US012636280B2

(12) United States Patent
Cho et al.

(10) Patent No.: US 12,636,280 B2
(45) **Date of Patent: *May 26, 2026**

(54) THERAPEUTIC TYROSINE KINASE INHIBITORS FOR RELAPSING MULTIPLE SCLEROSIS (RMS)

(71) Applicant: Principia Biopharma Inc., Morristown, NJ (US)

(72) Inventors: Meehyung Cho, Mountainside, NJ (US); Timothy J. Turner, Belmont, MA (US); Erik Wallstroem, Cambridge, MA (US)

(73) Assignee: Principia Biopharma Inc., Morristown, NJ (US)

( * ) Notice: Subject to any disclaimer, the term of this patent is extended or adjusted under 35 U.S.C. 154(b) by 80 days.

This patent is subject to a terminal disclaimer.

(21) Appl. No.: 18/613,641

(22) Filed: Mar. 22, 2024

(65) Prior Publication Data

US 2024/0366585 A1 Nov. 7, 2024

Related U.S. Application Data

(63) Continuation of application No. 17/151,954, filed on Jan. 19, 2021, now Pat. No. 11,969,418.

(60) Provisional application No. 63/013,895, filed on Apr. 22, 2020, provisional application No. 62/970,502, filed on Feb. 5, 2020, provisional application No. 62/963,238, filed on Jan. 20, 2020.

(51) Int. Cl.

| | |
|---|---|
| ***A61K 31/4545*** | (2006.01) |
| ***A61K 31/437*** | (2006.01) |
| ***A61P 25/00*** | (2006.01) |
| ***A61P 25/28*** | (2006.01) |

(52) U.S. Cl.

CPC .......... *A61K 31/4545* (2013.01); *A61P 25/28* (2018.01)

(58) Field of Classification Search

None

See application file for complete search history.

(56) References Cited

U.S. PATENT DOCUMENTS

| | | | |
|---|---|---|---|
| 3,760,984 | A | 9/1973 | Theeuwes |
| 3,952,741 | A | 4/1976 | Baker |
| 7,772,226 | B2 | 8/2010 | Yoshikawa et al. |
| 8,557,803 | B2 | 10/2013 | Yamamoto et al. |
| 9,199,997 | B2 | 12/2015 | Yamamoto et al. |
| 9,688,676 | B2 | 6/2017 | Owens |
| 9,695,164 | B2 | 7/2017 | Zhu et al. |
| 11,969,418 | B2 * | 4/2024 | Cho ........................ A61P 25/00 |
| 12,049,463 | B2 | 7/2024 | Chen et al. |
| 2006/0045822 | A1 | 3/2006 | Timmons et al. |
| 2013/0079327 | A1 | 3/2013 | Yamamoto et al. |
| 2013/0197014 | A1 | 8/2013 | Chen et al. |
| 2014/0142099 | A1 | 5/2014 | Owens |
| 2014/0179680 | A1 | 6/2014 | Christopher et al. |
| 2021/0113568 | A1 | 4/2021 | Ariza |
| 2021/0244720 | A1 | 8/2021 | Cho et al. |
| 2022/0389011 | A1 | 12/2022 | Chen et al. |
| 2024/0018142 | A1 | 1/2024 | Sheng et al. |
| 2024/0051955 | A1 | 2/2024 | Arabeyre et al. |
| 2024/0173313 | A1 | 5/2024 | Dukovic et al. |
| 2024/0238267 | A1 | 7/2024 | Calderone et al. |
| 2024/0366585 | A1 | 11/2024 | Cho et al. |
| 2024/0391915 | A1 | 11/2024 | Chen et al. |
| 2025/0034130 | A1 | 1/2025 | Chen et al. |
| 2025/0101021 | A1 | 3/2025 | Bailly et al. |
| 2025/0145618 | A1 | 5/2025 | Owens et al. |
| 2025/0197402 | A1 | 6/2025 | Goldstein et al. |
| 2025/0262193 | A1 | 8/2025 | Syed |
| 2025/0282777 | A1 | 9/2025 | Baltes et al. |
| 2025/0354998 | A1 | 11/2025 | Blazier et al. |

FOREIGN PATENT DOCUMENTS

| | | | |
|---|---|---|---|
| AU | 2022290946 | A1 | 1/2024 |
| CA | 2975072 | A1 | 8/2016 |
| CN | 101610676 | A | 12/2009 |
| CN | 103502249 | A | 1/2014 |
| CN | 104640861 | A | 5/2015 |
| CN | 105753863 | A | 7/2016 |
| EA | 020001 | B1 | 7/2014 |
| EP | 2578585 | A1 | 4/2013 |
| EP | 2786996 | A1 | 10/2014 |
| EP | 4328226 | A1 | 2/2024 |
| EP | 4342468 | A1 | 3/2024 |
| JP | 2010504324 | A | 2/2010 |
| JP | 2012246314 | A | 12/2012 |
| JP | 2013507448 | A | 3/2013 |
| JP | 2014517838 | A | 7/2014 |
| JP | 2016504277 | A | 2/2016 |
| JP | 2016094368 | A | 5/2016 |
| JP | 2018516935 | A | 6/2018 |
| JP | 2024544724 | A | 12/2024 |
| RU | 204139111 | A | 8/2005 |

(Continued)

OTHER PUBLICATIONS

"ASENT2021 Annual Meeting Abstracts ED—Vink Robert; Bullock M. Ross," Neurotherapeutics, 18(3), pp. 2134-2151 (2021).

Blazier A., "Tolebrutinib Can Reverse Multiple Sclerosis Induced Cerebrospinal Fluid Proteomic Alterations", Multiple Sclerosis Journal, 29(3) supplement, p. 564 (2023).

Blazier, A., "Evaluating Large Scale Proteomic Changes in Cerebrospinal Fluid of Multiple Sclerosis Patients Treated with Tolebrutinib", Multiple Sclerosis, 29(2) supplement, pp. 26-27 (2023).

(Continued)

*Primary Examiner* — Sun Jae Yoo

(74) *Attorney, Agent, or Firm* — McNeill PLLC

(57) ABSTRACT

This disclosure relates to the field of therapeutic tyrosine kinase inhibitors, in particular Bruton tyrosine kinase ("BTK") inhibitors for treatment of subjects with relapsing multiple sclerosis.

32 Claims, 9 Drawing Sheets

(56) References Cited

FOREIGN PATENT DOCUMENTS

| | | | |
|---|---|---|---|
| WO | 2003037890 | A2 | 5/2003 |
| WO | 2006031878 | A2 | 3/2006 |
| WO | 2006086634 | A2 | 8/2006 |
| WO | 2007142755 | A2 | 12/2007 |
| WO | 2008039218 | A2 | 4/2008 |
| WO | 2009010491 | A1 | 1/2009 |
| WO | 2010034796 | A1 | 4/2010 |
| WO | 2011046964 | A2 | 4/2011 |
| WO | 2011152351 | A1 | 12/2011 |
| WO | 2012158764 | A1 | 11/2012 |
| WO | 2012158785 | A1 | 11/2012 |
| WO | 2012170976 | A2 | 12/2012 |
| WO | 2013116382 | A1 | 8/2013 |
| WO | 2013184572 | A1 | 12/2013 |
| WO | 2013184757 | A1 | 12/2013 |
| WO | 2013191965 | A1 | 12/2013 |
| WO | 2014039899 | A1 | 3/2014 |
| WO | 2014078578 | A1 | 5/2014 |
| WO | 2014100620 | A2 | 6/2014 |
| WO | 2015132799 | A2 | 9/2015 |
| WO | 2016057500 | A1 | 4/2016 |
| WO | 2016089722 | A1 | 6/2016 |
| WO | 2016121777 | A1 | 8/2016 |
| WO | 2016196840 | A1 | 12/2016 |
| WO | 2017041536 | A1 | 3/2017 |
| WO | 2017066014 | A1 | 4/2017 |
| WO | 2017087445 | A1 | 5/2017 |
| WO | 2018096141 | A1 | 5/2018 |
| WO | 2021150476 | A1 | 7/2021 |
| WO | 2021247748 | A1 | 12/2021 |
| WO | 2022081512 | A1 | 4/2022 |
| WO | 2022140511 | A1 | 6/2022 |
| WO | 20220121670 | A1 | 6/2022 |
| WO | 2022223027 | A1 | 10/2022 |
| WO | 2022242740 | A1 | 11/2022 |
| WO | 2022257845 | A1 | 12/2022 |
| WO | 2023031840 | A1 | 3/2023 |
| WO | 2023122072 | A1 | 6/2023 |
| WO | 2023220370 | A1 | 11/2023 |
| WO | 2023244587 | A1 | 12/2023 |
| WO | 2023249980 | A1 | 12/2023 |
| WO | 2024006406 | A1 | 1/2024 |
| WO | 2024081168 | A1 | 4/2024 |
| WO | 2024137604 | A1 | 6/2024 |
| WO | 2024163542 | A2 | 8/2024 |
| WO | 2025188862 | A1 | 9/2025 |

OTHER PUBLICATIONS

International Search Report and Written Opinion issued in International Application No. PCT/US2024/013658 on Jul. 31, 2024 (25 pages).

Iwanowski et al., "CXCL10 and CXCL13 chemokines in patients with relapsing remitting and primary progressive multiple sclerosis", Journal of Neurological Sciences, vol. 380, pp. 22-26 (2017).

Kuhle J., "Evobrutinib, a Bruton's tyrosine kinase inhibitor, decreases neurofilament light chain levels over 2.5 years of treatment in patients with relapsing multiple sclerosis", Multiple Sclerosis Journal, 28(3 Supplement), pp. 822-823 (2022).

Martynova, E., "Serum and Cerebrospinal Fluid Cytokine Biomarkers for Diagnosis of Multiple Sclerosis", Mediators of Inflammation, vol. 2020, pp. 1-10 (2020).

Nuesslein-Hildesheim, B., "Remibrutinib inhibits neuroflammation driven by B cells and myeloid cells in preclinical models of multiple sclerosis," Multiple Sclerosis, vol. 28, No. 3 supplement, pp. 220-221 (2022).

Puthenparampil, M., "Wide Cytokine Analysis in Cerebrospinal Fluid at Diagnosis Identified CCL-3 as a Possible Prognostic Factor for Multiple Sclerosis," Frontiers in Immunology, vol. 11, p. 174 (2020).

Yang et al., "Current and Future Biomarkers in Multiple Sclerosis", International Journal of Molecular Sciences, 23(11), p. 5877 (2022).

Sanofi Press Release: "Tolebrutinib demonstrated a 31% delay in time to onset of confirmed disability progression in non-relapsing secondary progressive multiple sclerosis phase 3 study", 4 pages (Sep. 20, 2024).

Sanofi Press Release: "Tolebrutinib meets primary endpoint in HERCULES phase 3 study, the first and only to show reduction in disability accumulation in non-relapsing secondary progressive multiple sclerosis", 3 pages (Sep. 2, 2024).

Proposed *TM* Tolebrutinib Label, Genzyme Corporation/Sanofi (15 pages).

Lee et al., "Safety, pharmacokinetics, and pharmacodynamics of BMS-986142, a novel reversible BTK inhibitor, in healthy participants", European Journal of Clinical Pharmacology, 73(6), pp. 689-698 (2017).

Lehmann-Horn K, et al., "Deciphering the role of B cells in multiple sclerosis—towards specific targeting of pathogenic function.", Int J Mol Sci. 2017;18(10):2048.

Li et al., "Comparative efficacy and acceptability of disease-modifying therapies in patients with relapsing-remitting multiple sclerosis: a systematic review and network meta-analysis", J Neurol, pp. doi: 10.1007/s00415-019-09395-w (2019).

Linder et al., "Outcome in juvenile-onset myasthenia gravis: a retrospective study with long-term follow-up of 79 patients", J Neurol., 244(8), pp. 515-520 (Aug. 1997).

Lindstrom et al., "Antibody to acetylcholine receptor in myasthenia gravis. Prevalence, clinical correlates, and diagnostic value", Neurology., 26(11), pp. 1054-1059 (Nov. 1976).

Lipsky et al., "Incidence and risk factors of bleeding-related adverse events in patients with chronic lymphocytic leukemia treated with ibrutinib", Haematologica., 100(12), pp. 1571-1578 (Dec. 2015).

Liu et al., "Analysis of mortality and related factors in 2195 adult myasthenia gravis patients in a 10-year follow-up study", Neurol India, 65(3), pp. 518-524 (May-Jun. 2017).

Liu et al., "Disability outcome measures in therapeutic trials of relapsing-remitting multiple sclerosis: effects of heterogeneity of disease course in placebo cohorts", J Neurol Neurosurg Psychiatry, vol. 68, pp. 450-457 (2000).

Liu et al., "Tacrolimus Improves Symptoms of Children With Myasthenia Gravis Refractory to Prednisone", Pediatr Neurol., 77, pp. 42-47 (Dec. 2017).

Lublin F D, et. al., "Defining the clinical course of multiple sclerosis: the 2013 revisions.", Neurology. 2014;83(3):278-86.

Lynch et al., "Epidermal growth factor receptor inhibitor-associated cutaneous toxicities: an evolving paradigm in clinical management", Oncologist, 12(5), pp. 610-621 (May 2007).

Mangla et al., "Pleiotropic consequences of Bruton tyrosine kinase deficiency in myeloid lineages lead to poor inflammatory responses", Blood, 104, pp. 1191-1197 (2004).

Mansukhani et al., "Incidence and Ocular Features of Pediatric Myasthenias", Am J Ophthalmol., 200, pp. 242-249 (Apr. 2019).

Marta et al., "Microglial Fc receptors mediate physiological changes resulting from antibody cross-linking of myelin oligodendrocyte glycoprotein", J Neuroimmunol., 196(1-2), pp. 35-40 (2008).

Massimiliano et al., "Smoothness of gait detects early alterations of walking in persons with multiple sclerosis without disability", Gait & Posture, 58, pp. 307-309 (2017).

McGrogan et al., "The Incidence of Myasthenia Gravis: A Systematic Literature Review", Neuroepidemiology, 34, pp. 171-183 (2010).

McPherson et al., "Correlation of Quantitative Myasthenia Gravis and Myasthenia Gravis Activities of Daily Living scales in the MGTX study", Muscle Nerve, 62(2), pp. 261-266 (2020).

MedicineNet.com, Definition of Cancer (2004). (http://www.medterms.com) (1 page).

Merck Press release. Merck KGaA, Darmstadt, Germany, "Announces Positive Phase IIB Results for Evobrutinib in Relapsing Multiple Sclerosis.", Mar. 7, 2018.

Mexhitaj et al., "Abnormal effector and regulatory T cell subsets in paediatric-onset multiple sclerosis", Brain, 142(3), pp. 617-632 (2019).

Meyer-Moock et al., "Systematic literature review and validity evaluation of the expanded disability status scale (EDSS) and the multiple sclerosis functional composite (MSFC) in patients with multiple sclerosis", BMC Neurol., 14, p. 58 (Mar. 25, 2014).

(56) References Cited

OTHER PUBLICATIONS

Miller, R., "Chapter 10—Population Pharmacokinetics", Principles of clinical pharmacology, second edition, pp. 129-139 (2007).
Mohamed et al., "Bruton's tyrosine kinase (Btk): function, regulation, and transformation with special emphasis on the PH domain", Immunol Rev., 228, pp. 58-73 (2009).
Montalban et al., "Placebo-Controlled Trial of an Oral BTK Inhibitor in Multiple Sclerosis", The New England Journal of Medicine, 380(25), pp. 2406-2417 (Jun. 20, 2019).
Montalban X, et al. "Ocrelizumab versus placebo in primary progressive multiple sclerosis", N Engl J Med. 2017;376(3):209-20.
Morrow et al., "Predicting loss of employment over three years in multiple sclerosis: Clinically meaningful cognitive decline", Clin Neuropsychol, 24, pp. 1131-1145 (2010).
Mowry et al., "Multiple sclerosis susceptibility genes: associations with relapse severity and recovery", PLoS One 2013; 8:e75416.
Munot et al., "242nd ENMC international diagnosis and management of juvenile myasthenia gravis Hoofddorp, the Netherlands, Mar. 1-3, 2019", Neuromuscul Disord., 30, pp. 254-264 (2010).
Muppidi et al., "MG-ADL: Still a relevant outcome measure", Muscle Nerve, vol. 44, pp. 727-731 (2011).
Muppidi, "The myasthenia gravis-specific activities of daily living profile", Ann N.Y. Acad Sci, vol. 1274, pp. 114-119 (2012).
Murray et al., "Semiparametric Bayesian Commensurate Survival Model for Post-Market Medical Device Surveillance with Non-Exchangeable Historical Data", Biometrics, 70, pp. 185-191 (Mar. 2014).
Narayanaswami et al., "International Consensus Guidance for Management of Myasthenia Gravis: 2020 Update", Neurology, 96(3), pp. 114-122 (Jan. 19, 2021).
National MS Society web site (https://www.nationalmssociety.org/What-is-MS/MS-FAQ-s) (5 pages).
Navarro et al., "Antiviral Immunity", Curr Immunol Rev., 7, pp. 19-24 (2011).
Noêl, R. et al., "Synthesis and SAR of 4-(pyrazol-3-yl)-pyridines as novel c-jun N-terminal kinase inhibitors" Bioorganic & Medicinal Chemistry Letters, vol. 21, Issue 9, (2011) 2732-2735.
O'Connell et al., "Management of Juvenile Myasthenia Gravis", Front. Neurol., 11, p. 743 (2020).
O'Connor et al., "Randomized Trial of Oral Teriflunomide for Relapsing Multiple Sclerosis", N Engl J Med, 365, pp. 1293-1303 (2011).
Okun et al., "Involvement of Fc receptors in disorders of the central nervous system", Neuromolecular Med., 12(2), pp. 164-178 (2010).
Online "https://www.chemicalbook.com/Chemical ProductProperty_EN_CB6195326.htm" dated by google to Oct. 1, 2014, Accessed Jun. 18, 2020 (4 pages).
Otallah et al., "Pediatric Multiple Sclerosis: an Update", Curr Neurol Neurosci Rep., 18(11), p. 76 (Sep. 18, 2018).
Owens et al., "Phase 1 clinical trial evaluating safety, exposure and pharmacodynamics of BTK inhibitor tolebrutinib (PRN2246, SAR442168)", Clin Transl Sci., 00, pp. 1-9 (2021).
Parr et al., "How common is childhood myasthenia? The UK incidence and prevalence of autoimmune and congenital myasthenia", Arch Dis Child, 99(6), pp. 539-542 (Jun. 2014).
Patani, G., Bioisosterism: A Rational Approach in Drug Design. Chem. Rev. 1996, vol. 96, No. 8, pp. 3147-3176.
Pedersen et al., "Late-onset myasthenia not on the increase: a nationwide register study in Denmark", 1996-2009. Eur J Neurol., 20, pp. 309-314 (2013).
Pennington et al., "The Necessary Nitrogen Atom: A Versatile High-Impact Design Element for Multiparameter Optimization," J. Med. Chem., ePub Feb. 8, 2017, 28 pages, DOI: 10.1021/acs.jmedchem 6b01807.
Peragallo JH., "Pediatric Myasthenia Gravis", Semin Pediatr Neurol., 24(2), pp. 116-121 (May 2017).
Phillips et al., "Sustained improvement in Expanded Disability Status Scale as a new efficacy measure of neurological change in multiple sclerosis: treatment effects with natalizumab in patients with relapsing", Multiple Sclerosis Journal, 17(8), pp. 970-979 (2011).
Popperud et al., "Juvenile myasthenia gravis in Norway: HLA-DRB1_04:04 is positively associated with prepubertal onset", PLoS ONE, 12(10): e0186383 (2017).
Press Release: "Sanofi to acquire Principia Biopharma", 6 pages (Aug. 17, 2020).
Ragheb et al., "B-Cell-Activating Factor and Autoimmune Myasthenia Gravis", Autoimmune Dis., 2011; 939520.
"General Tests, Processes and Apparatus—2.58 X-Ray Powder Diffraction Method", Japanese Pharmacopoeia, 16th edition, 2011, pp. 75-79 (English version).
English Translation of Japanese Patent No. 2016-094368A, issued on May 26, 2016 (15 pages).
Sanofi Press Release, "Tolebrutinib designated Breakthrough Therapy by the FDA for non-relapsing secondary progressive multiple sclerosis", Dec. 13, 2024 (3 pages).
Absinta et al., "Association of Chronic Active Multiple Sclerosis Lesions With Disability In Vivo", JAMA Neurology, 76(12), pp. 1474-1483 (2019).
Akinsanya et al., "Toward the Use of Paramagnetic Rim Lesions in Proof-of-Concept Clinical Trials for Treating Chronic Inflammation in Multiple Sclerosis", P126, Multiple Sclerosis Journal, 27: (1S), pp. 74-75 (2021).
Akinsanya et al., "Toward the Use of Paramagnetic Rim Lesions in Proof-of-Concept Clinical Trials for Treating Chronic Inflammation in Multiple Sclerosis", National Institute of Neurological Disorders and Stroke, Actrims, P126, 2021 (10 pages).
Ali Raza et al., "(0058/1599) Cerebrospinal fluid myeloid modulation in patients with multiple sclerosis treated with tolebrutinib", Multiple Sclerosis Journal; 29: (3S), pp. 41-42 (2023).
Ali Raza et al., "Cerebrospinal fluid and serum proteome signature for chronic active multiple sclerosis", P253, National Institute of Neurological Disorders and Stroke, ECTRIMS (1 page) (2024).
Ali Raza et al., "Cerebrospinal fluid myeloid modulation in patients with multiple sclerosis treated with tolebrutinib", National Institute of Neurological Disorders and Stroke, ECTRIMS 2023, Italy (11 pages).
Ali Raza et al., "CSF and serum proteome signature for chronic active multiple sclerosis", P253/1586, Multiple Sclerosis Journal, 30: (3S), p. 303 (2024).
Arnold et al., "Effect of Evobrutinib on Slowly Expanding Lesion Volume in Relapsing Multiple Sclerosis. A Post Hoc Analysis of a Phase 2 Trial", Neurology®, 102:e208058 (2024) (11 pages).
Bagnato et al., "Associations between chronic active lesions and clinical outcomes in multiple sclerosis: A systematic literature review", JMCP.org, 31(7), pp. 694-721 (Jul. 2025).
Bagnato et al., "Imaging chronic active lesions in multiple sclerosis: a consensus statement", Brain, 147, pp. 2913-2933 (2024).
Baharlou, S., "International Preliminary Report on Patentability", issued in International Application No. PCT/US2023/022042 on Nov. 7, 2024 (9 pages).
Baharlou, S., "International Preliminary Report on Patentability", issued in International Application No. PCT/US2023/025170 on Dec. 10, 2024 (6 pages).
Barr et al., "Microglial BTK Signaling Regulates Immune-Mediated Cortical Demyelination", P196, Multiple Sclerosis Journal, 27: (1S), pp. 107-108 (2021).
Barr et al., "Microglial BTK signaling regulates immune-mediated cortical demyelination", Poster P196, Actrims (10 pages) (2021).
Baston, E., "Extended European Search Report", issued in European Application No. EP 21902377.7 on Oct. 28, 2024 (6 pages).
Becker et al., "Safety, Tolerability, Pharmacokinetics, Target Occupancy, and Concentration-QT Analysis of the Novel BTK Inhibitor Evobrutinib in Healthy Volunteers", Clin Transl Sci, 13, pp. 325-336 (2020).
Blazier et al., "Evaluating Large Scale Proteomic Changes in Cerebrospinal Fluid of Multiple Sclerosis Patients Treated with Tolebrutinib", P019, Presented at the 8th Annual Americas Committee for Treatment and Research in Multiple Sclerosis (ACTRIMS) Forum; San Diego, CA, USA; Feb. 23-25, 2023 (1 page).

(56) References Cited

OTHER PUBLICATIONS

Blazier et al., "Evaluating large scale proteomic changes in cerebrospinal fluid of multiple sclerosis patients", EP1037, Multiple Sclerosis Journal; 28: (3S), pp. 833-834 (2022).

Blazier et al., "Evaluating Large Scale Proteomic Changes in Cerebrospinal Fluid of Multiple Sclerosis Patients", Presented at the 38th Congress of the European Committee for Treatment and Research in Multiple Sclerosis, Oct. 26-28, 2022, Amsterdam, the Netherlands (1 page).

Blazier et al., "Tolebrutinib Can Reverse Multiple Sclerosis-Induced Cerebrospinal Fluid Proteomic Alterations", P645, Presented at the 9th Joint ECTRIMS-ACTRIMS Meeting; Milan, Italy; Oct. 11-13, 2023 (1 page).

Bojanowski et al., "Efficacy and Safety of the Bruton's Tyrosine Kinase Inhibitor Evobrutinib in Patients with Relapsing Multiple Sclerosis over 48 Weeks: a Randomised, Placebocontrolled, Phase 2 Study", Multiple Sclerosis Journal 2020; NP69-NP70 (2020).

Bosworth, Ted, "No Support for BTK Inhibitor in Phase 3 Multiple Sclerosis Trial", ACTRIMS 2024, Medscape Medical News, 4 pages (Mar. 7, 2024).

Cabanis et al., "A phase I trial assessing the safety, pharmacokinetics, cerebrospinal fluid penetrance, and food effect of BTK inhibitor tolebrutinib in healthy volunteers", Clin Transl Sci., 17:e13693 (2024) (12 pages).

Cagol et al., "Association of Spinal Cord Atrophy and Brain Paramagnetic Rim Lesions With Progression Independent of Relapse Activity in People With MS", Neurology, 102: e207768 (2024) (14 pages).

Calabresi, P.A., "Progress toward Mitigating Disability Progression in Multiple Sclerosis", The New England Journal of Medicine, 392;19, pp. 1966-1968 (2025).

Caldwell et al., "Discovery of Evobrutinib: An Oral, Potent, and Highly Selective, Covalent Bruton's Tyrosine Kinase (BTK) Inhibitor for the Treatment of Immunological Diseases", J. Med. Chem., 62, pp. 7643-7655 (2019).

Chertcoff et al., "Recent Advances in Diagnostic, Prognostic, and Disease-Monitoring Biomarkers in Multiple Sclerosis", Neurol Clin, 42, pp. 15-38 (2024).

Chomyk et al., "Transcript Profiles of Microglia/Macrophage Cells at the Borders of Chronic Active and Subpial Gray Matter Lesions in Multiple Sclerosis", Ann Neurol, 95, pp. 907-916 (2024).

Ciccarelli et al., "Using the Progression Independent of Relapse Activity Framework to Unveil the Pathobiological Foundations of Multiple Sclerosis", Neurology, 103: e209444 (2024) (10 pages).

ClincialTrials.gov, "A Study to Investigate Long-term Safety and Tolerability of Tolebrutinib in Participants With Multiple Sclerosis", NCT06372145, Record History Tab,Version 1, Last Updated Jul. 8, 2025 (13 pages).

ClincialTrials.gov, "Dose-finding Study for SAR442168 in Relapsing Multiple Sclerosis", NCT03889639, Record History Tab, Version 18, Last Updated Mar. 8, 2023 (21 pages).

ClincialTrials.gov, "Efficacy and Safety of Tolebrutinib (SAR442168) Tablets in Adult Participants With Generalized Myasthenia Gravis (URSA)", NCT05132569, Record History Tab, Version 10, Last Updated Apr. 8, 2024 (16 pages).

ClincialTrials.gov, "Efficacy and Safety of Tolebrutinib (SAR442168) Tablets in Adult Participants With Generalized Myasthenia Gravis (URSA)", NCT05132569, Record History Tab, Version 17, Last Updated Apr. 8, 2024 (62 pages).

ClincialTrials.gov, "Efficacy and Safety of Tolebrutinib (SAR442168) Tablets in Adult Participants With Generalized Myasthenia Gravis (URSA)", NCT05132569, Record History Tab, Version 2, Last Updated Apr. 8, 2024 (13 pages).

ClincialTrials.gov, "Long Term Safety and Efficacy Study of Tolebrutinib (SAR442168) in Participants With Relapsing Multiple Sclerosis", NCT03996291, Record History Tab, Version 13, Last Updated Dec. 27, 2024 (17 pages).

ClincialTrials.gov, "Long Term Safety and Efficacy Study of Tolebrutinib (SAR442168) in Participants With Relapsing Multiple Sclerosis", NCT03996291, Record History Tab, Version 1, Last Updated Dec. 27, 2024 (13 pages).

ClincialTrials.gov, "Long Term Safety and Efficacy Study of Tolebrutinib (SAR442168) in Participants With Relapsing Multiple Sclerosis", NCT03996291, Record History Tab, Version 3, Last Updated Dec. 27, 2024 (13 pages).

ClincialTrials.gov, "Long Term Safety and Efficacy Study of Tolebrutinib (SAR442168) in Participants With Relapsing Multiple Sclerosis", NCT03996291, Record History Tab, Version 17, Last Updated Dec. 27, 2024 (15 pages).

ClincialTrials.gov, "Long Term Safety and Efficacy Study of Tolebrutinib (SAR442168) in Participants With Relapsing Multiple Sclerosis", NCT03996291, Record History Tab, Version 15, Last Updated Dec. 27, 2024 (15 pages).

ClincialTrials.gov, "Study of Drug-drug Interaction of the Effects of Gemfibrozil and Rifampicin on SAR442168 in Healthy Adult Subjects", NCT06064539, Record History Tab, Version 1, Last Updated Oct. 3, 2023 (10 pages).

ClincialTrials.gov, "Study of the Tolerability and Pharmacokinetics of Oral Doses of SAR442168 With a Food Effect Investigation in Healthy Adult Participants", NCT06106074, Record History Tab, Version 1, Last Updated Oct. 30, 2023 (10 pages).

ClincialTrials.gov, "Study to Assess the Plasma Concentration of Tolebrutinib Given as a Tablet to Adult Participants with Mild Hepatic Impairment Compared to Participants with Normal Hepatic Function", NCT05283915, Record History Tab, Version 4, Last Updated Jan. 15, 2025 (11 pages).

ClincialTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 159, Last Updated Aug. 13, 2024 (29 pages).

ClincialTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 145, Last Updated Aug. 13, 2024 (29 pages).

ClincialTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 95, Last Updated Aug. 13, 2024 (29 pages).

ClincialTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 167, Last Updated Aug. 13, 2024 (41 pages).

ClinicalTrials.gov "Dose-finding Study for SAR442168 in Relapsing Multiple Sclerosis", NCT03889639, v1, Last Updated Mar. 8, 2023 (17 pages).

ClinicalTrials.gov "Dose-finding Study for SAR442168 in Relapsing Multiple Sclerosis", NCT03889639, ver 17, Last Updated Mar. 8, 2023 (21 pages).

ClinicalTrials.gov, "Dose-finding Study for SAR442168 in Relapsing Multiple Sclerosis", NCT03889639, Record History Tab, Version 20, Last Updated Mar. 8, 2023 (55 pages).

ClinicalTrials.gov, "Nonrelapsing Secondary Progressive Multiple Sclerosis (NRSPMS) Study of Bruton's Tyrosine Kinase (BTK) Inhibitor Tolebrutinib (SAR442168)(Hercules) (Hercules)", NCT04411641, Record History Tab, Version 1, Last Updated Jul. 2, 2025 (15 pages).

Nakamura, Y., "International Preliminary Report on Patentability", International Application No. PCT/US2023/034655 on Apr. 15, 2025 (9 pages).

NHS Oxford University Hospitals, "MOG Antibody Demyelination. Information for patients", Apr. 2019 (12 pages).

Nickitas-Etienne, A., "International Preliminary Report on Patentability", issued in International Application No. PCT/US2016/035588 on Dec. 5, 2017 (6 pages).

Nickitas-Etienne, A., "International Preliminary Report on Patentability", issued in International Application No. PCT/US2021/013883 on Jul. 26, 2022 (8 pages).

(56) References Cited

OTHER PUBLICATIONS

Nicolas et al., "Absorption, Metabolism, and Excretion of [14C]-Tolebrutinib After Oral Administration in Humans, Contribution of the Metabolites to Pharmacological Activity", Clinical Drug Investigation, 43, pp. 653-665 (2023).
Nicolas et al., "Tolebrutinib Demonstrates Cerebrospinal Fluid Exposure at Bioactive Levels in a Single-Ascending Dose Study in Healthy Volunteers", P151, Presented at the 8th Annual Americas Committee for Treatment and Research in Multiple Sclerosis (ACTRIMS) Forum; San Diego, CA, USA; Feb. 23-25, 2023 (1 page).
Nicolas et al., "Tolebrutinib Demonstrates Cerebrospinal Fluid Exposure at Bioactive Levels in a Single-Ascending Dose Study in Healthy Volunteers", P151, Multiple Sclerosis Journal, 29:(2S), p. 89 (2023).
Oh et al, "Safety and clinical efficacy outcomes from the Long-term extension study of tolebrutinib in patients with relapsing multiple sclerosis: 2-year results", P308, Multiple Sclerosis Journal, 28: (3S), pp. 342-343 (2022).
Oh et al., "Efficacy and Safety of Tolebrutinib Versus Teriflunomide in Relapsing Multiple Sclerosis: Results from the Phase 3 GEMINI 1 and 2 Trials", O135/4026, Multiple Sclerosis Journal; 30: (3S), pp. 1145-1146 (2024).
Oh et al., "Efficacy and Safety of Tolebrutinib Versus Teriflunomide in Relapsing Multiple Sclerosis: Results From the Phase 3 GEMINI 1 and 2 Trials", ECTRIMS 2024, Presentation #0135, Presented at the 40th Congress of the European Committee for Treatment and Research in Multiple Sclerosis; Sep. 18-20, 2024; Copenhagen, Denmark (16 pages).
Oh et al., "MRI, Safety, and Efficacy Outcomes in Patients with Relapsing MS: 18-month Results from the Long-term Extension Study of Tolebrutinib", P102, Presented at the American Committee for Treatment and Research in Multiple Sclerosis (ACTRIMS) Forum, Feb. 24-26, 2022, West Palm Beach, FL (1 page).
Oh et al., "MRI, Safety, and Efficacy Outcomes in Patients with Relapsing MS: 18-month Results from the Long-term Extension Study of Tolebrutinib", P102, Multiple Sclerosis Journal, 28: (1S), p. 66 (2022).
Oh et al., "Paramagnetic Rim Lesions as a Prognostic and Predictive Biomarker in the Tolebrutinib Phase 3 Trials for Disability Outcomes", LB1.1, Multiple Sclerosis Journal, 31: (2S), pp. 10-11 (2025).
Oh et al., "Paramagnetic Rim Lesions as a Prognostic and Predictive Biomarker in the Tolebrutinib Phase 3 Trials for Disability Outcomes", P755, Presented at the 10th Annual Americas Committee for Treatment and Research in Multiple Sclerosis (ACTRIMS) Forum, Feb. 27-Mar. 1, 2025; West Palm Beach, Florida (11 pages).
Oh et al., "Safety and Clinical Efficacy Outcomes From the Long-Term Extension Study of Tolebrutinib in Participants With Relapsing Multiple Sclerosis: 3-Year Results", P278, Presented at the 9th Joint ECTRIMS-ACTRIMS Meeting; Milan, Italy; Oct. 11-13, 2023 (1 page).
Oh et al., "Safety and Clinical Efficacy Outcomes from the Long-term Extension Study of Tolebrutinib in Participants with Relapsing Multiple Sclerosis:3-Year Results", P278/1470, Multiple Sclerosis Journal, 29: (3S), pp. 334-335 (2023).
Oh et al., "Safety and Clinical Efficacy Outcomes from the Long-term Extension Study of Tolebrutinib in Participants with Relapsing Multiple Sclerosis: 2.5-Year Results", (S16.010), Neurology, MS Clinical Trials and Therapeutics, 100 (17_supplement_2) (Apr. 28, 2023)(3 pages).
Oh et al., "Safety and Clinical Efficacy Outcomes From the Long-term Extension Study of Tolebrutinib in Participants With Relapsing Multiple Sclerosis: 2.5-Year Results", AAN 2023, Platform S16 010 (11 pages).
Oh et al., "Safety and Clinical Efficacy Outcomes from the Long-Term Extension Study of Tolebrutinib in Patients with Relapsing Multiple Sclerosis: 2-Year Results", P308, Presented at the 38th Congress of the European Committee for Treatment and Research in Multiple Sclerosis (ECTRIMS); Amsterdam, the Netherlands; Oct. 26-28, 2022 (1 page).
Oh et al., "Safety and efficacy outcomes from the long-term extension study of tolebrutinib in patients with relapsing MS: Year 1 results", P667, Multiple Sclerosis Journal, 27: (2S), pp. 571-572 (2021).
Oh et al., "Safety and Efficacy Outcomes From the Long-term Extension Study of Tolebrutinib in Patients With Relapsing MS: Year 1 Results", P667, Presented at the 37th Congress of the European Committee for Treatment and Research in Multiple Sclerosis, Oct. 13-15, 2021, Virtual (1 page).
Oh et al., "Safety and Efficacy Outcomes in Patients with Relapsing MS: 18-month Results from the Longterm Extension Study of Tolebrutinib", AAN 2022, Platform S 14:003 (10 pages).
Oh et al., "Tolebrutinib versus Teriflunomide in Relapsing Multiple Sclerosis", The New England Journal of Medicine, Apr. 8, 2025 (12 pages); DOI: 10.1056/NEJMoa2415985.
Orlandi et al., "Tolebrutinib. Bruton tyrosine kinase (BTK) inhibitor Treatment of multiple sclerosis", Drugs of the Future, 47(5), pp. 325-336 (2022).
Osborne, R., "MS Aubagio tableau: Sanofi talks tolebrutinib, Immunic the pick?", BioWorld, Sep. 20, 2024 (3 pages) (www.bioworld.com/articles/712670-ms-aubagio-tableau-sanofi-talks-tolebrutinib-immunic-the-pick.
Pachner et al., "Clinical utility of a molecular signature in inflammatory demyelinating disease", Neurol Neuroimmunol Neuroinflamm, 6:e520 (2019) (10 pages).
Papasouliotis et al., "Determination of a clinically effective evobrutinib dose: Exposure—response analyses of a phase II relapsing multiple sclerosis study", Clin Transl Sci., 15, pp. 2888-2898 (2022).
Polman et al., "Diagnostic Criteria for Multiple Sclerosis: 2005 Revisions to the McDonald Criteria", Ann Neurol, 58, pp. 840-846 (2005).
Real Talk MS, "ECTRIMS Extra: Results from the Tolebrutinib Phase 3 Clinical Trial for RRMS with Dr. Jiwon Oh", Oct. 4, 2024 (6 pages).
Real Talk MS, "Episode 373: ECTRIMS Research Roundup Part 2 with Dr. Bruce Bebo", with transcript, Oct. 22, 2024 (11 pages).
Real Talk MS, "RealTalk MS ECTRIMS Extra: Tolebrutinib and RRMS", with transcript, Dec. 15, 2024 (11 pages).
Real Talk MS, "RealTalk MS ECTRIMS Extra: Tolebrutinib and SPMS", with transcript, Dec. 15, 2024 (10 pages).
Real Talk MS, "RealTalk MS, Episode 369: ECTRIMS 2024 with Kristine Werner Ozug and Dr. Bruce Bebo", with translation, Sep. 24, 2024 (12 pages).
Reich et al., "A Phase 2 Trial of Tolebrutinib, a Bruton's Tyrosine Kinase Inhibitor, for Chronic Active Lesions in Multiple Sclerosis", National Institute of Neurological Disorders and Stroke, EPO-600, Presentation (1 page) (2024).
Reich et al., "A phase 2 trial of tolebrutinib, a Bruton's tyrosine kinase inhibitor, for chronic active lesions in multiple sclerosis", EPO-600, Ean, Abstract, 687 (2024).
Reich et al., "Efficacy and Safety Outcomes in Patients With Relapsing Forms of MS Treated With the CNS-Penetrating BTK Inhibitor SAR442168: Results From the Phase 2b Trial", Presentation from EAN 2020, O4010 (17 pages).
Reich et al., "Efficacy and safety outcomes in patients with relapsing forms of MS treated with the CNS-Penetrating BTK inhibitor SAR442168: results from the phase 2b trial", O4010, European Journal of Neurology, 27 (Suppl. 1), p. 91 (2020).
Reich et al., "MRI Outcomes from the Long-term Extension Study of Tolebrutinib in Participants with Relapsing Multiple Sclerosis: 3-Year Results", P684/1478, Multiple Sclerosis Journal, 29:592 (3S)(2023).
Reich et al., "MRI Outcomes From the Long-Term Extension Study of Tolebrutinib in Participants With Relapsing Multiple Sclerosis: 3-Year Results", P684, Presented at the 9th Joint ECTRIMS-ACTRIMS Meeting; Milan, Italy; Oct. 11-13, 2023 (1 page).
Reich et al., "MRI Outcomes from the Long-term Extension Study of Tolebrutinib in Patients with Relapsing MS: 18-Month Results", Presented at the American Academy of Neurology (AAN) Virtual Annual Meeting, Apr. 24-26, 2022 (1 page).

(56) References Cited

OTHER PUBLICATIONS

Reich et al., "MRI Outcomes from the Long-Term Extension Study of Tolebrutinib in Patients with Relapsing Multiple Sclerosis: 2-Year Results", P297, Presented at the 38th Congress of the European Committee for Treatment and Research in Multiple Sclerosis (ECTRIMS); Amsterdam, the Netherlands; Oct. 26-28, 2022 (1 page).
Reich et al., "MRI outcomes from the long-term extension study of tolebrutinib in patients with relapsing multiple sclerosis: 2-year results", P297, Multiple Sclerosis Journal, 28: (3S), pp. 334-335 (2022).
Reich et al., MRI Outcomes from the Long-term Extension Study of Tolebrutinib in Patients with Relapsing Multiple Sclerosis: 18-Month Results (P1-1. Virtual), Neurology, MS and CNS Inflammatory Disease Virtual, 98 (18_supplement) (May 3, 2022) (1 page).
Reich et al., "MRI outcomes from the long-term extension study of tolebrutinib in relapsing MS: Year 1 results", P666, Multiple Sclerosis Journal, 27: (2S), p. 571 (2021).
Reich et al., "MRI Outcomes From the Long-term Extension Study of Tolebrutinib in Relapsing MS: Year 1 Results", P666, Presented at the 37th Congress of the European Committee for Treatment and Research in Multiple Sclerosis, Oct. 13-15, 2021, Virtual (1 page).
Rijvers et al., "Human T-bet+ B cell development is associated with BTK activity and suppressed by evobrutinib", JCI insight, 7(16): e160909 (2022).
Rochaix, T., "International Preliminary Report on Patentability", issued in International Application No. PCT/US2023/026526 on Dec. 18, 2024 (9 pages).
Rocky Mountain MS Center, "BTK inhibitors Update: Tolebrutinib Phase 3 Clinical Trial Results", Sep. 16, 2024 (3 pages).
Sanofi Press Release, "Tolebrutinib phase 3 data published in NEJM demonstrate benefit on disability progression in multiple sclerosis", 4 pages, Apr. 8, 2025.
Sanofi Press Release, "Tolebrutinib regulatory submission accepted for priority review in the US for patients with multiple sclerosis", Mar. 25, 2025 (3 pages).
Sanofi, Amended Clinicial Trial Protocol 08, "An interventional, Phase 3 extension study to investigate long-term safety and tolerability of tolebrutinib in participants with relapsing multiple sclerosis, primary progressive multiple sclerosis, or nonrelapsing secondary progressive multiple sclerosis", LTS17043, EUCT 2023-503631-18 (Sep. 27, 2024) (140 pages).
Sanofi, Amended Clinicial Trial Protocol 14, "A Phase 3, randomized, double-blind, efficacy andsafety study comparing SAR442168 to placebo inparticipants with primary progressive multiplesclerosis (PERSEUS)", EFC16035, SAR442168 (Oct. 31, 2024) (163 pages).
Scalfari et al., "Smouldering-Associated Worsening in Multiple Sclerosis: An International Consensus Statement on Definition, Biology, Clinical Implications, and Future Directions", Annals of Neurology, 96, pp. 826-845 (2024).
Schwind et al., "Quantitative functional measures in MS: What is a reliable change?" Neurology, 58, pp. 1294-1296 (2002).
Smith et al., "Phase 1 Clinical Trial of PRN2246 (SAR442168), a Covalent BTK Inhibitor Demonstrates Safety, CNS Exposure and Therapeutic Levels of BTK Occupancy", ACTRIMS, P072, Feb. 28, 2019 (1 page).
Syed et al., "Efficacy and Safety of Tolebrutinib in Adults with Generalized Myasthenia Gravis: Phase 3 Study Design", eP03.04.09, J Neuromusc Dis, Abstracts, S246-S247 (2022).
Syed et al., "Efficacy and Safety of Tolebrutinib in Patients with Highly Active Relapsing MS: Subgroup Analysis of the Phase 2b Study (2260)", Neurology, MS and CNS Inflammatory Disease: Emerging Therapeutics and Biomarkers, 96 (15_supplement) (Apr. 13, 2021) (3 pages).
Syed et al., "Subgroup Analysis of Patients With Relapsing MS and Highly Active Disease in the Tolebrutinib Phase 2b Study", AAN 2021, Platform S25:004 (11 pages).
Traboulsee et al., "Lack of Rebound Disease Activity in Patients with Relapsing Multiple Sclerosis Following Placebo Run-Out in the Tolebrutinib Phase 2b Trial", P296, Presented at the 38th Congress of the European Committee for Treatment and Research in Multiple Sclerosis (ECTRIMS); Amsterdam, the Netherlands; Oct. 26-28, 2022 (1 page).
Turner et al., "Comparative CNS Pharmacology of the Bruton's Tyrosine Kinase (BTK) Inhibitor Tolebrutinib Versus Other BTK Inhibitor Candidates for Treating Multiple Sclerosis", Drugs in R&D, 24, pp. 263-274 (2024).
Turner et al., "Comparative CNS Pharmacology of Tolebrutinib Versus Other BTK Inhibitor Candidates for Treating MS (S46. 007)", Neurology, MS Therapeutics and Clinical Decision Making, AAN, 100 (17_supplement_2), Apr. 28, 2023 (2 pages).
Turner et al., "Comparative CNS Pharmacology of Tolebrutinib Versus Other BTK Inhibitor Candidates for Treating MS", AAN 2023, Presentation 007 (13 pages).
Turner et al., "Comparative CNS Pharmacology of Tolebrutinib Versus Other BTK Inhibitor Candidates for Treating MS", Presented at the Americas Committee for Treatment and Research in Multiple Sclerosis (ACTRIMS) Forum, Feb. 24-26, 2022, West Palm Beach, FL, USA (1 page).
Turner, T.J., "Comparative CNS Pharmacology of Tolebrutinib Versus Other BTK Inhibitor Candidates for Treating MS", P162, Multiple Sclerosis Journal, 28: (1S), pp. 94-95 (2022).
Unknown, International Search Report and Written Opinion of the International Searching Authority issued in International Application No. PCT/US2025/018520 on Jul. 28, 2025 (15 pages).
Vermersch et al., "Bruton's Tyrosine Kinase Inhibitor Tolebrutinib in Patients With Progressive MS: Design of the Phase 3 PERSEUS and HERCULES Trials", EPO-455, Presented at the 7th Congress/ 2nd Virtual Congress of the European Academy of Neurology (EAN), Jun. 19-22, 2021 (1 page).
Vermersch et al., BTK Inhibitor Tolebrutinib in Patients With Progressive MS: Design of Phase 3PERSEUS and HERCULES Trials, EPO-455, European Journal of Neurology, 28 (Suppl. 1), p. 727 (2021).
Waldron, James, "Sanofi's tolebrutinib fails 2 of trio of phase 3 MS trials, but pharma still plans FDA filing", Fierce Biotech, Sep. 2, 2024 (3 pages).
Wang, X., "International Preliminary Report on Patentability", issued in International Application No. PCT/US2023/025808 on Dec. 18, 2024 (14 pages).
WHO, "International Nonproprietary Names forPharmaceutical Substances (INN)", WHO Drug Information, List 84, vol. 34, No. 3, 2020 (115 pages).
WHO, "International Nonproprietary Names forPharmaceutical Substances (INN)", WHO Drug Information, Proposed List 112, vol. 33, No. 4, 2019 (139 pages).
Wiendl et al., "Baseline Characteristics in the Tolebrutinib Phase 3 Relapsing Multiple Sclerosis GEMINI 1 and 2 Trials", EPO-664, Presented at 9th Congress of the European Academy of Neurology (EAN), Jul. 1-4, 2023, Budapest, Hungary (1 page).
Wiendl et al.,"EPO-664, Baseline Characteristics in the Tolebrutinib Phase 3 Relapsing Multiple Sclerosis GEMINI 1 and 2 Trials", EPO-224, European Journal of Neurology, 30 (Suppl. 1), pp. 649-742 (2023).
Wirak et al., "Bruton's Tyrosine Kinase Regulates Microglial Proinflammatory Pathways—Implications for Multiple Sclerosis", P134, Presented at the 9th Joint ECTRIMS-ACTRIMS Meeting; Milan, Italy; Oct. 11-13, 2023 (1 page).
Wirak et al., "Bruton's tyrosine kinase regulates microglial proinflammatory pathways—implications for multiple sclerosis", P134/2063, Multiple Sclerosis Journal, 29: (3S), p. 229 (2023).
Wynford-Thomas et al., "Neurological update: MOG antibody disease", Journal of Neurology, 266, pp. 1280-1286 (2019).
ClinicalTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES) (HERCULES)", NCT04411641, Record History Tab, Version 20, Last Updated Jul. 2, 2025 (15 pages).
ClinicalTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES) (HERCULES)", NCT04411641, Record History Tab, Version 31, Last Updated Jul. 2, 2025 (39 pages).

(56) References Cited

OTHER PUBLICATIONS

ClinicalTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES) (HERCULES)", NCT04411641, Record History Tab, Version 14, Last Updated Jul. 2, 2025 (21 pages).
ClinicalTrials.gov, "Nonrelapsing Secondary Progressive Multiple Sclerosis (NRSPMS) Study of Bruton's Tyrosine Kinase (BTK) Inhibitor Tolebrutinib (SAR442168)(HERCULES)(HERCULES)", NCT04411641, Record History Tab, Version 32, Last Updated Jul. 2, 2025 (90 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 39, Last Updated Jan. 13, 2025 (56 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 25, Last Updated Jan. 13, 2025 (51 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 1, Last Updated Jan. 13, 2025 (15 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 43, Last Updated Jan. 13, 2025 (38 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 42, Last Updated Jan. 13, 2025 (39 pages).
ClinicalTrials.gov, "Primary Progressive Multiple Sclerosis (PPMS) Study of Bruton's Tyrosine Kinase (BTK) Inhibitor Tolebrutinib (SAR442168) (PERSEUS) (PERSEUS)", NCT04458051, Record History Tab, Version 11, Last Updated Jan. 13, 2025 (22 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 2) (GEMINI 2)", NCT04410991, Record History Tab, Version 40, Last Updated Jul. 2, 2025 (72 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 1)(GEMINI 1)", NCT04410978, Records History Tab, Version 1, Last Updated Jul. 2, 2025 (17 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 1)(GEMINI 1)", NCT04410978, Records History Tab, Version 17, Last Updated Jul. 2, 2025 (24 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 1)(GEMINI 1)", NCT04410978, Records History Tab, Version 26, Last Updated Jul. 2, 2025 (34 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 2) (GEMINI 2)", NCT04410991, Record History Tab, Version 26, Last Updated Jul. 2, 2025 (33 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 2) (GEMINI 2)", NCT04410991, Record History Tab, Version 18, Last Updated Jul. 2, 2025 (23 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 1)(GEMINI 1)", NCT04410978, Records History Tab, Version 44, Last Updated Jul. 2, 2025 (75 pages).
ClinicalTrials.gov, "Relapsing Forms of Multiple Sclerosis (RMS) Study of Bruton's Tyrosine Kinase (BTK) Inhibitor Tolebrutinib (SAR442168) (GEMINI 2) (GEMINI 2)", NCT04410991, Record History Tab, Version 1, Last Updated Jul. 2, 2025 (16 pages).
ClinicalTrials.gov, "Study of Excretion Balance and Pharmacokinetics of [14C]-SAR442168 in Healthy Male Subjects", NCT04171310, Record History Tab, Version 1, Last Updated Apr. 25, 2022 (9 pages).
ClinicalTrials.gov, "Study to Assess the Plasma Concentration of Tolebrutinib Given as a Tablet to Adult Participants With Mild Hepatic Impairment Compared to Participants With Normal Hepatic Function", NCT05283915, Record History Tab, Last Updated Jan. 15, 2025 (11 pages).
ClinicalTrials.gov, "Study to Assess the Plasma Concentration of Tolebrutinib Given as a Tablet to Adult Participants With Renal Impairment Compared to Healthy Participants", NCT05282030, Record History Tab, Version 1, Last Updated Feb. 6, 2025 (11 pages).
ClinicalTrials.gov, "Study to Assess the Plasma Concentration of Tolebrutinib Given as a Tablet to Adult Participants with Renal Impairment Compared to Healthy Participants", NCT05282030, Version 5, Record History Tab, Last Updated Feb. 6, 2025 (12 pages).
ClinicalTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 145, Last Updated Aug. 13, 2024 (29 pages).
ClinicalTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab, Version 1, Last Updated Aug. 13, 2024 (27 pages).
ClinicalTrials.gov, "Tolebrutinib, a Brain-penetrant Bruton's Tyrosine Kinase Inhibitor, for the Modulation of Chronically Inflamed White Matter Lesions in Multiple Sclerosis", NCT04742400, Record History Tab—V157, Last Updated Aug. 13, 2024 (29 pages).
Confaverux et al., "Oral terifl unomide for patients with relapsing multiple sclerosis (TOWER): a randomised, double-blind, placebocontrolled, phase 3 trial", Lancet Neurol, 13, pp. 247-256 (2014).
Correale, J., "BTK inhibitors as potential therapies for multiple sclerosis", The Lancet Neurology, 20, pp. 689-691 (Sep. 2021).
Dal-Bianco et al., "Chronic active lesions in multiple sclerosis: classification, terminology, and clinical significance", The Adv Neurol Disord, 17, pp. 1-25 (2024).
Disano et al., "Intrathecally produced CXCL13: A predictive biomarker in multiple sclerosis", Multiple Sclerosis Journal—Experimental, Translational and Clinical, pp. 1-12 (Oct.-Dec. 2020).
Doherty, F., "International Preliminary Report on Patentability", issued in International Application No. PCT/US2022/053479 on Jun. 20, 2024 (9 pages).
Doherty, F., "International Preliminary Report on Patentability", issued in International Application No. PCT/US2023/084784 on Jun. 24, 2025 (13 pages).
EU Clinical Trials Register, "A study to investigate long-term safety and tolerability of tolebrutinib in particpants with multipe sclerosis", EUCT 2023-503631-18-01, 2023 (141 pages).
EU Clinical Trials Register, "Clinical trial results: A Phase 3, randomized, double-blind efficacy and safety study comparing SAR442168 to teriflunomide (Aubagio®) in participants with relapsing forms of multiple sclerosis (GEMINI 2)", v1, EU-CTR2020-000644-55, Jul. 6, 2025 (32 pages).
EU Clinical Trials Register, "Clinical trial results: A Phase 3, randomized, double-blind, efficacy and safety study comparing SAR442168 to placebo in participants with nonrelapsing secondary progressive multiple sclerosis (HERCULES)", v1, 2020-000647-30, Jul. 6, 2025 (63 pages).
EU Clinical Trials Register, "Primary Progressive Multiple Sclerosis (PPMS) Study of Bruton's Tyrosine Kinase (BTK) Inhibitor tolebrutinib (SAR442168)(PERSEUS)", v1, 2024-514495-41-00, 2024 (91 pages).
EU Clinical Trials Register, Clinical trial results: A Phase 3, randomized, double-blind efficacy and safety study comparing SAR442168 to teriflunomide (Aubagio®) in participants with relapsing forms of multiple sclerosis (GEMINI 1), v1, EU-CTR2020-000637-41, Jul. 6, 2025 (35 pages).

(56) References Cited

OTHER PUBLICATIONS

European Medical Journal, "Sanofi's MS drug delivers surprising Phase III results", obtained from https://emjreviews.com/en-us/emj-gold/news/sanofis-ms-drug-delivers-suprising-phase-iii-results/, Sep. 3, 2024 (5 pages).
Fier et al., "A Multifunctional Reagent Designed for the Site-Selective Amination of Pyridines", Journal of the American Chemical Society, 142(19), pp. 8614-8618 (May 13, 2020).
Fox et al., "(DMT37) Baseline Characteristics in the Tolebrutinib Phase 3 Primary Progressive Multiple Sclerosis PERSEUS Clinical Trial", International Journal of MS Care, 27(1): 42 (May/Jun. 2025).
Fox et al., "(PLA-A4) Disability Outcomes in Tolebrutinib Phase 3 Trials in Nonrelapsing Secondary Progressive Multiple Sclerosis and Relapsing Multiple Sclerosis", International Journal of MS Care, 27(1), pp. 5-6 (May/Jun. 2025).
Fox et al., "Baseline Characteristics in the Tolebrutinib Phase 3 Non-Relapsing Secondary Progressive Multiple Sclerosis (nrSPMS) HERCULES Clinical Trial", P1476, Presented at the 9th Joint ECTRIMS-ACTRIMS Meeting; Milan, Italy; Oct. 11-13, 2023 (1 page).
Fox et al., "Baseline Characteristics in the Tolebrutinib Phase 3 Non-Relapsing Secondary Progressive Multiple Sclerosis (nrSPMS) HERCULES Clinical Trial", P1476/1293, Multiple Sclerosis Journal, 29: (3S), pp. 938-939 (2023).
Fox et al., "Baseline Characteristics in the Tolebrutinib Phase 3 Primary Progressive Multiple Sclerosis PERSEUS Clinical Trial", DMT37, Presented at the Consortium of Multiple Sclerosis Centers Annual Meeting, May 28-31, 2025; Phoenix, Arizona (1 page).
Fox et al., "Characteristics and Outcomes of COVID-19 Cases from the Long-term Extension Study of Tolebrutinib in Patients with Relapsing MS", P126, Presented at the Americas Committee for Treatment and Research in Multiple Sclerosis (ACTRIMS) Forum, Feb. 24-26, 2022, West Palm Beach, FL, USA (1 page).
Fox et al., "Characteristics and Outcomes of COVID-19 Cases from the Long-term Extension Study of Tolebrutinib in Patients with Relapsing MS", P126, Multiple Sclerosis Journal, 28: (1S), p. 77 (2022).
Fox et al., "Disability Outcomes in Tolebrutinib Phase 3 Trials in Non-Relapsing Secondary Progressive Multiple Sclerosis and Relapsing Multiple Sclerosis", Presentation PLA-A4, Presented at the Consortium of Multiple Sclerosis Centers Annual Meeting, May 28-31, 2025; Phoenix, Arizona (12 pages).
Fox et al., "Efficacy and Safety of Tolebrutinib Versus Placebo in Non-Relapsing Secondary Progressive Multiple Sclerosis: Results From the Phase 3 HERCULES Trial", Presentation #0136. Presented at the 40th Congress of the European Committee for Treatment and Research in Multiple Sclerosis; Sep. 18-20, 2024; Copenhagen, Denmark (15 pages).
Fox et al., "Efficacy and Safety of Tolebrutinib Versus Placebo in Non-Relapsing Secondary Progressive Multiple Sclerosis: Results from the Phase 3 HERCULES Trial", O136/4027, Multiple Sclerosis Journal, 30: (3S), pp. 1146-1147 (2024).
Fox et al., "MRI, efficacy, and safety of tolebrutinib in patients with highly active disease (HAD): 2-year data from the phase 2b Long-term safety (LTS) Study", P292, Multiple Sclerosis Journal, 28: (3S), p. 331 (2022).
Fox et al., "MRI, Efficacy, and Safety of Tolebrutinib in Patients with Highly Active Disease: 2-Year Data from the Phase 2b Long-Term Safety Study", P292, Presented at the 38th Congress of the European Committee for Treatment and Research in Multiple Sclerosis (ECTRIMS); Amsterdam, the Netherlands; Oct. 26-28, 2022 (1 page).
Bader, Saskia, "Invitation to Pay Additional Fees and, Where Applicable, Protest Fee with Annex to Form PCT/ISA/206 Communication Relating to the Results of the Partial International Search Report", mailed in International Application No. PCT/US2025/043964 on Dec. 16, 2025 (12 pages).
Bar-Or et al., "Blood Immunoglobulin Levels and Immune Cell Populations in the Phase 3 HERCULES Trial of Tolebrutinib in Non-Relapsing Secondary Progressive Multiple Sclerosis", ECTRIMS, P297, Presented at the 41st Congress of the European Committee for Treatment and Research in Multiple Sclerosis; Sep. 24-26, 2025; Barcelona, Spain (1 page).
Bar-Or, et al., "Blood Immunoglobulin Levels and Immune Cell Populations in the Phase 3 HERCULES Trial of Tolebrutinib in Non-Relapsing Secondary Progressive Multiple Sclerosis", P297, Multiple Sclerosis Journal, 31: (3S), 136-762, pp. 352-353 (2025).
Fox et al., "Subgroup Analyses of the Phase 3 Tolebrutinib in nrSPMS HERCULES Trial", ECTRIMS, P796, Presented at the 41st Congress of the European Committee for Treatment and Research in Multiple Sclerosis; Sep. 24-26, 2025; Barcelona, Spain (1 page).
Fox et al., "Subgroup Analyses of the Phase 3 Tolebrutinib in nrSPMS HERCULES Trial", Multiple Sclerosis Journal; 31: (3S) 136-762, pp. 671-672 (2025).
Giovannoni, G., "Tolebrutinib PPMS trial is negative. The PERSEUS phase 3 study of tolebrutinib in primary progressive multiple sclerosis (PPMS) did not meet its primary endpoint.", MS-Selfie Research, Dec. 15, 2025 (6 pages).
Gulf News, "Emirates Drug Establishment grants global first approval for 'Tolebrutinib' for secondary progressive multiple sclerosis (SPMS)", Aug. 26, 2025 (11 pages).
Kramer et al., "Bruton tyrosine kinase inhibitors in multiple sclerosis: evidence and expectations", Current Opinion in Neurology 37(3): pp. 237-244, Jun. 2024.
Nicolas et al., "Tolebrutinib Plasma Exposure and Efficacy Response in the Phase 3 HERCULES Trial in nrSPMS", ECTRIMS, P292, Presented at the 41st Congress of the European Committee for Treatment and Research in Multiple Sclerosis; Sep. 24-26, 2025; Barcelona, Spain (1 page).
Nicolas et al., "Tolebrutinib Plasma Exposure and Efficacy Response in the Phase 3 HERCULES Trial in nrSPMS", P292, Multiple Sclerosis Journal; 31: (3S) 136-762, pp. 347-348 (2025).
Oh et al., "Effects of Tolebrutinib on Progression Independent of Relapse Activity in the Phase 3 GEMINI Relapsing MS Trials", Multiple Sclerosis Journal 2025; 31: (3S) 136-762, p. 670 (2025).
Oh et al., "Effects of Tolebrutinib on Progression Independent of Relapse Activity in the Phase 3 GEMINI Relapsing MS Trials", ECTRIMS, P794, Presented at the 41st Congress of the European Committee for Treatment and Research in Multiple Sclerosis; Sep. 24-26, 2025; Barcelona, Spain (1 page).
Oh et al., "Tolebrutinib Phase 2b Long-Term Extension Study Two-Year Safety, MRI, and Clinical Efficacy Outcomes in Patients With Relapsing Multiple Sclerosis", Neurology Open Access, 1(3), 1: e000028 (Sep. 2025) (13 pages).
Sanofi Press Release, "Sanofi provides update on tolebrutinib in primary progressive multiple sclerosis", Dec. 15, 2025 (3 pages).
Schulte-Mecklenbeck et al., "Tolebrutinib treatment induces complex alterations of the peripheral immune-regulatory network in the blood of patients with non-relapsing secondary progressive MS—first results from the TOLEDYNAMIC study", ECTRIMS, P315, Poster Presentation Sep. 24, 2025 (1 page).
Schulte-Mecklenbeck et al., "Tolebrutinib treatment induces complex alterations of the peripheral immune-regulatory network in the blood of patients with non-relapsing secondary progressive MS—results from the TOLEDYNAMIC study", P315, Multiple Sclerosis Journal; 31: (3S) 136-762, pp. 364-365 (2025).
Vermersch et al., "Effects of Tolebrutinib on MSQOL-54 in the HERCULES Phase 3 Trial in nrSPMS", ECTRIMS, P810, Presented at the 41st Congress of the European Committee for Treatment and Research in Multiple Sclerosis; Sep. 24-26, 2025; Barcelona, Spain (1 page).
Vermersch et al., "Effects of Tolebrutinib on MSQOL-54 in the HERCULES Phase 3 trial in nrSPMS", Multiple Sclerosis Journal; 31: (3S) 136-762, pp. 684-685 (2025).
Wiendl et al., "Blood Immunoglobulin Levels and Immune Cell Populations in the Phase 3 GEMINI Trials of Tolebrutinib in Relapsing Multiple Sclerosis", ECTRIMS, P800, Presented at the 41st Congress of the European Committee for Treatment and Research in Multiple Sclerosis; Sep. 24-26, 2025; Barcelona, Spain (1 page).
Wiendl et al., "Blood Immunoglobulin Levels and Immune Cell Populations in the Phase 3 GEMINI Trials of Tolebrutinib in

(56) References Cited

OTHER PUBLICATIONS

Relapsing Multiple Sclerosis", P800, Multiple Sclerosis Journal 2025; 31: (3S) 136-762 (2 pages).
Fox et al., "Tolebrutinib in Nonrelapsing Secondary Progressive Multiple Sclerosis", The New England Journal of Medicine, Apr. 8, 2025 (DOI: 10.1056/NEJMoa2415988) (10 pages).
Francesco et al., "PRN2246, a potent and selective blood brain barrier penetrating BTK inhibitor, exhibits efficacy in central nervous system immunity", ECTRIMS, P072 (1 page) (2017).
Gaitan et al., "Primary Outcome of a Phase 2 Clinical Trial of Tolebrutinib, a Brain-Penetrant BTK Inhibitor, for the Modulation of Chronically Inflamed White Matter Lesions in MS", National Institute of Neurological Disorders and Stroke, ACTRIMS, 2024 (16 pages).
Gaitan et al., "Primary Outcome of a Phase 2 Clinical Trial of Tolebrutinib, a Brain-Penetrant BTK Inhibitor, for the Modulation of Chronically Inflamed White Matter Lesions in MS", LB1.2, Multiple Sclerosis Journal, ACTRIMS, 30:(IS), p. 11 (2024).
Gavriliu, D., "Extended European Search Report", issued in European Application No. 22188609.6 on Nov. 9, 2022 (7 pages).
Gavriliu, D., "Extended European Search Report", issued in European Patent Application No. 21169631.5 on Aug. 15, 2021 (13 pages).
Giovannoni, G., aka Prof G, "Breaking news—smouldering MS or the "real MS" becomes a tractable problem.", X, Sep. 2, 2024 (1 page).
Giovannoni, G., "Smouldering MS: the real MS becomes a tractable problem", Sep. 2, 2024 (7 pages).
Greenberg, B.M., "Bruton's Tyrosine Kinase Inhibitors for Multiple Sclerosis Treatment: A New Frontier", Neurol Clin, 42, pp. 155-163 (2024).
Gruber et al., "BTK regulates microglial function and neuroinflammation in human stem cell models and mouse models of multiple sclerosis", Nature Communications, 115:10116 (2024) (17 pages).
Gruber et al., "Central Effects of BTK Inhibition in Neuroinflammation (808)", Neurology, Multiple Sclerosis: Basic Science, 94(15_Supplement), Apr. 14, 2020 (2 pages).
Gruber et al., "Central Effects of BTK Inhibition in Neuroinflammation", AAN, Presentation 808, 2020 (12 pages).
Gruber et al., "Decoding Bruton's Tyrosine Kinase Signaling in Neuroinflammation", ECTRIMS-ACTRIMS 2020, P0311 (10 pages).
Gruber et al., "Decoding bruton's tyrosine kinase signalling in neuroinflammation", P0311, Multiple Sclerosis Journal, 26: (S3), p. 270 (2020).
Gruber et al., "Establishing a Role for the Bruton's Tyrosine Kinase Inhibitor Tolebrutinib in Modulating Neuroinflammation and Disease Progression in MS", AAN 2021, Platform S25:003 (13 pages).
Gruber et al., Establishing a Role for the Bruton's Tyrosine Kinase Inhibitor Tolebrutinib in Modulating Neuroinflammation and Disease Progression in MS (1974), Neurology, MS and CNS Inflammatory Disease: Emerging Therapeutics and Biomarkers, 96(15_supplement) (Apr. 13, 2021).
Gruber et al., "Evaluating the effect of a Bruton's tyrosine kinase inhibitor in a murine experimental autoimmune encephalomyelitis model of multiple sclerosis", P174, Multiple Sclerosis Journal, 28: (3S), pp. 244-245 (2022).
Gruber et al., "Evaluating the Effect of a Bruton's Tyrosine Kinase Inhibitor in a Murine Experimental Autoimmune Encephalomyelitis Model of Multiple Sclerosis", P174, Presented at the 38th Congress of the European Committee for Treatment and Research in Multiple Sclerosis (ECTRIMS); Amsterdam, the Netherlands; Oct. 26-28, 2022 (1 page).
Gruber et al., "Evaluating the effect of BTK inhibitor tolebrutinib in human microglia", P391, Multiple Sclerosis Journal, 27: (2S), pp. 376-377 (2021).
Gruber et al., "Evaluating the Effect of BTK Inhibitor Tolebrutinib in Human Microglia", P391, Presented at the 37th Congress of the European Committee for Treatment and Research in Multiple Sclerosis, Oct. 13-15, 2021, Virtual (1 page).
Gruber et al., "Evaluating the Effect of BTK Inhibitor Tolebrutinib in Human Tri-cultre", Presented at the American Academy of Neurology (AAN) Virtual Annual Meeting, 2594, Apr. 24-26, 2022 (1 page).
Gruber et al., "Evaluating the Effect of BTK Inhibitor Tolebrutinib in Human Tri-culture (P1-1. Virtual)", 2594, Neurology, MS and CNS Inflammatory Disease Virtual, 98(18_supplement), (May 3, 2022) (2 pages).
Gruber et al., "Evaluating the Effect of BTK Inhibitor Tolebrutinib in Modulating Microglia-Driven Neuroinflammation and MS Progression", EPR-182, European Journal of Neurology, 28 (Suppl. 1), p. 327 (2017).
Gruber et al., "Evaluating the Effect of BTK Inhibitor Tolebrutinib in Modulating Microglia-Driven Neuroinflammation and MS Progression", EAN 2021, EPR-182 (8 pages).
Guerra et al., "Cerebrospinal fluid proteomic dissection of chronic neuroinflammation in Multiple Sclerosis patients", National Institutes of Health National Institute of Neurological Disorders and Stroke, ACTRIMS, P362 (1 page) (2025).
Guerra et al., "Cerebrospinal Fluid Proteomic Dissection of Chronic Neuroinflammation in Multiple Sclerosis", P362, Multiple Sclerosis Journal, 31: (2S), pp. 194-195 (2025).
Hegen et al., "Recent developments in MOG-IgG associated neurological disorder", Ther Adv Neurol Disord, vol. 13, pp. 1-20 (2020).
Hilfiker et al., "Relevance of Solid-state Properties for Pharmaceutical Products", Polymorphism in the Pharmaceutical Industry, Wiley-VCL, XP002528052, pp. 1-19 (Jan. 1, 2006).
Kappos et al., "Contribution of Relapse-Independent Progression vs Relapse-AssociatedWorsening to Overall ConfirmedDisability Accumulation in Typical Relapsing Multiple Sclerosis in a Pooled Analysis of 2 Randomized Clinical Trials", JAMA Neurol., 77(9), pp. 1132-1140, Published online Jun. 8, 2020.
Kappos et al., "Efficacy of Siponimod in Secondary Progressive Multiple Sclerosis: Results of the Phase 3 Study (CT.002)", Neurology, Clinical Trials, 88(16_supplement) (Apr. 18, 2017) (5 pages).
Kappos et al., "Ponesimod compared with teriflunomide in patients with relapsing multiple sclerosis in the active-comparator phase 3 OPTIMUM Study", JAMA Neurol. Published online Mar. 29, 2021 (32 pages).
Kleidernigg, O., "Extended European Search Report", issued in European Application No. 22819443.7, mailed on May 23, 2025 (7 pages).
Kobayashi, M., "International Preliminary Report on Patentability", issued in International Application No. PCT/US2024/013658 on Jul. 31, 2025 (16 pages).
Kramer et al., "Bruton tyrosine kinase inhibitors for multiple sclerosis", Nature Reviews Neurology, 19, pp. 289-304 (May 2023).
Lee, S. H., "International Preliminary Report on Patentability", issued in International Application No. PCT/US2021/064800 on Jun. 13, 2023 (9 pages).
Lindsey Shapiro, PhD, "Target smoldering inflammation. Data from Phase 3 trials show therapy slows disability progression in MS", Presented at EuropeanCommittee for Treatment and Research in Multiple Sclerosis (ECTRIMS) annual meeting, Sep. 18-20, 2024, online and in-person in Copenhagen (9 pages).
Lublin et al., "Defining the clinical course of multiple sclerosis: Results of an international survey", Neurology, 46, pp. 907-911 (1996).
Martin et al., "Bruton's Tyrosine Kinase Inhibition Promotes Myelin Repair", Brain Plasticity 5, pp. 123-133 (2020).
Meglio, Marco, "BTK Inhibitor Tolebrutinib Slows Disability Progression in Phase 3 HERCULES Study of Non-Relapsing Secondary Progressive MS", NeurologyLive, MJH Life Sciences, Sep. 3, 2024 (5 pages).
Merck KGaA, Darmstadt, Germany, News Release, "Initiation of New Patients on Evobrutinib Paused in the U.S.; Fully Enrolled Phase III Evobrutinib Studies Continue", Apr. 12, 2023 (2 pages).
Merck KGaA, News Release, "Merck KGaA, Darmstadt, Germany Provides Update on Phase III Results for Evobrutinib in Relapsing Multiple Sclerosis", Darmstadt, Germany, Dec. 5, 2023 (3 pages).

(56) References Cited

OTHER PUBLICATIONS

Miniejew, C., International Search Report and Written Opinion of the International Searching Authority issued in International Application No. PCT/US2023/025170 on Sep. 29, 2023 (10 pages).
Montalban et al., "Bruton's tyrosine kinase inhibitor evobrutinib (M2951) in patients withrelapsing Multiple sclerosis: a randomised, placebo-controlled, phase 2 study", O1205, European Journal of Neurology, 26 (Suppl. 1), p. 32 (2019).
Montalban et al., "Characterisation of the safety profile of evobrutinib in over 1000 patients from phase II clinical trials in multiple sclerosis, rheumatoid arthritis and systemic lupus erythematosus: an integrated safety analysis", J Neurol Neurosurg Psychiatry; 94:1-9 (2023).
Montalban et al., "Effect of evobrutinib, a Bruton's tyrosine kinase inhibitor, on immune cell and immunoglobulin levels over 48 weeks in a phase 2 study in relapsing multiple sclerosis", P1358, Multiple Sclerosis Journal, 25: (S2), p. 748 (2019).
Montalban et al., "Efficacy and Safety of the Bruton's Tyrosine Kinase Inhibitor Evobrutinib (M2951) in Patients with Relapsing Multiple Sclerosis over 48 Weeks: a Randomized, Placebo-Controlled, Phase 2 Study (S56.004)", Neurology, MS Trials and Treatment, 92(15_supplement) (Apr. 9, 2019) (2 pages).
Montalban et al., "Efficacy and safety results after >3.5 years of treatment with the Bruton's tyrosine kinase inhibitor evobrutinib in relapsing multiple sclerosis: Long-term follow-up of a Phase II randomised clinical trial with a cerebrospinal fluid sub-study", Multiple Sclerosis Journal, vol. 30(4-5), pp. 558-570 (2024).
Montalban et al., "Rationale and Design of two Phase 3 Randomized Controlled Trials (Evolution RMS 1&2) Evaluation the Bruton's Tyrosine Kinase Inhibitor Evobrutinib in Patients with Relapsing Multiple Sclerosis (4071)", Neurology, Multiple Sclerosis: Clinical Trials and Therapeutics 3, 94(15_supplement) Apr. 14, 2020 (3 pages).
Montalban et al., "Safety and efficacy of evobrutinib in relapsing multiple sclerosis (evolutionRMS1 and evolutionRMS2): two multicentre, randomised, double-blind, active-controlled, phase 3 trials", Lancet Neurol, 23: 1119-1132 (2024).
Multiple Sclerosis Trust, "Tolebrutinib. Other names: SAR442168, PRN2246", Last Updated Sep. 5, 2024 (8 pages).
Waldman et al., "Pediatric multiple sclerosis: Clinical features and outcome", Neurology, 87(9 Suppl 2):S74-81. (Aug. 30, 2016).
Wang, M.L., "Targeting BTK with Ibrutinib in Relapsed or Refractory Mantle-Cell Lymphoma." N Engl J Med., 369(6), Jun. 19, 2013. [Epub ahead of print].
Wassmer et al., "International Pediatric MS Study Group Global Members Symposium report", Neurology, 87(Suppl 2): S110-S116 (2016).
Weber et al., "B cell activation influences T cell polarization and outcome of anti-CD20 B cell depletion in CNS autoimmunity", Ann Neurol., 68(3), pp. 369-383 (Sep. 2010).
WebMD. 10 Ways to Prevent Psoriasis Flare-Ups. (2016) Web< http://www.webmd.com/skin-problems-and-treatments/psoriasis/prevent-flare-ups>.
WebMD. Multiple Sclerosis (MS)-Prevention. (2015) Web: < http://wwwv.webmd.com/multiple-sclerosis/tc/multiple-sclerosis-ms-prevention>.
Wermuth, Camille G., "Molecular Variation Based on Isosteric Replacements" in Chapter 13, The Practice of Medicinal Chemistry, Academic: 1996, pp. 203-237.
Wong et al., "Real-world validation of the 2017 McDonald criteria for pediatric MS", Neurol, 6:e528 (2019).
Wu et al., "Second-generation inhibitors of Bruton tyrosine kinase", J Hematol Oncol., 9(1), p. 80 (2016).
Xu et al., "RN486, a selective Bruton's tyrosine kinase inhibitor, abrogates immune hypersensitivity responses and arthritis in rodents", J Pharmacol Exp Ther, 341(1), pp. 90-103 (2012).
Yan et al., "Comparison of anti-acetylcholine receptor profiles between Chinese cases of adult- and juvenile-onset myasthenia gravis using cell-based assays", J Neuroimmunol., 349:577403 (Dec. 15, 2020).
Yeh et al., "Pediatric multiple sclerosis", Nat. Rev. Neurol., 5, pp. 621-631 (2009).
Yeshokumar et al., "Pediatric multiple sclerosis", Curr Opin Neurol., 30(3), pp. 216-221 (Jun. 2017).
Yi et al., "B cells in the pathophysiology of myasthenia gravis", Muscle Nerve, 57(2), pp. 172-184 (Feb. 2018).
Zhao, et al., "The role of innate immunity in myasthenia gravis", Autoimmun Rev., 20(5): 102800 (2021).
Zhong et al., "HLA in myasthenia gravis: From superficial correlation to underlying mechanism", Autoimmun Rev., 18(9): 102349 (Sep. 2019).
Core Study Information and Informed Consent Form for Clinical Trial Identifier No. DRI15928, marked "Property of the Sanofi Group—strictly confidential" and dated Feb. 12, 2019.
Core Study Information and Informed Consent Form for Clinical Trial Identifier No. DRI15928, marked "Property of the Sanofi Group—strictly confidential" and dated Oct. 22, 2018 (18 pages).
Core Study Information and Informed Consent Form for Clinical Trial Identifier No. EFC16033, marked "Property of the Sanofi Group—strictly confidential" and dated, Jul. 6, 2023 (20 pages).
Core Study Information and Informed Consent Form for Clinical Trial Identifier No. EFC16034, marked "Property of the Sanofi Group—strictly confidential" and dated Feb. 27, 2023 (20 pages).
Core Study Information and Informed Consent Form for Clinical Trial Identifier No. EFC16035, marked "Property of the Sanofi Group—strictly confidential" and dated Feb. 27, 2023 (21 pages).
Core Study Information and Informed Consent Form for Clinical Trial Identifier No. EFC16645, marked "Property of the Sanofi Group—strictly confidential" and dated Feb. 27, 2023 (20 pages).
Core Study Information and Informed Consent Form for Clinical Trial Identifier No. EFC17262, marked "Property of the Sanofi Group—strictly confidential" and dated Sep. 14, 2022 (22 pages).
Core Study Information and Informed Consent Form for Clinical Trial Identifier No. LTS 16004, marked "Property of the Sanofi Group—strictly confidential" and dated Jun. 28, 2023 (19 pages).
Core Study Information and Informed Consent Form for Clinical Trial Identifier No. POP16398, marked "Property of the Sanofi Group—strictly confidential" and dated Jun. 16, 2022 (22 pages).
Core Study Information and Informed Consent Form for Clinical Trial Identifier No. POP16399, marked "Property of the Sanofi Group—strictly confidential" and dated May 31, 2022 (22 pages).
Participant Information Sheet and Informed Consent Form for Sponsor Study No. BEX16018, marked "Property of the Sanofi Group—strictly confidential" and dated Aug. 9, 2019 (30 pages).
Chen et al., "A 2-in-1 Adaptive Phase 2/3 Design for Expedited Oncology Drug Development", Contemporary Clinical Trials, vol. 64, pp. 238-242.
Chen et al., "The effect of Bruton's tyrosine kinase (BTK) inhibitors on collagen-induced platelet aggregation, BTK, and tyrosine kinase expressed in hepatocellular carcinoma (TEC)", Eur J Haematol., 2018;101, pp. 604-612.
Chiang et al., "Juvenile myasthenia gravis", Muscle Nerve, 39, pp. 423-431 (2009).
Chisari et al., "Rituximab for the treatment of multiple sclerosis: a review", J Neurol., 8, pp. 1-25 (Jan. 2021).
Chitnis et al., "Demographics of pediatric-onset multiple sclerosis in an MS center population from the Northeastern United States", Mult Scler., 15(5), pp. 627-631 (May 2009) doi: 10.1177/1352458508101933. Epub Mar. 19, 2009.
Clinical Trial Results of EU Clinical Trials Register No. 2018-003927-12, "A Phase2b dose-finding study for SAR442168, a Bruton's tyrosine kinase inhibitor, in participants with relapsing multiple sclerosis", Dec. 31, 2020 (23 pages).
ClinicalTrial. gov ID No. NCT05132569, "Efficacy and Safety of Tolebrutinib (SAR442168) Tablets in Adult Participants With Generalized Myasthenia Gravis (URSA)", Last Updated Mar. 10, 2023 (9 pages).
ClinicalTrials.gov ID No. NCT03889639, "Dose-finding Study for SAR442168 in Relapsing Multiple Sclerosis", Last Updated Mar. 8, 2023 (11 pages).

(56) References Cited

OTHER PUBLICATIONS

ClinicalTrials.gov ID No. NCT03996291, "Long Term Safety and Efficacy Study of Tolebrutinib (SAR442168) in Participants with Relapsing Multiple Sclerosis", Last Updated Apr. 24, 2023 (8 pages).
ClinicalTrials.gov ID No. NCT04171310, "Study of Excretion Balance and Pharmacokinetics of [14C]-SAR442168 in Healthy Male Subjects", Last Updated Apr. 25, 2022 (7 pages).
ClinicalTrials.gov ID No. NCT04410978, "Relapsing Forms of Multiple Sclerosis (RMS) Study of Bruton's Tyrosine Kinase (BTK) Inhibitor Tolebrutinib (SAR442168) (GEMINI 1)", Last Updated Aug. 8, 2022 (11 pages).
ClinicalTrials.gov ID No. NCT04410991, "Relapsing Forms of Multiple Sclerosis (RMS) Study of Bruton's Tyrosine Kinase (BTK) Inhibitor Tolebrutinib (SAR442168) (GEMINI 2)", Last Updated Aug. 8, 2022 (9 pages).
ClinicalTrials.gov ID No. NCT04411641, "Nonrelapsing Secondary Progressive Multiple Sclerosis (NRSPMS) Study of Bruton's Tyrosine Kinase (BTK) Inhibitor Tolebrutinib (SAR442168) (HERCULES)", Last Updated Feb. 10, 2023 (9 pages).
ClinicalTrials.gov ID No. NCT04458051, "Primary Progressive Multiple Sclerosis (PPMS) Study of Bruton's Tyrosine Kinase (BTK) Inhibitor Tolebrutinib (SAR442168) (PERSEUS)", Last Updated Feb. 1, 2023 (9 pages).
ClinicalTrials.gov ID No. NCT04742400, "Tolebrutinib, a Brain-penetrant Bruton s Tyrosine Kinase Inhibitor, for the Modulation of Chronically Inflamed White Matter Lesions in Multiple Sclerosis", Last Updated Jul. 3, 2023 (12 pages).
ClinicalTrials.gov ID No. NCT05282030, "Study to Assess the Plasma Concentration of Tolebrutinib Given as a Tablet to Adult Participants With Renal Impairment Compared to Healthy Participants", Last Updated Jan. 26, 2023 (8 pages).
ClinicalTrials.gov ID No. NCT05283915, "Study to Assess the Plasma Concentration of Tolebrutinib Given as a Tablet to Adult Participants with Mild Hepatic Impairment Compared to Participants With Normal Hepatic Function", Last Updated Nov. 8, 2022 (8 pages).
Coles et al., "Monoclonal antibody treatment exposes three mechanisms underlying the clinical course of multiple sclerosis", Ann Neurol, 46(3), pp. 296-304 (1999).
Common Terminology Criteria for Adverse Events (CTCAE) Quick Reference (May 28, 2009) (196 pages) (http://evs.nci.nih.gov/ftp1/CTCAE/CTCAE_4.03_2010-06-14_QuickReference_5x7.pdf).
Confavreux et al., "Natural history of multiple sclerosis: a unifying concept", Brain., 129(Pt 3), pp. 606-616 (Mar. 2006).
Corneth et al., "BTK Signaling in B Cell Differentiation and Autoimmunity. In: Kurosaki T., Wienands J. (eds) B Cell Receptor Signaling", Current Topics in Microbiology and Immunology, vol. 393. Springer, Cham. https://doi.org/10.1007/82_2015_478 (2015).
Cottrell et al., "The natural history of multiple sclerosis: a geographically based study. 5. The clinical features and natural history of pimary progressive multiple sclerosis", Brain, 122, pp. 625-639 (1999).
Crawford et al., "Discovery of GDC-0853: A Potent, Selective, and Noncovalent Bruton's Tyrosine Kinase Inhibitor in Early Clinical Development", J Med Chem., 22;61(6), pp. 2227-2245 (2018).
Cron, et al. "Thymus involvement in early-onset myasthenia gravis", Ann N Y Acad Sci., 1412(1), pp. 137-145 (Jan. 2018).
Dahl et al., "Radiosynthesis of a Bruton's tyrosine kinase inhibitor, [11C] Tolebrutinib, via palladium-NiXantphos-mediated carbonylation", J Label Compd Radiopharm., 63, pp. 482-487 (2020).
Debouverie et al., "Multiple sclerosis with a progressive course from onset in Lorraine-Eastern France", J Neurol, 254, pp. 1370-1375 (2007).
Deenen et al., "The Epidemiology of Neuromuscular Disorders: A Comprehensive Overview of the Literature", J Neuromuscul Dis., 2(1), pp. 73-85 (2015).
Dendrou et al., "Immunopathology of multiple sclerosis", Nature Reviews Immunology, 15, pp. 545-558 (2015).
Di Paolo, et al., "Specific Btk inhibition suppresses B cell- and myeloid cell-mediated arthritis", Nature Chemical Biology, vol. 7, pp. 41-50 (Jan. 2011).
Dilokthornsakul et al., "Multiple Sclerosis Prevalence in the United States Commercially Insured Population", Neurology, 86(11), pp. 1014-1021 (Mar. 15, 2016).
Duquette et al., "Multiple sclerosis in childhood: Clinical profile in 125 patients", Journal of Pediatrics, 111, pp. 359-363 (1987).
EMD Serono Inc., "Positive lake-breaking Phase II data evaluating investigational oral therapy, evobrutinib in RMS [Online]", Oct. 12, 2018. Available from: URL:http://media.emdserono.com/press-releases?item=122714 (7 pages).
English translation of CN 105753863 A, published Jul. 13, 2016 [57 pages].
English translation of WO 2022/223027, published Oct. 27, 2022, retrieved from Espacenet on Jan. 23, 2023 (2022) (17 pages).
Erickson et al., "Bruton's Tyrosine Kinase Small Molecule Inhibitors Induce a Distinct Pancreatic Toxicity in Rats." J Pharmacol Exp Ther. 2017;360(1):226-38.
Ethnic Factors in The Acceptability of Foreign Clinical Data E5(R1) http://www.ich.org (Sep. 1998) (15 pages).
EU Clinical Trials Register No. 2018-003927-12, "A Phase2b dose-finding study for SAR442168, a Bruton's tyrosine kinase inhibitor, in participants with relapsing multiple sclerosis", first entered into EudraCT Jan. 11, 2019 (5 pages).
EU Clinical Trials Register No. 2018-004731-76, "Long-term extension safety and efficacy study of SAR442168 in participants with relapsing multiple sclerosis", first entered into EudraCT Feb. 25, 2019 (6 pages).
EU Clinical Trials Register No. 2020-000637-41, "A Phase 3, randomized, double-blind efficacy and safety study comparing SAR442168 to teriflunomide (Aubagio®) in participants with relapsing forms of multiple sclerosis", first entered into EudraCT Jun. 17, 2020 (7 pages).
EU Clinical Trials Register No. 2020-000644-55, "A Phase 3, randomized, double-blind efficacy and safety study comparing SAR442168 to teriflunomide (Aubagio®) in participants with relapsing forms of multiple sclerosis", first entered into EudraCT Jun. 15, 2020 (7 pages).
EU Clinical Trials Register No. 2020-000645-14, A Phase 3, randomized, double-blind, efficacy and safety study comparing SAR442168 to placebo in participants with primary progressive multiple sclerosis (PERSEUS), first entered into EudraCT Jul. 27, 2020 (6 pages).
EU Clinical Trials Register No. 2020-00647-30, "A Phase 3, randomized, double-blind, efficacy and safety study comparing SAR442168 to placebo in participants with nonrelapsing secondary progressive multiple sclerosis", first entered into EudraCT Jun. 16, 2020 (6 pages).
EU Clinical Trials Register No. 2021-003898-59, "A Phase 3, randomized, double-blind, placebo-controlled, parallel-group study to evaluate the efficacy and safety of tolbrutinib (SAR442168) in adults with generalized myasthenia gravis (MG)", first entered into EudraCT Oct. 6, 2021 (7 pages).
European Medicines Agency. "Guideline on the investigation of drug interactions." Jun. 21, 2012.
Evans et al., "Inhibition of Btk with CC-292 Provides Early Pharmacodynamic Assessment of Activity in Mice and Humans", J Pharmacol Exp Ther, 346(2), pp. 219-228 (Aug. 2013).
Evoli A., "Acquired myasthenia gravis in childhood", Curr Opin Neurol., 23(5), pp. 536-540 (Oct. 2010).
Fadda et al., "Canadian Pediatric Demyelinating Disease Network. MRI and laboratory features and the performance of international criteria in the diagnosis of multiple sclerosis in children and adolescents: a prospective cohort study", Lancet Child Adolesc Health., 2(3), pp. 191-204 (Mar. 2018).
FDA Center for Drug Evaluation and Research. In Vitro Drug Interaction Studies—Cytochrome P450 Enzyme- and Transporter-Mediated Drug Interactions Guidance for Industry. Jan. 2020.
FDA Guidance for Industry: Estimating the maximum safe starting dose in initial clinical trials for therapeutics in adult healthy volunteers. Jul. 2005.

(56) References Cited

OTHER PUBLICATIONS

Fischer J S, et. al., "The Multiple Sclerosis Functional Composite Measure (MSFC): an integrated approach to MS clinical outcome assessment. National MS Society Clinical Outcomes Assessment Task Force.", Mult Scler. 1999;5(4):244-50.
Rahmanzadeh R, et. al., "Multiple sclerosis pathogenesis: missing pieces of an old puzzle.", Rev Neurosci. Jun. 8, 2018. pii: /j/revneuro.ahead-ofprint/revneuro-2018-0002/revneuro-2018-0002.XML. doi: 10.1515/revneuro-2018-0002.
Raisch et al., "Detection of cases of progressive multifocal leukoencephalopathy associated with new biologicals and targeted cancer therapies from the FDA's adverse event reporting system", Expert Opin Drug Saf., 15(8), pp. 1003-1011 (2016).
Ramanujam et al., "Utilizing twins concordance rates to infer the predisposition to myasthenia gravis", Twin Res. Hum. Genet., 13, pp. 129-136 (2011).
Rankin et al., "Selective inhibition of BTK prevents murine lupus and antibody-mediated glomerulonephritis", J Immunol., 191(9), pp. 4540-4550 (2013).
Rasche et al., "MRI Markers and Functional Performance in Patients With CIS and MS: A Cross-Sectional Study", Front Neurol, vol. 9(718), pp. 1-12 (2018).
Reich et al., "Safety and efficacy of tolebrutinib, an oral brain-penetrant BTK inhibitor, in relapsing multiple sclerosis: a phase 2b, randomised, double-blind, placebo-controlled trial", The Lancet Neurology, 20(9), pp. 729-738 (Sep. 1, 2021).
Renoux et al., "Natural History of Multiple Sclerosis with Childhood Onset", New England Journal of Medicine, 356, pp. 2603-2613 (2007).
Renoux et al., "The natural history of multiple sclerosis with childhood onset", Clin Neurol Neurosug., Nov. 2008;110(9), pp. 897-904. doi 10.1016/j.clineuro.2008.04.009. Epub Jun. 4, 2008.
Rigg et al., "Oral administration of Bruton's tyrosine kinase inhibitors impairs GPVI-mediated platelet function", Am J Physiol Cell Physiol., 310(5), pp C373-C380 (Mar. 2016).
Robinet et al., "Review on Toll-Like Receptor Activation in Myasthenia Gravis: Application to the Development of New Experimental Models", Clin Rev Allergy Immunol., 52(1), pp. 133-147 (Feb. 2017).
Roschewski et al., "Inhibition of Burton tyrosine kinase in patients with severe COVID-19", Sci. Immunol. 10.1126/sciimmunol.abd0110 (2020).
Rovaris et al., "MRI markers of destructive pathology in multiple sclerosis-related cognitive dysfunction", Journal of the Neurological Sciences 245(1-2), pp. 111-116 (2006).
Sanders, D., et al., "International consensus guidance for management of myasthenia gravis: Executive summary", Neurology., 87(4), pp. 419-425 (Jul. 26, 2016).
Scalfari et al., "Onset of secondary progressive phase and long-term evolution of multiple sclerosis", Neurol Neurosurg Psychiatry., pp. 67-75 (2013).
Scalfari, et al., "Mortality in patients with multiple sclerosis", Neurology, 81, pp. 184-192 (2013).
Scheers et al., "Absorption, Metabolism, and Excretion of Oral 14C Radiolabeled Ibrutinib: An Open-Label, Phase 1, Single-Dose Study in Healthy Men", Drug Metab Dispos, vol. 43, pp. 289-207 (2015).
Schutt, et al., "BTK knockout rat model demonstrates rat-specific BTK inhibitor-related pancreatic pathology is on-target and unlikely to be relevant for humans [abstract 70]", Presented at 35th Annual Symposium of the Society of Toxicologic Pathology; Jun. 26-29, 2016; San Diego, CA. p 77.
Selcen et al., "High-dose intravenous immunoglobulin therapy in juvenile myasthenia gravis", Pediatr Neurol, 22, pp. 40-43 (2000).
Sengupta et al., "MicroRNA and mRNA expression associated with ectopic germinal centers in thymus of myasthenia gravis", PLoS One, 13(10):e0205464 (Oct. 11, 2018).
Shatzel et al., "Ibrutinib-associated bleeding: pathogenesis, management and risk reduction strategies", J Thromb Haemost., 15(5), pp. 835-847., Epub Mar. 27, 2017. (May 2017).
Shi et al., "Purine derivatives as potent Bruton's tyrosine kinase (BTK) inhibitors for autoimmune diseases", Bioorganic & Medicinal Chemistry Letters, 24, pp. 2206-2211 (2014).
Sibaud et al., "Dermatological Toxicities of Bruton's Tyrosine Kinase Inhibitors", Am. J. Clin. Dermatol., 21, pp. 799-812 (2020).
Sideras et al., "Molecular and cellular aspects of X-linked agammaglobulinemia",, Adv Immunol., 59, pp. 135-223 (1995).
Smith P F et.al., "Phase 1 clinical trial of PRN2246 (SAR441268), a covalent BTK inhibitor demonstrates safety, CNS exposure and therapeutic levels of BTK occupancy", Database accession No. EMB 628003781 abstract & Multiple Sclerosis Journal Apr. 1, 2019 Sage Publications Ltd NLD, vol. 25, No. Supplement 1, Apr. 1, 2019 (Apr. 1, 2019), pp. 52 CONF Feb. 28, 2019 to Mar. 2, 2019 Dallas, TX-4th Annual.
Sobieszczuk et al., "Myasthenia Gravis in Poland: National Healthcare Database Epidemiological Study", Neuroepidemiology, 19, pp. 1-8 (Feb. 2021).
Sormani et al., "Magnetic resonance imaging as a potential surrogate for relapses in multiple sclerosis: a meta-analytic approach.", Ann Neurol.; 65(3), pp. 268-275 (2009).
Sormani et al., "MRI lesions as a surrogate for relapses in multiple sclerosis: a meta analysis of randomised trials", Lancet Neurol., 12(7), pp. 669-676 (Jul. 2013).
Sormani et al., "Surrogate endpoints for EDSS worsening in multiple sclerosis a meta-analytic approach.", Neurology.; 75(4), pp. 302-309 (2010).
Sparaco et al., "The Role of Wearable Devices in Multiple Sclerosis", Mult Scler Int.; Review Article, v. 2018.
Sprenger et al., "Association of brain volume loss and long-term disability outcomes in patients with multiple sclerosis treated with teriflunomide", Multiple Sclerosis Journal, pp. 1-10 (2019).
Stys, et. al., "Will the real multiple sclerosis please stand up?", Nat Rev Neurosci., 13(7), pp. 507-514 (2012).
Tan et al., "Targeting the SYK-BTK axis for the treatment of immunological and hematological disorders: Recent progress and therapeutic perspectives", Pharmacol Ther., 138(2), pp. 294-309 (2013).
Tang, et al., "Cardiac side effects of bruton tyrosine kinase (BTK) inhibitors", Leuk Lymphoma, 59(7), pp. 1554-1564 (Jul. 2018).
Thompson A J, et. al., "Diagnosis of multiple sclerosis: 2017 revisions of the McDonald criteria.", Lancet Neurol.;17(2): 162-73 (2018).
Thompson et al., "Multiple sclerosis", Lancet, 391(10130), 1622-1636 (2018).
Tomassini et al., "Predicting the profile of increasing disability in multiple sclerosis", Multiple Sclerosis Journal, 25(9), pp. 1306-1315 (2019).
Traboulsee Anthony et al., "Design of a Phase 2b Dose-finding Trial to Evaluate Safety and Efficacy of the CNS-penetrant BTK Inhibitor SAR442168 in Patients with Relapsing Forms of Multiple Sclerosis (804) : Neurology", Neurology, Apr. 14, 2020 (Apr. 14, 2020), XP055794139, Retrieved from the Internet: URL:https://n.neurology.org/content/94/15 Supplement/804.abstract—[retrieved by ISA on Apr. 12, 2021].
Tsai et al., "Increased subsequent risk of myasthenia gravis in children with allergic diseases", J Neuroimmunol., 276(1-2), pp. 202-206 (Nov. 15, 2014).
Tur et al., "Assessing treatment outcomes in multiple sclerosis trials and in the clinical setting", Neurology, 14, pp. 75-93 (2018).
US FDA. In vitro metabolism and transporter-mediated drug-drug interaction studies. [Online]. [Cited Nov. 20, 2018]. Available from: URL:https://www.fda.gov/downloads/Drugs/GuidanceComplianceRegulatoryInformation/Guidances/UCM581965.pdf.
Uzawa et al., "Roles of cytokines and T cells in the pathogenesis of myasthenia gravis", Clin Exp Immunol., 203, pp. 366-374 (2020).
Van Rosmalen et al., "Including historical data in the analysis of clinical trials: Is it worth the effort?", Statistical Methods in Medical Research., 27(10), pp. 3167-3182 (2018).
Vanderver et al., "Relative incidence of inherited white matter disorders in childhood to acquired pediatric demyelinating disorders", Semin Pediatr Neurol., 19(4), pp. 219-223. doi:10.1016/j.spen.2012.10.001. (2012).

(56) References Cited

OTHER PUBLICATIONS

Vandiedonck et al., “Genetics of autoimmune myasthenia gravis: the multifaceted contribution of the HLA complex”, J Autoimmun., 25 Suppl:6-11 (2005).
Venkateswaran et al., “Pediatric Multiple Sclerosis”, The Neurologist, 16(2), pp. 92-105 (Mar. 2010).
Volmering et al., “The Neutrophil Btk Signalosome Regulates Integrin Activation During Sterile Inflammation”, Immunity, 44, pp. 73-87 (2016).
Von Budingen, et al., “B cell exchange across the blood brain barrier in multiple sclerosis”, J. Clin. Invest., 122(12), pp. 4533-4543 (2012).
Von Lindern et al., “Control of erythropoiesis by erythropoietin and stem cell factor: A novel role for Bruton’s tyrosine kinase”, Cell Cycle, 3(7), pp. 876-879 (2004).
Wakefield, “Fluorinated Pharmaceuticals”, Innovations in Pharmaceutical Technology, pp. 74-78 (2003).
Waldman et al., “Multiple sclerosis in children: an update on clinical diagnosis, therapeutic strategies, and research”, Lancet Neurol., 13(9), pp. 936-948. doi: 10.1016/S1474-4422(14)70093-6. Review (Sep. 2014).
Caira, Mino R., “Crystalline Polymorphism of Organic Compounds”, Topics in Current Chemistry, 198, pp. 163-208 (Jan. 1, 1998).
Dalton et al., “Effect of natalizumab on conversion of gadolinium enhancing lesions to T1 hypointense lesions in relapsing multiple sclerosis”, J Neurol, 251, pp. 407-413 (2004).
English Translation of Japanese Patent No. 2012246314A, issued on Dec. 13, 2012 (120 pages).
Goldman et al., “Oral Bruton tyrosine kinase inhibitors block activation of the platelet Fc receptor CD32a (FcγRIIA): a new option in HIT?”, Thrombosis and hemostasis, 3(23_, pp. 4021-4033, Electronic resource, URL: https:// shpublications.org/bloodadvances/article/3/23/4021/429246/Oral-Bruton-tyrosine-kinase-inhibitors-block, date of access Apr. 22, 2024, p. 2028 right col. par. 1.
International Preliminary Report on Patentability issued in International Application No. PCT/CN2022/096779 on Nov. 21, 2023 (12 pages).
International Search Report and Written Opinion issued in International Application No. PCT/US2021/064800 on Apr. 4, 2022 (10 pages).
Zavalishin et al., “Multiple sclerosis: modern concept of pathogenesis and pathogenetic treatment”, Annals of Clinical and Experimental Neurology, 1(1), pp. 32-40 (2007) (English translation).
International Search Report and Written Opinion issued in International Application No. PCT/US2022/053479 on Apr. 11, 2023 (13 pages).
International Search Report and Written Opinion issued in International Application No. PCT/US2023/022042 on Aug. 11, 2023 (13 pages).
International Search Report and Written Opinion issued in International Application No. PCT/US2023/025808 on Oct. 2, 2023 (24 pages).
International Search Report and Written Opinion issued in International Application No. PCT/US2023/026526 on Oct. 12, 2023 (12 pages).
International Search Report and Written Opinion issued in International Application No. PCT/US2023/034655 on Feb. 2, 2024 (13 pages).
International Search Report and Written Opinion issued in International Application No. PCT/US2023/084784 on Mar. 18, 2024 (17 pages).
International Search Report for International Application No. PCT/CN2016/084057, mailed Sep. 2, 2016 (4 pages) (English translation).
Lee et al., “B cell depletion therapies in autoimmune disease: advances and mechanistic insights”, Nature Reviews Drug Discovery, 20(3), pp. 179-199 (Dec. 15, 2020).
Mader et al., “Pathomechanisms in demyelination and astrocytopathy: autoantibodies to AQP4, MOG, GFAP, GRP78 and beyond”, Current Opinion in Neurology, 35(3), pp. 427-435 (Jun. 1, 2022).
Mehta et al., “Iron is a Sensitive Biomarker for Inflammation in Multiple Sclerosis Lesions”, PLOS ONE, 8(3), p. e57573 (Mar. 14, 2013).
Montalban et al., “Evobrutinib Phase 2 MS manuscript—Supplement”, Electronic resource, URL: https:// scientiasalut.gencat.cat/bitstream/handle/11351/4593/placebo_controlled_trial_oral_BTK_inhibitor_multiple_sclerosis_2019_appe ndix.pdf?sequence=3&isAllowed=y, date of access Apr. 22, 2024, table S2.
Oh et al., “Emerging therapies to target CNS pathophysiology in multiple sclerosis”, Nature Review Neurology, 18(8), pp. 466-475 (Jun. 13, 2022).
Oh et al., “Safety and clinical outcomes from the long-term extension study of tolebrutinib in patients with relapsing Multiple Sclerosis: 18-month results”, Neurology, 98(18S, pp. 20220424-20220426 (May 3, 2022).
Panichi Zanin Ferreira et al., “Disease progression and oxidative stress are associated with higher serum ferritin levels in patients with multiple sclerosis”, J Neurol Sci, 373, pp. 236-241 (Epub Dec. 27, 2016).
Pellerin et al., “MOG autoantibodies trigger a tightly-controlled FcR and BTK-drive microglia proliferative response”, Brain, 144(8), pp. 2361-2374 (Sep. 4, 2021).
Rudko et al., “Monitoring increased iron levels in multiple sclerosis using MRI”, Future Neurology, 9(4), pp. 387-391 (Jul. 1, 2014).
Sfagos et al., “Serum ferritin, transferrin and soluble transferrin receptor levels in multiple sclerosis patients”, Multiple Sclerosis Journal, 11(3), pp. 272-275 (Jun. 1, 2005).
Stathopoulos et al., “Evolution of Anti-B Cell Therapeutics in Autoimmune Neurological Diseases”, Neurotherapeutics, 19(3), pp. 691-710 (Feb. 18, 2022).
Torke et al., “Inhibition of Bruton’s tyrosine kinase interfers with pathogenic B-cell development in inflammatory CNS demyelinating disease”, ACTA Neuropathologica, 140(4), pp. 535-548 (Aug. 6, 2020).
Traboulsee et al., “Lack of rebound disease activity in patients with relapsing multiple sclerosis following placebo run-out in the tolebrutinib phase 2b trial”, Multiple Sclerosis Journal, 28(3_suppl), pp. 130-691 (Oct. 12, 2022).
Francesco M R et.al, “PRN2246, a potent and selective blood brain barrier penetrating BTK inhibitor, exhibits efficacy in central nervous system immunity”, Database accession No. EMB-619358129abstract & Multiple Sclerosis Journal Oct. 1, 2017 Sage Publications Ltd NLD, vol. 23, No. 3, Supplement 1, Oct. 1, 2017 (Oct. 1, 2017), pp. 511; CONF Oct. 25, 2017 to Oct. 28, 2017 Paris-7th Joint.
Fu et al., “Ocular toxicities associated with targeted anticancer agents: an analysis of clinical data with management suggestions”, Oncotarget, 8(35), pp. 58709-58727 (May 2017).
Futatani et al., “Bruton’s tyrosine kinase is present in normal platelets and its absence identifies patients with X-linked agammaglobulinaemia and carrier females”, Br J Haematol., 114(1), pp. 141-149 (2001).
Ghezzi et al., “Long-Term Effect of Immediate Versus Delayed Fingolimod Treatment in Young Adult Patients with Relapsing—Remitting Multiple Sclerosis: Pooled Analysis from the FREEDOMS/FREEDOMS II Trials”, Neurology and Therapy, 8, pp. 461-475 (2019).
Ghezzi et al., “Multiple sclerosis in childhood: clinical features of 149 cases”, Multiple Sclerosis, 3, pp. 443-446 (1997).
Gilhus et al., “Myasthenia gravis”, Nat Rev Dis Primers., 5(30), pp. 1-19 (2019).
Gilhus et al., “Myasthenia gravis: subgroup classification and therapeutic strategies”, Lancet Neurol., 14(10), pp. 1023-1036 (Oct. 2015).
Giovannoni et al., “The COVID-19 pandemic and the use of MS disease-modifying therapies” [published online ahead of print, Mar. 27, 2020]. Mult Scler Relat Disord., vol. 39, 102073 (Apr. 2020).
Gough et al., “Assessment of dose proportionality: report from the statisticians in the pharmaceutical industry / pharmacokinetics UK joint working party”, Drug Information J, 29, pp. 1039-1048 (1995).

(56) References Cited

OTHER PUBLICATIONS

Harding et al., "Modelling the Natural History of Primary Progressive Multiple Sclerosis", J Neurol Neurosurg Psychiatry, 86(1), pp. 13-19 (Jan. 2015).
Hata et al., "Involvement of Bruton's tyrosine kinase in FcepsilonRI-dependent mast cell degranulation and cytokine production", J Exp Med., 187(8), pp. 1235-1247 (1998).
Hauser et al., "B-Cell Depletion with Rituximab in Relapsing-Remitting Multiple Sclerosis", N Engl J Med., 358, pp. 676-688 (2008).
Hauser, SL, et al., "Ocrelizumab versus Interferon Beta-1a in Relapsing Multiple Sclerosis." N Engl J Med. 2017;376(3):221-34. Epub Dec. 21, 2016.
Hehir et al., "Generalized Myasthenia Gravis: Classification, Clinical Presentation, Natural History, and Epidemiology", Neurol Clin., 36(2), pp. 253-260 (May 2018).
Hemmer B, et. al., "Immunopathogenesis and immunotherapy of multiple sclerosis.", Nat Clin Pract Neurol. 2006;2(4):201-11.
Hemmer B, et. al., "Role of the innate and adaptive immune responses in the course of multiple sclerosis.", Lancet Neurol. 2015; 14(4):406-19.
Holcmann et al., "Mechanisms underlying skin disorders induced by EGFR inhibitors", Mol Cell Oncol., 2(4):e1004969 (Jun. 2015).
Honigberg et al., "The Bruton tyrosine kinase inhibitor PCI-32765 blocks B-cell activation and is efficacious in models of autoimmune disease and B-cell malignancy", Proc. Natl Acad Sci USA, 107(29), pp. 13075-13080 (Jul. 20, 2010).
Horwood et al., "Bruton's tyrosine kinase is required for lipopolysaccharide induced tumor necrosis factor alpha production", J Exp Med, 197(12), pp. 1603-1611 (2003).
Howard et al., "QMG and MG-ADL Correlations: Study of Eculizumab Treatment of Myasthenia Gravis", Muscle & Nerve, 56(2), pp. 328-330 (Aug. 2017).
Howard et al., "Safety and efficacy of eculizumab in anti-acetylcholine receptor antibody-positive refractory generalized myasthenia gravis (REGAIN): a phase 3, randomised, double-blind, placebo-controlled, multicentre study", Lancet Neurol., 16(12), pp. 976-986 (Dec. 2017).
Huang et al., "Clinical characteristics of juvenile myasthenia gravis in southern China", Front Neurol., 9, p. 77 (2018).
Hundelshausen et al., "Bleeding by Bruton tyrosine kinase-inhibitors: Dependency on drug type and disease", Cancers, 13(5), p. 1103 (Jan. 2021).
Hutcheson et al., "Modulating proximal cell signaling by targeting Btk ameliorates humoral autoimmunity and end-organ disease in murine lupus", Arthritis Res Ther., 14: R243 (2012).
Ibrahim et al., "The power prior: theory and applications", Statist. Med., 34, pp. 3724-3749 (2015).
Ibrutinib [prescribing information]. Horsham, PA: Janssen Biotech, Inc.; 2013 [Revised Jan. 2015; cited Aug. 12, 2021]. Available from: https://www.accessdata.fda.gov/drugsatfda_docs/label/2015/205552s002lbl.pdf.
Imbruvica [package insert]. Pharmacyclics, Inc., Sunnyvale, CA; 2017.
Ingle et al., "Magnetic resonance imagin in primary progressive multiple sclerosis", Journal of Rehabilitation Research and Development, 39(2), pp. 261-272 (Mar./Apr. 2002).
International Search Report and Written Opinion in corresponding International Patent Application No. PCT/US2021/013883, mailed Apr. 28, 2021 (12 pages).
International Search Report and Written Opinion issued in International Application No. PCT/CN2021/132028, dated Feb. 18, 2022 (English translation provided) (2 pages).
International Search Report and Written Opinion mailed Aug. 16, 2016, issued in corresponding International Application No. PCT/US2016/035588 (9 pages).
Irwin, S., "Comprehensive observational assessment: Ia. A systematic, quantitative procedure for assessing the behavioral and physiologic state of the mouse", Psychopharmacologia, 13(3), pp. 222-257 (1968).
Itachaki et al., "Experience with ibrutinib for first-line use in patients with chronic lymphocytic leukemia", Ther Adv Hematol., 9(1), pp. 3-19 (Jan. 2018).
Jaretzki et al., "Myasthenia gravis: recommendations for clinical research standards. Task Force of the Medical Scientific Advisory Board of the Myasthenia Gravis Foundation of America", Neurology,55(1), pp. 16-23 (Jul. 12, 2000).
Johnson, "Modelling approaches to dose estimation in children", Br J Clin Pharmacol, 59(6), pp. 663-669 (2005).
Kalincik et al., "Treatment effectiveness of alemtuzumab compared with natalizumab, fingolimod, and interferon beta in relapsing-remitting multiple sclerosis: a cohort study", Lancet Neurol, 16, pp. 271-281 (2017).
Kaminski, "Treatment of Myasthenia Gravis. In: Kaminski HJ, Kusner LL, editors", Current Clinical Neurology: Myasthenia Gravis and Related Disorders 3rd edition, pp. 169-187 (2018).
Kapoor et al., "Effect of natalizumab on disease progression in secondary progressive multiple sclerosis (ASCEND): a phase 3, randomised, double-blind, placebo-controlled trial with an open-label extension", Lancet Neurol, 17: 405-415 (2018).
Kappos et al., "Ocrelizumab in relapsing-remitting multiple sclerosis: a phase 2, randomised, placebo-controlled, multicentre trial", The Lancet, 378(9805), pp. 1779-1787 (Nov. 19, 2011).
Kappos L, et; al., "Siponimod versus placebo in secondary progressive multiple sclerosis (EXPAND): a double-blind, randomised, phase 3 study.", Lancet. 2018;391(10127):1263-73.
Kappos, L., et al., "Natalizumab treatment for multiple sclerosis: recommendations for patient selection and monitoring", Lancet Neurol, 6(5), pp. 431-441 (2007).
Kim et al., "Imidazo[1,5-a]quinoxalines as irreversible BTK inhibitors for the treatment of rheumatoid arthritis", Bioorg Med Chem Lett., 21, pp. 6258-6263 (2011).
Kozuki, T., "Skin problems and EGFR-tyrosine kinase inhibitor." Jpn J Clin Oncol., 46(4), pp. 291-298. (Apr. 2016).
Krupp et al., "International Pediatric Multiple Sclerosis Study Group. International Pediatric Multiple Sclerosis Study Group", Multiple Sclerosis Journal., 19, pp. 1261-1267 (2011).
Kuks J.B.M., "Clinical Presentations of Myasthenia Gravis: Myasthenia Gravis and Related Disorders", Current Clinical Neurology, 2018. p. 58-100.
Kurtzke J F, "Rating neurologic impairment in multiple sclerosis: an expanded disability status scale (EDSS).", Neurology. 1983;33(11):1444-52.
Langer-Gould et al., "Incidence of acquired CNS demyelinating syndromes in a multiethnic cohort of children", Neurology, 77(12), pp. 1143-1148 (Sep. 2011).
Lazaridis et al., "Myasthenia Gravis: Autoantibody Specificities and Their Role in MG Management", Front Neurol, p. 30;11:59698 (2020).
Lebakken et al., "Development and applications of a broad-coverage, TR-FRET-based kinase binding assay platform", J Biomol Screen, 14, pp. 924-935 (2009).
Lee et al., "Juvenile Myasthenia Gravis in Korea: Subgroup Analysis According to Sex and Onset Age", J Child Neurol, 31(14), pp. 1561-1568 (Dec. 2016).
Acalabrutinib [prescribing information]. Wilmington, DE: AstraZeneca Pharmaceuticals LP;2017 [Revised Oct. 2017; cited Aug. 12, 2021]. Available from:https://www.accessdata.fda.gov/drugsatfda_docs/label/2017/210259s000lbl.pdf.
Advani, et al., "Bruton tyrosine kinase inhibitor ibrutinib (PCI-32765) has significant activity in patients with relapsed/refractory B-cell malignancies." Journal of Clinical Oncology, 31, pp. 88-94 (2013).
Aguilar, C, "Ibrutinib-related bleeding: pathogenesis, clinical implications and management." Blood Coagul Fibrinolysis, 29(6), pp. 481-487 (Sep. 2018).
Alabbad, et al. "Monoclonal Antibody Based Therapies for Myasthenia Gravis." BioDrugs., 34(5), pp. 557-566 (Oct. 2020).
Alroughani et al., "Pediatric multiple sclerosis—a review", BMC Neurology, 18:27 (2018) (8 pages).
Amato et al, "Interrater reliability in assessing functional systems and disability on the Kurtzke scale in multiple sclerosis", Arch Neurol., 45(7), pp. 746-748 (Jul. 1988).

(56) References Cited

OTHER PUBLICATIONS

American Cancer Society. Can Non-Hodgkins Lymphoma Be Prevented? (2016) Web: https://www.cancer.org/cancer/non-hodgkin-lymphoma/causes-risks-prevention/prevention.html (3 pages).
Aragonès et al, "Prevalence of myasthenia gravis in the Catalan county of Osona", Neurologia., 32(1), pp. 1-5 (Jan.-Feb. 2017).
Arora, et al., "Role of Tyrosine Kinase Inhibitors in Cancer Therapy," J. Pharmacol. Exp. Ther., 2005, 315:971-979.
Auto-immune Diseases: Medlineplus (2014). Web: http://www.nlm.nih.gov/medlineplus/autoimmunediseases.html.
Azevedo et al., "Whole-brain atrophy: ready for implementation into clinical decision-making in multiple sclerosis?", Curr Opin Neurol., 29(3), pp. 237-242 (Jun. 2016).
Balto et al., "Accuracy and precision of smartphone applications and commercially available motion sensors in multiple sclerosis", Mult Scler J Exp Transl Clin (Mar. 4, 2016).
Banwell et al., "Incidence of acquired demyelination of the CNS in Canadian children", Neurology, 72(3), pp. 232-239 (Jan. 20, 2009). doi: 10.1212/01.wnl.0000339482. 84392.bd.
Banwell et al., "Multiple sclerosis in children: clinical diagnosis, therapeutic strategies, and future directions", Lancet Neurology, 6, pp. 887-902 (2007).
Barnett et al., "Measuring Clinical Treatment Response in Myasthenia Gravis", Neurol Clin, 36(2), pp. 339-353 (2018).
Barnett et al., "A conceptual framework for evaluating impairments in myasthenia gravis", PLoS One, 9(5), pp. 1-9 (2014).
Barnett et al., "Development and validation of the Myasthenia Gravis Impairment Index", Neurology, 87(9), pp. 879-886 (Aug. 30, 2016).
Barnett et al., "Myasthenia Gravis Impairment Index: Responsiveness, meaningful, change, and relative efficiency", Neurology, 5:89(23), pp. 2357-2364 (2017).
Barohn et al., "Reliability testing of the quantitative myasthenia gravis score", Ann N.Y. Acad Sci, 841, pp. 769-772 (1998).
Bar-Or et al., Clinical Perspectives on the Molecular and Pharmacological Attributes of Anti-CD20 Therapies for Multiple Sclerosis, CNS Drugs, 35(9), pp. 985-997 (Sep. 2021).
Barraud et al., "Clinical features and evolution of juvenile myasthenia gravis in a French cohort", Muscle Nerve, 57(4), pp. 603-609 (Apr. 2018).
Bedlack et al., "Quantitative myasthenia gravis score: Assessment of responsiveness and longitudinal validity", Neurology, vol. 64, pp. 1968-1970 (2005).
Benedict et al., "Characterizing cognitive function during relapse in multiple sclerosis", Mult Scler., 20(13), pp. 1745-1752 (Nov. 2014) doi: 10.1177/1352458514533229.
Benedict et al., "Improved cognitive outcomes in patients with relapsing-remitting multiple sclerosis treated with daclizumab beta: results from the DECIDE study", Mult Scler J, 24(6), pp. 795-804 (2018).
Berger, et al., "PML diagnostic criteria: consensus statement from the AAN Neuroinfectious Disease Section", Neurology, vol. 80, No. 15, pp. 1430-1438 (Apr. 9, 2013).
Bergsland et al., "Subcortical and Cortical Gray Matter Atrophy in a Large Sample of Patients with Clinically Isolated Syndrome and Early Relapsing-Remitting Multiple Sclerosis", Am J Neuroradiol, 33(8), pp. 1573-1578 (2012).
Berrih-Aknin, et al., "Myasthenia Gravis: a comprehensive review of immune dysregulation and etiological mechanisms", J Autoimmun., vol. 52, pp. 90-100 (Aug. 2014).
Bhaskaran, et al., "Pancreatic Effects of a Bruton's Tyrosine Kinase Small-molecule Inhibitor in Rats Are Strain-dependent", Toxicol Pathol., vol. 46(4), pp. 460-472 (Jun. 2018).
Blauth, et al., "The ins and outs of B cells in multiple sclerosis", Front. Immunol., vol. 6, p. 565 (Nov. 5, 2015).
Boiko et al., "Early onset multiple sclerosis: a longitudinal study", Neurology, 59, pp. 1006-1010 (2002).
Bornkamp et al., "Package 'DoseFinding': Planning and analyzing dose finding experiments," Version 0.9-16, CRAN. Jan. 4, 2018.
Breiner et al., "Epidemiology of myasthenia gravis in Ontario, Canada", Neuromuscul Disord., 26(1), pp. 41-46 (Jan. 2016).
Brenneman et al., "Mechanistic investigations of test article-induced pancreatic toxicity at the endocrine-exocrine interface in the rat", Toxicol Pathol., 42(1), pp. 229-242 (Jan. 2014).
Brittain, Harry, "Polymorphism in Pharmaceutical Solids, 2nd Edition", CRC Press, 2009 (229 pages).
Brown et al. "Incidence of and risk factors for major haemorrhage in patients treated with ibrutinib: An integrated analysis.", Br. J. Haematol., 184(4), pp. 558-569 ( Feb. 2019).
Bubuioc et al. "The epidemiology of myasthenia gravis.", J Med Life., 14(1), pp. 7-16 (Jan.-Mar. 2021).
Buoen, C., et al. "How first-time-in-human studies are being performed: a survey of phase I dose-escalation trials in healthy volunteers published between 1995 and 2004." J Clin Pharmacol. Oct. 2005, vol. 45, No. 10, pp. 1123-1136.
Burdick et al., "Confidence intervals on variance components.", Marcel Dekker, NY. 1992.
Burger J A, et. al., "Targeting B cell receptor signalling in cancer: preclinical and clinical advances.", Nat Rev Cancer. 2018;18(3):148-67.
Bye et al., "Severe platelet dysfunction in NHL patients receiving ibrutinib is absent in patients receiving acalabrutinib", Blood Adv., 1(26), pp. 2610-2623 (Dec. 12, 2017).
Byrd et al., "Acalabrutinib (ACP-196) in relapsed chronic lymphocytic leukemia", N Engl J Med., 374(4), pp. 323-332 (2016).
Byrd et al., "Targeting BTK with Ibrutinib in Relapsed Chronic Lymphocytic Leukemia", N Engl J Med., 369(1), pp. 32-42 (Jun. 19, 2013).
Cadavid et al., "The EDSS-Plus, an improved endpoint for disability progression in secondary progressive multiple sclerosis", Multiple Sclerosis Journal, 23(1), pp. 94-105 (2017).
Carr et al., "A systematic review of population based epidemiological studies in Myasthenia Gravis", BMC Neurology, 10(46), pp. 1-9 (Jun. 18, 2010).
Case et al., "Accuracy of smartphone applications and wearable devices for tracking physical activity data", JAMA, 313(6), pp. 625-626.
Cavalcante et al., "Etiology of myasthenia gravis: innate immunity signature in pathological thymus", Autoimmun Rev., 12(9), pp. 863-874 (Jul. 2013).
Cavalcante et al., "Toll-like receptors 7 and 9 in myasthenia gravis thymus: amplifiers of autoimmunity?" Annals of the New York Academy of Science, Feb. 2018;1413(1):11-24.
Center for Drug Evaluation and Research, Summary Basis of Approval, Acalabrutinib, Application No. 210259Orig1s000, 2017.
Center for Drug Evaluation and Research, Summary Basis of Approval, Ibrutinib, Application No. 205552Orig1s000, 2013.
Chang, Betty Y., et al., "The Bruton tyrosine kinase inhibitor PCI-32765 ameliorates autoimmune arthritis by inhibition of multiple effector cells." Arthritis Research & Therapy, 2011; vol. 13, Article No. R115.
Aaltonen et al., "Solid form screening—A review", European Journal of Pharmaceutics and Biopharmaceutics, 2009, vol. 71(1), 23-37 (see part 1 Introduction and background (1.1, 1.2) doi:10.1016/j.ejpb.2008.07.014).
Bernstein, J., "Polymorphism of molecular crystals", Moscow, Nauka, Ch. 7.3.2., Bioavailability, pp. 324-330 (2007).
Council for International Organizations of Medical Sciences (CIOMS), "Drug-induced liver injury (DILI): Current status and future directions for drug development and the post-market setting" (2020) (176 pages).
FDA Guidance for Industry Drug-Induced Liver Injury: Premarketing Clinical Evaluation; U.S. Department of Health and Human Services, Food and Drug Administration, Center for Drug Evaluation and Research (CDER), Center for Biologics Evaluation and Research (CBER), Jul. 2009 (28 pages).
Kümmerer, Pharmaceuticals in the environment, Annual Review of Environment and Resources, v. 35, pp. 57-75, doi:10.1146/annurev-environ-052809-161223 (see the abstract, p. 60) (2010).
Sarma et al., "Solid formation of pharmaceuticals: Polymorphs, salt and cocrystals", Korean J.Chem. Eng., 28(2), pp. 315-322 (p. 315-317 section "Introduction", "Polymorphism") (2011).

(56) References Cited

OTHER PUBLICATIONS

Sanofi Press Release, "Patient enrollment of phase III tolebrutinib trials paused in the U.S.", (Jun. 30, 2022) (2 pages).

* cited by examiner

C1: Cohort 1; C2: Cohort 2; R: randomization; Schedule of Activities (SoA)

THERAPEUTIC TYROSINE KINASE INHIBITORS FOR RELAPSING MULTIPLE SCLEROSIS (RMS)

This application is a continuation of U.S. application Ser. No. 17/151,954, filed Jan. 19, 2021, which claims priority to U.S. Provisional Application No. 62/963,238, filed Jan. 20, 2020, U.S. Provisional Application No. 62/970,502, filed Feb. 5, 2020, and U.S. Provisional Application No. 63/013,895, filed Apr. 22, 2020, the contents of each of which are incorporated herein by reference for all purposes.

INTRODUCTION AND SUMMARY

This disclosure relates to the field of therapeutic tyrosine kinase inhibitors, in particular Bruton tyrosine kinase ("BTK") inhibitors, to treat relapsing multiple sclerosis (RMS).

Multiple Sclerosis (MS) is a neurological disease affecting more than 1 million people worldwide. It is the most common cause of neurological disability in young and middle-aged adults and has a major physical, psychological, social and financial impact on subjects and their families. MS involves an immune-mediated process in which an abnormal response of the body's immune system is directed against the central nervous system (CNS). In the course of the disease, scleroses, i.e., lesions or scars, appear in the myelin sheath of nerve cells, disrupting transmission of electrical signals. Scleroses accumulate over time and result in the debilitating symptoms experienced by MS patients. MS patients generally experience one of four clinical courses of disease, each of which might be mild, moderate, or severe: clinically isolated syndrome, relapsing remitting, secondary progressive and primary progressive. About 85% of MS patients have the relapsing remitting form of the disease, in which they experience clearly defined relapses (also called flare-ups or exacerbations), which are episodes of acute worsening of neurologic function, followed by partial or complete recovery periods (remissions) that are free of disease progression. Within the scope of the present disclosure, "relapsing multiple sclerosis," "relapsing MS," or "RMS" may include clinically isolated syndrome ("CIS"), relapsing remitting multiple sclerosis ("RRMS"), and relapsing secondary progressive multiple sclerosis ("R-SPMS.") See, e.g., Lublin et al., Defining the clinical course of multiple sclerosis; the 2013 revisions, *Neurology* 2014; 83:278-286.

Immunomodulatory drugs have been the mainstay of MS therapy. Recent results from clinical studies have demonstrated efficacy of agents that target B lymphocytes, especially B-cell-depleting agents like ocrelizumab (anti-CD20) (Hauser et al., *N Engl J Med.* 2017; 376(3):221-34). Targeting B-cells represents a departure from the prevailing dogma based on animal models that demonstrated therapeutic benefits from modulating T-cell activity and positions the B cell as the centerpiece of current MS drug development (Lehmann-Horn K et al., *Int J Mol Sci.* 2017; 18(10):2048). The importance of immune cells residing in the CNS is also well known and needs to be considered in MS pathogenesis (Hemmer B et al, *Nat Clin Pract Neurol.* 2006; 2(4):201-11).

Despite these recent advances, there is still a significant unmet need for therapies that target neuroinflammation in the CNS with a goal of halting long-term disability and neurodegeneration in people with relapsing multiple sclerosis (RMS) and with progressive forms of the disease (primary progressive multiple sclerosis, ("PPMS") and non-relapsing secondary progressive multiple sclerosis, ("NR-SPMS")) (Stys P K et al, *Nat Rev Neurosci.* 2012; 13(7):507-14). Even the most recent high-efficacy disease-modifying therapies act mainly on adaptive immunity in the periphery with only modest or temporary ability to halt neuroinflammatory and neurodegenerative processes and stop disease progression, as also demonstrated by recent studies in progressive forms of MS (Montalban X et al, *N Engl J Med.* 2017; 376(3):209-20; Kappos L et al, *Lancet* 2018; 391(10127):1263-73).

Beyond the existing strategy to modulate cellular elements of adaptive immunity, there is mounting evidence that innate immunity, mediated by myeloid cell lineages (bone-marrow-derived monocytes/macrophages and CNS-resident microglial cells), is responsible for many of the neurodegenerative aspects of MS that persist in spite of the effectiveness of approved disease-modifying therapies in preventing acute relapses (Hemmer B et al., *Lancet Neurol.* 2015; 14(4):406-19; Rahmanzadeh R et al., *Rev Neurosci.* 2018 Jun. 8). Immunomodulation directed at innate immunity has potential to curtail "smoldering neuroinflammation" and other manifestations of disease progression that remain unaddressed by current, approved therapies.

The Bruton's tyrosine kinase (BTK) pathway is critical to signaling in B lymphocytes and myeloid cells including CNS microglia. Each of these cell types has been implicated in the pathophysiology of multiple sclerosis (MS). Further, as BTK signaling is vital for maturation of B cells into antibody-secreting plasma cells, BTK inhibition can modulate both cellular and humoral immunity. Accordingly, an inhibitor of BTK signaling represents a dual mechanism targeting both aspects of the immune system.

Accordingly, compounds that inhibit BTK that are able to both inhibit antigen-induced B-cell activation responsible for neuroinflammation and modulate maladaptive microglial cells linked to neuroinflammation in the brain and spinal cord may be useful in treating RMS with superior benefits when compared to currently available therapies.

Accordingly, the following embodiments are provided. In some embodiments, a method of treating relapsing multiple sclerosis (RMS) is provided comprising administering to a subject in need thereof a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the number of new gadolinium (Gd)-enhancing T1 hyperintense lesions is provided comprising administering to a subject having relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the number of new or enlarging T2 lesions is provided comprising administering to a subject having relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the total number of gadolinium (Gd)-enhancing T1 hyperintense lesions is provided comprising administering to a subject having relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the rate of relapse in a subject having multiple sclerosis (MS) is provided comprising administering to the subject a BTK inhibitor comprising (R)-1-(1-acryloylpiperidin-3-yl)-4-amino-3-(4-phenoxyphenyl)-1H-imidazo[4,5-c]pyridin-2(3H)-one.

In another embodiment, the dose of the BTK inhibitor is about 5 mg to about 60 mg. In another embodiment, the dose is 5 mg. In another embodiment, the dose is 15 mg. In another embodiment, the dose is 30 mg. In another embodiment, the dose is 60 mg. In some embodiments, a method of treating relapsing multiple sclerosis (RMS) comprises administering to a subject in need thereof a BTK inhibitor comprising (R)-1-(1-acryloylpiperidin-3-yl)-4-amino-3-(4-phenoxyphenyl)-1H-imidazo[4,5-c]pyridin-2(3H)-one, wherein administration of the BTK inhibitor inhibits the formation of new active brain lesions as measured by MRI. In another embodiment, the BTK inhibitor compound is administered as monotherapy. In some embodiments, RMS is chosen from clinically isolated syndrome (CIS), relapsing remitting multiple sclerosis (RRMS), and relapsing secondary progressive multiple sclerosis (R-SPMS). In another embodiment, the subject is a human.

In some embodiments, the dose is once daily. In some embodiments, the dose is administered once daily with food. In some embodiments, a dose of 15 mg is administered once daily with food. In some embodiments, a dose of 30 mg is administered once daily with food. In some embodiments, a dose of 60 mg is administered once daily with food.

In some embodiments, administration of the BTK inhibitor reduces RGS1 expression in a brain cell. In some embodiments, the brain cell comprises microglia.

In some embodiments, administration of the BTK inhibitor reduces the number of new gadolinium (Gd)-enhancing T1 hyperintense lesions as measured by MRI. In some embodiments, the number of new Gd-enhancing T1 hyperintense lesions is equal to or less than 1. In some embodiments, the number of new Gd-enhancing T1 hyperintense lesions is zero. In some embodiments, no new Gd-enhancing T1 hyperintense lesions is formed after 12 weeks of BTK inhibitor treatment. In some embodiments, one or fewer new Gd-enhancing T1 hyperintense lesions is formed after 12 weeks of BTK inhibitor treatment.

In some embodiments, a method of reducing the number of new gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one.

In some embodiments, a method of reducing the number of new or enlarging T2 lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one.

In some embodiments, a method of reducing the total number of gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one.

In some embodiments, a method of reducing the rate of relapse in a subject having multiple sclerosis (MS) is provided, comprising administering to the subject a BTK inhibitor comprising (R)-1-(1-acryloylpiperidin-3-yl)-4-amino-3-(4-phenoxyphenyl)-1H-imidazo[4,5-c]pyridin-2(3H)-one.

In some embodiments, administration of the BTK inhibitor reduces the number of new or enlarging T2 lesions as measured by MRI. In some embodiments, the number of new or enlarging T2 lesions is equal to or less than 2. In some embodiments, the number of new or enlarging T2 lesions is equal to or less than 1. In some embodiments, the number of new or enlarging T2 lesions is zero. In some embodiments, equal to or less than 2 new or enlarging T2 lesion is formed after 12 weeks of BTK inhibitor treatment. In some embodiments, equal to or less than 1 new or enlarging T2 lesion is formed after 12 weeks of BTK inhibitor treatment. In some embodiments, no new or enlarging T2 lesion is formed after 12 weeks of BTK inhibitor treatment.

In some embodiments, administration of the BTK inhibitor reduces the total number of Gd-enhancing T1-hyperintense lesions after 12 weeks of the BTK inhibitor treatment.

In some embodiments, the dose is 60 mg, and one or zero new Gd-enhancing T1 hyperintense lesions is formed after 12 weeks of BTK inhibitor treatment. In some embodiments, zero new Gd-enhancing T1 hyperintense lesions is formed after 12 weeks of BTK inhibitor treatment. In some embodiments, the number of new or enlarging T2 lesions is equal to or less than 2.

In some embodiments, the administration of the BTK inhibitor reduces the total number of Gd-enhancing T1-hyperintense lesions after 12 weeks of the BTK inhibitor treatment.

In one embodiment, a method of treating relapsing multiple sclerosis (RMS) is provided, the method comprising administering to a subject in need thereof 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein no new Gd-enhancing T1 hyperintense lesions are formed after 12 weeks of BTK administration.

In some embodiments, a BTK inhibitor comprising (R)-1-(1-acryloylpiperidin-3-yl)-4-amino-3-(4-phenoxyphenyl)-1H-imidazo[4,5-c]pyridin-2(3H)-one for use in a method for treating relapsing multiple sclerosis (RMS) in a subject in need thereof is provided. In some embodiments, a BTK inhibitor comprising (R)-1-(1-acryloylpiperidin-3-yl)-4-amino-3-(4-phenoxyphenyl)-1H-imidazo[4,5-c]pyridin-2(3H)-one for use in a method for reducing the number of new or enlarging T2 lesions in a subject that has relapsing multiple sclerosis (RMS) is provided. In some embodiments, a BTK inhibitor comprising (R)-1-(1-acryloylpiperidin-3-yl)-4-amino-3-(4-phenoxyphenyl)-1H-imidazo[4,5-c]pyridin-2(3H)-one for use in a method for reducing the total number of gadolinium (Gd)-enhancing T1 hyperintense lesions in a subject that has relapsing multiple sclerosis (RMS) is provided. In some embodiments, a BTK inhibitor comprising (R)-1-(1-acryloylpiperidin-3-yl)-4-amino-3-(4-phenoxyphenyl)-1H-imidazo[4,5-c]pyridin-2(3H)-one for use in a method for reducing the rate of relapse in a subject having multiple sclerosis (MS) is provided.

DETAILED DESCRIPTION

Figure 1:
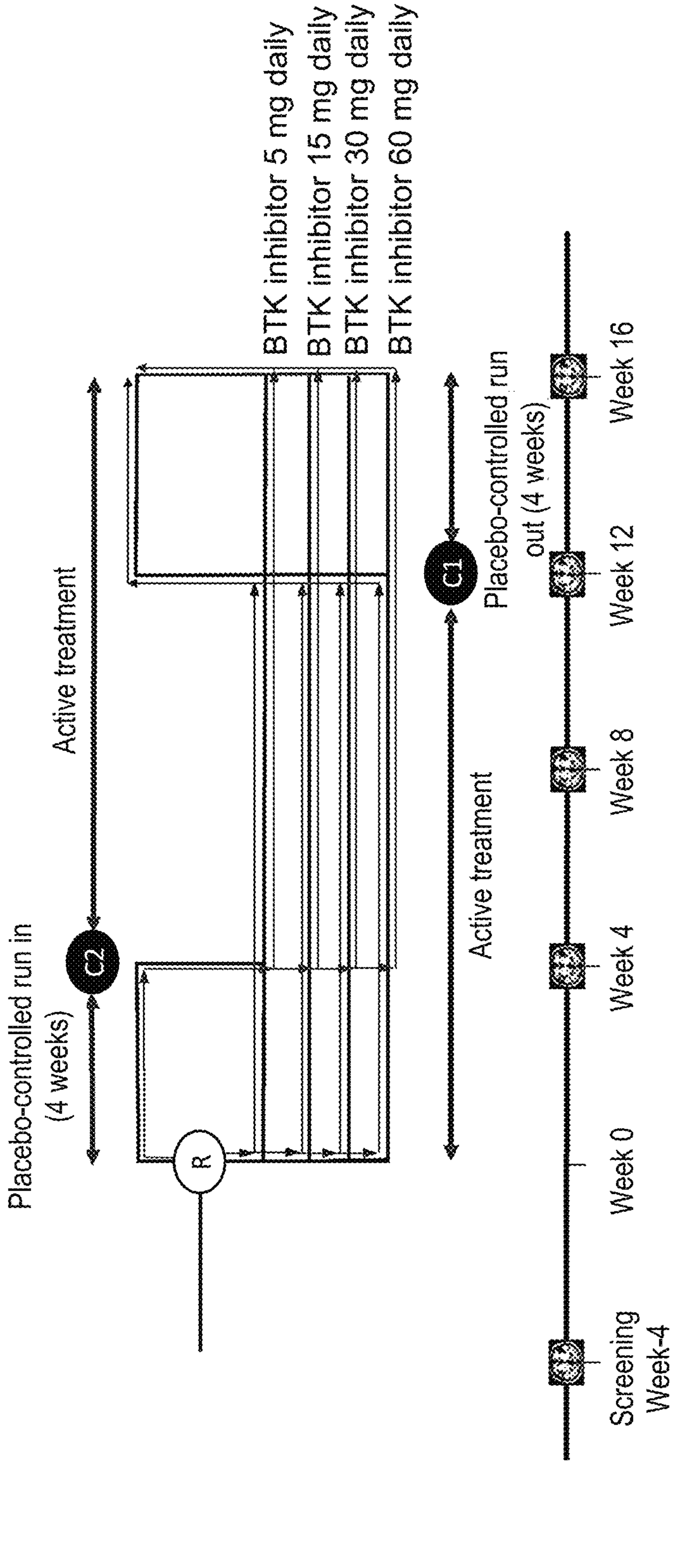
FIG. 1 shows an exemplary overall design of treatment.

Reference will now be made in detail to certain embodiments, examples of which are illustrated in the accompanying drawings. While the disclosure provides illustrated embodiments, it will be understood that they are not intended to limit the invention to those embodiments. On the contrary, the invention is intended to cover all alternatives, modifications, and equivalents, which may be included within the disclosure as defined by the appended claims.

The section headings used herein are for organizational purposes only and are not to be construed as limiting the desired subject matter in any way. In the event that any literature incorporated by reference contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

I. Definitions

Unless otherwise stated, the following terms used in the specification and claims are defined for the purposes of this disclosure and have the following meaning:

As used herein, "the BTK inhibitor," "the BTK inhibitor compound," and "the compound", refers to (R)-1-(1-acryloylpiperidin-3-yl)-4-amino-3-(4-phenoxyphenyl)-1H-imidazo[4,5-c]pyridin-2(3H)-one having the following structure:

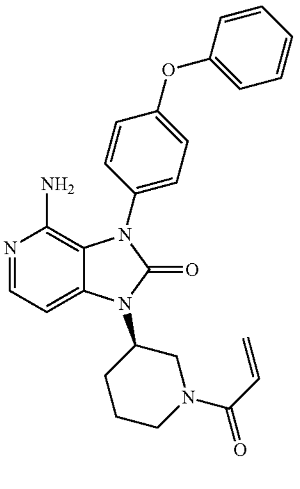

which is also known as 4-amino-3-(4-phenoxyphenyl)-1-[(3R)-1-(prop-2-enoyl)piperidin-3-yl]-1,3-dihydro-2H-imidazo[4,5-c]pyridin-2-one having the following structure:

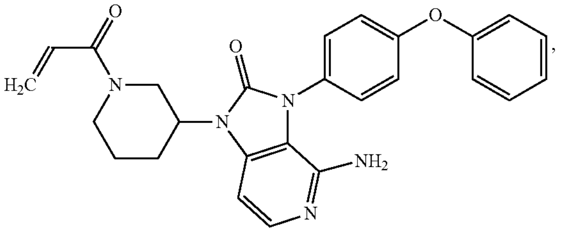 [SMILES: C=CC(=O)N1CCCC(n2c(=O)n(-c3ccc(Oc4ccccc4)cc3)c3c(N)nccc32)C1]

and/or a pharmaceutically acceptable salt thereof.

A "pharmaceutically acceptable carrier" or a "pharmaceutically acceptable excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Treating" or "Treatment" of a Disease Includes:

(1) preventing the disease, e.g., causing the clinical symptoms of the disease not to develop in a mammal that may be exposed to or predisposed to the disease but does not yet experience or display symptoms of the disease;

(2) inhibiting the disease, e.g., arresting or reducing the development of the disease or its clinical symptoms; or (3) relieving the disease, e.g., causing regression of the disease or its clinical symptoms.

"Optional" or "optionally" means that the subsequently described event or circumstance may but need not occur, and that the description includes instances where the event or circumstance occurs and instances in which it does not.

A "therapeutically effective amount" means the amount of the BTK inhibitor compound, that, when administered to a mammal for treating a disease, is sufficient to effect such treatment for the disease. The "therapeutically effective amount" will vary depending on the compound, the disease and its severity and the age, weight, etc., of the mammal to be treated.

Before describing the present teachings in detail, it is to be understood that the disclosure is not limited to specific compositions or process steps, as such may vary.

It should be noted that, as used in this specification and the appended claims, the singular form "a", "an" and "the" include plural references unless the context clearly dictates otherwise. Thus, for example, reference to "a conjugate" includes a plurality of conjugates and reference to "a cell" includes a plurality of cells and the like.

Numeric ranges are inclusive of the numbers defining the range. Measured and measurable values are understood to be approximate, taking into account significant digits and the error associated with the measurement. Also, the use of "comprise", "comprises", "comprising", "contain", "contains", "containing", "include", "includes", and "including" are not intended to be limiting. It is to be understood that both the foregoing general description and detailed description are exemplary and explanatory only and are not restrictive of the teachings.

Unless specifically noted in the above specification, embodiments in the specification that recite "comprising" various components are also contemplated as "consisting of" or "consisting essentially of" the recited components; embodiments in the specification that recite "consisting of" various components are also contemplated as "comprising" or "consisting essentially of" the recited components; and embodiments in the specification that recite "consisting essentially of" various components are also contemplated as "consisting of" or "comprising" the recited components (this interchangeability does not apply to the use of these terms in the claims.)

The terms "or a combination thereof" and "or combinations thereof" as used herein refers to any and all permutations and combinations of the listed terms preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

"Or" is used in the inclusive sense, i.e., equivalent to "and/or," unless the context requires otherwise.

II. Administered BTK Inhibitor Compound

In some embodiments, a BTK inhibitor compound, (R)-1-(1-acryloylpiperidin-3-yl)-4-amino-3-(4-phenoxyphenyl)-1H-imidazo[4,5-c]pyridin-2(3H)-one is administered for treating relapsing multiple sclerosis (RMS) in a subject in need thereof. In some embodiments, the BTK inhibitor compound is a pharmaceutically acceptable salt of (R)-1-(1-acryloylpiperidin-3-yl)-4-amino-3-(4-phenoxyphenyl)-1H-imidazo[4,5-c]pyridin-2(3H)-one. In some embodiments, a therapeutically effective amount of the BTK inhibitor compound is administered. In some embodiments, a dose of 5 to 60 mg of the BTK inhibitor compound is administered.

The BTK inhibitor compound can be prepared according to the methods and schemes described in, e.g., U.S. Pat. No. 9,688,676 B2, in particular the content of column 62, line 8 to column 65 line 32, and column 67, line 28 to column 69, which is incorporated herein by reference.

The following preparation of the compound of (R)-1-(1-acryloylpiperidin-3-yl)-4-amino-3-(4-phenoxyphenyl)-1H-imidazo[4,5-c]pyridin-2(3H)-one, is given to enable those skilled in the art to prepare the BTK inhibitor compound. The synthetic route should not be considered as limiting the scope of the disclosure, but merely as being illustrative and representative thereof.

Exemplary synthesis of (R)-1-(1-acryloylpiperidin-3-yl)-4-amino-3-(4-phenoxyphenyl)-1H-imidazo[4,5-c]pyridin-2(3H)-one

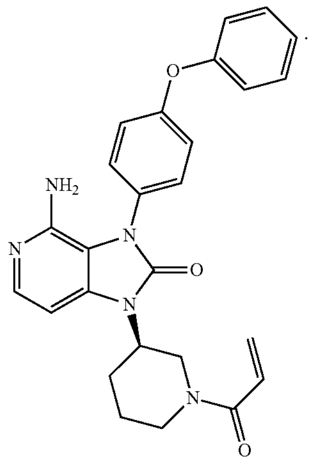 [SMILES: C=CC(=O)N1CCC[C@@H](n2c(=O)n(-c3ccc(Oc4ccccc4)cc3)c3c(N)nccc32)C1]

Into a 100 mL round-bottom flask was placed (R)-4-amino-3-(4-phenoxyphenyl)-1-(piperidin-3-yl)-1H-imidazo[4,5-c]pyridin-2(3H)-one (150 mg, 0.37 mmol, 1.00 equiv), DCM-$CH_3OH$ (6 mL), TEA (113 mg, 1.12 mmol, 3.00 equiv). This was followed by the addition of prop-2-enoyl chloride (40.1 mg, 0.44 mmol, 1.20 equiv) dropwise with stirring at 0° C. in 5 min. The resulting solution was stirred for 2 h at 0° C. The resulting mixture was concentrated under vacuum. The residue was applied onto a silica gel column with dichloromethane/methanol (30:1). The crude product (100 mg) was purified by Prep-HPLC under the following conditions (Column, XBridge Prep $C_{18}$ OBD Column, 5 μm, 19*150 mm; mobile phase, water with 0.05% TFA and ACN (25.0% ACN up to 45.0% in 8 min). 54.5 mg product of (R)-1-(1-acryloylpiperidin-3-yl)-4-amino-3-(4-phenoxyphenyl)-1H-imidazo[4,5-c]pyridin-2(3H)-one was obtained as a white solid. LC-MS m/z: 465.2 (M+1).

III. Therapeutic Methods

Provided herein are methods of treating relapsing multiple sclerosis (RMS) comprising administering to a subject in need thereof a therapeutically effective amount of the BTK inhibitor compound comprising (R)-1-(1-acryloylpiperidin-3-yl)-4-amino-3-(4-phenoxyphenyl)-1H-imidazo[4,5-c]pyridin-2(3H)-one, and/or a pharmaceutically acceptable salt thereof. In some embodiments the therapeutically effective amount is about 5 to about 60 mg. In some embodiments, the subject is a mammal. In some embodiments, the mammal is a human. In some embodiments, the subject has one or more symptoms of RMS prior to treatment and the treatment reduces or eliminates the one or more symptoms. In some embodiments, the subject suffers from neuropathic pain, musculoskeletal pain, or spasticity caused by RMS.

In some embodiments, a subject with RMS has at least one documented relapse within the previous year, and/or greater than two documented relapses within the previous two years, and/or greater than one active Gd-enhancing brain lesion on an MRI scan in the past six months and prior to screening.

In some embodiments, a dose of about 5-10 mg, 10-15 mg, 15-20 mg, 20-25 mg, 25-30 mg, 30-35 mg, 35-40 mg, 40-45 mg, 45-50 mg, 50-55 mg, or 55-60 mg is administered. In some embodiments, the dose is 5 mg, 10 mg, 15 mg, 20 mg, 25 mg, 30 mg, 35 mg, 40 mg, 45 mg, 50 mg, 55 mg, or 60 mg. In some embodiments, the dose is 5 mg. In some embodiments, the dose is 15 mg. In some embodiments, the dose is 30 mg. In some embodiments, the dose is 60 mg.

In some embodiments, the dose is administered daily. The daily dose can be delivered as a single dose or split into multiple parts. For example, in some embodiments, the dose is administered once a day (e.g., about every 24 hours). In some embodiments, the dose is administered twice daily. In some embodiments, the dose is subdivided in two parts to be administered twice per day (e.g., about every 12 hours). In some embodiments, the dose is subdivided in three parts to be administered three times per day (e.g., about every 8 hours). In some embodiments, the dose is subdivided in four parts to be administered four times per day (e.g., about every 6 hours).

In some embodiments, the dose is administered orally. In some embodiments, the dose is administered in a form of tablets. In some embodiments, the dose is administered in the form of pills, capsules, semisolids, powders, sustained release formulations, solutions, suspensions, elixirs, aerosols, or any other appropriate compositions.

In some embodiments, the subject is administered the BTK inhibitor compound for a period of about 4, 8, 12, 16, or 20 weeks. In some embodiments, the subject is administered the BTK inhibitor compound for a period of about 12 weeks. In some embodiments, the dose is once daily.

In some embodiments, the dose is administered with food. In some embodiments, the dose is administered once daily with food. In some embodiments, the dose of 5 mg, 15 mg, 30 mg, or 60 mg is administered with food. In some embodiments, the dose of 5 mg, 15 mg, 30 mg, or 60 mg is administered once daily with food. In some embodiments, the dose of 60 mg is administered once daily with food. In some embodiments, the dose is administered in oral solution or tablets. In some embodiments, the dose is administered in oral solution or tablets with food. In some embodiments, the dose is administered once daily in oral solution or tablets. In some embodiments, the dose is administered once daily in oral solution or tablets with food. In some embodiments, the dose of 60 mg is administered in oral solution or tablets. In some embodiments, the dose of 60 mg is administered in oral solution or tablets with food. In some embodiments, the dose of 60 mg is administered once daily in oral solution or tablets. In some embodiments, the dose of 60 mg is administered once daily in oral solution or tablets with food.

RGS1 (regulator of G protein signaling 1) functions as a negative regulator of G protein signaling pathways and has been implicated in various inflammatory diseases. RGS1 has been identified as a MS risk factor and also found to be enriched in microglia (International Multiple Sclerosis Genetics Consortium, *Science* 365:6460 (2019)). As detailed below in Example 3, RNA sequencing showed BTK-dependent transcriptional signature in mouse microglia, and RGS1 was identified as one of the genes upregulated in this BTK-dependent microglial signature. The in vitro and in vivo study of Example 3 further shows that BTK inhibition normalizes the signature of mouse microglia activated by IgG, including downregulation of RGS1. Accordingly, in some embodiments, administration of the BTK inhibitor reduces RGS1 expression in a brain cell. The brain cell may comprise microglia. In some embodiments, levels of RGS1 expression are measured in a brain cell in vitro or in vivo.

In some embodiments, administration of the BTK inhibitor reduces new active brain lesions. In some embodiments, administration of the BTK inhibitor reduces new active gadolinium (Gd)-enhancing T1 hyperintense lesions. In some embodiments, administration of the BTK inhibitor reduces new or enlarging T2 lesions.

In some embodiments, administration of the BTK inhibitor reduces the number of new gadolinium (Gd)-enhancing T1 hyperintense lesions as measured by MRI. In some embodiments, the number of new Gd-enhancing T1 hyperintense lesions is less than 1. In some embodiments, the number of new Gd-enhancing T1 hyperintense lesions is equal to or less than 0.77, 0.7, 0.6. 0.5, 0.4, 0.3, 0.2, or 0.1. In some embodiments, no new Gd-enhancing T1 hyperintense lesions is formed after 12 weeks of BTK inhibitor treatment.

In some embodiments, administration of the BTK inhibitor reduces the number of new or enlarging T2 lesions as measured by MRI. In some embodiments, the number of new or enlarging T2 lesions is equal to or less than 2. In some embodiments, the number of new or enlarging T2 lesions is equal to or less than 1.9, 1.8, 1.7, 1.6, 1.5, 1.4, 1.3, 1.2, 1.1, 1.0, 0.9, 0.8, 0.7, 0.6. 0.5, 0.4, 0.3, 0.2, or 0.1. In some embodiments, no new or enlarging T2 lesion is formed after 12 weeks of BTK inhibitor treatment.

In some embodiments, administration of the BTK inhibitor reduces the total number of Gd-enhancing T1-hyperintense lesions after 12 weeks of the BTK inhibitor treatment.

In some embodiments, the dose is 60 mg, and one or zero new Gd-enhancing T1 hyperintense lesions is formed after 12 weeks of BTK inhibitor treatment. In some embodiments, zero new Gd-enhancing T1 hyperintense lesions is formed after 12 weeks of BTK inhibitor treatment. In some embodiments, the number of new or enlarging T2 lesions is equal to or less than 2. In some embodiments, the number of new or enlarging T2 lesions is equal to or less than 2, 1.9, 1.8, 1.7, 1.6, 1.5, 1.4, 1.3, 1.2, 1.1, 1.0, 0.9, 0.8, 0.7, 0.6. 0.5, 0.4, 0.3, 0.2, or 0.1.

In some embodiments, the administration of the BTK inhibitor reduces the total number of Gd-enhancing T1-hyperintense lesions after 12 weeks of the BTK inhibitor treatment.

In one embodiment, a method of treating relapsing multiple sclerosis (RMS) is provided, the method comprising administering to a subject in need thereof 60 mg BTK inhibitor comprising (R)-1-(1-acryloylpiperidin-3-yl)-4-amino-3-(4-phenoxyphenyl)-1H-imidazo[4,5-c]pyridin-2(3H)-one, wherein no new Gd-enhancing T1 hyperintense lesions are formed after 12 weeks of BTK administration.

In some embodiments, a method of treating relapsing multiple sclerosis (RMS) is provided, comprising administering to a subject in need thereof a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of treating relapsing multiple sclerosis (RMS) is provided, comprising administering to a subject in need thereof a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of treating relapsing multiple sclerosis (RMS) is provided, comprising administering to a subject in need thereof a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily. In some embodiments, a method of treating relapsing multiple sclerosis (RMS) is provided, comprising administering to a subject in need thereof a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of treating relapsing multiple sclerosis (RMS) is provided, comprising administering to a subject in need thereof a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of treating relapsing multiple sclerosis (RMS) is provided, comprising administering to a subject in need thereof a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of treating relapsing multiple sclerosis (RMS) is provided, comprising administering to a subject in need thereof a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily. In some embodiments, a method of treating relapsing multiple sclerosis (RMS) is provided, comprising administering to a subject in need thereof a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks.

In some embodiments, a method of treating relapsing multiple sclerosis (RMS) is provided, comprising administering to a subject in need thereof 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of treating relapsing multiple sclerosis (RMS) is provided, comprising administering to a subject in need thereof 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of treating relapsing multiple sclerosis (RMS) is provided, comprising administering to a subject in need thereof 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of treating relapsing multiple sclerosis (RMS) is provided, comprising administering to a subject in need thereof 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of treating relapsing multiple sclerosis (RMS) is provided, comprising administering to a subject in need thereof 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of treating relapsing multiple sclerosis (RMS) is provided, comprising administering to a subject in need thereof 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of treating relapsing multiple sclerosis (RMS) is provided, comprising administering to a subject in need thereof 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of treating relapsing multiple sclerosis (RMS) is provided, comprising administering to a subject in need thereof 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks.

In some embodiments, a method of reducing the number of new gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the number of new gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily. In some embodiments, a method of reducing the number of new gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the number of new gadolinium (Gd)-enhancing T1 hyperintense lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the number of new gadolinium (Gd)-enhancing T1 hyperintense lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2

(3H)-one, wherein the BTK inhibitor compound is administered once daily. In some embodiments, a method of reducing the number of new gadolinium (Gd)-enhancing T1 hyperintense lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new gadolinium (Gd)-enhancing T1 hyperintense lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments of the methods provided above, the BTK inhibitor is administered to a subject having relapsing multiple sclerosis (RMS) in need of reducing the number of new gadolinium (Gd)-enhancing T1 hyperintense lesions.

In some embodiments, a method of reducing the number of new gadolinium (Gd)-enhancing T1 hyperintense lesions is provided, comprising administering to a subject that has relapsing multiple sclerosis (RMS) 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new gadolinium (Gd)-enhancing T1 hyperintense lesions is provided, comprising administering to a subject that has relapsing multiple sclerosis (RMS) 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new gadolinium (Gd)-enhancing T1 hyperintense lesions is provided, comprising administering to a subject that has relapsing multiple sclerosis (RMS) 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new gadolinium (Gd)-enhancing T1 hyperintense lesions is provided, comprising administering to a subject that has relapsing multiple sclerosis (RMS) 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new gadolinium (Gd)-enhancing T1 hyperintense lesions is provided, comprising administering to a subject that has relapsing multiple sclerosis (RMS) 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the number of new gadolinium (Gd)-enhancing T1 hyperintense lesions is provided, comprising administering to a subject that has relapsing multiple sclerosis (RMS) 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the number of new gadolinium (Gd)-enhancing T1 hyperintense lesions is provided, comprising administering to a subject that has relapsing multiple sclerosis (RMS) 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the number of new gadolinium (Gd)-enhancing T1 hyperintense lesions is provided, comprising administering to a subject that has relapsing multiple sclerosis (RMS) 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments of the methods provided above, the BTK inhibitor is administered to a subject having relapsing multiple sclerosis (RMS) in need of reducing the number of new gadolinium (Gd)-enhancing T1 hyperintense lesions.

In some embodiments, a method of reducing the number of new or enlarging T2 lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the number of new or enlarging T2 lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new or enlarging T2 lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily. In some embodiments, a method of reducing the number of new or enlarging T2 lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the number of new or enlarging T2 lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the number of new or enlarging T2 lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new or enlarging T2 lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2

(3H)-one, wherein the BTK inhibitor compound is administered once daily. In some embodiments, a method of reducing the number of new or enlarging T2 lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments of the methods provided above, the BTK inhibitor is administered to a subject having relapsing multiple sclerosis (RMS) in need of reducing the number of new or enlarging T2 lesions.

In some embodiments, a method of reducing the number of new or enlarging T2 lesions is provided, comprising administering to a subject that has relapsing multiple sclerosis (RMS) 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new or enlarging T2 lesions is provided, comprising administering to a subject that has relapsing multiple sclerosis (RMS) 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new or enlarging T2 lesions is provided, comprising administering to a subject that has relapsing multiple sclerosis (RMS) 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new or enlarging T2 lesions is provided, comprising administering to a subject that has relapsing multiple sclerosis (RMS) 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the number of new or enlarging T2 lesions is provided, comprising administering to a subject that has relapsing multiple sclerosis (RMS) 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the number of new or enlarging T2 lesions is provided, comprising administering to a subject that has relapsing multiple sclerosis (RMS) 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the number of new or enlarging T2 lesions is provided, comprising administering to a subject that has relapsing multiple sclerosis (RMS) 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the number of new or enlarging T2 lesions is provided, comprising administering to a subject that has relapsing multiple sclerosis (RMS) 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments of the methods provided above, the BTK inhibitor is administered to a subject having relapsing multiple sclerosis (RMS) in need of reducing the number of new or enlarging T2 lesions.

In some embodiments, a method of reducing the total number of gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the total number of gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the total number of gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily. In some embodiments, a method of reducing the total number of gadolinium (Gd)-enhancing T1 hyperintense lesions is provided, comprising administering to a subject that has relapsing multiple sclerosis (RMS) a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the total number of gadolinium (Gd)-enhancing T1 hyperintense lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the total number of gadolinium (Gd)-enhancing T1 hyperintense lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the total number of gadolinium (Gd)-enhancing T1 hyperintense lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the total number of gadolinium (Gd)-enhancing T1 hyperintense lesions is provided, comprising administering to a subject that has relapsing multiple sclerosis (RMS) a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments of the methods provided above, the BTK inhibitor is administered to a subject having relapsing multiple sclerosis (RMS) in need of reducing the total number of gadolinium (Gd)-enhancing T1 hyperintense lesions.

In some embodiments, a method of reducing the total number of gadolinium (Gd)-enhancing T1 hyperintense lesions is provided, comprising administering to a subject that has relapsing multiple sclerosis (RMS) 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the total number of gadolinium (Gd)-enhancing T1 hyperintense lesions is provided, comprising administering to a subject that has relapsing multiple sclerosis (RMS) 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the total number of gadolinium (Gd)-enhancing T1 hyperintense lesions is provided, comprising administering to a subject that has relapsing multiple sclerosis (RMS) 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the total number of gadolinium (Gd)-enhancing T1 hyperintense lesions is provided, comprising administering to a subject that has relapsing multiple sclerosis (RMS) 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the total number of gadolinium (Gd)-enhancing T1 hyperintense lesions is provided, comprising administering to a subject that has relapsing multiple sclerosis (RMS) 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the total number of gadolinium (Gd)-enhancing T1 hyperintense lesions is provided, comprising administering to a subject that has relapsing multiple sclerosis (RMS) 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the total number of gadolinium (Gd)-enhancing T1 hyperintense lesions is provided, comprising administering to a subject that has relapsing multiple sclerosis (RMS) 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the total number of gadolinium (Gd)-enhancing T1 hyperintense lesions is provided, comprising administering to a subject that has relapsing multiple sclerosis (RMS) 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments of the methods provided above, the BTK inhibitor is administered to a subject having relapsing multiple sclerosis (RMS) in need of reducing the total number of gadolinium (Gd)-enhancing T1 hyperintense lesions.

In some embodiments, a method of reducing the rate of relapse in a subject having multiple sclerosis (MS) is provided, comprising administering to the subject a BTK inhibitor comprising (R)-1-(1-acryloylpiperidin-3-yl)-4-amino-3-(4-phenoxyphenyl)-1H-imidazo[4,5-c]pyridin-2(3H)-one. In some embodiments, a method of reducing the rate of relapse in a subject having multiple sclerosis (MS) is provided, comprising administering to the subject a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the rate of relapse in a subject having multiple sclerosis (MS) is provided, comprising administering to the subject a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily. In some embodiments, a method of reducing the rate of relapse in a subject having multiple sclerosis (MS) is provided, comprising administering to the subject a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the rate of relapse in a subject having multiple sclerosis (MS) is provided, comprising administering to the subject a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the rate of relapse in a subject having multiple sclerosis (MS) is provided, comprising administering to the subject a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily. In some embodiments, a method of reducing the rate of relapse in a subject having multiple sclerosis (MS) is provided, comprising administering to the subject a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments of the methods provided above, the BTK inhibitor is administered to a subject having multiple sclerosis in need of reducing the rate of relapse.

In some embodiments, a method of reducing the rate of relapse in a subject having multiple sclerosis (MS) is provided, comprising administering to the subject 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the rate of relapse in a subject having multiple sclerosis (MS) is provided, comprising administering to the subject 15 mg of a BTK inhibitor comprising (R)-1-(1-acryloylpiperidin-3-yl)-4-amino-3-(4-phenoxyphenyl)-1H-imidazo[4,5-c]pyridin-2

(3H)-one, wherein the BTK inhibitor compound is administered for a period of at least about 12 weeks. In some embodiments, a method of reducing the rate of relapse in a subject having multiple sclerosis (MS) is provided, comprising administering to the subject 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments, a method of reducing the rate of relapse in a subject having multiple sclerosis (MS) is provided, comprising administering to the subject 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered for a period of at least about 12 weeks. In some embodiments of the methods provided above, the BTK inhibitor is administered to a subject having multiple sclerosis in need of reducing the rate of relapse.

In some embodiments, a method of reducing the rate of relapse in a subject having multiple sclerosis (MS) is provided, comprising administering to the subject 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the rate of relapse in a subject having multiple sclerosis (MS) is provided, comprising administering to the subject 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the rate of relapse in a subject having multiple sclerosis (MS) is provided, comprising administering to the subject 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments, a method of reducing the rate of relapse in a subject having multiple sclerosis (MS) is provided, comprising administering to the subject 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, wherein the BTK inhibitor compound is administered once daily for a period of at least about 12 weeks. In some embodiments of the methods provided above, the BTK inhibitor is administered to a subject having multiple sclerosis in need of reducing the rate of relapse.

In some embodiments, a BTK inhibitor comprising (R)-1-(1-acryloylpiperidin-3-yl)-4-amino-3-(4-phenoxyphenyl)-1H-imidazo[4,5-c]pyridin-2(3H)-one for use in a method for treating relapsing multiple sclerosis (RMS) in a subject in need thereof is provided. In some embodiments, a BTK inhibitor comprising (R)-1-(1-acryloylpiperidin-3-yl)-4-amino-3-(4-phenoxyphenyl)-1H-imidazo[4,5-c]pyridin-2(3H)-one for use in a method for reducing the number of new or enlarging T2 lesions in a subject that has relapsing multiple sclerosis (RMS) is provided. In some embodiments, a BTK inhibitor comprising (R)-1-(1-acryloylpiperidin-3-yl)-4-amino-3-(4-phenoxyphenyl)-1H-imidazo[4,5-c]pyridin-2(3H)-one for use in a method for reducing the total number of gadolinium (Gd)-enhancing T1 hyperintense lesions in a subject that has relapsing multiple sclerosis (RMS) is provided. In some embodiments, a BTK inhibitor comprising (R)-1-(1-acryloylpiperidin-3-yl)-4-amino-3-(4-phenoxyphenyl)-1H-imidazo[4,5-c]pyridin-2(3H)-one for use in a method for reducing the rate of relapse in a subject having multiple sclerosis (MS) is provided In some embodiments, the BTK inhibitor compound is administered as monotherapy. In some embodiments, the method comprises administering the BTK inhibitor compound and at least one additional therapeutic agent. The additional therapeutic agent may be administered concurrently or sequentially with the BTK inhibitor compound.

Determination of the frequency of administration can be made by persons skilled in the art, such as an attending physician based on considerations of the condition being treated, age of the subject being treated, severity of the condition being treated, general state of health of the subject being treated and the like. In some embodiments, BTK inhibitor compounds are administered in a therapeutically effective amount for treatment of RMS. The therapeutically effective amount is typically dependent on the weight of the subject being treated, his or her physical or health condition, the extensiveness of the condition to be treated, or the age of the subject being treated, pharmaceutical formulation methods, and/or administration methods (e.g., administration time and administration route).

In some embodiments, a method of treating relapsing multiple sclerosis (RMS) is provided, the method comprising administering to a subject in need thereof a dose of about 5 to about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, and/or a pharmaceutically acceptable salt thereof. In some embodiments, the administration of the inhibitor reduces the number of new active brain lesions. In some embodiments, the lesions are Gd-enhancing T1-hyperintense lesions. In some embodiments, the number of lesions is detected by magnetic resonance imaging (MRI).

In some embodiments, a method of treating RMS is provided, the method comprising administering to a subject in need thereof a dose of about 5-10 mg, 10-15 mg, 15-20 mg, 20-25 mg, 25-30 mg, 30-35 mg, 35-40 mg, 40-45 mg, 45-50 mg, 50-55 mg, or 55-60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, and/or a pharmaceutically acceptable salt thereof. In some embodiments, a method of treating RMS is provided, the method comprising administering to a subject in need thereof a dose of about 5 mg of a BTK inhibitor comprising (R)-1-(1-acryloylpiperidin-3-yl)-4-amino-3-(4-phenoxyphenyl)-1H-imidazo[4,5-c]pyridin-2(3H)-one, and/or a pharmaceutically acceptable salt thereof. In some embodiments, a method of treating RMS is provided, the method comprising administering to a subject in need thereof a dose of about 15 mg of a BTK inhibitor comprising (R)-1-(1-acryloylpiperidin-3-yl)-4-amino-3-(4-phenoxyphenyl)-1H-imidazo[4,5-c]pyridin-2(3H)-one, and/or a pharmaceutically acceptable salt thereof. In some embodiments, a method of treating RMS is provided, the method comprising administering in a subject in need thereof a dose of about 30 mg of a BTK inhibitor comprising (R)-1-(1-acryloylpiperidin-3-yl)-4-amino-3-(4-phenoxyphenyl)-1H-imidazo[4,5-c]pyridin-2(3H)-one, and/or a pharmaceutically acceptable salt thereof. In some embodiments, a method of treating RMS is provided, the method comprising administering to a subject in need thereof a dose of about 60 mg of a BTK inhibitor comprising (R)-1-(1-acryloylpiperidin-3-yl)-4-amino-3-(4-phenoxyphenyl)-1H-imidazo[4,5-c]pyridin-2(3H)-one, and/or a pharmaceutically acceptable salt thereof.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability. Bioavailability of drugs that decompose at stomach pH can be increased by administration of such drugs in a formulation that releases the drug intraduodenally.

The compositions are comprised of in general, the BTK inhibitor compound and/or a pharmaceutically acceptable salt thereof in combination with a pharmaceutically acceptable excipient such as binders, surfactants, diluents, buffering agents, antiadherents, glidants, hydrophilic or hydrophobic polymers, retardants, stabilizing agents or stabilizers, disintegrants or superdisintegrants, antioxidants, antifoaming agents, fillers, flavors, colors, lubricants, sorbents, preservatives, plasticizers, or sweeteners, or mixtures thereof, which facilitate processing of the BTK inhibitor compound and/or a pharmaceutically acceptable salt thereof into preparations which can be used pharmaceutically. Any of the well-known techniques and excipients may be used as suitable and as understood in the art, see for example, Remington: The Science and Practice of Pharmacy, Twenty-first Ed., (Pharmaceutical Press, 2005); Liberman, H. A., Lachman, L., and Schwartz, J. B. Eds., Pharmaceutical Dosage Forms, Vol. 1-2 Taylor & Francis 1990; and R. I. Mahato, Ansel's Pharmaceutical Dosage Forms and Drug Delivery Systems, Second Ed. (Taylor & Francis, 2012).

In certain embodiments, the formulations may include one or more pH adjusting agents or buffering agents, for example, acids such as acetic, boric, citric, fumaric, maleic, tartaric, malic, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate, ammonium chloride, and the like. Such buffers used as bases may have other counterions than sodium, for example, potassium, magnesium, calcium, ammonium, or other counterions. Such acids, bases and buffers are included in an amount required to maintain pH of the composition in an acceptable range.

In certain embodiments, the formulations may also include one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In certain embodiments, the formulations may also include one or more antifoaming agents to reduce foaming during processing which can result in coagulation of aqueous dispersions, bubbles in the finished film, or generally impair processing. Exemplary anti-foaming agents include silicon emulsions or sorbitan sesquioleate.

In certain embodiments, the formulations may also include one or more antioxidants, such as non-thiol antioxidants, for example, butylated hydroxytoluene (BHT), sodium ascorbate, ascorbic acid or its derivative, and tocopherol or its derivatives. In certain embodiments, antioxidants enhance chemical stability where required. Other agents such as citric acid or citrate salts or EDTA may also be added to slow oxidation.

In certain embodiments, the formulations may also include one or more preservatives to inhibit microbial activity. Suitable preservatives include mercury-containing substances such as merfen and thiomersal; stabilized chlorine dioxide; and quaternary ammonium compounds such as benzalkonium chloride, cetyltrimethylammonium bromide, and cetylpyridinium chloride.

In certain embodiments, the formulations may also include one or more binders. Binders impart cohesive qualities and include, e.g., alginic acid and salts thereof, cellulose derivatives such as carboxymethylcellulose, methylcellulose (e.g., Methocel®), hydroxypropylmethylcellulose, hydroxyethylcellulose, hydroxypropylcellulose (e.g., Klucel®), ethylcellulose (e.g., Ethocel®), and microcrystalline cellulose (e.g., Avicel®); microcrystalline dextrose; amylose; magnesium aluminum silicate; polysaccharide acids; bentonites; gelatin; polyvinyl-pyrrolidone/vinyl acetate copolymer; crosspovidone; povidone; starch; pregelatinized starch; tragacanth, dextrin, a sugar, such as sucrose (e.g., Dipac®), glucose, dextrose, molasses, mannitol, sorbitol, xylitol (e.g., Xylitab®), and lactose; a natural or synthetic gum such as acacia, tragacanth, ghatti gum mucilage of isapol husks, polyvinylpyrrolidone (e.g., Polyvidone® CL, Kollidon® CL, Polyplasdone® XL-10), larch arabogalactan, Veegum®, polyethylene glycol, polyethylene oxide, waxes, sodium alginate, and the like.

In certain embodiments, the formulations may also include dispersing agents and/or viscosity modulating agents. Dispersing agents and/or viscosity modulating agents include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween®60 or 80, PEG, polyvinylpyrrolidone (PVP; commercially known as Plasdone®), and the carbohydrate-based dispersing agents such as, for example, hydroxypropyl celluloses (e.g., HPC, H-PC-SL, and HPC-L), hydroxypropyl methylcelluloses (e.g., HPMC K100, RPMC K4M, HPMC K15M, and HPMC K100M), carboxymethylcellulose sodium, methylcellulose, hydroxyethylcellulose, hydroxypropyl-cellulose, hydroxypropylmethylcellulose phthalate, hydroxypropyl-methylcellulose acetate stearate (HPMCAS), noncrystalline cellulose, polyethylene oxides, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F10©8, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol can have a molecular weight of about 300 to about 6000, or about 3350 to about 4000, or about 7000 to 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose can also be used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate. In general, binder levels of about 10 to about 70% are used in powder-filled gelatin capsule formulations. Binder usage level in tablet formulations varies whether direct compression, wet granulation, roller compaction, or usage of other excipients such as fillers which itself can act as moderate binder. Formulators skilled in art can determine the binder level for the formulations, but binder usage level of up to 90% and more typically up to 70% in tablet formulations is common.

In certain embodiments, the formulations may also include one or more diluents which refer to chemical compounds that are used to dilute the compound of interest prior to delivery. Diluents can also be used to stabilize compounds because they can provide a more stable environment Salts dissolved in buffered solutions (which also can provide pH control or maintenance) are utilized as diluents in the art, including, but not limited to a phosphate buffered saline solution. In certain embodiments, diluents increase bulk of the composition to facilitate compression or create sufficient bulk for homogenous blend for capsule filling. Such compounds include e.g., e.g., lactose, starch, mannitol, sorbitol, dextrose, microcrystalline cellulose such as Avicel®; dibasic calcium phosphate, dicalcium phosphate dihydrate; tricalcium phosphate, calcium phosphate; anhydrous lactose, spray-dried lactose; pregelatinized starch, compressible sugar, such as Di-Pac® (Amstar); hydroxypropyl-methylcellulose, hydroxypropylmethylcellulose acetate stearate, sucrose-based diluents, confectioner's sugar; monobasic calcium sulfate monohydrate, calcium sulfate dihydrate; calcium lactate trihydrate, dextrates; hydrolyzed cereal solids, amylose; powdered cellulose, calcium carbonate; glycine, kaolin; mannitol, sodium chloride; inositol, bentonite, and the like.

In certain embodiments, the formulations may also include one or more disintegrants which includes both the dissolution and dispersion of the dosage form when contacted with gastrointestinal fluid. Disintegration agents or disintegrants facilitate the breakup or disintegration of a substance. Examples of disintegration agents include a starch, e.g., e.g., a natural starch such as corn starch or potato starch, a pregelatinized starch such as National 1551 or sodium starch glycolate such as Promogel® or Explotab®, a cellulose such as a wood product, methylcrystalline cellulose, e.g., e.g., Avicel®, Avicel® PH101, Avicel® PH 102, Avicel® PH105, Elceme® P100, Emcocel®, Vivacel®, and Solka-Floc®, methylcellulose, croscarmellose, or a cross-linked cellulose, such as cross-linked sodium carboxymethyl-cellulose (Ac-Di-Sol®), cross-linked carboxymethylcellulose, or cross-linked croscarmellose, a cross-linked starch such as sodium starch glycolate, a cross-linked polymer such as crosspovidone, a cross-linked polyvinylpyrrolidone, alginate such as alginic acid or a salt of alginic acid such as sodium alginate, a clay such as Veegum® HV (magnesium aluminum silicate), a gum such as agar, guar, locust bean, Karaya, pectin, or tragacanth, sodium starch glycolate, bentonite, a natural sponge, a surfactant, a resin such as a cation-exchange resin, citrus pulp, sodium lauryl sulfate, sodium lauryl sulfate in combination starch, and the like.

In certain embodiments, the formulations may also include erosion facilitators. Erosion facilitators include materials that control the erosion of a particular material in gastrointestinal fluid. Erosion facilitators are generally known to those of ordinary skill in the art. Exemplary erosion facilitators include, e.g., hydrophilic polymers, electrolytes, proteins, peptides, and amino acids.

In certain embodiments, the formulations may also include one or more filling agents which include compounds such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

In certain embodiments, the formulations may also include one or more flavoring agents and/or sweeteners e.g., acacia syrup, acesulfame K, alitame, anise, apple, aspartame, banana, Bavarian cream berry, black currant, butterscotch, calcium citrate, camphor, caramel, cherry, cherry cream chocolate, cinnamon, bubble gum, citrus, citrus punch, citrus cream, cotton candy, cocoa, cola, cool cherry, cool citrus, cyclamate, cyclamate, dextrose, eucalyptus, eugenol, fructose, fruit punch, ginger, glycyrrhizinate, glycyrrhiza (licorice) syrup, grape, grapefruit, honey, isomalt, lemon, lime, lemon cream, monoammonium glyrrhizinate, maltol, mannitol, maple, marshmallow, menthol, mint cream, mixed berry, neohesperidine DC, neotame, orange, pear, peach, peppermint, peppermint cream, Powder, raspberry, root beer, rum, saccharin, safrole, sorbitol, spearmint, spearmint cream, strawberry, strawberry cream, stevia, sucralose, sucrose, sodium saccharin, saccharin, aspartame, acesulfame potassium, mannitol, talin, xylitol, sucralose, sorbitol, Swiss cream, tagatose, tangerine, thaumatin, tutti frutti, vanilla, walnut, watermelon, wild cherry, wintergreen, xylitol, or any combination of these flavoring ingredients, e.g., anise-menthol, cherry-anise, cinnamon-orange, cherry-cinnamon, chocolate-mint, honey-lemon, lemon-lime, lemon-mint, menthol-eucalyptus, orange-cream, vanilla-mint, and mixtures thereof.

In certain embodiments, the formulations may also include one or more lubricants and glidants which are compounds that prevent, reduce or inhibit adhesion or friction of materials. Exemplary lubricants include, e.g., stearic acid, calcium hydroxide, talc, sodium stearyl lumerate, a hydrocarbon such as mineral oil, or hydrogenated vegetable oil such as hydrogenated soybean oil, higher fatty acids and their alkali-metal and alkaline earth metal salts, such as aluminum, calcium, magnesium, zinc, stearic acid, sodium stearates, glycerol, talc, waxes, boric acid, sodium benzoate, sodium acetate, sodium chloride, leucine, a polyethylene glycol (e.g., PEG4000) or a methoxypolyethylene glycol such as Carbowax®, sodium oleate, sodium benzoate, glyceryl behenate, polyethylene glycol, magnesium or sodium lauryl sulfate, colloidal silica such as Syloid®, Cab-O-Sil©, a starch such as corn starch, silicone oil, a surfactant, and the like.

In certain embodiments, the formulations may also include one or more plasticizers which are compounds used to soften the enteric or delayed release coatings to make them less brittle. Suitable plasticizers include, e.g., polyethylene glycols such as PEG 300, PEG 400, PEG 600, PEG 1450, PEG 3350, and PEG 800, stearic acid, propylene glycol, oleic acid, triethyl citrate, dibutyl sebacate, triethyl cellulose and triacetin. In some embodiments, plasticizers can also function as dispersing agents or wetting agents.

In certain embodiments, the formulations may also include one or more solubilizers which include compounds such as triacetin, triethylcitrate, ethyl oleate, ethyl caprylate, sodium lauryl sulfate, sodium doccusate, vitamin E TPGS, dimethylacetamide, N-methylpyrrolidone, N-hydroxyethylpyrrolidone, polyvinylpyrrolidone, hydroxypropylmethyl cellulose, hydroxypropyl cyclodextrins for example Captisol®, ethanol, n-butanol, isopropyl alcohol, cholesterol, bile salts, polyethylene glycol 200-600, glycofurol, transcutol, propylene glycol, and dimethyl isosorbide and the like. In one embodiment, the solubilizer is vitamin E TPGS and/or Captisol® or 8-hydroxypropylcyclodextrin.

In certain embodiments, the formulations may also include one or more suspending agents which include compounds such as polyvinylpyrrolidone, e.g., polyvinylpyrrolidone K112, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol can have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monoleate, povidone and the like.

In certain embodiments, the formulations may also include one or more surfactants which include compounds such as sodium lauryl sulfate, sodium docusate, Tween 20, 60 or 80, triacetin, vitamin E TPGS, sorbitan monooleate, polyoxyethylene sorbitan monooleate, polyoxyethylene sorbitan monolaurate, polysorbates, polaxomers, bile salts, glyceryl monostearate, copolymers of ethylene oxide and propylene oxide, e.g., Pluronic® (BASF), and the like. Some other surfactants include polyoxyethylene fatty acid glycerides and vegetable oils, e.g., polyoxyethylene (60) hydrogenated castor oil; and polyoxyethylene alkylethers and alkylphenyl ethers, e.g. octoxynol 10, octoxynol 40. In some embodiments, surfactants may be included to enhance physical stability or for other purposes.

In certain embodiments, the formulations may also include one or more viscosity enhancing agents which include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol alginates, acacia, chitosans and combinations thereof.

In certain embodiments, the formulations may also include one or more wetting agents which include compounds such as oleic acid, glyceryl monostearate, sorbitan monooleate, sorbitan monolaurate, triethanolamine oleate, polyoxyethylene sorbitan monooleate, polyoxyethylene sorbitan monolaurate, sodium docusate, sodium oleate, sodium lauryl sulfate, sodium doccusate, triacetin, Tween 80, vitamin E TPGS, ammonium salts and the like.

Pharmaceutical preparations disclosed herein can be obtained by mixing one or more solid excipient such as carrier, binder, filling agent, suspending agent, flavoring agent, sweetening agent, disintegrating agent, dispersing agent, surfactant, lubricant, colorant diluent, solubilizer, moistening agent, plasticizer, stabilizer, penetration enhancer, wetting agent, anti-foaming agent, antioxidant, preservative, or one or more combination thereof with one or more of the compounds described herein, optionally grinding the resulting mixture, and processing the mixture of granules, after adding suitable excipients, if desired, to obtain tablets.

Pharmaceutical preparations disclosed herein also include capsules made of gelatin, as well as soft, sealed capsules made of gelatin and a plasticizer, such as glycerol or sorbitol. Capsules may also be made of polymers such as hypromellose. The capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, lipids, solubilizers, or liquid polyethylene glycols. In addition, stabilizers may be added. All formulations for oral administration should be in dosages suitable for such administration.

These formulations can be manufactured by conventional pharmacological techniques. Conventional pharmacological techniques include, e.g., one or a combination of methods: (1) dry mixing, (2) direct compression, (3) milling, (4) dry or non-aqueous granulation, (5) wet granulation, (6) fusion, or (7) extrusion. See, e.g., Lachman et al., The Theory and Practice of Industrial Pharmacy, 3$^{rd}$ ed. (1986). Other methods include, e.g., spray drying, pan coating, melt granulation, granulation, fluidized bed spray drying or coating (e.g., wurster coating), tangential coating, top spraying, tableting, extruding, extrusion/spheronization, and the like.

It should be appreciated that there is considerable overlap between excipients used in the solid dosage forms described herein. Thus, the above-listed additives should be taken as merely exemplary, and not limiting, of the types of excipient that can be included in solid dosage forms described herein. The type and amounts of such excipient can be readily determined by one skilled in the art, according to the particular properties desired.

In some embodiments, the solid dosage forms described herein are enteric coated oral dosage forms, i.e., as an oral dosage form of a pharmaceutical composition as described herein which utilizes an enteric coating to effect the release of the compound in the intestine of the gastrointestinal tract. An "enterically coated" drug and/or tablet refers to a drug and/or tablet that is coated with a substance that remains intact in the stomach but dissolves and releases the drug once the intestine (in one embodiment small intestine) is reached. As used herein "enteric coating", is a material, such as a polymer material or materials which encase the therapeutically active agent core either as a dosage form or as particles. Typically, a substantial amount or all of the enteric coating material is dissolved before the therapeutically active agent is released from the dosage form, so as to achieve delayed dissolution of the therapeutically active agent core or particles in the small and/or large intestine. Enteric coatings are discussed, for example, Loyd, V. Allen, Remington: The Science and Practice of Pharmacy, Twenty-first Ed., (Pharmaceutical Press, 2005; and P. J. Tarcha, Polymers for Controlled Drug Delivery, Chapter 3, CRC Press, 1991. Methods for applying enteric coatings to pharmaceutical compositions are well known in the art, and include for example, U.S. Patent Publication No. 2006/0045822.

The enteric coated dosage form may be a compressed or molded or extruded tablet (coated or uncoated) containing granules, powder, pellets, beads or particles of the BTK inhibitor compound and/or a pharmaceutically acceptable salt thereof and/or other excipients, which are themselves coated or uncoated provided at least the tablet or the BTK inhibitor compound is coated. The enteric coated oral dosage form may also be a capsule (coated or uncoated) containing pellets, beads or granules of the BTK inhibitor compound and/or a pharmaceutically acceptable salt thereof and/or other excipients, which are themselves coated or uncoated provided at least one of them is coated. Some examples of coatings that were originally used as enteric coatings are beeswax and glyceryl monostearate; beeswax, shellac and cellulose; and cetyl alcohol, mastic and shellac as well as shellac and stearic acid (U.S. Pat. No. 2,809,918); polyvinylacetate and ethyl cellulose (U.S. Pat. No. 3,835,221). More recently, the coatings used are neutral copolymers of polymethacrylic acid esters (Eudragit L30D). (F. W. Goodhart et al, *Pharm. Tech*., p. 64-71, April, 1984); copolymers of methacrylic acid and methacrylic acid methyl ester (Eudragit S), or a neutral copolymer of polymethacrylic acid esters containing metallic stearates (Mehta et al U.S. Pat. Nos. 4,728,512 and 4,794,001), cellulose acetate succinate, and hypromellose phthalate.

Any anionic polymer exhibiting a pH-dependent solubility profile can be used as an enteric coating in the methods and compositions described herein to achieve delivery to the intestine. In one embodiment, delivery can be to the small intestine. In another embodiment, delivery can be to the duodenum. In some embodiments the polymers described herein are anionic carboxylic polymers. In other embodiments, the polymers and compatible mixtures thereof, and some of their properties, include, but are not limited to:

Shellac: Also called purified lac, it is a refined product obtained from the resinous secretion of an insect. This coating dissolves in media of pH>7;

Acrylic polymers: The performance of acrylic polymers (primarily their solubility in biological fluids) can vary based on the degree and type of substitution. Examples of suitable acrylic polymers include methacrylic acid copolymers and ammonium methacrylate copolymers. The Eudragit series L, S, and RS (manufactured Rohm Pharma and known as Evonik®) are available as solubilized in organic solvent, aqueous dispersion, or dry powders. The Eudragit series RL, NE, and RS are insoluble in the gastrointestinal tract but are permeable and are used primarily for colonic targeting. The Eudragit series L, L-30D and S are insoluble in stomach and dissolve in the intestine and may be selected and formulated to dissolve at a value of pH greater than 5.5 or as low as greater than 5 or as high as greater than 7;

Cellulose Derivatives: Examples of suitable cellulose derivatives are: ethyl cellulose; reaction mixtures of partial acetate esters of cellulose with phthalic anhydride. The performance can vary based on the degree and type of substitution. Cellulose acetate phthalate (CAP) dissolves in pH>6. Aquateric (FMC) is an aqueous based system and is a spray dried CAP pseudolatex with particles <1 μm. Other components in Aquateric can include pluronics, Tweens, and acetylated monoglycerides. Other suitable cellulose derivatives include; cellulose acetate tritnellitate (Eastman); methylcellulose (Pharmacoat, Methocel); hydroxypropylmethyl cellulose phthalate (HPMCP); hydroxypropylmethyl cellulose succinate (HPMCS); and hydroxypropylmethylcellulose acetate succinate (HPMCAS e.g., AQOAT (Shin Etsu)). The performance can vary based on the degree and type of substitution. For example, HPMCP such as, HP-50, HP-55, HP-555, HP-55F grades are suitable. The performance can vary based on the degree and type of substitution. For example, suitable grades of hydroxypropylmethylcellulose acetate succinate include, but are not limited to, AS-LG (LF), which dissolves at pH 5, AS-MG (MF), which dissolves at pH 5.5, and AS-HG (HF), which dissolves at higher pH. These polymers are offered as granules, or as fine powders for aqueous dispersions;

Poly Vinyl Acetate Phthalate (PVAP): PVAP dissolves in pH>5, and it is much less permeable to water vapor and gastric fluids. Detailed description of above polymers and their pH-dependent solubility can be found at in the article titled "Enteric coated hard gelatin capsules" by Professor Karl Thoma and Karoline Bechtold at http://pop.www.capsugel.com/media/library/enteric-coated-hard-gelatin-capsules.pdf. In some embodiments, the coating can, and usually does, contain a plasticizer and possibly other coating excipients such as colorants, talc, and/or magnesium stearate, which are well known in the art. Suitable plasticizers include triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, anionic carboxylic acrylic polymers usually contain 10-25% by weight of a plasticizer, especially dibutyl phthalate, polyethylene glycol, triethyl citrate and triacetin. Conventional coating techniques such as fluid bed or Wurster coaters, or spray or pan coating are employed to apply coatings. The coating thickness must be sufficient to ensure that the oral dosage form remains intact until the desired site of topical delivery in the intestinal tract is reached.

Colorants, surfactants, anti-adhesion agents, antifoaming agents, lubricants (e.g., carnauba wax or PEG) and other additives may be added to the coatings besides plasticizers to solubilize or disperse the coating material, and to improve coating performance and the coated product.

To accelerate the dissolution of the enteric coat, a half-thickness, double coat of enteric polymer (for instance, Eudragit L30 D-55) may be applied, and the inner enteric coat may have a buffer up to pH 6.0 in the presence of 10% citric acid, followed by a final layer of standard Eudragit L 30 D-55. Applying two layers of enteric coat, each half the thickness of a typical enteric coat, Liu and Basit were able to accelerate enteric coating dissolution compared to a similar coating system applied, unbuffered, as a single layer (Liu, F. and Basit, A. Journal of Controlled Release. 147 (2010) 242-245.)

The intactness of the enteric coating may be measured, for example, by the degradation of the drug within the micropellets. The enteric coated dosage forms or pellets may be tested in dissolution testing first in gastric fluid and separately in intestinal fluid as described in USP to determine its function.

The enteric coated tablets and capsules formulation containing the disclosed compounds can be made by methods well known in the art. For example, tablets containing a compound disclosed herein can be enterically coated with a coating solution containing Eudragit®, diethylphthalate, isopropyl alcohol, talc, and water using a side vented coating pan (Freund Hi-Coater).

Alternatively, a multi-unit dosage form comprising enteric-coated pellets that can be incorporated into a tablet or into a capsule can be prepared as follows.

Core material: The core material for the individually enteric coating layered pellets can be constituted according to different principles. Seeds layered with the active agent (i.e., the BTK inhibitor compound and/or a pharmaceutically acceptable sale thereof), optionally mixed with alkaline substances or buffer, can be used as the core material for the further processing. The seeds which are to be layered with the active agent can be water insoluble seeds comprising different oxides, celluloses, organic polymers and other materials, alone or in mixtures or water-soluble seeds comprising different inorganic salts, sugars, non-perils and other materials, alone or in mixtures. Further, the seeds may comprise the active agent in the form of crystals, agglomerates, compacts etc. The size of the seeds is not essential for the present disclosure but may vary between approximately 0.1 and 2 mm. The seeds layered with the active agent are produced either by powder or solution/suspension layering using for instance granulation or spray coating layering equipment.

Before the seeds are layered, active agent may be mixed with further components. Such components can be binders, surfactants, fillers, disintegrating agents, alkaline additives or other and/or pharmaceutically acceptable ingredients alone or in mixtures. The binders are for example polymers such as hydroxypropyl methylcellulose (HPMC), hydroxypropyl-cellulose (HPC), carboxymethylcellulose sodium, polyvinyl pyrrolidone (PVP), or sugars, starches or other pharmaceutically acceptable substances with cohesive properties. Suitable surfactants are found in the groups of pharmaceutically acceptable non-ionic or ionic surfactants such as for instance sodium lauryl sulfate.

Alternatively, the active agent optionally mixed with suitable constituents can be formulated into a core material. Said core material may be produced by extrusion/spheronization, balling or compression utilizing conventional process equipment. The size of the formulated core material is approximately between 0.1 and 4 mm and for example, between 0.1 and 2 mm. The manufactured core material can further be layered with additional ingredients comprising the active agent and/or be used for further processing.

The active agent is mixed with pharmaceutical constituents to obtain preferred handling and processing properties and a suitable concentration of the active agent in the final preparation. Pharmaceutical constituents such as fillers, binders, lubricants, disintegrating agents, surfactants and other pharmaceutically acceptable additives may be used.

Alternatively, the aforementioned core material can be prepared by using spray drying or spray congealing technique.

Enteric Coating Layer(s): Before applying the enteric coating layer(s) onto the core material in the form of individual pellets, the pellets may optionally be covered with one or more separating layer(s) comprising pharmaceutical excipients optionally including alkaline compounds such as pH-buffering compounds. This/these separating layer(s), separate(s) the core material from the outer layers being enteric coating layer(s). This/these separating layer(s) protecting the core material of active agent should be water soluble or rapidly disintegrating in water.

A separating layer(s) can be optionally applied to the core material by coating or layering procedures in suitable equipment such as coating pan, coating granulator or in a fluidized bed apparatus using water and/or organic solvents for the coating process. As an alternative the separating layer(s) can be applied to the core material by using powder coating technique. The materials for the separating layers are pharmaceutically acceptable compounds such as, for instance, sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium, water soluble salts of enteric coating polymers and others, used alone or in mixtures. Additives such as plasticizers, colorants, pigments, fillers anti-tacking and anti-static agents, such as for instance magnesium stearate, titanium dioxide, talc and other additives may also be included into the separating layer(s).

When the optional separating layer is applied to the core material it may constitute a variable thickness. The maximum thickness of the separating layer(s) is normally only limited by processing conditions. The separating layer may serve as a diffusion barrier and may act as a pH-buffering zone. The optionally applied separating layer(s) is not essential for the embodiments of the present disclosure. However, the separating layer(s) may improve the chemical stability of the active substance and/or the physical properties of the novel multiple unit tableted dosage form.

Alternatively, the separating layer may be formed in situ by a reaction between an enteric coating polymer layer applied on the core material and an alkaline reacting compound in the core material. Thus, the separating layer formed comprises a water-soluble salt formed between the enteric coating layer polymer(s) and an alkaline reacting compound which is in the position to form a salt.

One or more enteric coating layers are applied onto the core material or onto the core material covered with separating layer(s) by using a suitable coating technique. The enteric coating layer material may be dispersed or dissolved in either water or in suitable organic solvents. As enteric coating layer polymers, one or more, separately or in combination, of the following can be used, e.g. solutions or dispersions of methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s).

The enteric coating layers contain pharmaceutically acceptable plasticizers to obtain the desired mechanical properties, such as flexibility and hardness of the enteric coating layers. Such plasticizers are for instance, but not restricted to triacetin, citric acid esters, phthalic acid esters, dibutyl sebacate, cetyl alcohol, polyethylene glycols, polysorbates or other plasticizers.

The amount of plasticizer is optimized for each enteric coating layer formula, in relation to the selected enteric coating layer polymer(s), selected plasticizer(s) and the applied amount of said polymer(s), in such a way that the mechanical properties, i.e. flexibility and hardness of the enteric coating layer(s), for instance exemplified as Vickers hardness, are adjusted so that if a tablet is desired the acid resistance of the pellets covered with enteric coating layer(s) does not decrease significantly during compression of pellets into tablets. The amount of plasticizer is usually above 5% by weight of the enteric coating layer polymer(s), such as 15-50% and further such as 20-50%. Additives such as dispersants, colorants, pigments polymers e.g. poly(ethylacrylate, methylmethacrylate), anti-tacking and anti-foaming agents may also be included into the enteric coating layer(s). Other compounds may be added to increase film thickness and to decrease diffusion of acidic gastric juices into the acid susceptible material. The maximum thickness of the applied enteric coating is normally only limited by processing conditions and the desired dissolution profile.

Over-Coating Layer: Pellets covered with enteric coating layer(s) may optionally further be covered with one or more over-coating layer(s). The over-coating layer(s) should be water soluble or rapidly disintegrating in water. The over-coating layer(s) can be applied to the enteric coating layered pellets by coating or layering procedures in suitable equipment such as coating pan, coating granulator or in a fluidized bed apparatus using water and/or organic solvents for the coating or layering process. The materials for over-coating layers are chosen among pharmaceutically acceptable compounds such as, for instance sugar, polyethylene glycol, polyvinylpyrrolidone, polyvinyl alcohol, polyvinyl acetate, hydroxypropyl cellulose, methylcellulose, ethylcellulose, hydroxypropyl methyl cellulose, carboxymethylcellulose sodium and others, used alone or in mixtures. Additives such as plasticizers, colorants, pigments, fillers, anti-tacking and anti-static agents, such for instance magnesium stearate, titanium dioxide, talc and other additives may also be included into the over-coating layer(s). The over-coating layer may further prevent potential agglomeration of enteric coating layered pellets, further it may protect the enteric coating layer towards cracking during the compaction process and enhance the tableting process. The maximum thickness of the applied over-coating layer(s) is normally limited by processing conditions and the desired dissolution profile. The over-coating layer may also be used as a tablet film coating layer.

Enteric coating of soft gelatin capsules may contain an emulsion, oil, microemulsion, self-emulsifying system, lipid, triglycerides, polyethylene glycol, surfactants, other solubilizers and the like, and combinations thereof, to solubilize the active agent. The flexibility of the soft gelatin capsule is maintained by residual water and plasticizer. Moreover, for gelatin capsules the gelatin may be dissolved in water so that spraying must be accomplished at a rate with relatively low relative humidity such as can be accomplished in a fluid bed or Wurster. In addition, drying should be accomplished without removing the residual water or plasticizer causing cracking of the capsule shell. Commercially available blends optimized for enteric coating of soft gelatin capsules such as Instamodel EPD (Enteric Polymeric Dispersion), available from Ideal Cures, Pvt. Ltd. (Mumbai, India). On a laboratory scale enteric coated capsules may be prepared by: a) rotating capsules in a flask or dipping capsules in a solution of the gently heated enteric coating material with plasticizer at the lowest possible temperature or b) in a lab scale sprayer/fluid bed and then drying.

For aqueous active agents, it can be especially desirable to incorporate the drug in the water phase of an emulsion. Such "water-in-oil" emulsion provides a suitable biophysical environment for the drug and can provide an oil-water interface that can protect the drug from adverse effects of pH or enzymes that can degrade the drug. Additionally, such water-in-oil formulations can provide a lipid layer, which can interact favorably with lipids in cells of the body, and can increase the partition of the formulation onto the membranes of cells. Such partition can increase the absorption of drugs in such formulations into the circulation and therefore can increase the bioavailability of the drug.

In some embodiments the water-in-oil emulsion contains an oily phase composed of medium or long chain carboxylic acids or esters or alcohols thereof, a surfactant or a surface-active agent, and an aqueous phase containing primarily water and the active agent.

Medium and long chain carboxylic acids are those ranging from $C_8$ to $C_{22}$ with up to three unsaturated bonds (also branching). Examples of saturated straight chain acids are n-dodecanoic acid, n-tetradecanoic acid, n-hexadecanoic acid, caproic acid, caprylic acid, capric acid, lauric acid, myristic acid, palmitic acid, stearic acid, arachidic acid, behenic acid, montanic acid and melissic acid. Also useful are unsaturated monoolefinic straight chain monocarboxylic acids. Examples of these are oleic acid, gadoleic acid and erucic acid. Also useful are unsaturated (polyolefinic) straight chain monocarboxylic acids. Examples of these are linoleic acid, ricinoleic acid, linolenic acid, arachidonic acid and behenolic acid. Useful branched acids include, for example, diacetyl tartaric acid. Unsaturated olefinic chains may also be hydroxylated or ethoxylated to prevent oxidation or to alter the surface properties.

Examples of long chain carboxylic acid esters include, but are not limited to, those from the group of: glyceryl monostearates; glyceryl monopalmitates; mixtures of glyceryl monostearate and glyceryl monopalmitate; glyceryl monolinoleate; glyceryl monooleate; mixtures of glyceryl monopalmitate, glyceryl monostearate, glyceryl monooleate and glyceryl monolinoleate; glyceryl monolinoleate; glyceryl monogadoleate; mixtures of glyceryl monopalmitate, glyceryl monostearate, glyceryl monooleate, glyceryl monolinoleate, glyceryl monolinolenate and glyceryl monogadoleate; acetylated glycerides such as distilled acetylated monoglycerides; mixtures of propylene glycol monoesters, distilled monoglycerides, sodium stearoyl lactylate and silicon dioxide; d-alpha tocopherol polyethylene glycol 1000 succinate; mixtures of mono- and di-glyceride esters such as Atmul; calcium stearoyl lactylate; ethoxylated mono- and di-glycerides; lactated mono- and di-glycerides; lactylate carboxylic acid ester of glycerol and propylene glycol; lactylic esters of long chain carboxylic acids; polyglycerol esters of long chain carboxylic acids, propylene glycol mono- and di-esters of long chain carboxylic acids; sodium stearoyl lactylate; sorbitan monostearate; sorbitan monooleate; other sorbitan esters of long chain carboxylic acids; succinylated monoglycerides; stearyl monoglyceryl citrate; stearyl heptanoate; cetyl esters of waxes; stearyl octanoate; $C_8$-$C_{30}$ cholesterol/lavosterol esters; and sucrose long chain carboxylic acid esters. Examples of the self-emulsifying long chain carboxylic acid esters include those from the groups of stearates, palmitates, ricinoleates, oleates, behenates, ricinoleates, myristates, laurates, caprylates, and caproates. In some embodiments the oily phase may comprise a combination of 2 or more of the long chain carboxylic acids or esters or alcohols thereof. In some embodiments medium chain surfactants may be used and the oil phase may comprise a mixture of caprylic/capric triglyceride and $C_8$/$C_{10}$ mono-/di-glycerides of caprylic acid, glyceryl caprylate or propylene glycol monocaprylate or their mixtures.

The alcohols that can be used are exemplified by the hydroxyl forms of the carboxylic acids exemplified above and also stearyl alcohol.

Surface active agents or surfactants are long chain molecules that can accumulate at hydrophilic/hydrophobic (water/oil) interfaces and lower the surface tension at the interface. As a result, they can stabilize an emulsion. In some embodiments, the surfactant may comprise: Tween® (polyoxyethylene sorbate) family of surfactants, Span® (sorbitan long chain carboxylic acid esters) family of surfactants, Pluronic® (ethylene or propylene oxide block copolymers) family of surfactants, Labrasol®, Labrafil® and Labrafac® (each polyglycolyzed glycerides) families of surfactants, sorbitan esters of oleate, stearate, laurate or other long chain carboxylic acids, poloxamers (polyethylene-polypropylene glycol block copolymers or Pluronic®), other sorbitan or sucrose long chain carboxylic acid esters, mono and diglycerides, PEG derivatives of caprylic/capric triglycerides and mixtures thereof or mixture of two or more of the above. In some embodiments the surfactant phase may comprise a mixture of Polyoxyethylene (20) sorbitan monooleate (Tween 80®) and sorbitan monooleate (Span 80®).

The aqueous phase may optionally comprise the active agent suspended in water and a buffer.

In some embodiments, such emulsions are coarse emulsions, microemulsions and liquid crystal emulsions. In other embodiments such emulsion may optionally comprise a permeation enhancer. In other embodiments, spray-dried dispersions or microparticles or nanoparticles containing encapsulated microemulsion, coarse emulsion or liquid crystal can be used.

In some embodiments, the solid dosage forms described herein are non-enteric time-delayed release dosage forms. The term "non-enteric time-delayed release" as used herein refers to the delivery so that the release of the drug can be accomplished at some generally predictable location in the intestinal tract more distal to that which would have been accomplished if there had been no delayed release alterations. In some embodiments the method for delay of release is a coating that becomes permeable, dissolves, ruptures, and/or is no longer intact after a designed duration. The coating in the time-delayed release dosage forms can have a fixed time to erode after which the drug is released (suitable coating include polymeric coating such as HPMC, PEO, and the like) or has a core comprised of a superdisintegrant(s) or osmotic agent(s) or water attractant such as a salt, hydrophilic polymer, typically polyethylene oxide or an alkylcellulose, salts such as sodium chloride, magnesium chloride, sodium acetate, sodium citrate, sugar, such as glucose, lactose, or sucrose, or the like, which draw water through a semi-permeable membrane or a gas generating agent such as citric acid and sodium bicarbonate with or without an acid such as citric acid or any of the aforementioned acids incorporated in dosage forms. The semi-permeable membrane, while mostly not permeable to the drug nor the osmotic agent, is permeable to water that permeates at a near constant rate to enter the dosage form to increase the pressure and ruptures after the swelling pressure exceeds a certain threshold over a desired delay time. The permeability through this membrane of the drug should be less than 1/10 than water and in one embodiment less than 1/100 the water permeability. Alternatively, a membrane could become porous by leaching an aqueous extractable over a desired delay time.

Osmotic dosage forms have been described in Theeuwes U.S. Pat. No. 3,760,984, and an osmotic bursting dosage form is described in Baker U.S. Pat. No. 3,952,741. This osmotic bursting dosage form can provide a single pulse of release or multiple pulses if different devices with different timings are employed. The timing of the osmotic burst may be controlled by the choice of polymer and the thickness or the area of the semipermeable membrane surrounding the core that contains both the drug and the osmotic agent or attractant. As the pressure in the dosage form increase with additional permeated water, the membrane elongates until its breaking point, and then the drug is released. Alternatively, specific areas of rupture can be created in the membrane by having a thinner, weaker area in the membrane or by adding a weaker material to an area of the coating membrane. Some preferred polymers with high water permeabilities that may be used as semipermeable membranes are cellulose acetate, cellulose acetate butyrate, cellulose nitrate, crosslinked polyvinyl, alcohol, polyurethanes, nylon 6, nylon 6.6, and aromatic nylon. Cellulose acetate is an especially preferred polymer.

In another embodiment, the time-delayed coating that begins its delay to releasing drug after the enteric coating is at least partially dissolved is comprised of hydrophilic, erodible polymers that upon contact with water begin to gradually erode over time. Examples of such polymers include cellulose polymers and their derivatives including, but not limited to, hydroxyalkyl celluloses, hydroxymethyl cellulose, hydroxyethyl cellulose, hydroxypropyl cellulose, hydroxypropylmethyl cellulose, carboxymethylcellulose, microcrystalline cellulose; polysaccharides and their derivatives; polyalkylene oxides, such as polyethylene oxide or polyethylene glycols, particularly high molecular weight polyethylene glycols; chitosan; poly(vinyl alcohol); xanthan gum; maleic anhydride copolymers; poly(vinyl pyrrolidone); starch and starch-based polymers; maltodextrins; poly (2-ethyl-2-oxazoline); poly(ethyleneimine); polyurethane; hydrogels; crosslinked polyacrylic acids; and combinations or blends of any of the foregoing.

Some preferred erodible hydrophilic polymers suitable for forming the erodible coating are poly(ethylene oxide), hydroxypropyl methyl cellulose, and combinations of poly (ethylene oxide) and hydroxypropyl methyl cellulose. Poly (ethylene oxide) is used herein to refer to a linear polymer of unsubstituted ethylene oxide. The molecular weight of the poly(ethylene oxide) polymers can range from about $10^5$ Daltons to about $10^7$ Daltons. A preferred molecular weight range of poly(ethylene oxide) polymers is from about $2\times10^5$ to $2\times10^6$ Daltons and is commercially available from The Dow Chemical Company (Midland, Mich.) referred to as SENTRYR POLYOX™ water-soluble resins, NF (National Formulary) grade. When higher molecular weights of polyethylene oxide are used, other hydrophilic agents, such as salts or sugars, like glucose, sucrose, or lactose, that promote erosion or disintegration of this coating, are also included.

The time-delayed dosage form can be a mechanical pill such as an Enterion® capsule or pH sensitive capsule which can release the drug after a pre-programmed time or when it receives a signal which can be transmitted or once it leaves the stomach.

The amount of the compound of the disclosure in a formulation can vary within the full range employed by those skilled in the art. Typically, the formulation will contain, on a weight percent (wt %) basis, from about 0.01-99.99 wt % of the BTK inhibitor compound based on the total formulation, with the balance being one or more suitable pharmaceutical excipients. In one embodiment, the compound is present at a level of about 1-80 wt %.

The foregoing disclosure has been described in some detail by way of illustration and example, for purposes of clarity and understanding. Therefore, it is to be understood that the above description is intended to be illustrative and not restrictive. The scope of the disclosure should, therefore, be determined not with reference to the above description, but should instead be determined with reference to the following appended claims, along with the full scope of equivalents to which such claims are entitled.

EXAMPLES

The following examples are provided to illustrate certain disclosed embodiments and are not to be construed as limiting the scope of this disclosure in any way. In the Examples discussed below, the BTK inhibitor, as defined above, may be also referred as "the compound" or "the drug" interchangeably.

Example 1—Dose-Finding Study for the BTK Inhibitor in Relapsing Multiple Sclerosis

Example 1.1—Introduction and Summary

The goal of this Phase 2b study is to define a safe, optimal dose of the BTK inhibitor. The proposed mechanism of action for the BTK inhibitor is inhibition of formation of new active brain lesions in MS as measured by MRI and thus predicted to demonstrate clinical efficacy in further trials in MS patients. This study assesses dose-response by measuring changes in the number of gadolinium (Gd)-enhancing T1-hyperintense lesions associated with inflammation. This radiographic outcome has been established as a highly-reliable predictive biomarker for clinical efficacy in pivotal studies in MS and has been demonstrated to be a predictive biomarker for clinical efficacy (reduction in ARR) in Phase 3 registration studies (Sormani et al, Ann Neurol. 2009; 65(3):268-75; Sormani et al, Neurology, 2010; 75(4):302-9)). Dose-response for lesion suppression is assessed, based on 4 dose levels and a short placebo period, with a 2-step statistical approach. The BTK inhibitor efficacy relative to placebo is assessed by evaluating inhibition of the formation of new active brain lesions as measured by MRI. The study is also to characterize safety and tolerability of the BTK inhibitor in participants with RMS.

This study employs a number of secondary outcome measures in an effort to collect additional data on the potential benefit of the BTK inhibitor in neuroinflammation.

Exploratory assessments, such as analysis of NfL levels in serum and advanced imaging methods, are expected to start to build evidence for the BTK inhibitor activity on neuroinflammation and neurodegeneration, and potential effects on remyelination and tissue preservation. FIG. 1 shows a graphic of the overall design of the study and Table 1 shows the Schedule of Activities (SOA).

TABLE 1

Schedule of Activities (SOA)

| Phase Week (a window of ±3 days is allowed for all visits after screening) | Screening W-4 to D-1[b] | Baseline/Start of IMP D1 | Intervention Phase | | | | | | Follow-up phase Follow-up visit (W18 to W20)[a,c] | Unscheduled Visit UNSCH | Premature end of treatment[a] |
|---|---|---|---|---|---|---|---|---|---|---|---|
| | | | W2 | W4 | W6 | W8 | W12 | W16 | | | |
| Informed Consent | X | | | | | | | | | | |
| Visit at clinical site | X | X | X | X | X | X | X | X | X | X | X |
| Inclusion/Exclusion criteria | X | | | | | | | | | | |
| Medical/surgical history | X | | | | | | | | | | |
| Prior/concomitant history | X | X | | X | | X | X | X | X | X | X |
| Randomization | | X | | | | | | | | | |
| Study Treatment Administration | | | | | | | | | | | |
| the BTK inhibitor/placebo (dispensation and accountability) | | X[l] | | X[l] | | X[l] | X[l] | Accountability[l] | | | |
| Treatment adherence diary[m] | | X | | X | | X | X | X | | | |
| SAFETY | | | | | | | | | | | |
| Physical Examination[d] | X | X[e] | | X | | X | X | X | X | X | X |
| Height | X | | | | | | | | | | |
| Body weight | X | X | | X | | X | X | X | X | If needed | X |
| Serology tests for hepatitis B, C, other infectious disease if locally required | X | | | | | | | | | | |

TABLE 1-continued

Schedule of Activities (SOA)

| Phase Week (a window of ±3 days is allowed for all visits after screening) | Screening W-4 to D-1[b] | Baseline/ Start of IMP D1 | Intervention Phase W2 | W4 | W6 | W8 | W12 | W16 | Follow-up phase Follow-up visit (W18 to W20)[a,c] | Unscheduled Visit UNSCH | Premature end of treatment[a] |
|---|---|---|---|---|---|---|---|---|---|---|---|
| Vital signs | X | X[e] | | X[e] | | X | X | X | X | X | X |
| 12-lead ECG | X | X[e] | | X[e] | | X | X | X | X | If needed | X |
| Body temperature | X | X[e] | | X[e] | | X | X | X | X | X | X |
| Hematology, biochemistry[f] | X | X[e] | X[g] | X[e] | X[g] | X | X | X | X | If needed | X |
| Coagulation[f] | X | | | | | | | | | If needed | |
| Urinalysis[f] | X | X[e] | | X[e] | | X | X | X | X | If needed | X |
| TB/QuantiFERON-TB Gold ® test or equivalent | X | | | | | | | | | | |
| β-HCG test (if applicable)[h] | X | X[e] | | X[e] | | X | X | X | | If needed | |
| Serum FSH | X | | | | | | | | | | |
| Suicidality assessment (C-SSRS) | X | X[e] | | X | | X | X | X | X | If needed | X |
| Adverse event collection | X | X | | X | | X | X | X | X | X | X |
| **Efficacy** | | | | | | | | | | | |
| EDSS | X | X[e,i] | | | | | X | | | If MS relapse suspected | X |
| MRI[j] | X | | | X[e] | | X | X | X | | | X |
| **Pharmacokinetics (PK)** | | | | | | | | | | | |
| the BTK inhibitor pharmacokinetic plasma samples (sampling to be done as indicated ±0.5 hour) | | X (1 hour post-dose)[l] | | X (1 and 3 hours post-dose)[l] | | X (1 ± 0.5 hour post-dose)[l] | X (1 and 3 hours post-dose)[l] | X (1 hour post-dose)[l] | | | X (1 hour post-dose) |
| **Pharmacogenetics** | | | | | | | | | | | |
| DNA sample | | X[k] | | | | | | | | | |
| **Pharmacodynamics/Biomarkers** | | | | | | | | | | | |
| Blood sample for archiving | X | | | | | | | | | | |
| Exploratory biomarkers: PBMC samples collection (lymphocyte phenotypes, BTK occupancy), (subset of participants) | | X (pre-dose and 1 ± 0.5 hour post-dose) | | | | | X (pre-dose and 1 ± 0.5 hour post-dose) | X (pre-dose and 1 ± 0.5 hour post-dose) | | If MS relapse suspected | X |

TABLE 1-continued

| Schedule of Activities (SOA) | | | | | | | | | | | | |
|---|---|---|---|---|---|---|---|---|---|---|---|---|
| Phase Week (a window of ±3 days is allowed for all visits after screening) | Screening W-4 to D-1[b] | Baseline/ Start of IMP D1 | Intervention Phase W2 | W4 | W6 | W8 | W12 | W16 | Follow-up phase Follow-up visit (W18 to W20)[a,c] | Unscheduled Visit UNSCH | Premature end of treatment[a] |
| Exploratory biomarker plasma samples (NfL, CHI3L1, Ig levels) | | X (pre-dose and 1 ± 0.5 hour post-dose) | | | | | X (pre-dose and 1 ± 0.5 hour post-dose) | X (pre-dose and 1 ± 0.5 hour post-dose) | | | X |

Abbreviations:
β-HCG: beta human chorionic gonadotropin;
BTK: Bruton's tyrosine kinase;
C-SSRS: Columbia Suicide Severity Rating Scale;
CHI3L1: chitinase-3-like 1;
D: day;
DME: drug-metabolizing enzymes;
DNA: deoxyribonucleic acid;
ECG: electrocardiogram;
EDSS: Expanded Disability Status Scale;
FSH: follicle-stimulating hormone;
Ig: immunoglobulin;
MRI: magnetic resonance imaging;
NfL: neurofilament light;
PBMC: peripheral blood mononuclear cell;
TB: tuberculosis;
W: week

[a]The participant should return for a follow-up visit 2 to 4 weeks after premature end-of-treatment.
[b]Screening activities can be done any time starting from 4 weeks to Day 1 before intervention.
[c]Only participants who do not enroll into the LTS study should come for a Week 18 to 20 follow-up visit
[d]A full physical examination is performed at screening; a brief physical examination is sufficient thereafter. The brief physical examination needs to be extended as needed as per the judgment of the Investigator if any new findings occur.
[e]Sample or measurement to be taken before treatment.
[f]For a detailed list of laboratory tests, refer to Example 1.16. Pre-study tests may be accepted, if they are performed in the period Week −4 to Day −1.
[g]Hematology only
hSerum β-HCG is tested at screening; urine β-HCG is sufficient thereafter unless a pregnancy is detected or the urine test it is inconclusive and a serum test needs to be used for verification.
[i]Baseline EDSS can be done in the frame of 3 days before Day 1.
[j]MRI can be performed within a window of ±5 days. The screening MRI should be performed as close before Day 1 as feasible.
[k]Participants are consented for pharmacogenetics sampling.
[l]On site visit days, participants should not take the IMP before the visit but should bring their drug wallets to the visit in order that the time of administration can be recorded in order to schedule PK sampling.
[m]Treatment adherence diaries are dispensed for a 4-week period, collected, and clarified at the following visits. Treatment compliance is reported with the help of diary data.

Objectives and endpoints for the treatment are shown in Table 2.

TABLE 2

| Objectives and endpoints | |
|---|---|
| **Objectives** | **Endpoints** |
| Primary | |
| To determine the dose-response relationship for the BTK inhibitor to reduce the number of new active brain lesions | Number of new Gd-enhancing T1-hyperintense lesions at the end of 12 weeks of the BTK inhibitor treatment as detected by brain MRI |
| Secondary | |
| To evaluate efficacy of the BTK inhibitor on disease activity as assessed by imaging measures | Number of new or enlarging T2 lesions at the end of 12 weeks of the BTK inhibitor treatment<br>Number of Gd-enhancing T1-hyper-intense lesions at the end of 12 weeks of the BTK inhibitor treatment |

TABLE 2-continued

| Objectives and endpoints | |
|---|---|
| **Objectives** | **Endpoints** |
| To evaluate the safety and tolerability of the BTK inhibitor | Adverse events (AEs), serious adverse events (SAEs), potentially clinically significant abnormalities in laboratory tests, electrocardiogram (ECG), or vital signs during the study period |
| Tertiary/exploratory | |
| To evaluate efficacy of the BTK inhibitor on disease activity, assessed by clinical and imaging measures | Number of new Gd-enhancing T1-hyperintense lesions over time<br>Change in volume of T2 lesions from baseline over time<br>Change in brain volume, including regional changes, from baseline to the end of 12 weeks of the BTK inhibitor treatment and over time<br>Change in the number of T1-hypo-intense lesions from baseline to the end of 12 weeks of the BTK inhibitor treatment and over time |

TABLE 2-continued

| Objectives and endpoints | |
|---|---|
| Objectives | Endpoints |
| | Change in myelin integrity and other features of MRI lesions as measured by magnetization transfer ratio and susceptibility-weighted imaging MRI from baseline to the end of 12 weeks of the BTK inhibitor treatment and over time |
| | Proportion of participants with no new MRI disease activity at the end of 12 weeks of the BTK inhibitor treatment and at the end of the study |
| | Number of relapses (ARR) over 12 weeks of the BTK inhibitor treatment |
| | Proportion of relapse-free participants at the end of 12 weeks of the BTK inhibitor treatment |
| | Change in EDSS from baseline over time |
| To explore genetic, and plasma-based biochemical biomarkers that correlate with disease pathophysiology | Neurofilament light (NfL) chain levels<br>Chitinase-3-like-1 concentrations<br>Drug metabolism enzyme gene variant correlations with PK/PD, efficacy and safety endpoints |
| To evaluate PK and PD of the BTK inhibitor | Pharmacokinetics of the BTK inhibitor<br>BTK occupancy changes over study period<br>Lymphocyte phenotype subset changes over the 12 weeks of the BTK inhibitor treatment<br>Immunoglobulin level changes over study period |

Appropriateness of Measurements

Magnetic resonance imaging (MRI) markers of inflammatory activity in the brain are collected as in most RMS clinical trials. Number of new Gd-enhancing T1-hyperintense lesions is used as the primary endpoint to assess the efficacy of the BTK inhibitor. Because MS results in a leaky blood-brain barrier, accumulation of Gd contrast agent in brain tissue is related to inflammatory activity in MS patients. This radiographic outcome has been established as a highly-reliable predictive biomarker for clinical efficacy in pivotal studies in MS. Central review is used to identify new Gd-enhancing T1-hyperintense lesions not present at the previous MRI. The total count of Gd-enhancing T1-hyperintense lesions are also used as a secondary endpoint to detect any effect on pre-existing inflammatory foci. The number of new and enlarging T2 lesions, a marker of inflammatory activity and brain tissue destruction in RMS, also is evaluated in central review to collect additional data with respect to the efficacy of the BTK inhibitor. The total volume of T2 lesions (MS burden) and the number of T1-hypointense lesions (black holes) also are assessed as supportive data with respect to efficacy.

Magnetic resonance imaging (MRI) measurements include change in brain volume, which is considered to be a marker of CNS degeneration but is also related to inflammatory events in RMS patients. Several MS drugs are known for their capacity to slow down brain atrophy, which is assessed in search of a possible signal.

Clinical relapse is the main clinical expression of RMS. Relapse-related endpoints (ARR, proportion of relapse-free participants) are widely used as endpoints in clinical trials. Although the short duration of this trial does not allow expectation of a significant difference between dose groups in occurrence of relapse and relapse is considered rare in PPMS, it is assessed due to its clinical importance and in an attempt to collect additional efficacy data.

The EDSS is widely used to measure neurological disability in clinical trials and routine settings (Kurtzke J F, Neurology. 1983; 33(11):1444-52). Large changes are not expected during the period of this study, but it is used as supportive data for efficacy.

Example 1.2—Study Design

Overall design: a Phase 2b, randomized, double-blind, placebo-controlled, cross-over, dose-ranging study to investigate the MRI efficacy and the safety of 12 weeks administration of the BTK inhibitor. People diagnosed with RMS are eligible for enrollment as long as they meet all inclusion and no exclusion criteria.

All participants are centrally assigned to 1 of 8 arms (4 dose groups in each of 2 cohorts at equal ratio to start with the BTK inhibitor (in Cohort 1) or placebo (in Cohort 2) period before cross-over, using an Interactive Voice/Web Response System (IVRS/IWRS).

Within each cohort, participants are randomly assigned equally to 1 of 4 the BTK inhibitor doses, 5, 15, 30, or 60 mg once daily, in a blinded manner.

Cohort 1: Participants receive 1 of the BTK inhibitor doses for the first 12 weeks, then cross-over to placebo for 4 weeks.

Cohort 2: Participants receive placebo for the first 4 weeks, then cross over to 1 of the BTK inhibitor doses for 12 weeks.

Upon completing the double-blinded treatment period, participants are given the option to enroll in a long-term safety (LTS) follow-up study to assess safety and tolerability of the BTK inhibitor.

Number of participants: Approximately 160 people are screened to randomize approximately 120 participants (based on a 25% screening failure rate) to the study intervention such that approximately 105 evaluable participants (based on an approximately 15% dropout rate, providing at least 26 participants for each dose level of the BTK inhibitor) complete 12 weeks of the BTK inhibitor treatment. Participants from Cohort 2 (n=60) receive 4 weeks of placebo before crossing over to the BTK inhibitor, providing data that can be utilized in estimating a dose-response curve and comparison to placebo. This approach is based on the assumption of a theoretical constant rate of new Gd-enhancing T1-hyperintense lesions over 12 weeks under placebo. The approach minimizes placebo exposure to study participants. A brief description of handling placebo data and analysis and additional details including sample size determination is provided in Example 1.14.

Intervention groups and duration: The 4-week period of placebo is introduced either after or before 12-week treatment with the BTK inhibitor (Cohorts 1 and 2, respectively). Participants are randomly assigned in an equal ratio to each of 8 groups (4 dose groups within each of 2 cohorts). See Table 5 for the overview of the study intervention.

Rationale: This study is blinded for dose and for administration sequence. It is focused on dose finding but also takes into account the need to minimize participant exposure to placebo. Accordingly, the dose range is evaluated using 4 doses: 5, 15, 30, and 60 mg once daily. In addition, to minimize exposure to placebo while maintaining the blinding of Investigators and participants, each participant is assigned to a 4-week placebo period that occurs during either the first or the last 4 weeks of the study. The 4-week period of placebo is introduced either after or before 12-week treatment with the BTK inhibitor (Cohorts 1 and 2, respectively). Participants are randomly assigned to 1 of 8 arms (4 dose groups at an equal ratio in each of the 2 cohorts). The duration of administration of placebo is limited to 4 weeks to minimize placebo exposure; a cross-over design allows all participants to be treated with the BTK inhibitor. This cross-over design blinds for administered intervention and permits a more objective evaluation of safety events at the beginning of the study and of efficacy endpoints. The duration of treatment period of the BTK inhibitor of 12 weeks should allow to detect its effect on suppressing the formation of new Gd-enhancing T1 lesions. Recent communication on an evobrutinib study in RMS patients confirms that meaningful reduction of such lesions may be observed from the Week 12 already (Merck Press release—Merck KGaA, Darmstadt, Germany, Announces Positive Phase IIB Results for Evobrutinib in Relapsing Multiple Sclerosis. 7 Mar. 2018).

Dose regimen: The dose range chosen for this study is informed by several assessments. First, allometric modeling intended to translate BTK occupancy by the BTK inhibitor in preclinical animals (mouse, rat, and dog) predicts an optimal dose range between 1 and 100 mg once daily in humans. Second, Phase 1 multiple-ascending-dose measurements of BTK occupancy in human peripheral blood mononuclear cells (PBMCs) show an asymptotic approach to saturation of the receptor by the BTK inhibitor at the 7.5 mg once daily dose with a more rapid approach to saturation at higher doses. Finally, measurements of absolute CD19+ B-cell counts show a dose-dependent increase (observed maximally at Day 4) of up to 80% relative to baseline. The BTK-induced increase in circulating B-cells is predicted from the literature, as BTK inhibition alters expression of cell surface adhesion molecules leading to egress from lymph nodes (Burger J A et al., *Nat Rev Cancer.* 2018; 18(3):148-67). The dose-response relationship for this effect is maximal at approximately 30 mg once daily. Taking all of these elements into consideration, a dose range between 5 and 60 mg once daily has been set to provide the best chance of capturing the optimal dose for the BTK inhibitor in RMS.

End of Study Definition: A participant is considered to have completed the study if he/she has completed all phases of the study including the last visit. The end of the study is defined as the date of the last visit of the last participant in the study.

Example 1.3—Study Population

Example 1.3A—Inclusion Criteria

Participants are eligible to be included in the study only if all of the following criteria apply as shown in Table 3.

TABLE 3

Inclusion Criteria

| Category | | Criteria |
|---|---|---|
| Age | I 01. | The participant must be 18 to 55 years of age, inclusive, at the time of signing the informed consent. |
| Type of participant and disease characteristics | I 02. | The participant must have been diagnosed with RMS according to the 2017 revision of the McDonald diagnostic criteria (Thompson A J et al., Lancet Neurol. 2018; 17(2): 162-73). |
| | I 03. | The participant must have at least 1 documented relapse within the previous year OR ≥ 2 documented relapses within the previous 2 years OR ≥ 1 active Gd-enhancing brain lesion on an MRI scan in the past 6 months and prior to screening. |
| | I 04. | A female participant must use a double contraception method including a highly effective method of birth control from inclusion and up to 2 months after the last study dose, except if she has undergone sterilization at least 3 months earlier or is postmenopausal. Menopause is defined as being amenorrheic for ≥12 months with serum follicle-stimulating hormone (FSH) level ≥30 UI/L. |
| | I 05. | Male participants, whose partners are of childbearing potential (including breastfeeding women), must accept to use, during sexual intercourse, a double contraceptive method according to the following algorithm: (condom) plus (intrauterine device or hormonal contraceptive) from inclusion up to 3 months after the last dose. |
| | I 06. | Male participants whose partners are pregnant must use, during sexual intercourse, a condom from inclusion up to 3 months after the last dose. |
| | I 07. | Male participants must have agreed not to donate sperm from the inclusion up to 3 months after the last dose. |
| Weight | Not Applicable | |
| Sex | I 08. | Male or Female |
| Informed Consent | I 09. | The participant must have given written informed consent prior to undertaking any study-related procedure. |

Example 1.3B—Exclusion Criteria

Participants are excluded from the study if any of the following criteria apply as shown in Table 4.

TABLE 4

Exclusion Criteria

| Category | | Criteria |
|---|---|---|
| Medical conditions | E 01. | The participant has been diagnosed with PPMS according to the 2017 revision of the McDonald diagnostic criteria or with non-relapsing SPMS (Thompson A J et al,. Lancet Neurol. 2018; 17(2): 162-73; Lublin F D et al., Neurology. 2014; 83(3): 278-86). |
| | E 02. | The participant has conditions or situations that would adversely affect participation in this study, including but not limited to: A short life expectancy due to pre-existing health condition(s) as determined by their treating neurologist |

TABLE 4-continued

| Exclusion Criteria | |
|---|---|
| | Medical condition(s) or concomitant disease(s) making them nonevaluable for the primary efficacy endpoint or that would adversely affect participation in this study, as judged by the Investigator<br>A requirement for concomitant treatment that could bias the primary evaluation<br>Contraindication for MRI, i.e., presence of pacemaker, metallic implants in high-risk areas (i.e., artificial heart valves, aneurysm/vessel clips), presence of metallic material (e.g., shrapnel) in high risk areas, known history of allergy to any contrast medium, or history of claustrophobia that would prevent completion of all protocol-scheduled MRI<br>Contraindications to use MRI Gd contrast-enhancing preparations |
| E 03. | The participant has a history of or currently has concomitant medical or clinical conditions that would adversely affect participation in this study, including but not limited to:<br>A history of T-lymphocyte or T-lymphocyte-receptor vaccination, transplantation (including solid organ, stem cell, and bone marrow transplantation) and/or antirejection therapy<br>A history of diagnosis of progressive multifocal leukoencephalopathy (PML) or evidence of findings suggestive of PML on the baseline MRI<br>As the investigational medical product (IMP) has the potential to diminish immunocompetence, people with a history of infection with human immunodeficiency virus are excluded<br>A history of active or latent tuberculosis (unless the participant has completed a full course of anti-tuberculosis therapy or it is documented by a specialist that the participant has been adequately treated and can begin treatment with an immunosuppressive agent); screening tuberculosis testing should be performed as per local health care authority recommendations prior to study start and during the study if clinically indicated. Blood testing (e.g., QuantiFERON®-TB Gold test) is preferred; skin testing (e.g., tuberculin skin test) is allowed if blood testing is not available or the blood test result is indeterminate<br>Any other active infections that would adversely affect participation or IMP administration in this study, as judged by the Investigator<br>A history of malignancy within 10 years prior to the first screening visit, except effectively treated carcinoma in situ of the cervix or adequately treated non-metastatic squamous or basal cell carcinoma of the skin<br>A history of alcohol or drug abuse within 1 year prior to the first screening visit<br>A history of any psychiatric disease, behavioral condition, or depression requiring hospitalization within 2 years prior to the first screening visit<br>Presence of any screening laboratory or ECG values outside normal limits that are considered in the Investigator's judgment to be clinically significant<br>Presence of liver injury defined as underlying hepatobiliary disease or screening alanine aminotransferase (ALT) >3 x upper limit of normal (ULN) |
| E 04. | At screening, the participant is positive for hepatitis B surface antigen and/or hepatitis B core antibody and/or is positive for hepatitis C antibody. |
| E 05. | The participant has any of the following:<br>A bleeding disorder or known platelet dysfunction at any time prior to the first screening visit<br>A platelet count <150 000/μL at the screening visit |

TABLE 4-continued

| Exclusion Criteria | | |
|---|---|---|
| | E 06. | The participant has a lymphocyte count less than the lower limit of normal (LLN) at the screening visit. |
| | E 07. | The participant has received any live (attenuated) vaccine (including but not limited to varicella zoster, oral polio, and nasal influenza) within 2 months before the first treatment visit. |
| Prior/ concomitant therapy | E 08. | The participant has received any of the following medications/treatments within the specified time frame before any baseline assessment (no wash-out is required for interferons beta or glatiramer acetate treatments): |
| | E 09. | |

| Medication | Exclusionary if used/used within required wash-out period |
|---|---|
| Systemic corticosteroids, adrenocorticotropic hormone | 1 month prior to screening MRI scan |
| Dimethyl fumarate | 1 month prior to randomization |
| Intravenous (IV) immunoglobulin, fingolimod, natalizumab (participants who have discontinued natalizumab in the 6 months prior to randomization should be evaluated to rule out PML) | 2 months prior to randomization |
| Teriflunomide | 2 years prior to randomization or 1 month prior to randomization if participant undergoes an accelerated elimination procedure and has documented teriflunomide plasma level below 0.02 mg/L before randomization |
| B-cell-depleting therapies such as ocrelizumab and rituximab | 6 months prior to randomization or until return of B-cell counts to normal levels, whichever is longer |
| Mildly to moderately immunosuppressive/ chemotherapeutic medications such azathioprine and methotrexate | 6 months prior to randomization |
| Highly immunosuppressive/ chemotherapeutic medications: mitoxantrone up to 120 $mg/m^2$ body surface area, cyclophosphamide, cladribine | 2 years prior to randomization |
| Alemtuzumab | 4 years prior to randomization |
| Lymphoid irradiation, bone marrow transplantation, mitoxantrone (with evidence of cardiotoxicity following treatment, or cumulative lifetime dose >120 $mg/m^2$), other strongly immunosuppressive treatments with very long-lasting effects | Any time |

TABLE 4-continued

| Exclusion Criteria | | |
|---|---|---|
| | E 10. | The participant is receiving strong inducers or inhibitors of CYP3A or CYP2C8 hepatic enzymes as listed in Table 12. |
| | E 11. | The participant is receiving anticoagulant/antiplatelet therapies, including:<br>Acetylsalicylic acid (aspirin)<br>Antiplatelet drugs (e.g., clopidogrel)<br>Warfarin (vitamin K antagonist)<br>Heparin, including low molecular weight heparin (antithrombin agents)<br>Dabigatran (direct thrombin inhibitor)<br>Apixaban, edoxaban, rivaroxaban (direct factor Xa inhibitors) |
| | Note: All above drugs need to be stopped at least 5 half-lives before study drug administration except for aspirin, which needs to be stopped at least 8 days before. | |
| Prior/concurrent clinical study experience | E 12. | The participant has previously participated in any clinical trial of a BTK inhibitor. |
| | E 13. | The participant has taken other investigational drugs within 3 months or 5 half-lives, whichever is longer, before the first screening visit |
| Diagnostic assessments | E 14. | The participant has an EDSS score >5.5 at the first screening visit. |
| | E 15. | The participant has had a relapse in the 30 days prior to randomization. |
| Other exclusions | E 16. | The participant is accommodated in an institution because of a regulatory or legal order, is a prisoner, or is legally institutionalized. |
| | E 17. | The participant is dependent on the Sponsor or Investigator (in conjunction with Section 1.61 of the International Council for Harmonization (ICH) Good Clinical Practice (GCP) Ordinance E6). |
| | E 18. | The participant has sensitivity to any of the study interventions, or components thereof or has a drug or other allergy that, in the opinion of the Investigator, contraindicates participation in the study. |
| | E 19. | The participant is pregnant or a breastfeeding woman. |
| | E 20. | The participant has any of the following within 4 weeks of the first screening visit:<br>Fever (≥38° C.)<br>Persistent chronic or active recurring infection requiring treatment with antibiotics, antivirals, or antifungals |
| | E 21. | The participant has a documented history of attempted suicide over the 6 months prior to the screening visit, presents with suicidal ideation of category 4 or 5 on the Columbia Suicide Severity Rating Scale (C-SSRS) during the study, OR if in the Investigator's judgment, the participant is at risk for a suicide attempt. |
| | E 22. | The participant has had major surgery within 4 weeks prior to the first screening visit, which could affect participant's safety or affect immune response (as judged by the Investigator) or has planned any elective surgery during the course of the study. |
| | E23. | The participant has a history or presence of significant other concomitant illness according to the Investigator's judgment such as, but not limited to cardiovascular (including Stage III or IV cardiac failure according to New York Heart Association [NYHA] classification), or renal, neurological, endocrine, gastrointestinal, hepatic, metabolic, pulmonary, or lymphatic disease that would adversely affect participation in this study. |
| | E 24. | The participant is uncooperative or has any condition that could make the participant potentially non-compliant with the study procedures. |

Example 1.4—Study Intervention

Study intervention is defined as any investigational intervention(s), marketed product(s), placebo, or medical device(s) intended to be administered to a study participant according to the study protocol.

Example 1.4A—Study Intervention(s) Administered

This study intervention includes an IMP and a noninvestigational medicinal product (NIMP). To maintain blinding, participants receive 4 tablets once per day of the BTK inhibitor and/or placebo in a blinded fashion. Details for the interventions are provided in Table 5.

TABLE 5

Overview of study interventions administered

| Study intervention name | The BTK inhibitor | Matching Placebo |
|---|---|---|
| Dosage formulation | Film coated tablet | Film coated tablet |
| Unit dose strength(s)/ dosage level(s) | Up to 4 tablets daily to achieve 5, 15, 30, and 60 mg doses | N/A |
| Route of administration | Oral | Oral |
| Dosing instructions | Up to 4 tablets daily to achieve 5, 15, 30, and 60 mg doses | Up to 4 tablets daily to maintain double-blind |

NIMP: A radiological, signal-enhancing, intravenous (IV) contrast medium is used for T1 contrast-enhanced MRI sequences. A locally approved medium is used.

Example 1.4A1—Measures to Minimize Bias: Randomization and Blinding

All participants are centrally assigned to 1 of 8 arms (4 dose groups in each of the 2 cohorts at equal ratio to start with the BTK inhibitor (in Cohort 1) or placebo (in Cohort 2) period before cross-over, using an IVRS/IWRS. A participant cannot be randomly assigned more than once in the study. Before the study is initiated, the telephone number and call-in directions for the IVRS and/or the log in information and directions for the IWRS are provided to each site. Study interventions are dispensed at the study visits summarized in the Schedule of Activities (Table 1). Returned study interventions should not be re-dispensed to the participants.

Blind Breaks (IVRS/IWRS): The IVRS/IWRS is programmed with blind-breaking instructions. In case of an emergency, the Investigator has the sole responsibility for determining if unblinding of a participant's treatment assignment is warranted. Participant safety must always be the first consideration in making such a determination. If the Investigator decides that unblinding is warranted, the Investigator should make every effort to contact the Sponsor prior to unblinding a participant's treatment assignment unless this could delay emergency treatment of the participant. If a participant's treatment assignment is unblinded, the Sponsor must be notified within 24 hours after breaking the blind. The date and reason that the blind was broken must be recorded in the source documentation and case report form, as applicable.

This study is blinded for dose and the BTK inhibitor-placebo administration sequence. Tablets of different BTK inhibitor dose levels and placebo are identical. Due to ethical considerations, placebo duration is restricted to 4 weeks, which allows more objective evaluation of safety events at the beginning of the study period, and also adds to objectivity of evaluation of clinical endpoints.

Investigators do not have access to MRI data except for any non-MS-related findings, which are communicated in order to evaluate the safety of the participant. The radiology service for the site is in charge of timely reporting of any non-MS findings on MRI to the Investigator The Independent Data Monitoring Committee (IDMC) is used to periodically monitor safety of this study. Unblinded data are provided for IDMC review by an unblinded independent statistician. Study team members, Investigators, and study participants do not have access to unblinded data.

Example 1.4B—Concomitant Therapy

Any medication or vaccine (including over-the-counter or prescription medicines, vitamins, and/or herbal supplements) that the participant is receiving at the time of enrollment or receives during the study is recorded along with reasons for use, dates of administration including start and end dates, and dosage information including dose and frequency.

The same data are collected for all prior medications received during the 4 weeks before enrollment, also for all prior MS treatments and treatments considered clinically important to assess MS or concomitant disease. Standard treatment of MS relapse with high-dose glucocorticoids is permitted. Local guidance is to be followed for such treatments.

In addition to the medicines excluded in Table 4, the following medications are prohibited throughout the study:

Other MS disease-modifying treatments

Acetylsalicylic acid (aspirin)

Anti-platelet drugs (e.g., clopidogrel)

Anticoagulants, including: warfarin, heparin, including low-molecular-weight heparins, dabigatran, and apixaban, edoxaban, rivaroxaban.

Paracetamol/acetaminophen, at doses of ≤3 grams/day, is permitted for use at any time during the study. Short courses (up to 5 days) of NSAIDs (other than acetylsalicylic acid) at the recommended dose may be given during the course of the study if clinically necessary for the treatment of an existing medical condition or a new event. The Investigator records the use of NSAIDs (and any other comedication) in the CRY.

In vitro experimentation and in silico modeling have demonstrated the potential for gastric acid reducing agents to reduce plasma exposure of the BTK inhibitor. Use of proton pump inhibitors (e.g., omeprazole) should be avoided. Use of antacids (e.g., calcium carbonate) should be staggered with respect to the BTK inhibitor dosing, with antacid administration occurring no less than 2 hours before or 2 hours after the BTK inhibitor administration. Use of H2-receptor antagonists (e.g., ranitidine) should also be staggered with respect to the BTK inhibitor dosing, with H2-receptor antagonist administration occurring no less than 10 hours before or 2 hours after the BTK inhibitor administration. See Table 13 for a list of example drugs with a potential to affect plasma exposure of the BTK inhibitor via reduction of gastric acid.

Based on preclinical drug metabolism studies, the BTK inhibitor is a substrate of the CYP3A and CYP2C8 isoenzymes, and therefore, it is possible that plasma exposures of the BTK inhibitor would be altered if co-administered with other drugs that either induce or inhibit CYP3A and/or CYP2C8 metabolism. This has not been studied in humans to date and therefore, drugs that strongly inhibit or induce CYP3A or CYP2C8 should be avoided, if possible. See Table 12 for the list of drugs not to be used.

Example 1.4C—Dose Modification

Dose reduction is not foreseen in this study. Participants, Investigators, and the Sponsor's team are blinded with respect to assigned dose levels. Treatment might need to be interrupted or permanently discontinued if deemed necessary due to an AE (Examples 1.4E and 1.8).

Example 1.4D—Intervention after the End of the Study

A separate, open-label, LTS study is offered to participants completing the Week 16 visit of this study. Upon completing the double-blinded treatment period, participants already enrolled in the DRI study and all subsequent participants are given the option to enroll in an LTS follow-up study to assess safety and tolerability of the BTK inhibitor.

Example 1.4E—Discontinuation of Study Intervention and Participant Discontinuation/Withdrawal Withdrawal of consent for treatment should be distinguished from (additional) withdrawal of consent for follow-up visits and from withdrawal of consent for nonparticipant contact (e.g., medical record checks) follow up. The site should document any case of withdrawal of consent.

Example 1.4E1—Discontinuation of Study Intervention

Definitive Discontinuation: The IMP should be continued whenever possible. In case the IMP is stopped, it should be determined whether the stop can be made temporarily; definitive IMP discontinuation should be a last resort. Any IMP discontinuation is fully documented in the eCRF. In any case, the participant should remain in the study as long as possible. Definitive intervention discontinuation is any intervention discontinuation associated with the definitive decision from the Investigator not to re-expose the participant to the IMP at any time during the study, or from the participant not to be re-exposed to the IMP, whatever the reason. Discontinuation of the study intervention for abnormal liver function should be considered by the Investigator when a participant meets one of the conditions outlined in the Section 10.6 or if the Investigator believes that it is in best interest of the participant. If a clinically significant finding is identified in the ECG (including, but not limited to changes from baseline in QT interval corrected using Fridericia's formula [QTcF]) after enrollment, the Investigator or qualified designee determines if the participant can continue in the study and if any change in participant management is needed. Review of ECG findings by a cardiologist needs to be taken into consideration for a decision of a definitive discontinuation of study intervention because of ECG changes. This review of the ECG printed at the time of collection is documented. Any new clinically relevant finding is reported as an AE.

See the SoA (Table 1) for data to be collected at the time of intervention discontinuation (end-of-treatment visit) and follow up and for any further evaluations that need to be completed. Any abnormal laboratory value or ECG parameter is immediately rechecked for confirmation after 24 hours before a decision of definitive discontinuation of the intervention for the concerned participant is made. In case of premature discontinuation of the intervention, the end-of-treatment visit is conducted.

Participants are followed up according to the study procedures specified in this protocol up to study completion, or up to recovery or stabilization of any AE to be followed up as specified in this protocol, whichever comes last. If possible, and after the definitive discontinuation of intervention, the participants are assessed using the procedure normally planned for the last treatment day with the IMP including a PK sample. Details are provided in the SoA (Table 1). All cases of definitive intervention discontinuation are recorded by the Investigator in the appropriate pages of the eCRF when considered as confirmed.

Temporary intervention discontinuation may be considered by the Investigator because of suspected AEs and/or laboratory abnormalities and/or ECG abnormalities. For all temporary intervention discontinuations, the duration of the discontinuation should be recorded by the Investigator in the appropriate pages of the eCRF. Temporary intervention discontinuation decided by the Investigator corresponds to >1 dose not administered to the participant.

Re-initiation of intervention with the IMP is done under close and appropriate clinical/and or laboratory monitoring once the Investigator has considered, according to his/her best medical judgment, that the responsibility of the IMP(s) in the occurrence of the concerned event was unlikely and if the selection criteria for the study are still met (refer to Table 3).

Example 1.4E2—Participant Discontinuation/Withdrawal

A participant may withdraw from the study at any time at his/her own request or may be withdrawn at any time at the discretion of the Investigator for safety, behavioral, compliance, or administrative reasons.

- If a participant withdraws consent for disclosure of future information, the Sponsor may retain and continue to use any data collected before such a withdrawal of consent
- If a participant withdraws from the study, he/she may request destruction of any samples taken and not tested, and the Investigator must document this in the site study records
- See the SoA (Table 1) for data to be collected at the time of study discontinuation and follow up and for any further evaluations that need to be completed
- If participants no longer wish to take the IMP, they are encouraged to remain in the study.

Investigators should discuss key visits with participants. The value of all study data should be emphasized as important to the public health value of the study.

Participants who withdraw from the study intervention should be explicitly asked about the contribution of possible AEs to their decision, and any AE information elicited must be documented.

All study withdrawals should be recorded by the Investigator in the appropriate screens of the eCRF and in the participant's medical records. In the medical record, at least the date of the withdrawal and the reason should be documented.

In addition, a participant may withdraw consent to participate in the study. Withdrawal of consent for intervention should be distinguished from withdrawal of consent for follow-up visits and from withdrawal of consent for non-participant contact follow up, e.g., medical record checks. The site should document any case of withdrawal of consent.

Participants who have withdrawn from the study cannot be re-randomized (treated) in the study. Their participant and kit numbers are not reused.

Example 1.4E3—Lost to Follow Up

A participant is considered lost to follow-up if he or she repeatedly fails to return for scheduled visits and is unable to be contacted by the study site.

The following actions are taken if a participant fails to return to the clinic for a required study visit:

The site must attempt to contact the participant and reschedule the missed visit as soon as possible and counsel the participant on the importance of maintaining the assigned visit schedule and ascertain whether or not the participant wishes to and/or should continue in the study.

Before a participant is deemed lost to follow up, the Investigator or designee must make every effort to regain contact with the participant (where possible, 3 telephone calls, and if necessary, a certified letter to the participant's last known mailing address or local equivalent methods). These contact attempts should be documented in the participant's medical record.

A participant, whom continues to be unreachable, is considered to have withdrawn from the study.

Example 1.5—Study Assessments and Procedures

Study procedures and their timing are summarized in the SoA (Table 1). Protocol waivers or exemptions are not allowed. Procedures conducted as part of the potential participant's routine clinical management (e.g., blood count) and obtained before signing of the informed consent form (ICF) may be utilized for screening or baseline purposes, provided the procedures meet the protocol-specified criteria and were performed within the time frame defined in the SoA (Table 1). In case of premature discontinuation of study intervention, the end-of-treatment visit is conducted. The participant returns 2 to 4 weeks after a premature end-of-treatment visit.

Example 1.6—Efficacy Assessments

Example 1.6A—Magnetic Resonance Imaging Assessments

Cranial (brain) MRI with and without Gd contrast is performed. Basic MRIs are performed for all participants at all study sites and consist of T2- and T1-weighted sequences without and with Gd contrast. Due to a potential safety risk related to deposition of certain IV Gd contrast agents in the brain, these agents should be used in accordance with local recommendations/regulations (Fischer J S et al. "The Multiple Sclerosis Functional Composite Measure (MSFC): an integrated approach to MS clinical outcome assessment," National MS Society Clinical Outcomes Assessment Task Force. *Mult Scler.* 1999; 5(4):244-50).

New T1 Gd-enhancing hyperintense and new and enlarging T2 lesions are evaluated at each visit as per the SoA (Table 1), comparing lesion count to that from the previous MRI scan. Unless specified otherwise, the baseline brain MRI is used as the reference to assess all MRI-derived endpoints. The baseline MRI is the last MRI performed before the randomization visit. Standardized endpoint evaluation is assured by central review of brain MRI scans. Blinded central review is performed for all MRI-derived endpoints. Magnetic resonance imaging reviewers are blinded to treatment assignments and to other participant data. Spinal MRIs may be required if spine MS lesions are suspected by the Investigator. Spinal MRIs are evaluated locally and reported in the eCRF. No central review is performed for spinal MRIs.

Magnetic resonance imaging for exploratory efficacy evaluation employs regional and whole brain volume evaluation, additional analyses of T1 and T2 imaging, and sequences such as magnetic transfer ratio and susceptibility-weighted imaging.

Example 1.6B—Multiple Sclerosis Relapse

Unscheduled assessment visits for a suspected multiple sclerosis relapse: Participants are instructed to immediately report new neurological symptoms and recurring or worsening of previous symptoms to the Investigator. Any reported symptoms are be collected. If a participant reports symptoms that may be consistent with relapse, an unscheduled assessment visit with the Investigator is scheduled as soon as possible (whenever possible within 7 days of onset of the symptoms). The Investigator assesses whether the reported episode is consistent with the definition of MS relapse (see Example 1.6B). If it is consistent with the definition of MS relapse or if there is any doubt and relapse cannot be ruled out, an EDSS assessment should be performed. Unscheduled visit activities are detailed in SoA (Table 1), they need to be adapted, if other pathology than MS is cause for it, and additional examinations or laboratory tests are needed for safety follow up and optimal treatment decisions.

Multiple sclerosis relapse: For the purposes of this study, MS relapse is defined as acute, new neurological symptoms or worsening of previous neurological symptoms with an objective change on neurological examination. Symptoms must:

Be attributable to MS

Last for ≥24 hours, and

Be present at normal body temperature (i.e., no infection, excessive exercise, or excessively high ambient temperature)

Note: An exacerbation or recurrence of symptoms and signs that can be reasonably attributed to transient impairment of conduction in previously demyelinated pathways due to drugs (such as rarely occurs a few hours after injection of interferon beta), raised core body temperature (the Uhthoff phenomenon), or systemic cytokine release (such as occurs with the administration of alemtuzumab) are not considered a relapse.

Example 1.6C—Expanded Disability Status Scale Evaluation

The Investigator performs the EDSS evaluation (Kurtzke J F, Neurology. 1983; 33(11):1444-52) as indicated in the SoA (Table 1).

The Investigator rates functional systems in the context of a standard neurological examination and reports these ratings as per the EDSS reporting instructions together with information on the participant's mobility, gait, and use of assistive devices. Standard EDSS assessments of neurological symptoms in each of 7 functional domains (visual, brainstem, pyramidal [motor], cerebellar [coordination], sensory, cerebral and bowel/bladder) are performed. Ambulation also is scored as part of the evaluation. Fatigue may optionally be evaluated, but it does not contribute to the EDSS score.

Example 1.7—Safety Assessments

Time points for all safety assessments are provided in the SoA (Table 1). The definitions of AEs and SAEs can be found in Example 1.8B. For the purpose of this protocol, MS relapses (Example 1.6B) are waived from reporting as AEs except if they meet the criteria of an SAE. Nonserious MS relapses are collected on a special eCRF page and are analyzed as an efficacy endpoint. Following an MS relapse assessment, (Example 1.6B), events that are concluded as not meeting the criteria of an MS relapse are reported as AEs.

Example 1.7A—Physical Examinations

A complete physical examination includes, at a minimum, assessments of general appearance, head and neck, abdomen, lymph nodes, skin (signs of bleeding include bruises, petechial rash), cardiovascular, respiratory, gastrointestinal, musculoskeletal, and neurological systems. Height and weight also are measured and recorded. The brief physical examination includes, at a minimum, assessments of the skin, lungs, cardiovascular system, and abdomen (liver and spleen). Investigators should pay special attention to clinical signs related to previous serious illnesses. Any new finding or worsening of a previous finding should be reported as a new AE. The SoA (Table 1) provides a schedule of physical examinations.

Example 1.7B—Vital Signs

Temperature, pulse rate, respiratory rate, and blood pressure are assessed. The same method for temperature measurement should be used throughout the study. Blood pressure and pulse measurements are assessed in sitting or supine position with a completely automated device. Same position measurements should be used throughout the study for the same participant. Manual techniques are used only if an automated device is not available. Caffeinated drinks to be avoided before blood pressure measurements. Blood pressure and pulse measurements should be preceded by at least 5 minutes of rest for the participant in a quiet setting without distractions (e.g., television, cell phones). Vital signs (to be taken before blood collection for laboratory tests) consist of 1 pulse, 3 blood pressure measurements (3 consecutive blood pressure readings are recorded at intervals of at least 1 minute), and respiratory rate. The average of the 3 blood pressure readings is recorded.

Example 1.7C—Electrocardiograms

Single twelve-lead ECGs are obtained as outlined in the SOA (Table 1) using an ECG machine that automatically calculates the heart rate and measures PR, QRS, QT, and QTc intervals. At least one longer rhythm monitoring recording needs to be part of each ECG testing. The ECG is reviewed by a cardiologist for confirmation of abnormality and clinical evaluation. Refer to Example 1.4E for QTc withdrawal criteria and any additional QTc readings that may be necessary.

Example 1.7D—Clinical Safety Laboratory Assessments

See Example 1.16 for the list of clinical laboratory tests to be performed and to the SoA (Table 1) for the timing and frequency. The Investigator will review the laboratory report, document this review, and record any clinically relevant changes occurring during the study in the AE section of the eCRF. Clinically significant abnormal laboratory findings are those that are not associated with the underlying disease, unless judged by the Investigator to be more severe than expected for the participant's condition. All laboratory tests with values considered clinically significantly abnormal during participation in the study or within 4 weeks after the last dose of study intervention should be repeated until the values return to normal or baseline or are no longer considered clinically significant by the Investigator or medical monitor. If such values do not return to normal/baseline within a period of time judged reasonable by the Investigator, the etiology should be identified and the Sponsor notified. All protocol-required laboratory assessments, as defined in Example 1.16, are conducted in accordance with the laboratory manual and the SoA (Table 1). If laboratory values from non-protocol specified laboratory assessments performed at the institution's local laboratory require a change in participant management or are considered clinically significant by the Investigator (e.g., SAE or AE or dose modification), then the results are recorded in the eCRF.

Example 1.7E—Suicide Risk Monitoring

The BTK inhibitor is considered to be CNS-active, and therefore routine suicide risk monitoring is performed. The Columbia Suicide Severity Rating Scale (C-SSRS) and thorough clinical evaluation of complaints are used for suicide risk assessment. Any observations or events of clinical importance are reported as AEs. The C-SSRS is a tool used to assess the lifetime suicidality of a participant and to track suicidal events through the study. The structured interview prompts recollection of suicidal ideation, including the intensity of the ideation, behavior and attempts with actual/potential lethality. The scale is administered by the Investigator or a qualified designee at the time points indicated in the SoA (Table 1).

Example 1.8—Adverse Events and Serious Adverse Events

Example 1.8A—Adverse Event of Special Interest

An AESI is an AE (serious or nonserious) of scientific and medical concern specific to the Sponsor's product or program, for which ongoing monitoring and immediate notification by the Investigator to the Sponsor is required. Such events may require further investigation in order to characterize and understand them. Adverse events of special interest may be added, modified or removed during a study by protocol amendment.

Acute hypersensitivity/anaphylaxis

Pregnancy of a female participant entered in a study as well as pregnancy occurring in a female partner of a male participant entered in a study with IMP/NIMP;

Pregnancy occurring in a female participant entered in the clinical study or in a female partner of a male participant entered in the clinical study. It is qualified as an SAE only if it fulfills one of the seriousness criteria (see Example 1.8B). In the event of pregnancy in a female participant, IMP should be discontinued. Follow up of the pregnancy in a female participant or in a female partner of a male participant is mandatory until the outcome has been determined (See Example 1.17)

Symptomatic overdose (serious or nonserious) with IMP/NIMP: An overdose (accidental or intentional) with the IMIP/NIMP is an event suspected by the Investigator or spontaneously notified by the participant (not based on systematic pills count) and defined as at least twice the intended dose within the intended therapeutic interval, adjusted according to the tested drug. Of note, asymptomatic overdose is reported as a standard AE.

Increase in ALT: any increase of ALT>3×ULN.

Other Project Specific AESIs

ECG observation of QTc≥500 ms or of clinically significant arrhythmia (e.g., atrial fibrillation, atrial flutter) confirmed by a cardiologist, including serious infection, particularly any opportunistic infection; major hemorrhagic events, including symptomatic bleeding in a critical area or organ, such as CNS or intraocular bleeding resulting in an SAE; thrombocytopenia platelet count $<100\times10^9$/L.

AE is reported by the participant (or, when appropriate, by a caregiver, surrogate, or the participant's legally authorized representative).

The Investigator and any qualified designees are responsible for detecting, documenting, and recording events that meet the definition of an AE or SAE and remain responsible for following up AEs that are serious, considered related to the study intervention or study procedures, or that caused the participant to discontinue the study intervention (See Example 1.4E).

The definition of an AE or SAE can be found in Example 1.8B.

Example 1.8B—Adverse Events: Definitions and Procedures for Recording, Evaluating, Follow-Up, and Reporting Adverse Event (AE): An AE is any untoward medical occurrence in a participant or clinical study participant, temporally associated with the use of study intervention, whether or not considered related to the study intervention. AE can therefore be any unfavorable and unintended sign (including an abnormal laboratory finding), symptom, or disease (new or exacerbated) temporally associated with the use of study intervention.

Events Meeting the AE Definition:

Any abnormal laboratory test results (e.g., hematology, clinical chemistry, or urinalysis) or other safety assessments (e.g., ECG, radiological scans, vital signs measurements), including those that worsen from baseline, considered clinically significant in the medical and scientific judgment of the Investigator (i.e., not related to progression of underlying disease).

Exacerbation of a chronic or intermittent pre-existing condition including either an increase in frequency and/or intensity of the condition.

New conditions detected or diagnosed after study intervention administration even though it may have been present before the start of the study.

Signs, symptoms, or the clinical sequelae of a suspected drug-drug interaction.

Signs, symptoms, or the clinical sequelae of a suspected overdose of either study intervention or a concomitant medication.

Lack of efficacy or failure of expected pharmacological action per se is reported as an AE or SAE, but is captured in the efficacy assessments.

Events NOT Meeting the AE Definition:

Any clinically significant abnormal laboratory findings or other abnormal safety assessments associated with the underlying disease, unless judged by the Investigator to be more severe than expected for the participant's condition The disease/disorder being studied or expected progression, signs, or symptoms of the disease/disorder being studied, unless more severe than expected for the participant's condition.

Medical or surgical procedure (e.g., endoscopy, appendectomy): the condition that leads to the procedure is the AE.

Situations in which an untoward medical occurrence did not occur (social and/or convenience admission to a hospital).

Anticipated day-to-day fluctuations of pre-existing disease(s) or condition(s) present or detected at the start of the study that do not worsen If an event is not an AE per definition above, then it cannot be an SAE even if serious conditions are met (e.g., hospitalization for signs/symptoms of the disease under study, death due to progression of disease).

Serious Adverse Event (SAE): A SAE is any Untoward Medical Occurrence that at any Dose:

a) Results in death;

b) Is life threatening (the term "life-threatening" refers to an event/reaction in which the participant was at risk of death at the time of the event/reaction; it does not refer to an event/reaction which hypothetically might have caused death if it were more severe);

c) Requires inpatient hospitalization or results in prolongation of existing hospitalization (in general, hospitalization signifies that the participant has been detained (usually involving at least an overnight stay) at the hospital or emergency ward for observation and/or treatment that would not have been appropriate in the physician's office or outpatient setting. Complications that occur during hospitalization are AEs. If a complication prolongs hospitalization or fulfills any other serious criteria, the event is serious. When in doubt as to whether "hospitalization" occurred or was necessary, the AE should be considered serious. Hospitalization for elective treatment of a pre-existing condition that did not worsen from baseline is not considered an AE);

d) Results in persistent disability/incapacity (the term disability means a substantial disruption of a person's ability to conduct normal life functions. This definition is not intended to include experiences of relatively minor medical significance such as uncomplicated headache, nausea, vomiting, diarrhea, influenza, and accidental trauma (e.g., sprained ankle) that may interfere with or prevent everyday life functions but do not constitute a substantial disruption);

e) Is a congenital anomaly/birth defect;

f) Other situations such as important medical events that may not be immediately life-threatening or result in death or hospitalization but may jeopardize the participant or may require medical or surgical intervention to prevent one of the other outcomes listed in the above definition. These events should usually be considered serious. Examples of such events include invasive or malignant cancers, intensive treatment in an emergency room or at home for allergic bronchospasm, blood dyscrasias or convulsions that do not result in hospitalization, or development of drug dependency or drug abuse.

Recording and Follow-Up of AE and/or SAE

AE and SAE recording: When an AE/SAE occurs, all documentation (e.g., hospital progress notes, laboratory reports, and diagnostics reports) related to the event are reviewed and all relevant AE/SAE information in the eCRF are recorded. It is not acceptable for the Investigator to send photocopies of the participant's medical records to the Sponsor's representative instead of completion of the AE/SAE eCRF page. Medical records may need to be submitted as additional data for SAE and AESI reporting. They are anonymized in such a case by replacing the participant's name and initials by the participant number of this study. There may be instances when copies of medical records for certain cases are requested by the Sponsor. In this case, all participant identifiers, with the exception of the participant number, are redacted on the copies of the medical records before submission to the Sponsor. The Investigator attempts to establish a diagnosis of the event based on signs, symptoms, and/or other clinical information. Whenever possible, the diagnosis (not the individual signs/symptoms) is documented as the AE/SAE.

Assessment of intensity: Intensity of AE/SAE reported during the study is assessed and assigned to one of the following categories:

Mild: An event that is easily tolerated by the participant, causing minimal discomfort and not interfering with everyday activities.

Moderate: An event that causes sufficient discomfort and interferes with normal everyday activities.

Severe: An event that prevents normal everyday activities. An AE that is assessed as severe should not be confused with an SAE. Severe is a category utilized for rating the intensity of an event; and both AEs and SAEs can be assessed as severe.

An event is defined as "serious" when it meets at least one of the predefined outcomes as described in the definition of an SAE, NOT when it is rated as severe.

Assessment of causality: The Investigator is obligated to assess the relationship between study intervention and each occurrence of each AE/SAE. A "reasonable possibility" of a relationship conveys that there are facts, evidence, and/or arguments to suggest a causal relationship, rather than a relationship cannot be ruled out. The Investigator uses clinical judgment to determine the relationship. Alternative causes, such as underlying disease(s), concomitant therapy, and other risk factors, as well as the temporal relationship of the event to study intervention administration are considered and investigated. The Investigator also consults the Investigator's Brochure (IB) and/or Product Information, for marketed products, in his/her assessment.

For each AE/SAE, the Investigator documents in the medical notes that he/she has reviewed the AE/SAE and has provided an assessment of causality. There may be situations in which an SAE has occurred, and the Investigator has minimal information to include in the initial report to the Sponsor. However, it is very important that the Investigator always assess causality for every event before the initial transmission of the SAE data to the Sponsor. The Investigator may change his/her opinion of causality in light of follow-up information and send a SAE follow-up report with the updated causality assessment. The causality assessment is one of the criteria used when determining regulatory reporting requirements.

Follow-up of AEs and SAEs: The Investigator is obligated to perform or arrange for the conduct of supplemental measurements and/or evaluations as medically indicated or as requested by the representative of the monitoring team to elucidate the nature and/or causality of the AE or SAE as fully as possible. This may include additional laboratory tests or investigations, histopathological examinations, or consultation with other health care professionals. New or updated information are recorded in the originally completed eCRF. If a participant dies during participation in the study or during a recognized follow-up period, the Investigator provides the Sponsor's representative with a copy of any post-mortem findings including histopathology. New or updated information is recorded in the originally completed eCRF. The Investigator submits any updated SAE data to the Sponsor within 24 hours of receipt of the information.

REPORTING OF SAEs: SAE reporting to the Sponsor via an electronic data collection tool. The primary mechanism for reporting an SAE to the Sponsor is the electronic data collection tool. If the electronic system is unavailable for more than 24 hours, then the site uses the paper SAE data collection tool (see herein). The site enters the SAE data into the electronic system as soon as it becomes available. After the study is completed at a given site, the electronic data collection tool is taken off-line to prevent the entry of new data or changes to existing data. If a site receives a report of a new SAE from a study participant or receives updated data on a previously reported SAE after the electronic data collection tool has been taken off-line, then the site can report this information on a paper SAE form (see Example 1.8C) or to the Sponsor by telephone.

SAE reporting to the Sponsor via case report form (CRF): Facsimile transmission of the SAE paper CRF is the preferred method to transmit this information to the Sponsor. In rare circumstances and in the absence of facsimile equipment, notification by telephone is acceptable with a copy of the SAE data collection tool sent by overnight mail or courier service. Initial notification via telephone does not replace the need for the Investigator to complete and sign the SAE CRF pages within the designated reporting time frames.

Example 1.8C—Time Period and Frequency for Collecting AE and SAE Information

All AEs (including SAEs) are collected from the signing of the ICF until EOT at the time points specified in the SOA (Table 1). All SAEs and AESI are recorded and reported to the Sponsor or designee within 24 hours, as indicated in Example 1.8B. The Investigator submits any updated SAE data to the Sponsor within 24 hours of it being available. Investigators are not obligated to actively seek AE or SAE after conclusion of the study participation. However, if the Investigator learns of any SAE, including a death, at any time after a participant has been discharged from the study, and he/she considers the event to be reasonably related to the study intervention or study participation, the Investigator promptly notifies the Sponsor. The method of recording, evaluating, and assessing causality of AE and SAE and the procedures for completing and transmitting SAE reports are provided in Example 1.8B.

Example 1.8D—Method of Detecting AEs and SAEs

Care is taken not to introduce bias when detecting AEs and/or SAEs. Open-ended and non-leading verbal questioning of the participant is the preferred method to inquire about AE occurrences.

Example 1.8E—Follow-Up of AEs and SAEs

After the initial AE/SAE report, the Investigator is required to proactively follow each participant at subsequent visits/contacts. At the prespecified study end date, all SAEs, and nonserious AESIs (as defined in Example 1.8B), are followed until resolution, stabilization, the event is otherwise explained, or the participant is lost to follow up (as defined in Example 1.4E3).

Example 1.8F—Pregnancy

Details of all pregnancies in female participants and female partners of male participants are collected after the start of study intervention and until the last visit of the study. If a pregnancy is reported, the Investigator informs the Sponsor within 24 hours of learning of the pregnancy and should the procedures outlined in Example 1.17. Abnormal pregnancy outcomes (e.g., spontaneous abortion, fetal death, stillbirth, congenital anomalies, ectopic pregnancy) are considered SAEs.

Example 1.8G—Cardiovascular and Death Events

Atrial fibrillation, atrial flutter, observation of QTc≥500 ms, or other clinically significant arrhythmia are AESIs in this study and subject to expedited reporting to the Sponsor. All other cardiovascular events are reported per standard safety reporting and safety oversight practices (including data review by IDMC). Central ECG review is performed to assure consistency in ECG evaluation. Death events are reported per standard SAE reporting rules to clarify the cause of death and to report the diagnosis of the fatal event as an SAE.

Example 1.8H—Multiple Sclerosis Relapse Reporting

Multiple sclerosis relapses, determined from the evaluations described in Example 1.6B, as with all efficacy endpoints, are exempt from being reported as AEs except when they meet the definition of an SAE. Hospitalization for MS relapse, if done routinely at the site (e.g., for high dose IV methylprednisolone), is not considered as a seriousness criterion for this study. Other worsening of neurological symptoms that do not meet the definition of MS relapse is reported as AEs according to general safety reporting rules.

Example 1.8I—Reporting of Safety Findings from Magnetic Resonance Imaging

Magnetic resonance imaging scans need to be reviewed locally for any non-MS pathology. In case of such findings, the MRI report needs to be provided to the Investigator for appropriate safety reporting. When available, a diagnosis of pathology as a cause of such MRI findings or the findings themselves are reported as an AE until the diagnosis is clear. Multiple sclerosis findings on MRI do not need to be reported unless they are deemed unusual and thus a distinct safety finding.

Example 1.9—Treatment of Overdose

Sponsor does not recommend specific treatment for an overdose. In the event of an overdose, the Investigator should:

- Contact the Medical Monitor immediately.
- Closely monitor the participant for any AE/SAE and laboratory abnormalities until study intervention can no longer be detected systemically and activity is over (at least 9 days).
- Obtain a plasma sample for PK analysis within 1 day from the date of the last dose of study intervention if possible or later if requested by the Medical Monitor (determined on a case-by-case basis).
- Document the quantity of the excess dose as well as the duration of the overdose in the eCRF.

Decisions regarding dose interruptions or modifications are made by the Investigator in consultation with the Medical Monitor based on clinical evaluation of the participant.

Example 1.10—Pharmacokinetics

Example 1.10A—Sampling Time

Samples for the BTK inhibitor PK analysis are collected 1 hour post-dose (±0.5 hour) at visits during Weeks 1, 4, 8, 12, and 16 for all participants in both cohorts. An additional PK sample is collected 3 hours post-dose (±0.5 hour) at visits during Weeks 4 and 12 for all participants in both cohorts. Data of the most recent meal prior to PK sampling are noted in the eCRF.

Example 1.10B—Pharmacokinetics Handling Procedure

A total of 2 mL of blood is to be collected for each PK sample. The total amount of blood for PK per participant and the total number of samples taken in the study are presented in Table 6.

TABLE 6

| Blood volume per participant and total number of samples | | |
|---|---|---|
| Number of pharmacokinetics samples by participant | Blood volume per participant for pharmacokinetics | Total number of samples in the study for pharmacokinetics |
| 7 | 7 × 2 mL = 14 mL | 7 × 120 samples = 840 samples |

Example 1.10C—Bioanalytical Method

The BTK inhibitor is assayed by a validated LC/MS method.

Example 1.10D—PK Parameters

The BTK inhibitor concentrations at selected time points after IMP intake are reported using descriptive statistics.

Additional PK parameters such as $C_{max}$, $t_{max}$, and AUC at steady state are estimated using a population PK approach.

Example 1.11—Pharmacodynamics

Example 1.11A—Sampling Time

Venous blood samples collected for PBMCs are used for measurement of lymphocyte subset analysis BTK occupancy at baseline (pre-dose) and 1 hour post-dose (±0.5 hour) of the BTK inhibitor dosing at visits during Weeks 12 and 16 (as part of a biomarker substudy).

Example 1.11B—Bioanalytical Method for Pharmacodynamics Parameters

Peripheral blood mononuclear cells are prepared from whole blood to determine BTK occupancy. Percentage of BTK occupancy at selected time points are reported using descriptive statistics.

Example 1.12—Pharmacogenetics

A 6 mL blood sample is collected for DNA isolation from participants who have consented to participate in the genetic analysis component of the study. Participants who do not wish to participate in the genetic research may still participate in the study. Samples are collected to investigate allelic variants of drug-metabolizing enzymes and/or drug transporters as intrinsic factors associated with PK or PD variability of the BTK inhibitor (Example 1.18).

In the event of DNA extraction failure, a replacement genetic blood sample may be requested from the participant.

Example 1.13—Biomarkers

Plasma and serum samples for biomarker research are collected from all participants in this study as specified in the SoA (Table 1). Samples from all participants are tested for neurofilament light chain and chitinase-3-like 1 protein and immunoglobulin levels to evaluate their associations with observed clinical responses. Samples of blood for PBMC isolation are also collected in all participants from sites selected by their capability to send them rapidly to the central laboratory for processing. Peripheral blood mononuclear cell samples are used for evaluation of BTK receptor occupancy (Example 1.11B), for selected lymphocyte subsets analysis over the period of the study, as well as other possible biomarkers. Approximately 50 mL of blood is drawn for all of these samples.

Example 1.14—Statistical Considerations

Example 1.14A—Statistical Hypotheses

The primary objective of this study is to assess the dose-response relationship based on the primary endpoint (number of new Gd-enhancing T1-hyperintense lesions as detected by brain MRI) at the end of 12 weeks of the BTK inhibitor treatment. The null hypothesis is a flat, no dose-response curve for the primary endpoint and the alternative is that there is a dose-response signal Example 1.14B—Sample Size Determination The study has 120 participants equally randomly assigned to 1 of 4 BTK inhibitor doses in 2 cohorts (60 participants in each of Cohorts 1 and 2). Cohorts 1 and 2 represent different treatment sequences, and participants in each crossover to the BTK inhibitor or placebo in a blinded manner.

The 60 participants in Cohort 2 start with a 4-week placebo run-in that is utilized as the placebo data in analyses for the primary endpoint based on the assumption of the constant monthly mean number of new Gd-enhancing T1-hyperintense lesions over 12 weeks of placebo treatment. Assuming 15% of participants without the primary endpoint at the end of 12 weeks of the BTK inhibitor, 105 participants (26 per the BTK inhibitor dose) has at least 83% power to detect the maximum reduction of 85% using a 2-step MCP-Mod with 6 pre-defined dose response curves (2 $E_{max}$ models, a quadratic model, a linear model, a logistic model, and an exponential model). This calculation assumes the dispersion parameter of 2, within-subject correlation ranging from −0.9 to 0.9 in measurements between 4-week placebo and 12-week BTK inhibitor in Cohort 2, and placebo mean number of ≥1 for new Gd-enhancing T1-hyperintense lesions at 4 weeks. This power was calculated using the package Dose Finding from the Comprehensive R Archive Network (CRAN) (Bornkamp B, Pinheiro J, Bretz F. Package 'DoseFinding', Jan. 4, 2018), using the 6 candidate curves considered for dose-response modelling in a negative binomial regression framework.

Example 1.14C—Populations for Analyses

For purposes of analysis, the following populations are defined as shown in Table 7:

TABLE 7

Populations for analyses

| Population | Description |
|---|---|
| Enrolled | All participants who sign the informed consent form |
| Randomly assigned to study intervention | All participants who are randomly assigned to the study intervention |
| Modified intent-to-treat (mITT) | The primary efficacy population is the mITT population, defined as all randomly assigned participants exposed to study intervention. The efficacy analyses are conducted according to the treatment group allocated by the randomization schedule, irrespective of the treatment received |
| Safety | All participants randomly assigned to the study intervention and who take at least 1 dose of the study intervention. Participants are analyzed according to the intervention they actually receive. |

Example 1.14D—Statistical Analyses

Efficacy Analyses

Primary Analysis: The primary objective of dose-response relationship of the BTK inhibitor with the primary endpoint, number of new Gd-enhancing T1-hyperintense lesions as detected by brain MRI at the end of 12 weeks of the BTK inhibitor treatment, is evaluated in the modified intent-to-treat (mITT) population by a 2-step multiple comparison procedure with modelling techniques (MCP-Mod). The first step of this procedure tests for an efficacy signal (compared to the null hypothesis of a flat, no dose-response curve) in a procedure that controls the type 1 error. To account for the uncertainty of the dose-response shape, 6 candidate models have been considered to cover diverse and potential dose-response profiles: 2 $E_{max}$ models ($ED_{50}$=10 mg, $ED_{50}$=30 mg), a linear model, a quadratic model, a logistic model, and an exponential model. The second step is the Dose estimation of the dose-response curve, provided that an efficacy signal is established in the first step.

A negative binomial regression model with covariates for baseline Gd-enhancing T1-hyperintense lesion count, treatment, and cohort (Cohort 1 or Cohort 2) is used to assess the mean count of new Gd-enhancing T1-hyperintense lesions in each of the 4 dose groups at the end of 12 weeks of the BTK inhibitor treatment and at the end of 4 weeks of placebo. The 4-week post-randomization placebo data from Cohort 2 (i.e., Week 4 data from Cohort 2) is utilized as the placebo data at Week 12 in analysis, under the assumption of a constant rate of Gd-enhancing T1-hyperintense lesion formation if participants would be receiving placebo over 12 weeks. Participants in Cohort 2 contribute to the placebo data (at Week 4) as well as the data for 4 BTK inhibitor doses (at Week 16). Thus, in order to account for the potential correlation between the measurements in the 4-week placebo period and the subsequent 12-week BTK inhibitor treatment period in Cohort 2, a generalized estimating equation (GEE) approach is used to fit the negative binomial model accounting for the within-participant correlation via the repeated statement in SAS PROC GENMOD. A minus log transformation of the mean lesion count id entered into the MCP-Mod procedure. The null hypothesis of a flat dose-response curve (i.e., no dose-response relationship) at the end of 12 weeks of the BTK inhibitor treatment for the primary endpoint is jointly evaluated for each of the 6 candidate dose response models with a contrast test that controls the family wise error rate at 2-sided alpha=0.05. If step 1 yields significant results, the best fitting model from the 6 predefined candidate models is chosen using the generalized Akaike information criterion (AIC).

The primary analysis is based on pooled data of Cohorts 1 and 2 for each of the BTK inhibitor doses (i.e., data at Week 12 for Cohort 1 and at Week 16 for Cohort 2 for the number of new Gd-enhancing T1-hyperintense lesions). Data from Cohorts 1 and 2 may also be separately explored as necessary.

Analysis of Secondary Points: For the secondary endpoint of number of Gd-enhancing T1-hyperintense lesions at the end of 12 weeks of the BTK inhibitor treatment, a similar negative binomial model and MCP-Mod procedure is used. As it is reasonable to assume a constant rate of lesion formation over 12 weeks under placebo for total number of Gd-enhancing T1-hyperintense lesions, the same approach as that utilized for the primary endpoint is used, by using the Week 4 data in Cohort 2 as the Week 12 placebo data while accounting for the within-participant correlation. Descriptive summary statistics over time is provided for each of the 4 BTK inhibitor doses.

For the number of new or enlarging T2 lesions, descriptive summary statistics over time (4, 8, 12, and 16 weeks) is provided for each of the 4 BTK inhibitor doses. Further, a similar MCP-Mod approach is explored if it is deemed reasonable to extrapolate the Week 4 data from Cohort 2 to the Week 12 placebo data.

The primary efficacy analysis is based on the mITT population. For the endpoints assessed by change from baseline, the baseline values are defined as the last measurements collected on or before the randomization visit (Day 1) prior to initiation of the first dose of study intervention.

Data from Cohorts 1 and 2 are combined for the primary analysis (i.e., data at Week 12 for Cohort 1 and at Week 16 for Cohort 2 for the number of new Gd-enhancing T1-hyperintense lesions). For each cohort, descriptive statistics are summarized over time (Weeks 4, 8, 12, and 16) when appropriate. The summary from Cohort 1 includes descriptive statistics for the 4-week placebo period after 12 weeks of the BTK inhibitor treatment. Additional efficacy analyses are described in the SAP.

TABLE 8

Efficacy Analyses

| Endpoint | Statistical Analysis Methods |
|---|---|
| Primary | |
| Number of new Gd-enhancing T1-hyperintense lesions at the end of 12 weeks of the BTK inhibitor treatment as detected by brain MRI | For the mITT population, the dose-response relationship is evaluated by a 2-step MCP-Mod procedure. The first step of this procedure tests for an efficacy signal (compared to the null hypothesis of a flat, no dose-response curve) in a procedure that controls the type 1 error. To account for the uncertainty of the dose-response shape, 6 candidate models have been considered to cover diverse and potential dose-response profiles: 2 $E_{max}$ models ($ED_{50}$ = 10 mg, $ED_{50}$ = 30 mg), a linear model, a quadratic model, a logistic model, and an exponential model. The second step is the estimation of the dose-response curve, provided that an efficacy signal is established in the first step.<br>A negative binomial regression model with covariates for baseline Gd-enhancing T1-hyperintense lesion count, treatment, and cohort (Cohort 1 or Cohort 2) are used to assess the mean count of new Gd-enhancing T1-hyperintense lesions in each of the 4 dose groups at the end of 12 weeks of the BTK inhibitor treatment and at the end of 4 weeks of placebo. The 4-week post-randomization placebo data from Cohort 2 (i.e., Week 4 data from Cohort 2) are utilized as the placebo data at Week 12 in analysis, under the assumption of a constant rate of Gd-enhancing T1-hyperintense lesion formation if participants would be receiving placebo over 12 weeks. Participants in Cohort 2 contribute to the placebo data (at Week 4) as well as the data of 5 doses of the BTK inhibitor (at Week 16). Thus, in |

TABLE 8-continued

| Efficacy Analyses | |
|---|---|
| Endpoint | Statistical Analysis Methods |
| | order to account for the potential correlation between the measurements in the 4-week placebo period and the subsequent 12-week BTK inhibitor treatment period in Cohort 2, a GEE approach is used to fit the negative binomial model accounting for the within-participant correlation via the repeated statement in SAS PROC GENMOD. A minus log transformation of the mean lesion count is entered into the MCP-Mod procedure. The null hypothesis of a flat dose-response curve (i.e., no dose-response relationship) at the end of 12 weeks of the treatment for the primary endpoint is jointly evaluated for each of the 6 candidate dose response models with a contrast test that controls the family wise error rate at 2-sided alpha = 0.05. If step 1 yields significant results, the best fitting model from the 6 predefined candidate models is chosen using the generalized AIC. The dose for the Phase 3 program is then estimated from the final selected model. Data from Cohorts 1 and 2 are combined for the primary analysis (i.e., data at Week 12 for Cohort 1 and at Week 16 for Cohort 2 for the number of new Gd-enhancing T1-hyperintense lesions). Data from each cohort may be separately explored.<br>Descriptive statistics also are provided for the 4 doses of the BTK inhibitor for number of new Gd-enhancing T1-hyperintense lesions over time (i.e., Week 4/Week 8, Week 8/Week 12, and Week 12/Week 16 for Cohort 1/Cohort 2). |
| Secondary | |
| Number of new or enlarging T2 lesions at the end of 12 weeks of the BTK inhibitor treatment<br>Total number of Gd-enhancing T1-hyperintense lesions at the end of 12 weeks of the BTK inhibitor treatment | For the secondary endpoint of number of Gd-enhancing T1-hyperintense lesions at the end of 12 weeks of the BTK inhibitor treatment, a similar negative binomial model and MCP-Mod procedure is used. As it is reasonable to assume a constant rate of lesion formation over 12 weeks under placebo for total number of Gd-enhancing T1-hyperintense lesions, the same approach as that utilized for the primary endpoint are used, by using the Week 4 data in Cohort 2 as the Week 12 placebo data while accounting for the within-participant correlation. Descriptive statistics over time also are provided for the 4 doses.<br>For the secondary endpoint of number of new or enlarging T2 lesions, descriptive summary statistics over time (4, 8, 12, and 16 weeks) are provided for each of the 4 doses. Further, a similar MCP-Mod approach is explored if it is deemed reasonable to extrapolate the Week 4 data from Cohort 2 to the Week 12 placebo data. |
| Exploratory | The exploratory efficacy endpoints listed in Table 2 are descriptively summarized with no inferential testing or comparison to placebo. Note that it may not be appropriate to assume constant rate of Gd-enhancing T1-hyperintense lesion formation for placebo treatment over 12 weeks for these endpoints. Thus, in absence of no placebo data at Week 12, for each dose of the BTK inhibitor, summary statistics over time are provided for each dose. A brief description of analyses of each exploratory endpoint is provided in the SAP. |

Safety Analyses

All safety analyses are performed on the safety population. All safety summaries are descriptive. No statistical significance tests are performed on safety data. Safety endpoints are described in Table 9.

The baseline value is defined generally as the last available value before the first administration of randomized study intervention. Safety data for the first 4 weeks following randomization (where participants in Cohort 2 receive placebo) are summarized by the BTK inhibitor and placebo. Safety data during the 4-week placebo period (i.e., 4 weeks) in Cohort 1 are summarized separately and displayed by the BTK inhibitor dose group and overall. For the BTK inhibitor treatment safety data, summaries by dose group, by time on the BTK inhibitor, and overall are provided.

For safety variables, the following observation periods are defined and used for classification of AEs, determination of on-treatment PCSA values, and the last on-treatment value for laboratory and vital sign parameters. The pretreatment period is defined as the time from the signed ICF to the first administration of randomized study intervention. For the purpose of defining 'treatment-emergent', the on-treatment period is defined as the time from the first administration of randomized study intervention until the last study visit. The treatment periods are further defined as:

The "Weeks 1 to 4 period" is defined as the time from first administration of randomized study treatment to the administration of the Week 4 study treatment. For Cohort 1 this is the BTK inhibitor treatment for 4 weeks and for Cohort 2 is placebo treatment for 4 weeks The "BTK inhibitor treatment period" is defined as Weeks 1 to 12 for Cohort 1 and Weeks 4 to 16 for Cohort 2. Note: participants from the Cohort 1 Weeks 1 to 4 period are also included in the 12 weeks of the BTK inhibitor treatment period.

The "placebo/post-BTK inhibitor dose period" is defined as Week 12 to Week 16 for Cohort 1. This is the 4 weeks of placebo treatment following 12 weeks of the BTK inhibitor treatment The analyses of AEs focus on treatment-emergent adverse events (TEAEs). Pretreatment AEs are defined as AEs that developed, or worsened, or become serious during the pretreatment period. Treatment-emergent AEs (TEAEs) are defined as AEs that develop, worsen, or become serious during the on-treatment period The Following Definitions are Applied to Laboratory Parameters, ECG, and Vital Sign Results:

Potentially clinically significant abnormality (PCSA) values are defined as abnormal values considered medically important by the Sponsor according to predefined criteria/thresholds based on literature review and are defined by the Sponsor for clinical laboratory tests and vital signs.

Potentially clinically significant abnormality criteria determine which participants had at least 1 PCSA during the on-treatment period, taking into account all evaluations performed during the on-treatment period including unscheduled or repeated evaluations. The number of all such participants is the numerator for the on-treatment PCSA percentage

TABLE 9

Safety analyses

| Endpoint | Statistical Analysis Methods |
|---|---|
| Adverse events | |
| AEs<br>TEAEs<br>SAEs<br>AEs leading to IMP or study discontinuation<br>AEs leading to death<br>AESIs | Adverse event incidence tables are presented by system organ class (sorted by internationally agreed order), high-level group term, high level term, and preferred term sorted in alphabetical order and present the number (n) and percentage (%) of participants experiencing an AE, by treatment period for: the Weeks 1 to 4 period for each BTK inhibitor dose group or placebo, for the BTK inhibitor dose period, by the BTK inhibitor dose group, and for the placebo/post-BTK inhibitor dose period. Multiple occurrences of the same event in the same participant are counted only once within a treatment period in the tables. The denominator for computation of percentages is the number of participants in the safety population (N) within each BTK inhibitor dose group or placebo, for the treatment period.<br>The incidence of TEAEs are summarized by severity grade/intensity, and relationship to IMP, by treatment period for: the Weeks 1 to 4 period for each BTK inhibitor dose group or placebo, for the BTK inhibitor period, by the BTK inhibitor dose group, and for the placebo/post-BTK inhibitor period.<br>Deaths and serious TEAEs are summarized and presented as numbers and percentages of participants, by treatment period for: the Weeks 1 to 4 period for each BTK inhibitor dose group or placebo, for the BTK inhibitor period, by the BTK inhibitor dose group, and for the placebo/post-BTK inhibitor period.<br>The following summaries are generated for deaths:<br>Numbers (%) of participants who died by the following categories and reasons for death summarized for the safety population by treatment received<br>Numbers (%) of participants who died by the following categories and reasons for death summarized for the safety population by treatment received<br>Death on study: deaths from any cause occurring after the randomization, and to the end of the study: e.g., to the date of last protocol planned visit if participants complete the whole study period as defined in the protocol<br>Death on treatment: deaths from any cause occurring during the on-treatment AE period<br>Death post-study: deaths from any cause occurring after the end of study, if any, e.g., after the date of last protocol planned visit if participants complete the whole study period<br>Deaths in nonrandomized participants<br>Treatment-emergent AEs leading to treatment discontinuation are summarized and presented as numbers and percentages of participants by treatment period for: the 'Weeks 1-4' period for each BTK inhibitor dose group |

TABLE 9-continued

| Safety analyses | |
|---|---|
| Endpoint | Statistical Analysis Methods |
| | or placebo, for the 'Active Dose' period, by the BTK inhibitor dose group, and for the 'Placebo-Post Active Dose' period.<br>Numbers (%) of participants for each AESI are summarized, by treatment period for: the Weeks 1 to 4 period for each BTK inhibitor dose group or placebo, for the BTK inhibitor period, by the BTK inhibitor dose group, and for the placebo/post-BTK inhibitor period. |
| Vital signs, ECG and laboratory data | Vital signs and ECG data are summarized by treatment period for: the Weeks 1 to 4 period for each BTK inhibitor dose group or placebo, for the BTK inhibitor period by the BTK inhibitor dose group, and for the placebo/post-BTK inhibitor period by baseline and change from baseline at scheduled visits with descriptive statistics. Numbers and percentages of participants with at least 1 PCSA by treatment period for: the Weeks 1 to 4 period for each BTK inhibitor dose group or placebo, for the BTK inhibitor period by the BTK inhibitor dose group, and for the placebo/post-BTK inhibitor period are summarized for each vital sign and ECG variable.<br>Clinical laboratory test results are summarized by treatment period for: the Weeks 1 to 4 period for each BTK inhibitor dose group or placebo, for the BTK inhibitor period by the BTK inhibitor dose group, and for the placebo/post-BTK inhibitor period by baseline value and change from baseline value at each scheduled visit using descriptive statistics.<br>Numbers and percentages of participants with at least 1 incident of PCSA during the on-treatment period are summarized by treatment period for: the Weeks 1 to 4 period for each BTK inhibitor dose group or placebo, for the BTK inhibitor period by the BTK inhibitor dose group, and for the placebo/post-BTK inhibitor period. Shift tables showing change from baseline are provided as necessary.<br>Potentially clinically significant abnormality values with flags indicating out-of-range values are provided. |

The individual PK concentrations are descriptively summarized by visit. Additional PK parameters as stated in Example 1.10D, and population PK and PD analyses are presented in a separate document.

Example 1.15—Interim Analyses

If deemed necessary due to a slower recruitment than anticipated, one interim analysis is performed when at least 44 participants have completed the 16 weeks of the study (12 weeks of the BTK inhibitor treatment and 4 weeks of placebo). The interim analysis is not performed if the trial recruits quickly since the interim analysis would be too close in time (i.e., less than 3 to 4 months) to the final analysis to be worthwhile. The purpose of the interim analysis would be to explore an efficacy signal and to optimize the planning of Phase 3 studies. Operational documents prespecify the conditions for performing the interim analysis (e.g., recruitment rate) and the decision of whether or not the interim analysis is conducted are made prior to the SAP finalization. If the interim analysis is conducted, the reduction in the number of new Gd-enhancing T1-hyperintense lesions (in the 60 mg group only or in the combined 60 and 30 mg groups) compared to placebo (using the 4-week post-randomization placebo data from Cohort 2), as well as the potential dose-response curves, is explored. The interim analysis would be performed by an unblinded, independent statistician. Since the study is not stopped early for efficacy claims based on this potential exploratory interim analysis, no alpha adjustment is made at the final analysis if the interim analysis is performed. The SAP describes the planned one interim analysis in greater detail, if it is to be performed.

An IDMC is used to monitor safety of the study.

Example 1.16—Clinical Laboratory Tests

Details of the clinical laboratory tests are provided in Table 10. Additional tests are performed at any time during the study as determined necessary by the Investigator or required by local regulations.

TABLE 10

| Protocol-required safety laboratory assessments | | | | |
|---|---|---|---|---|
| Laboratory assessments | Parameters | | | |
| Hematology | Platelet count<br>Red blood cell (RBC) count<br>Hemoglobin<br>Hematocrit | RBC indices:<br>MCV<br>MCH<br>% reticulocytes | White blood cell (WBC) count with differential:<br>Neutrophils<br>Lymphocytes<br>Monocytes<br>Eosinophils<br>Basophils | |
| Coagulation | PT/INR | aPTT | | |
| Clinical chemistry[a] | Blood urea nitrogen (BUN) | Potassium | Aspartate aminotransferase (AST)/Serum glutamic-oxaloacetic transaminase (SGOT) | Total and direct bilirubin |
| | Creatinine | Sodium | Alanine aminotransferase (ALT)/Serum glutamic-pyruvic transaminase (SGPT) | Total protein |
| | Lipase | Amylase | Creatine phosphokinase<br>Total protein | Total and direct bilirubin<br>Albumin |
| | Glucose (nonfasting) | Calcium | Alkaline phosphatase | Serum FSH<br>Serum human chorionic gonadotropin (hCG) pregnancy test |
| Routine urinalysis | Specific gravity<br>pH, glucose, protein, blood, ketones, bilirubin, urobilinogen, nitrite, leukocyte esterase by dipstick, urine drug screen<br>Microscopic examination (if blood or protein) | | | |
| Other tests | Hepatitis B surface antigen (HBsAg), and hepatitis C virus antibody, other infectious disease if locally required | | | |
| Other screening tests | Urine human chorionic gonadotropin (hCG) pregnancy test (as needed for women of childbearing potential)[b]<br>Serology (HIV antibody, or other tests)] if locally required<br>TB/QuantiFERON-TB Gold ® test or equivalent | | | |

[a]All events of ALT ≥3 × upper limit of normal (ULN) and bilirubin ≥2 × ULN (>35% direct bilirubin) or ALT ≥3 × ULN and international normalized ratio (INR) >1.5, if INR measured that may indicate severe liver injury (possible Hy's Law) are reported as an SAE.

[b]Local urine testing is standard for the protocol except screening, unless only serum testing is required by local regulation or IRB/IEC, or needed for inconclusive urine test.

Example 1.17—Contraceptive Guidance and Collection of Pregnancy Information

Woman of childbearing potential (WOCBP): A woman is considered fertile following menarche and until becoming post-menopausal unless permanently sterile.

Women in the Following Categories are not Considered WOCBP:

1) Premenarchal
2) Premenopausal female with 1 of the following: documented hysterectomy, documented bilateral salpingectomy, documented bilateral oophorectomy.
3) Postmenopausal female
   - A postmenopausal state is defined as no menses for 12 months without an alternative medical cause. A high FSH level in the postmenopausal range may be used to confirm a postmenopausal state in women not using hormonal contraception or hormonal replacement therapy (HRT). However, in the absence of 12 months of amenorrhea, a single FSH measurement is insufficient.
   - Females on HRT and whose menopausal status is in doubt are required to use one of the nonestrogen hormonal highly effective contraception methods if they wish to continue their HRT during the study. Otherwise, they must discontinue HRT to allow confirmation of postmenopausal status before study enrollment.

Contraception Guidance

Male participants

Male participants with female partners of childbearing potential are eligible to participate if they agree to ONE of the following from inclusion up to 3 months after the last dose of study intervention:

- Are abstinent from penile-vaginal intercourse as their usual and preferred lifestyle (abstinent on a long term and persistent basis) and agree to remain abstinent
- Agree to use a male condom plus partner use of a contraceptive method with a failure rate of <1% per year as described in Table 11 when having penile-vaginal intercourse with a woman of childbearing potential who is not currently pregnant In addition, male participants must refrain from donating sperm for the duration of the study and for 6 months after the last dose of study intervention Male participants with a pregnant or breastfeeding partner must agree to remain abstinent from penile vaginal intercourse or use a male condom during each episode of penile penetration for 3 months after the last dose.

Female participants

As definitive reproduction toxicity studies have yet to be conducted with the BTK inhibitor, the Investigator is directed to take appropriate precautions during exposure of WOCBP in this clinical trial. Female participants of childbearing potential are eligible to participate if they agree to use a double contraception method including a highly effective method of contraception consistently and correctly as described in Table 9 from inclusion and up to 2 months after the last study dose. In addition, WOCBP must refrain from donating ova for the duration of the study and for 2 months after the last dose of study intervention.

TABLE 11

| Highly effective contraceptive methods |
|---|
| Highly effective contraceptive methods that are user dependent<br>Failure rate of <1% per year when used consistently and correctly.<br>i) Combined (estrogen and progestogen containing) hormonal contraception associated with inhibition of ovulation: Oral, Intravaginal, or Transdermal<br>ii) Progestogen only hormonal contraception associated with inhibition of ovulation: Oral or Injectable<br>Notes: Typical use failure rates may differ from those when used consistently and correctly. Use should be consistent with local regulations regarding the use of contraceptive methods for participants participating in clinical studies.<br>Highly effective methods that are user independent:<br>Implantable progestogen only hormonal contraception associated with inhibition of ovulation: Intrauterine device (IUD), Intrauterine hormone-releasing system (IUS), or Bilateral tubal occlusion<br>Vasectomized partner: A vasectomized partner is a highly effective contraception method provided that the partner is the sole male sexual partner of the WOCBP and the absence of sperm has been confirmed. If not, an additional highly effective method of contraception is used.<br>Sexual abstinence: Sexual abstinence is considered a highly effective method only if defined as refraining from heterosexual intercourse during the entire period of risk associated with the study intervention. The reliability of sexual abstinence is evaluated in relation to the duration of the study and the preferred and usual lifestyle of the participant.<br>Pregnancy Testing: WOCBP is included only after a confirmed menstrual period and a negative highly sensitive serum pregnancy test. Additional pregnancy testing is performed at monthly intervals during the intervention period and at 1 month after the last dose of study intervention and as required locally. Pregnancy testing is performed whenever a menstrual cycle is missed or when pregnancy is otherwise suspected. |

Collection of Pregnancy Information:

Male participants with partners who become pregnant—The Investigator attempts to collect pregnancy information on any male participant's female partner who becomes pregnant while the male participant is in this study. This applies only to male participants who receive the BTK inhibitor. After obtaining the necessary signed informed consent from the pregnant female partner directly, the Investigator records pregnancy information on the appropriate form and submits it to the Sponsor within 24 hours of learning of the partner's pregnancy. The female partner is also be followed to determine the outcome of the pregnancy. Information on the status of the mother and child is forwarded to the Sponsor. Generally, the follow-up is no longer than 6 to 8 weeks following the estimated delivery date. Any termination of the pregnancy is reported regardless of fetal status (presence or absence of anomalies) or indication for the procedure.

Female participants who become pregnant—The Investigator collects pregnancy information on any female participant who becomes pregnant while participating in this study. Information is recorded on the appropriate form and submitted to the Sponsor within 24 hours of learning of a participant's pregnancy. The participant is followed to determine the outcome of the pregnancy. The Investigator collects follow-up information on the participant and the neonate and the information is forwarded to the Sponsor. Generally, follow-up is not required for longer than 6 to 8 weeks beyond the estimated delivery date. Any termination of pregnancy is reported, regardless of fetal status (presence or absence of anomalies) or indication for the procedure. Any pregnancy complication or elective termination of a pregnancy is reported as an AE or SAE. A spontaneous abortion is always considered to be an SAE and is reported as such. Any post-study pregnancy related SAE considered reasonably related to the study intervention by the Investigator is reported to the Sponsor. While the Investigator is not obligated to actively seek this information in former study participants, he or she may learn of an SAE through spontaneous reporting. Any female participant becoming pregnant while participating in the study discontinues the study intervention and is withdrawn from the study.

Example 1.18—Genetics

Use/Analysis of DNA

Genetic variation may impact a participant's response to study intervention, susceptibility to, and severity and progression of disease. Variable response to study intervention may be due to genetic determinants that impact drug absorption, distribution, metabolism, and excretion; mechanism of action of the drug; disease etiology; and/or molecular subtype of the disease being treated. Therefore, where local regulations and IRB/IEC allow, a blood sample is collected for DNA analysis from consenting participants.

DNA samples are used for research related to the study intervention or MS and related diseases. They may also be used to develop tests/assays including diagnostic tests related to the study intervention and indication. Genetic research may consist of the analysis of one or more candidate genes or the analysis of genetic markers throughout the genome (as appropriate). DNA samples are analyzed to investigate allelic variants of drug-metabolizing enzymes and/or drug transporters as intrinsic factors associated with PK or PD variability of the BTK inhibitor. Additional analyses may be conducted if it is hypothesized that this may help further understand the clinical data. The samples may be analyzed as part of a multi-study assessment of genetic factors involved in the response to the BTK inhibitor or study interventions of this class to understand study disease or related conditions.

Example 1.19—List of Example Drugs Prohibited

The following drugs should not be taken during the study due to their potential to change the BTK inhibitor kinetics due to interaction with P450-mediated metabolism, being potent inducers or inhibitors of CYP3A or CYP2C8 liver enzymes (per the lists of the Drug Interaction Database Program of the University of Washington (www.druginteractioninfo.org). Please note that the lists provided are not exhaustive and that the product information of drugs intended for concomitant use should be consulted.

TABLE 12

List of example drugs with a potential to change with the BTK inhibitor metabolism

| | | |
|---|---|---|
| Strong CYP3A Inhibitors | Viekira Pak | Mibefradil |
| | Indinavir/RIT | LCL161 |
| | Tipranavir/RIT | Clarithromycin |
| | Ritonavir | Posaconazole |
| | Cobicistat (GS-9350) | Telithromycin |
| | | Conivaptan |
| | Ketoconazole | Nefazodone |
| | Indinavir | Nelfinavir |
| | Troleandomycin | Saquinavir |
| | Telaprevir | Ribociclib |
| | Danoprevir/RIT | Idelalisib |
| | Elvitegravir/RIT | Boceprevir |
| | Saquinavir/RIT | Note: VIEKIRA PAK = |
| | Lopinavir/RIT | 150/100 mg |
| | Itraconazole | paritaprevir/ritonavir + 25 mg |
| | Voriconazole | ombitasvir + 800 mg dasabuvir |
| | | for 28 days |
| Potent CYP3A Inducers | Rifampin | Carbamazepine |
| | Mitotane | Enzalutamide |
| | Avasimibe | St John's Wort extract |
| | Rifapentine | Lumacaftor |
| | Apalutamide | Rifabutin |
| | Phenytoin | Phenobarbital |
| Strong CYP2C8 Inhibitors: | Gemfibrozil | |
| | Clopidogrel | |
| | Letermovir | |
| | Teriflunomide D eferasirox | |

TABLE 13

List of example drugs with a potential to affect plasma exposure of the BTK inhibitor via reduction of gastric acid

| | |
|---|---|
| Proton Pump Inhibitors | Esomeprazole |
| | Lansoprazole |
| | Omeprazole |
| | Pantoprazole |
| | Rabeprazole |
| H2-receptor Antagonists | Cimetidine |
| | Famotidine |
| | Nizatidine |
| | Ranitidine |

TABLE 13-continued

List of example drugs with a potential to affect plasma exposure of the BTK inhibitor via reduction of gastric acid

| | |
|---|---|
| Other Agents | Antacids, e.g., aluminum hydroxide/carbonate |
| | Calcium hydroxide/carbonate |
| | Bismuth subsalicylate |
| | Buffered medications, e.g., didanosine |

TABLE 14

Abbreviations

| | |
|---|---|
| AEs | adverse event |
| AESI | adverse event of special interest |
| AIC | Akaike information criterion |
| ALT | alanine aminotransferase |
| ARR | annualized relapse rate |
| BTK | Bruton's tyrosine kinase |
| CNS | central nervous system |
| CSF | cerebrospinal fluid |
| C-SSRS | Columbia Suicide Severity Rating Scale |
| DNA | deoxyribonucleic acid |
| DTP | duties and taxes paid |
| ECG | electrocardiogram |
| eCRF | electronic case report form |
| EDSS | Expanded Disability Status Scale |
| FSH | follicle-stimulating hormone |
| GCP | Good Clinical Practice |
| Gd | gadolinium |
| GEE | generalized estimating equation |
| HRT | hormone replacement therapy |
| ICF | informed consent form |
| ICH | International Council for Harmonization |
| IDMC | Independent Data Monitoring Committee |
| IEC | Independent Ethics Committee |
| IMP | investigational medicinal product |
| IRB | Institutional Review Board |
| IV | intravenous(ly) |
| IVRS | interactive voice response system |
| IWRS | interactive web response system |
| LLN | lower limit of normal |
| LTS | long-term safety, long-term safety |
| MCP-Mod | multiple comparison procedure with modelling techniques |
| mITT | modified intent-to-treat |
| MRI | magnetic resonance imaging |
| MS | multiple sclerosis |
| NfL | neurofilament light chain |
| NIMP | noninvestigational medicinal product |
| NOAEL | no observed adverse effect level |
| PBMC | peripheral blood mononuclear cell |
| PCSA | potentially clinically significant abnormality |
| PD | pharmacodynamic(s) |
| PK | pharmacokinetic(s) |
| PML | progressive multifocal leukoencephalopathy |
| PPMS | primary progressive multiple sclerosis |
| QTcF | QT interval corrected using Fridericia's formula |
| RMS | relapsing multiple sclerosis |
| SAE | serious adverse event |
| SAP | Statistical Analysis Plan |
| SPMS | secondary progressive multiple sclerosis |
| TEAE | treatment-emergent adverse event |
| ULN | upper limit of normal |

Example 2: Results of the Dose-Finding and Safety Studies for the BTK Inhibitor in Relapsing Multiple Sclerosis We herein provide results of the dose-finding and safety studies described in Example 1. We determined the dose-response relationship for the BTK inhibitor to reduce the number of new active brain lesions, including the number of new gadolinium (Gd)-enhancing T1-hyperintense lesions. We also evaluated efficacy of the BTK inhibitor on disease activity as assessed by imaging measures, by measuring the number of new or enlarging T2 lesions and the total number of Gd-enhancing T1-hyperintense lesions. We also evaluated the safety and tolerability of for the BTK inhibitor dose-response.

As described in Example 1, this study was a multi-center study with a total of 40 active sites in Europe and North America. All participants were centrally assigned to 1 of 8 arms (4 dose groups in each of 2 cohorts at equal ratio to start with the BTK inhibitor (in Cohort 1) or placebo (in Cohort 2) period before cross-over, using an Interactive Voice/Web Response System.

Within each cohort, participants were randomly assigned equally to 1 of 4 of the BTK inhibitor doses of 5, 15, 30, or 60 mg once daily, in a blinded manner.

Cohort 1: Participants received 1 of the BTK inhibitor doses for the first 12 weeks, then crossed over to placebo for 4 weeks.

Cohort 2: Participants received placebo for the first 4 weeks, then crossed over to 1 of the BTK inhibitor doses for 12 weeks.

All brain scans were reviewed and interpreted by 1 or more rater-blinded radiologists at an independent, central facility who were blinded to treatment, thereby avoiding bias and assuring standardized endpoint evaluation.

Diagnosis and criteria for inclusion: Participants ages 18 to 55 years, diagnosed with RMS according to the 2017 revision of the McDonald diagnostic criteria, and had at least 1 documented relapse within the previous year OR≥2 documented relapses within the previous 2 years OR≥1 active Gd-enhancing brain lesion on an MRI scan in the 6 months prior to screening.

Primary and Main Secondary Key Endpoints

Efficacy:

Primary: Number of new gadolinium (Gd)-enhancing T1 hyperintense lesions at the end of 12 weeks of the BTK inhibitor treatment as detected by brain MRI.

Secondary:

Number of new or enlarging T2 lesions at the end of 12 weeks of the BTK inhibitor treatment;

Number of Gd-enhancing T1-hyperintense lesions at the end of 12 weeks of the BTK inhibitor treatment Safety:

Adverse events (AEs), serious adverse events (SAEs), potentially clinically significant abnormalities in laboratory tests, electrocardiogram (ECG), or vital signs during the study period Statistical Methods:

Analysis of Primary Endpoint:

The primary analysis was based on pooled data of Cohorts 1 and 2 for each of the BTK inhibitor doses (i.e., data at Week 12 for Cohort 1 and at Week 16 for Cohort 2 for the number of new Gd-enhancing T1-hyperintense lesions).

The primary objective of dose-response relationship of the BTK inhibitor with the primary endpoint, number of new Gd-enhancing T1-hyperintense lesions as detected by brain MRI at the end of 12 weeks of the BTK inhibitor treatment was evaluated in the modified intent-to-treat (mITT) population by a 2-step multiple comparison procedure with modeling techniques (MCP-Mod). The first step of this procedure tested for an efficacy signal (compared to the null hypothesis of a flat, no dose-response curve) in a procedure that controls the type 1 error. To account for the uncertainty of the dose-response shape, 6 candidate models were considered to cover diverse and potential dose-response profiles: 2 $E_{max}$ models ($ED_{50}$=10 mg, $ED_{50}$=30 mg), a linear model, a quadratic model, a logistic model, and an exponential model. In the second step, a dose-response curve was estimated, because an efficacy signal was established in the first step.

In MCP-Mod Step 1, a negative binomial regression model with covariates for baseline Gd-enhancing T1-hyperintense lesion activity (presence/absence) and treatment, was used to assess the mean count of new Gd-enhancing T1-hyperintense lesions in each of the 4 dose groups at the end of 12 weeks of the BTK inhibitor treatment and at the end of 4 weeks of placebo. The MRI assessments were excluded from the analyses if the participant was receiving systemic corticosteroids within the 30 days prior to the MRI assessment date. The 4-week post-randomization placebo data from Cohort 2 (i.e., Week 4 data from Cohort 2) was utilized as the placebo data at Week 12 in analysis under the assumption of a constant rate of Gd-enhancing T1-hyperintense lesion formation if participants were to receive placebo over 12 weeks. Participants in Cohort 2 contributed to the placebo data (at Week 4) as well as the data for 4 BTK inhibitor doses (at Week 16). The 4-week placebo run-out data from Cohort 1 was not included in the analysis. Thus, in order to account for the potential correlation between the measurements in the 4-week placebo period and the subsequent 12-week BTK inhibitor treatment period in Cohort 2, a generalized estimating equation (GEE) approach was used to fit the negative binomial model accounting for within-participant correlation by using the "REPEATED" statement in SAS PROC GENMOD. A minus log transformation of the mean lesion count was entered into the MCP-Mod procedure. The null hypothesis of a flat dose-response curve (i.e., no dose-response relationship) at the end of 12 weeks of the BTK inhibitor treatment for the primary endpoint was jointly evaluated for each of the 6 candidate dose response models using a contrast test that controls the family-wise error rate at a 2-sided alpha of 0.05. Test statistics and adjusted p-values were provided for all 6 candidate models.

In MCP-Mod Step 2, all candidate models with adjusted p-values <0.05 in Step 1 were fitted. The generalized Akaike information criterion (AIC) and model parameters were provided. The best fitting model was chosen as the one with the smallest generalized AIC. The dose for the Phase 3 program was then estimated from the final selected model.

In addition, the relative reduction in mean counts of new Gd-enhancing T1-hyperintense lesion relative to the placebo group and corresponding 95% confidence intervals (CIs) were provided for each of the 4 BTK inhibitor dose groups based on the negative binomial regression model described above.

Descriptive statistics were also provided for the 4 BTK inhibitor dose groups for observed number of new Gd-enhancing T1-hyperintense lesions over time (Week 4/Week 8, Week 8/Week 12, and Week 12/Week 16 for Cohort 1/Cohort 2) and the placebo group (Week 4 Cohort 2).

Analysis of Secondary Endpoints:

For each secondary endpoint, a similar negative binomial model and the MCP-Mod procedure were used. As it is reasonable to assume a constant rate of lesion formation over 12 weeks under placebo treatment, the same approach as that utilized for the primary endpoint was used, i.e., using the Week 4 data in Cohort 2 as the Week 12 placebo data while accounting for within-participant correlation. Descriptive summary statistics over time were provided for each of the 4 BTK inhibitor dose groups.

All safety summaries are descriptive and were performed on the safety population. Safety data for the first 4 weeks following randomization (when participants in Cohort 2 receive placebo) are summarized by the BTK inhibitor and placebo treatments. Safety data during the BTK inhibitor treatment period (from first BTK inhibitor administration) are summarized by the BTK inhibitor dose group and overall.

Population Characteristics:

130 patients were randomized.

Participant demographics and characteristics at baseline were generally well balanced between the 8 treatment arms (2 cohorts of 4 treatment arms each). The median age of participants was 36.3 years (range: 19 to 55 years). The majority of participants was female (91; 70.0%). Of note, 119 (91.5%) of 130 participants were white.

All 130 participants were diagnosed with RMS (128 with relapsing RMS and 2 with secondary progressive MS) with a mean EDSS score of 2.50, a median time since first diagnosis of 3.5 years, and a median time since first symptoms of MS of 4.9 years. 127 (97.7%) participants had at least one relapse in the year prior to screening, and 61 (46.9%) participants had highly active disease (HAD) defined by 1 relapse in the year prior to screening AND ≥1 Gd-enhancing lesion in MRI done within 6 months prior to screening OR 9 or more T2 lesions at baseline OR 2 or more relapses in the year prior to screening).

129 of 130 patients completed the treatment period. One participant permanently discontinued treatment after Week 12 for declining to meet contraception requirements.

Table 15 provides details of patient disposition. Tables 16A-16B summarizes demographic and baseline characteristics of patients. Table 17 shows details of duration of exposure in each group and Table 18 shows details of exposure by dosage in each group.

Efficacy Results:

Primary efficacy endpoint: The study met its primary objective, demonstrating a dose-response relationship for the BTK inhibitor as evidenced by a reduction in the number of new active Gd-enhancing T1-hyperintense brain lesions detected by brain MRI after 12 weeks of treatment.

Figure 2A:
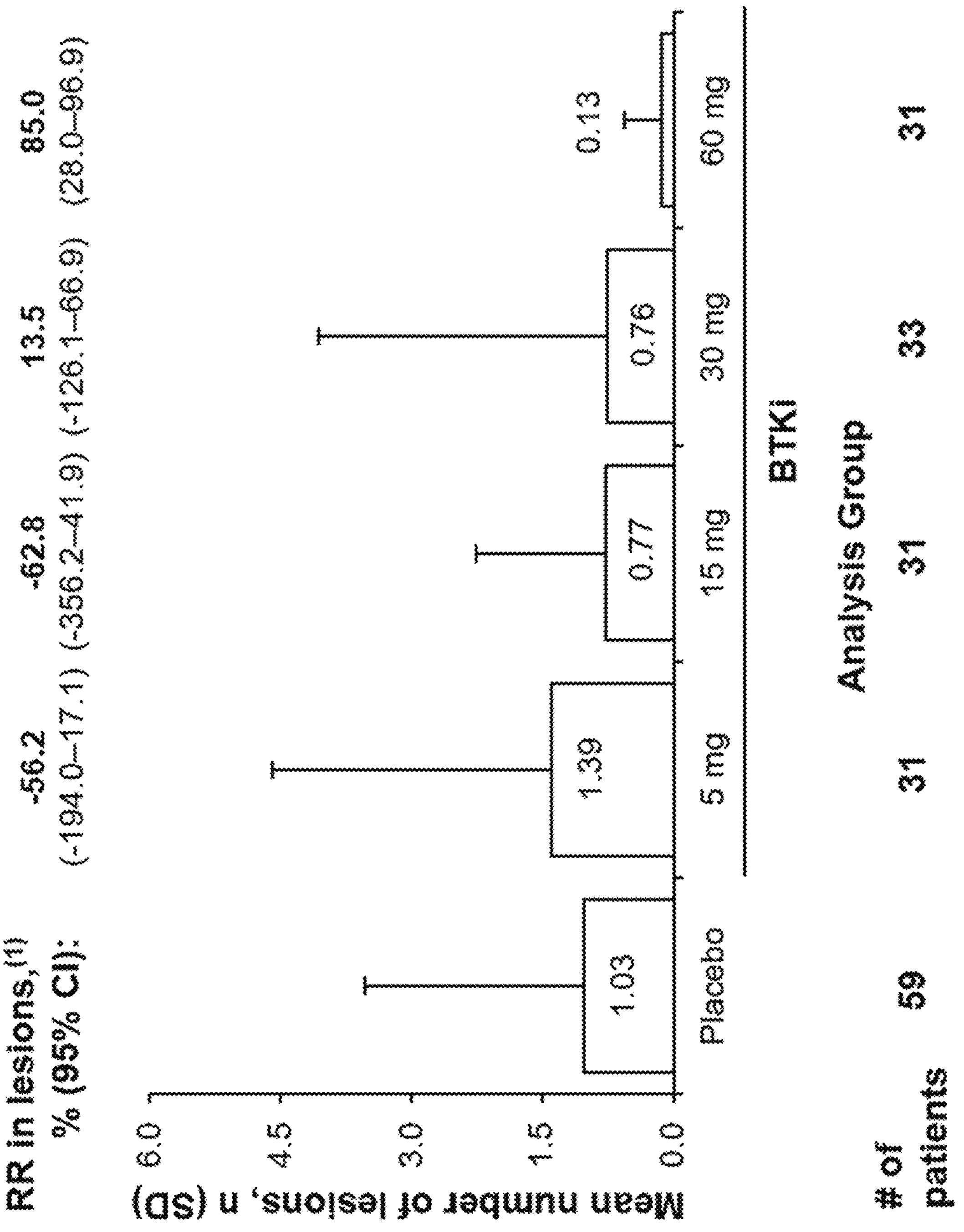
FIG. 2A shows the primary endpoint results, the number of new Gd-enhancing T1-hyperintense lesion after 12 weeks of the BTK inhibitor treatment (Cohort 1: Week 12; Cohort 2: Week 16), or 4 weeks of placebo for Cohort 2 patients. Relative reduction (RR) in lesions were adjusted for baseline Gd-enhancing T1-hyperintense lesion activity (presence/absence) using a negative binomial model. CI: confidence interval.

Table 19 provides a summary of relative reductions vs. placebo of new Gd-enhancing T1-hyperintense brain lesions after 12 weeks of treatment, as also shown in FIG. 2A. Table 20 shows MCP-Mod of new Gd-enhancing T1-hyperintense brain lesions after 12 weeks of treatment. The MCP-Mod evaluation was performed as described above in the statistical methods section.

Figure 2B:
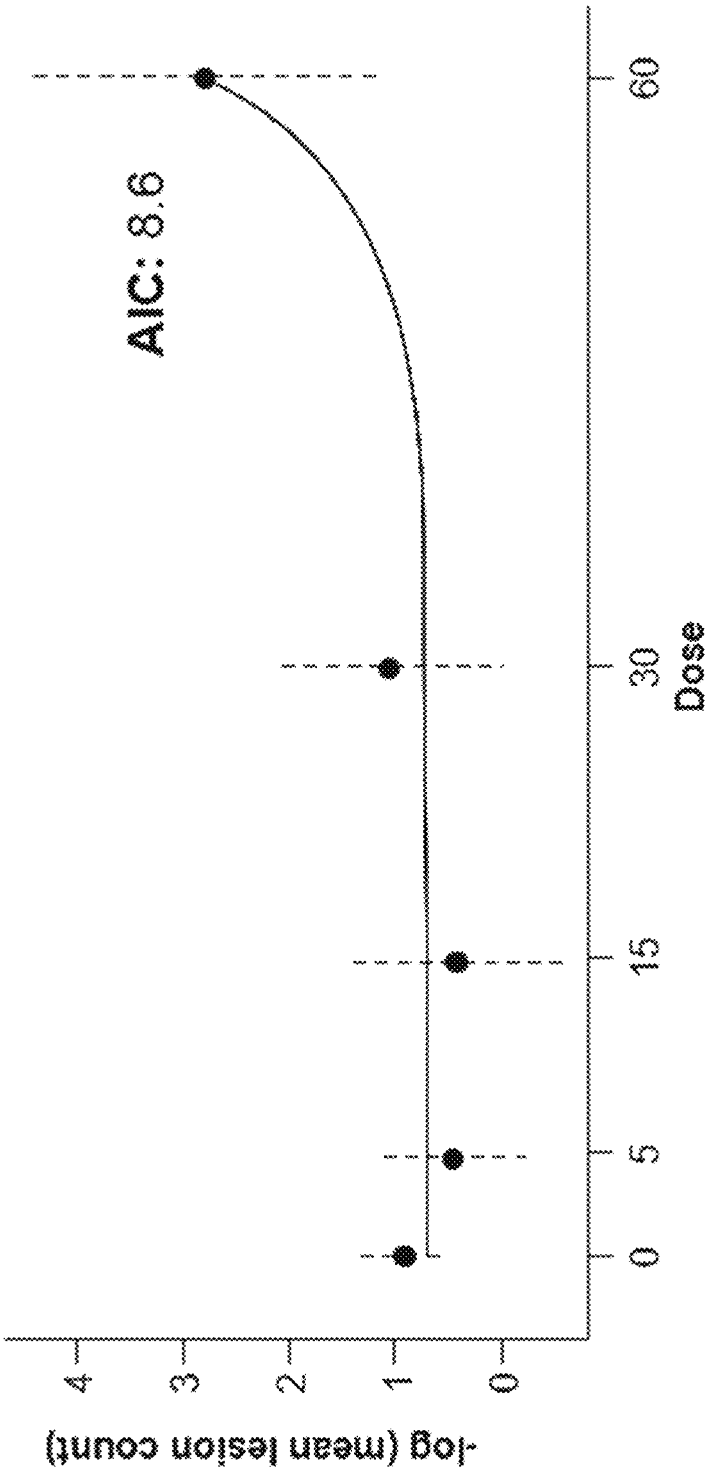
FIG. 2B shows an estimated dose response curve for new Gd-enhancing T1-hyperintense brain lesions (primary endpoint) after the BTK inhibitor treatment based on the multiple comparison procedure and modelling (MCP-Mod). The best fitting model was chosen as the one with the smallest generalized AIC (Akaike information criterion).

FIG. 2B shows MCP-Mod Step 2 to assess estimated dose response curve for new Gd-enhancing T1-hyperintense brain lesions. To account for the potential correlation for cohort 2 between the measurements in the run-in period and the treatment period, a generalized estimating equation approach (GEE) was used to fit the model accounting for the within-subject correlation. Mean lesion count at Week 12 for the BTK inhibitor treatment and Week 4 for placebo, estimated from a negative binomial regression model and accounted for the potential correlation between the measurements in the 4-week placebo period and the subsequent 12-week the BTK inhibitor treatment period in Cohort 2. The MRI assessment was excluded from the analyses if the participant was receiving systemic corticosteroids within the 30 days prior to the MRI assessment date.

As shown in FIG. 2A and Table 19, the observed means (SD) of new Gd-enhancing T1-hyperintense lesion counts at 12 weeks post treatment were 1.03 (2.50) in the placebo group, 1.39 (3.20) in the BTK inhibitor 5 mg group, 0.77 (1.48) in the BTK inhibitor 15 mg group, 0.76 (3.31) in the BTK inhibitor 30 mg group, and 0.13 (0.43) in the BTK inhibitor 60 mg group. The relative reduction in lesions at 12 weeks as compared with placebo from the negative binomial regression model adjusted for baseline Gd-enhancing T1-hyperintense lesion activity was statistically significant in the 60 mg dose group (85.02%; 95% CI [28.02%, 96.88%]; nominal p-value=0.0178) but not in the lower dose groups. Of note, 90.30% of participants (28 of 31) in the BTK inhibitor 60 mg dose group with evaluable MRI data had no new Gd-enhancing T1-hyperintense lesions at the end of 12 weeks of treatment. The exponential model was selected as the best-fitting dose-response curve and shown in FIG. 2B.

Figure 3A:
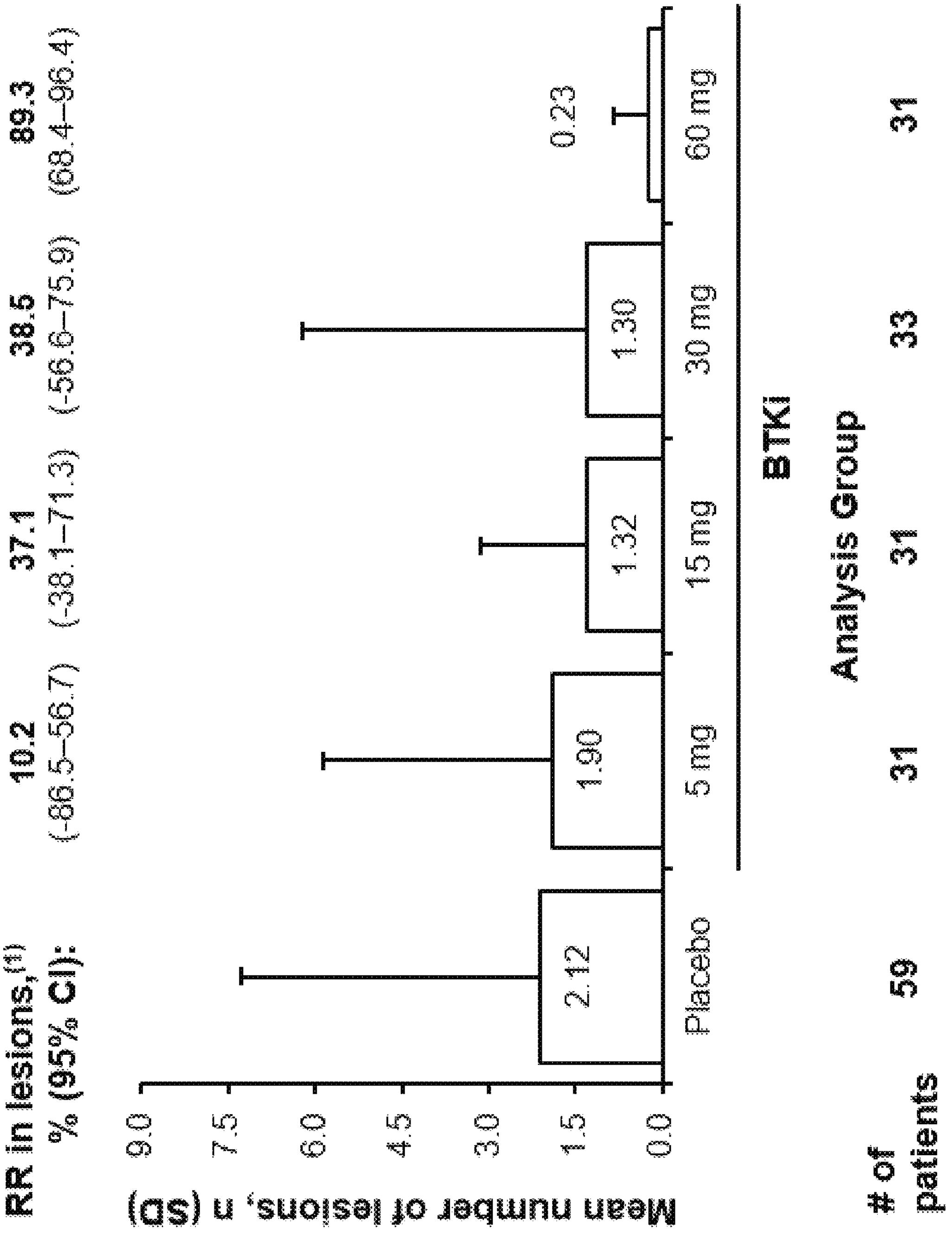
FIG. 3A shows the secondary endpoint results, the number of new or enlarging T2 lesions after 12 weeks of the BTK inhibitor treatment (Cohort 1: Week 12; Cohort 2: Week 16), or 4 weeks of placebo for Cohort 2 patients. Relative reductions (RR) in lesions were adjusted for baseline Gd-enhancing T2-hyperintense lesion activity using a negative binomial model. CI: confidence interval.
Figure 3B:
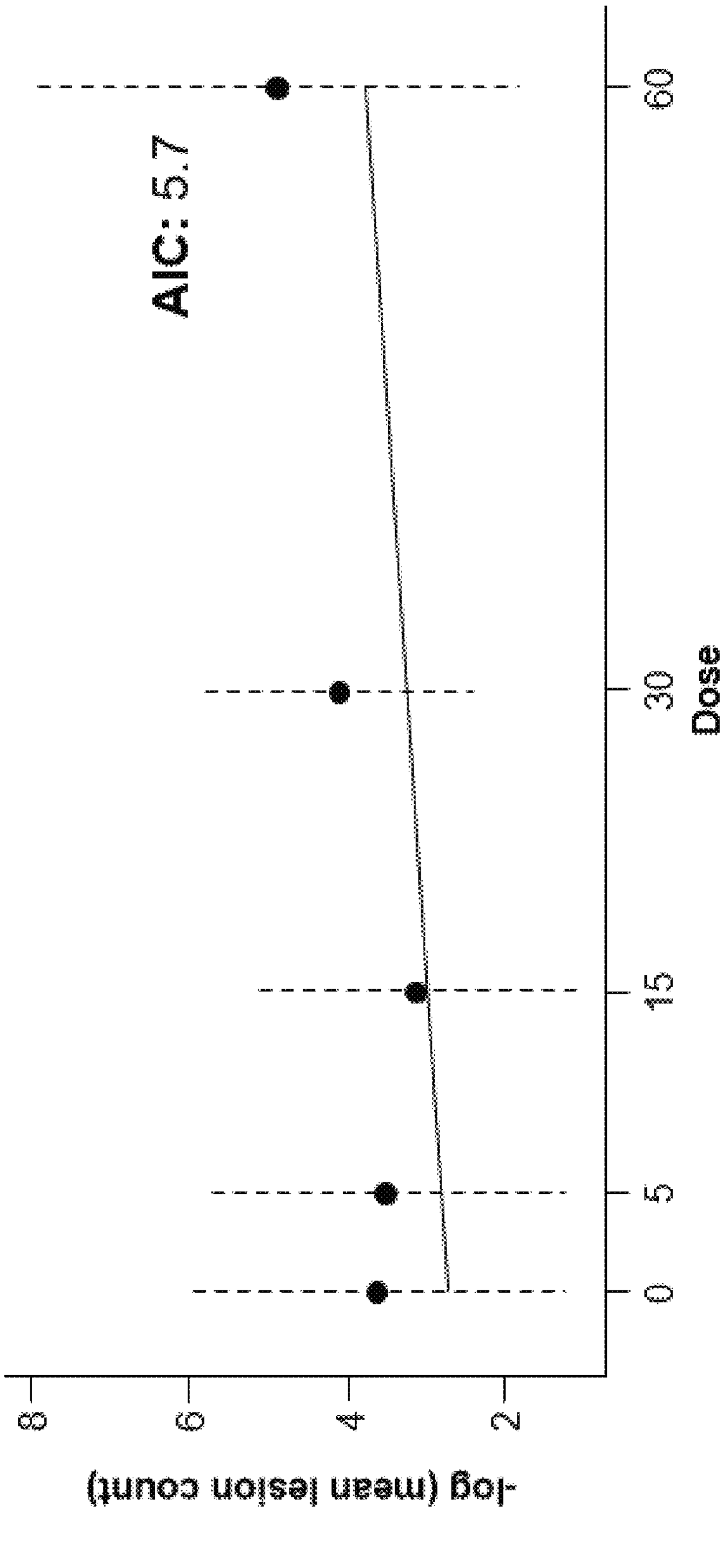
FIG. 3B shows an estimated dose response curve for new and enlarging T2 lesion counts (secondary endpoint) after the BTK inhibitor treatment based on the MCP-Mod analysis.

Main Secondary efficacy endpoints: Table 21 provides a summary of relative reductions vs. placebo of new or enlarging T2 lesion counts after 12 weeks of treatment, as also shown in FIG. 3A. Table 22 shows MCP-Mod of new and enlarging T2 lesions counts after 12 weeks of treatment, as also shown in FIG. 3B. Table 23 provides summary of relative reductions vs. placebo of total T2 Gd-enhancing T1-hyperintense lesion counts after 12 weeks of treatment. Table 24 shows MCP-Mod of total count of Gd-enhancing T1-hyperintense lesions after 12 weeks of treatment. After 12 weeks of the treatment stands for Week 12 for Cohort 1 for the BTK inhibitor treatment, Week 16 for Cohort 2 for the BTK inhibitor treatment, and Week 4 for Cohort 2 placebo. The MRI assessment was excluded from the analyses if the participant was receiving systemic corticosteroids within the 30 days prior to the MRI assessment date. MCP-Mod 1 failed to claim significance.

As shown in Table 21 and FIG. 3A, for the secondary endpoint count of new and enlarging T2 lesions at the end of 12 weeks of the BTK inhibitor treatment, the observed means (SD) were 2.12 (5.16) in the placebo group, 1.90 (3.97) in the BTK inhibitor 5 mg group, 1.32 (1.83) in the BTK inhibitor 15 mg group, 1.30 (4.90) in the BTK inhibitor 30 mg group, and 0.23 (0.62) in the BTK inhibitor 60 mg group. The 60 mg group showed a statistically significant adjusted relative reduction in the count of new and enlarging T2 lesions relative to the placebo group (89.34%; 95% CI. [68.39%, 96.41%]; nominal p-value=0.0001) unlike the other dose groups. 87.1% of participants (27 of 31) in the BTK inhibitor 60 mg group with evaluable MRI data had no new and enlarging T2 lesions at the end of 12 weeks of treatment. The linear model was selected as the best-fitting dose-response curve and shown in FIG. 3B.

As shown in Table 23, for the secondary endpoint count of Gd-enhancing T1-hyperintense lesions at 12 weeks of the BTK inhibitor treatment, the observed means (SD), were 1.36 (3.52) in the placebo group, 1.77 (4.10) in the BTK inhibitor 5 mg group, 0.87 (1.59) in the BTK inhibitor 15 mg group, 1.18 (4.87) in the BTK inhibitor 30 mg group, and 0.29 (0.86) in the BTK inhibitor 60 mg group. No statistically significant relative reduction in count of lesions was observed at any of the BTK inhibitor doses tested relative to placebo. However, a higher percentage of participants in the BTK inhibitor 60 mg group (87.1%, 27 of 31) compared to the placebo group (74.6%, 44 of 59) with evaluable MRI data was observed to have no Gd-enhancing T1-hyperintense lesions at the end of 12 weeks of treatment.

Safety results: the BTK inhibitor was well-tolerated over the 12 weeks of treatment. Table 25A provides overview of treatment-emergent adverse events in Weeks 1-4 period. Table 25B provides overview of adverse events during the 4-week period. Table 25C provide overview of adverse events during the 12-week period. Table 26 provides overview of treatment-emergent adverse events in the BTK inhibitor treatment period. Table 27 provides overview of serious treatment-emergent adverse events in the BTK inhibitor treatment period. Table 28 provides overview of treatment-emergent adverse events of special interest in Weeks 1-4 period. Table 29 provides overview of treatment-emergent adverse events of special interest in the BTK inhibitor treatment period. Table 30 provides overview of adverse events occurring in more than two patients across doses during the 12 weeks treatment.

As shown in Table 17, mean durations of the BTK inhibitor exposure were 82.1, 81.5, 83.6, and 82.1 days for the 5, 15, 30, and 60 mg the BTK inhibitor groups, respectively, and 28.0 days for the placebo group during the first 16 weeks. Mean exposure time to the BTK inhibitor across dosing groups was 82 days.

No deaths were reported in the study. One treatment-emergent SAE was reported in a participant in Cohort 1 treated with 60 mg BTK inhibitor. The event, MS relapse occurring in a 32-year-old female participant, occurred approximately 8 weeks after starting treatment with the BTK inhibitor. The participant had difficulties with her speech and an inability to drink fluids without drooling. No dysphagia was reported in the hospitalization records. She was hospitalized 2 days after experiencing the symptoms to rule out a possible stroke. The event was assessed as severe by the Investigator. MS relapse was confirmed, treatment continued without interruption, and the participant completed the study and was successfully enrolled in the long-term extension study.

All TEAEs reported were of mild or moderate intensity except for one severe TEAE reported in the 60 mg BTK inhibitor group, the SAE of severe MS relapse described above.

There were no TEAEs leading to permanent treatment discontinuation. The proportions of participants who experienced TEAEs in Weeks 1 to 4 were 34.8%, 31.3%, 18.8%, 12.5%, and 31.3% in the placebo and 5, 15, 30, and 60 mg groups, respectively. The proportions of participants with TEAEs were similar in the 4 BTK inhibitor groups (57.6%, 53.1%, 54.5%, and 50.0% in the 5, 15, 30, and 60 mg BTK inhibitor groups, respectively) during the treatment period.

The most frequently reported TEAEs (>3 events total) by primary SOC in the Weeks 1 to 4 (placebo controlled) period were headache (4 cases in the placebo group, 3 in the BTK inhibitor 5 mg group, 2 in the BTK inhibitor 15 mg group, and 1 in the BTK inhibitor 60 mg group), upper respiratory tract infection (1 case in each treatment group, including placebo), and nausea (1 case in the placebo group, 2 in the BTK inhibitor 5 mg group, and 1 in the BTK inhibitor 30 mg group).

As shown in Table 30, the most frequently reported TEAEs by primary SOC in the 12-week BTK inhibitor treatment period were: headache (1 in the BTK inhibitor 5 mg group, 3 in the BTK inhibitor 15 mg group, 1 in the BTK inhibitor 30 mg group, and 4 in the BTK inhibitor 60 mg group), upper respiratory tract infection (2 in the BTK inhibitor 5 mg group, 2 in the BTK inhibitor 15 mg group, 1 in the BTK inhibitor 30 mg group, and 1 in the BTK inhibitor 60 mg group), nasopharyngitis (1 in the BTK inhibitor 5 mg group, 1 in the BTK inhibitor 30 mg group, and 3 in the BTK inhibitor 60 mg group), back pain (1 in the BTK inhibitor 5 mg group, 1 in the BTK inhibitor 15 mg group, and 2 in the BTK inhibitor 30 mg group), oedema peripheral (2 in the BTK inhibitor 5 mg group and 2 in the BTK inhibitor 60 mg group), gastroenteritis (1 in the BTK inhibitor 5 mg group and 2 in the BTK inhibitor 60 mg group), respiratory tract infection (1 in the BTK inhibitor 15 mg group, 1 in the BTK inhibitor 30 mg group, and 1 in the BTK inhibitor 60 mg group), muscle spasticity (1 in the BTK inhibitor 30 mg group and 2 in the BTK inhibitor 60 mg group), oropharyngeal pain (1 in the BTK inhibitor 5 mg group, 1 in the BTK inhibitor 30 mg group, and 1 in the BTK inhibitor 60 mg group), alopecia (1 in the BTK inhibitor 5 mg group, 1 in the BTK inhibitor 15 mg group, and 1 in the BTK inhibitor 60 mg group), alanine aminotransferase increased (1 in the BTK inhibitor 5 mg group, 1 in the BTK inhibitor 30 mg group, and 1 in the BTK inhibitor 60 mg group) and accidental overdose (3 in the BTK inhibitor 60 mg group). Each of the 3 participants who experienced alopecia had a medical history of conditions that could potentially account for the event.

As shown in Table 29, two AESIs (alanine aminotransferase increased >3×ULN) were reported in the study, 1 during the 30 mg BTK inhibitor treatment period and 1 during the 60 mg BTK inhibitor treatment period. In both cases, the liver enzymes elevation was transient, the IMP was not discontinued, liver enzymes returned to normal levels, and the participants completed the study. The event in the participant receiving 60 mg was assessed as mild by the Investigator and with concomitant pruritus reported while the other was assessed as moderate with no concomitant symptoms. One participant (60 mg group) had ALT levels above the ULN (34 U/L) at screening and randomization (48 and 50 U/L, respectively) and reached the >3×ULN level (107 U/L) at the Week 4 visit. The ALT level decreased gradually, reaching the normal level (28 U/L) at Week 12. The other participant (30 mg group) had an ALT level >3×ULN (105 U/L) at the Week 8 visit, and the level returned to a normal level (32 U/L) within 4 days. Both participants were female.

PCSAs related to vital signs (systolic blood pressure, weight), labs (hemoglobin ≤115 g/L [male]; ≤95 g/L [female], hematocrit ≤0.37 v/v [male]; ≤0.32 v/v [female], ALT>3×ULN, bilirubin >1.5×ULN) and ECGs (eg, heart rate <50 beats/min, heart rate >90 beats/min, heart rate >100 beats/min, PR>200 msec, QRS>110 msec, QTc Bazett >450 msec, QTc Fridericia >450 msec) were reported in multiple treatment groups with no dose relationship.

Conclusions

The study met its primary objective, demonstrating a dose-response relationship for the BTK inhibitor as evidenced by a reduction in the number of new active Gd-enhancing T1-hyperintense brain lesions detected by brain MRI after 12 weeks of treatment with a statistically significant difference in the BTK inhibitor 60 mg group as compared to placebo; differences in the other BTK inhibitor treatment groups were not statistically significant compared to placebo. Consistently, efficacy on disease activity was also demonstrated by the reduction in the number of new and enlarging T2 lesions detected by brain MRI after 12 weeks of 60 mg BTK inhibitor treatment, but not so for the 5, 15, and 30 mg BTK inhibitor doses. However, the data did not show a statistically significant reduction in the total count of Gd-enhancing T1-hyperintense lesions after 12 weeks of BTK inhibitor treatment whatever the tested dose.

There was no direct correlation between the dose of the BTK inhibitor administered and number of TEAEs. The most common events (preferred terms) observed in participants in the BTK inhibitor treatment arms were headache, upper respiratory tract infection, and nasopharyngitis. There were low numbers of AESIs and PCSAs observed in multiple dose groups. No new risks were identified in this trial.

These findings indicate that the BTK inhibitor treatment within the dose ranges was well-tolerated and effective at lowering MRI lesions in relapsing MS patients.

TABLE 15

| Patient disposition | | | | | | | | |
|---|---|---|---|---|---|---|---|---|
| n (%) | Placebo/ BTKi 5 (N = 17) | Placebo/ BTKi 15 (N = 16) | Placebo/ BTKi 30 (N = 17) | Placebo/ BTKi 60 (N = 16) | BTKi 5/ Placebo (N = 16) | BTKi 15/ Placebo (N = 16) | BTKi 30/ Placebo (N = 16) | BTKi 60/ Placebo (N = 16) |
| Treated but not randomized/enrolled | 0 | 0 | 0 | 0 | 0 | 0 | 0 | 0 |
| Randomized and not treated | 0 | 0 | 0 | 0 | 0 | 0 | 0 | 0 |
| Randomized and treated | 17 (100) | 16 (100) | 17 (100) | 16 (100) | 16 (100) | 16 (100) | 16 (100) | 16 (100) |
| Completed the treatment period as per protocol | 17 (100) | 16 (100) | 17 (100) | 15 (93.8) | 16 (100) | 16 (100) | 16 (100) | 16 (100) |
| Did not complete the treatment period | 0 | 0 | 0 | 1 (6.3) | 0 | 0 | 0 | 0 |
| Main reason for premature end of treatment | | | | | | | | |
| Adverse event | 0 | 0 | 0 | 0 | 0 | 0 | 0 | 0 |
| Lack of efficacy | 0 | 0 | 0 | 0 | 0 | 0 | 0 | 0 |
| Progressive disease | 0 | 0 | 0 | 0 | 0 | 0 | 0 | 0 |
| Poor compliance to protocol | 0 | 0 | 0 | 0 | 0 | 0 | 0 | 0 |
| Withdrawal by subject | 0 | 0 | 0 | 1 (6.3) | 0 | 0 | 0 | 0 |
| Other | 0 | 0 | 0 | 0 | 0 | 0 | 0 | 0 |
| Reason for treatment withdrawn for participant | | | | | | | | |
| Adverse event | 0 | 0 | 0 | 0 | 0 | 0 | 0 | 0 |
| Study procedure | 0 | 0 | 0 | 1 (6.3) | 0 | 0 | 0 | 0 |
| Other | 0 | 0 | 0 | 0 | 0 | 0 | 0 | 0 |
| Completed the study period | 17 (100) | 16 (100) | 17 (100) | 16 (100) | 16 (100) | 16 (100) | 16 (100) | 16 (100) |
| Did not complete the study period | 0 | 0 | 0 | 0 | 0 | 0 | 0 | 0 |
| Main reason for study discontinuation | | | | | | | | |
| Adverse event | 0 | 0 | 0 | 0 | 0 | 0 | 0 | 0 |
| Poor compliance to protocol | 0 | 0 | 0 | 0 | 0 | 0 | 0 | 0 |
| Study terminated by sponsor | 0 | 0 | 0 | 0 | 0 | 0 | 0 | 0 |
| Other | 0 | 0 | 0 | 0 | 0 | 0 | 0 | 0 |

n: number of participants in the category,
N: number of participants randomized,
BTKi: the BTK inhibitor
Note:
Percentages are calculated using the number of participants randomized as denominator.

TABLE 16A

| Demographic and baseline characteristics<br>Demographics and participant characteristics at baseline - Randomized population | | | | | | |
|---|---|---|---|---|---|---|
| | Placebo (N = 66) | BTKi 5 (N = 33) | BTKi 15 (N = 32) | BTKi 30 (N = 33) | BTKi 60 (N = 32) | All (N = 130) |
| Age (years) | | | | | | |
| Number | 66 | 33 | 32 | 33 | 32 | 130 |
| Mean (SD) | 36.3 (9.8) | 36.0 (9.8) | 35.9 (9.3) | 39.1 (10.2) | 37.1 (8.8) | 37.1 (9.5) |
| Median | 35.5 | 34.0 | 36.5 | 42.0 | 36.5 | 16.0 |

TABLE 16A-continued

Demographic and baseline characteristics
Demographics and participant characteristics at baseline - Randomized population

| | Placebo (N = 66) | BTKi 5 (N = 33) | BTKi 15 (N = 32) | BTKi 30 (N = 33) | BTKi 60 (N = 32) | All (N = 130) |
|---|---|---|---|---|---|---|
| Q1; Q3 | 28.0; 45.0 | 28.0; 44.0 | 28.5; 43.0 | 30.0; 48.0 | 31.0; 43.0 | 29.0; 45.0 |
| Min; Max | 19; 55 | 22; 54 | 19; 54 | 23; 54 | 20; 55 | 19; 55 |
| Sex [n (%)] | | | | | | |
| Number | 66 | 33 | 32 | 33 | 32 | 130 |
| Male | 20 (30.3) | 8 (24.2) | 11 (34.4) | 12 (36.4) | 8 (25.0) | 39 (30.0) |
| Female | 46 (69.7) | 25 (75.8) | 21 (65.6) | 21 (63.6) | 24 (75.0) | 91 (70.0) |
| Race [n (%)] | | | | | | |
| Number | 66 | 33 | 32 | 33 | 32 | 130 |
| White | 61 (92.4) | 32 (97.0) | 29 (90.6) | 29 (87.9) | 29 (90.6) | 119 (91.5) |
| Black or African American | 2 (3.0) | 1 (3.0) | 1 (3.1) | 2 (6.1) | 2 (6.3) | 6 (4.6) |
| Asian | 1 (1.5) | 0 | 0 | 0 | 1 (3.1) | 1 (0.8) |
| Multiple | 1 (1.5) | 0 | 1 (3.1) | 0 | 0 | 1 (0.8) |
| Not Reported | 1 (1.5) | 0 | 1 (3.1) | 2 (6.1) | 0 | 3 (2.3) |
| Ethnicity [n (%)] | | | | | | |
| Number | 66 | 33 | 32 | 33 | 32 | 130 |
| Hispanic or Latino | 1 (1.5) | 0 | 2 (6.3) | 1 (3.0) | 1 (3.1) | 4 (3.1) |
| Not Hispanic or Latino | 62 (93.9) | 32 (97.0) | 29 (90.6) | 31 (93.9) | 29 (90.6) | 121 (93.1) |
| Unknown | 1 (1.5) | 1 (3.0) | 0 | 0 | 1 (3.1) | 2 (1.5) |
| Not Reported | 2 (3.0) | 0 | 1 (3.1) | 1 (3.0) | 1 (3.1) | 3 (2.3) |
| Baseline BMI (kg/m2) | | | | | | |
| Number | 66 | 33 | 32 | 33 | 32 | 130 |
| Mean (SD) | 26.1 (6.2) | 26.5 (6.3) | 24.4 (5.7) | 25.6 (5.2) | 26.1 (4.9) | 25.6 (5.5) |
| Median | 24.3 | 24.3 | 22.9 | 26.6 | 24.3 | 24.3 |
| Q1; Q3 | 22.2; 28.6 | 22.5; 29.4 | 20.9; 26.4 | 22.2; 28.4 | 22.3; 30.1 | 22.1; 28.4 |
| Min; Max | 13; 46 | 18; 46 | 18; 42 | 13; 41 | 19; 36 | 13; 46 |

BMI: body mass index,
n: number of participants in the category,
N: number of participants randomized,
Placebo: the Cohort 2 4-week placebo period,
BTKi: BTK inhibitor

TABLE 16B

Patient baseline characteristics

| | | | BTKi | | | |
|---|---|---|---|---|---|---|
| | All Patients (N = 130) | Placebo[a] (N = 66) | 5 mg (N = 33) | 15 mg (N = 32) | 30 mg (N = 33) | 60 mg (N = 32) |
| Age, years | 37.1 (9.5) | 36.3 (9.8) | 36.0 (9.8) | 35.9 (9.3) | 39.1 (10.2) | 37.1 (8.8) |
| Female, n (%) | 91 (70%) | 46 (70%) | 25 (76%) | 21 (66%) | 21 (64%) | 24 (75%) |
| RRMS, n (%) | 128 (99%) | 65 (99%) | 33 (100%) | 32 (100%) | 32 (97%) | 31 (97%) |
| Time since initial relapse, years | 7.8 (7.4) | 7.7 (7.4) | 7.7 (7.8) | 8.0 (7.6) | 8.1 (7.8) | 7.3 (6.7) |
| Relapses in previous year | 1.2 (0.6) | 1.2 (0.5) | 1.2 (0.5) | 1.3 (0.6) | 1.3 (0.6) | 1.2 (0.4) |
| Relapses in previous 2 years | 1.7 (0.9) | 1.7 (0.7) | 1.7 (0.8) | 1.5 (0.8) | 1.8 (1.1) | 1.6 (0.9) |
| EDSS score, median ($25^{th}$-$75^{th}$ percentiles) | 2.5 (1.5-3.5) | 2.5 (1.5-3.5) | 2.5 (2.0-3.0) | 2.0 (1.5-3.0) | 2.5 (1.5-3.5) | 2.5 (1.5-3.8) |
| Highly active disease, n (%) | 61 (47%) | 29 (44%) | 12 (36%) | 19 (59%) | 16 (49%) | 14 (44%) |

TABLE 16B-continued

Patient baseline characteristics

| | All Patients (N = 130) | Placebo[a] (N = 66) | BTKi 5 mg (N = 33) | BTKi 15 mg (N = 32) | BTKi 30 mg (N = 33) | BTKi 60 mg (N = 32) |
|---|---|---|---|---|---|---|
| Number of Gd-enhancing lesions | 1.8 (4.7) | 2.2 (5.9) | 2.3 (5.9) | 0.7 (1.8) | 1.9 (4.9) | 2.1 (4.9) |
| Patients with baseline Gd-enhancing lesions, n (%) | 44 (35%)[b] | 25 (38%) | 11 (34%)[c] | 7 (23%)[d] | 11 (34%)[c] | 15 (47%) |

EDSS = Expanded Disability Status Scale;

Gd = gadolinium;

RRMS = relapsing-remitting multiple sclerosis. Highly active disease was defined as 1 relapse in the year prior to screening and ≥1 Gd-enhancing lesion on MRI performed within 6 months prior to screening or ≥9 T2 lesions at baseline or ≥2 relapses in the year prior to screening.
Values are mean (SD) except where noted;

[a]Includes Cohort 2 placebo arm only, which began the BTKi treatment at Week 4;

[b]N = 127;

[c]N = 32;

[d]N = 31.

TABLE 17

Duration of exposure: safety population
Extent of exposure to investigational medicinal product - Safety population

| | Placebo (N = 66) | BTKi 5 (N = 33) | BTKi 15 (N = 33) | BTKi 30 (N = 33) | BTKi 60 (N = 32) | All (N = 130) |
|---|---|---|---|---|---|---|
| Duration of study treatment (days) | | | | | | |
| Number | 66 | 33 | 33 | 33 | 32 | 131 |
| Mean (SD) | 28.0 (1.8) | 82.1 (5.5) | 81.5 (10.1) | 83.6 (1.5) | 82.1 (7.0) | 82.3 (6.7) |
| Median | 28.0 | 83.0 | 84.0 | 84.0 | 84.0 | 84.0 |
| Min; Max | 18; 32 | 54; 91 | 29; 89 | 78; 86 | 51; 89 | 29; 91 |
| Duration of study treatment by category [n (%)] | | | | | | |
| Number | 66 | 33 | 33 | 33 | 32 | 131 |
| Missing duration | 0 | 0 | 0 | 0 | 0 | 0 |
| 1 to 28 days [Week 4] | 48 (72.7) | 0 | 0 | 0 | 0 | 0 |
| 29 to 56 days [Week 8] | 18 (27.3) | 1 (3.0) | 1 (3.0) | 0 | 1 (3.1) | 3 (2.3) |
| 57 to 84 days [Week 12] | 0 | 31 (93.9) | 24 (72.7) | 26 (78.8) | 23 (71.9) | 104 (79.4) |
| 85 to 112 days [Week 16] | 0 | 1 (3.0) | 8 (24.2) | 7 (21.2) | 8 (25.0) | 24 (18.3) |
| >112 days | 0 | 0 | 0 | 0 | 0 | 0 |
| Cumulative duration of study treatment by category [n (%)] | | | | | | |
| Number | 66 | 33 | 33 | 33 | 32 | 131 |
| >=1 day | 66 (100.0) | 33 (100.0) | 33 (100.0) | 33 (100.0) | 32 (100.0) | 131 (100.0) |
| >=29 days | 18 (27.3) | 33 (100.0) | 33 (100.0) | 33 (100.0) | 32 (100.0) | 131 (100.0) |
| >=57 days | 0 | 32 (97.0) | 32 (97.0) | 33 (100.0) | 31 (96.9) | 128 (97.7) |
| >=85 days | 0 | 1 (3.0) | 8 (24.2) | 7 (21.2) | 8 (25.0) | 24 (18.3) |
| >112 days | 0 | 0 | 0 | 0 | 0 | 0 |

n: number of participants in the category,

N: number of participants in safety population,

Placebo: the Cohort 2 4-week placebo period,

BTKi: the BTK inhibitor

Duration of IMP exposure is defined as last dose date - first dose date +1 day, regardless of unplanned intermittent discontinuations

TABLE 18

| Duration of exposure: safety population | | | | |
|---|---|---|---|---|
| | BTKi 5 (N = 33) | BTKi 15 (N = 33) | BTKi 30 (N = 33) | BTKi 60 (N = 32) |
| Total cumulative dose (mg) | | | | |
| Number | 33 | 33 | 33 | 32 |
| Mean (SD) | 410.3 (27.5) | 1222.7 (151.5) | 2507.3 (43.8) | 4929.4 (415.2) |
| Median | 415.0 | 1260.0 | 2520.0 | 5040.0 |
| Min; Max | 270; 455 | 435; 1335 | 2340; 2580 | 3060; 5340 |
| Mean daily dose (mg/day) | | | | |
| Number | 33 | 33 | 33 | 32 |
| Mean (SD) | 5.0 (0.0) | 15.0 (0.0) | 30.0 (0.0) | 60.0 (0.2) |
| Median | 5.0 | 15.0 | 30.0 | 60.0 |
| Min; Max | 5; 5 | 15; 15 | 30; 30 | 60; 61 |

TABLE 19

| Descriptive summary and relative reductions vs. placebo of New Gd-enhancing T1-hyperintense lesion after 12 weeks of treatment | | | | | |
|---|---|---|---|---|---|
| Efficacy parameters (unit) | Placebo (N = 66) | BTKi 5 (N = 33) | BTKi 15 (N = 32) | BTKi 30 (N = 33) | BTKi 60 (N = 32) |
| Patients with at least 1 MRI scan** | 66 | 33 | 32 | 33 | 32 |
| After 12 weeks of the BTK inhibitor treatment | | | | | |
| Number of lesions[n (%)] | 59 | 31 | 31 | 33 | 31 |
| 0 | 44 (74.6) | 22 (71.0) | 21 (67.7) | 27 (81.8) | 28 (90.3) |
| 1 | 4 (6.8) | 2 (6.5) | 5 (16.1) | 4 (12.1) | 2 (6.5) |
| 2 | 3 (5.1) | 3 (9.7) | 1 (3.2) | 1 (3.0) | 1 (3.2) |
| >=3 | 8 (13.6) | 4 (12.9) | 4 (12.9) | 1 (3.0) | 0 |
| Number | 59 | 31 | 31 | 33 | 31 |
| Mean (SD) | 1.03 (2.50) | 1.39 (3.20) | 0.77 (1.48) | 0.76 (3.31) | 0.13 (0.43) |
| Median | 0.00 | 0.00 | 0.00 | 0.00 | 0.00 |
| Q1; Q3 | 0.00; 1.00 | 0.00; 1.00 | 0.00; 1.00 | 0.00; 0.00 | 0.00; 0.00 |
| Min; Max | 0.0; 14.0 | 0.0; 12.0 | 0.0; 5.0 | 0.0; 19.0 | 0.0; 2.0 |
| Relative reduction in lesions vs. placebo (%) (95% CI) | | | | | |
| Unadjusted | NA | −34.16 (−214.64, 42.79) | 25.85 (−87.05, 70.60) | 26.73 (−128.23, 76.48) | 87.52 (57.48, 96.34) |
| Adjusted# | NA | −56.16 (−193.99, 17.05) | −62.80 (−356.24, 41.91) | 13.49 (−126.05, 66.89) | 85.02 (28.02, 96.88) |
| Nominal p-value*** | | 0.1673 | 0.3540 | 0.7674 | 0.0178 |

BTKi: the BTK inhibitor mg daily.

* After 12 weeks of the BTK inhibitor treatment stands for Week 12 for Cohort 1 for the BTK inhibitor treatment, Week 16 for Cohort 2 for the BTK inhibitor treatment, and Week 4 for Cohort 2 placebo.

**The MRI assessment was excluded from the analyses if the participant was receiving systemic corticosteroids within the 30 days prior to the MRI assessment date.

#Negative binomial model adjusting for baseline Gd enhancing T1 hyperintense lesion activity (presence/absence).

***p-value without multiplicity adjustment.

TABLE 20

| MCP-Mod for new Gd-enhancing T1 hyperintense lesion after 12 weeks of treatment | | | | | |
|---|---|---|---|---|---|
| | Linear | Quadratic | Logistic | Emax ED50 = 10 mg & ED50 = 30 mg | Exponential |
| Test statistic | 1.4874 | 0.4096 | 1.6095 | 0.2 & 0.7064 | 2.4654 |
| Adjusted p-value | 0.2632 | 0.9223 | 0.2112 | 0.9891 & 0.7437 | 0.0315 |
| AIC criteria | — | — | — | — | 8.517 |
| Model parameters | — | — | — | — | e0 = 0.7116<br>e1 = 0.0001<br>delta = 6 |

BTKi: the BTK inhibitor mg daily.

* After 12 weeks of the BTK inhibitor treatment stands for Week 12 for Cohort 1 for the BTK inhibitor treatment, Week 16 for Cohort 2 for the BTK inhibitor treatment, and Week 4 for Cohort 2 placebo.

Note 1:

The MRI assessment was excluded from the analyses if the participant was receiving systemic corticosteroids within the 30 days prior to the MRI assessment date.

Note 2:

Exponential model with the smallest AIC was selected.

TABLE 21

| Descriptive summary and relative reductions vs. placebo of new or enlarging T2 lesion counts after 12 weeks of treatment | | | | | |
|---|---|---|---|---|---|
| Efficacy parameters (unit) | Placebo (N = 66) | BTKi 5 (N = 33) | BTKi 15 (N = 32) | BTKi 30 (N = 33) | BTKi 60 (N = 32) |
| Patients with at least 1 MRI scan** | 66 | 33 | 32 | 33 | 32 |
| After 12 weeks of the BTK inhibitor treatment | | | | | |
| Number of lesions[n (%)] | 59 | 31 | 31 | 33 | 31 |
| 0 | 39 (66.1) | 19 (61.3) | 15 (48.4) | 24 (72.7) | 27 (87.1) |
| 1 | 5 (8.5) | 3 (9.7) | 7 (22.6) | 5 (15.2) | 1 (3.2) |
| 2 | 3 (5.1) | 4 (12.9) | 3 (9.7) | 1 (3.0) | 3 (9.7) |
| >=3 | 12 (20.3) | 5 (16.1) | 6 (19.4) | 3 (9.1) | 0 |
| Number | 59 | 31 | 31 | 33 | 31 |
| Mean (SD) | 2.12 (5.16) | 1.90 (3.97) | 1.32 (1.83) | 1.30 (4.90) | 0.23 (0.62) |
| Median | 0.00 | 0.00 | 1.00 | 0.00 | 0.00 |
| Q1; Q3 | 0.00; 2.00 | 0.00; 2.00 | 0.00; 2.00 | 0.00; 1.00 | 0.00; 0.00 |
| Min; Max | 0.0; 30.0 | 0.0; 14.0 | 0.0; 6.0 | 0.0; 28.0 | 0.0; 2.0 |
| Relative reduction in lesions vs. placebo (%) (95% CI) | | | | | |
| Unadjusted | NA | 10.17 (−86.49, 56.73) | 37.07 (−38.08, 71.32) | 38.50 (−56.61, 75.85) | 89.34 (68.39, 96.41) |
| Adjusted# | NA | 10.17 (−86.49, 56.73) | 37.07 (−38.08, 71.32) | 38.50 (−56.61, 75.85) | 89.34 (68.39, 96.41) |
| Nominal p-value*** | | 0.7736 | 0.2480 | 0.3081 | 0.0001 |

BTKi: the BTK inhibitor mg daily.

* After 12 weeks of the BTK inhibitor treatment stands for Week 12 for Cohort 1 for the BTK inhibitor treatment, Week 16 for Cohort 2 for the BTK inhibitor 8 treatment, and Week 4 for Cohort 2 placebo.

**The MRI assessment was excluded from the analyses if the participant was receiving systemic corticosteroids within the 30 days prior to the MRI assessment date.

#Negative binomial model adjusting for baseline T2 hyperintense lesion activity (presence/absence).

***p-value without multiplicity adjustment.

TABLE 22

| MCP-Mod for new and enlarging T2 lesions counts after 12 weeks of treatment | | | | | |
|---|---|---|---|---|---|
| | Linear | Quadratic | Logistic | Emax ED50 = 10 mg & ED50 = 30 mg | Exponential |
| Test statistic | 4.3227 | 3.3452 | 4.1482 | 3.3509 & 3.7829 | 4.335 |
| Adjusted p-value | <0.0001 | 0.0017 | <0.0001 | 0.002 & 0.0006 | <0.0001 |
| AIC criteria | 5.7243 | 6.4205 | 8.3756 | 9.6229 | 6.3585 |
| Model parameters | e0 = −0.6878 | e0 = −0.6112 | e0 = −0.979 | e0 = −0.7087 | e0 = −0.6211 |
| | delta = 0.0296 | b1 = 0.0099<br>b2 = 0.0004 | eMax = 9.7148<br>ed50 = 90<br>delta = 27.6733 | eMax = 3.7664<br>ed50 = 90 | e1 = 0.4753<br>delta = 35.5224 |

BTKi: the BTK inhibitor mg daily.

* After 12 weeks of the BTK inhibitor treatment stands for Week 12 for Cohort 1 for the BTK inhibitor treatment, Week 16 for Cohort 2 for the BTK inhibitor treatment, and Week 4 for Cohort 2 placebo.

Note 1:

The MRI assessment was excluded from the analyses if the participant was receiving systemic corticosteroids within the 30 days prior to the MRI assessment date.

Note 2:

Linear model with the smallest AIC was selected.

TABLE 23

| Descriptive summary and relative reductions vs. placebo of Total Gd-enhancing T1-hyperintense lesion after 12 weeks of treatment* | | | | | |
|---|---|---|---|---|---|
| Efficacy parameters (unit) | Placebo (N = 66) | BTKi 5 (N = 33) | BTKi 15 (N = 32) | BTKi 30 (N = 33) | BTKi 60 (N = 32) |
| Patients with at least 1 MRI scan** | 66 | 33 | 32 | 33 | 32 |
| Baseline | | | | | |
| Number of lesions[n (%)] | 66 | 32 | 31 | 32 | 32 |
| 0 | 41 (62.1) | 21 (65.6) | 24 (77.4) | 21 (65.6) | 17 (53.1) |
| 1 | 12 (18.2) | 4 (12.5) | 3 (9.7) | 4 (12.5) | 6 (18.8) |
| 2 | 2 (3.0) | 1 (3.1) | 1 (3.2) | 2 (6.3) | 1 (3.1) |
| >=3 | 11 (16.7) | 6 (18.8) | 3 (9.7) | 5 (15.6) | 8 (25.0) |
| Number | 66 | 32 | 31 | 32 | 32 |
| Mean (SD) | 2.20 (5.86) | 2.28 (5.93) | 0.71 (1.83) | 1.91 (4.91) | 2.09 (4.89) |
| Median | 0.00 | 0.00 | 0.00 | 0.00 | 0.00 |
| Q1; Q3 | 0.00; 1.00 | 0.00; 1.00 | 0.00; 0.00 | 0.00; 1.00 | 0.00; 2.50 |
| Min; Max | 0.0; 30.0 | 0.0; 30.0 | 0.0; 8.0 | 0.0; 25.0 | 0.0; 25.0 |
| After 12 weeks of the BTKi inhibitor treatment | | | | | |
| Number of lesions[n (%)] | 59 | 31 | 31 | 33 | 31 |
| 0 | 44 (74.6) | 20 (64.5) | 20 (64.5) | 25 (75.8) | 27 (87.1) |
| 1 | 4 (6.8) | 4 (12.9) | 6 (19.4) | 4 (12.1) | 1 (3.2) |
| 2 | 2 (3.4) | 2 (6.5) | 0 | 2 (6.1) | 2 (6.5) |
| >=3 | 9 (15.3) | 5 (16.1) | 5 (16.1) | 2 (6.1) | 1 (3.2) |
| Number | 59 | 31 | 31 | 33 | 31 |
| Mean (SD) | 1.36 (3.52) | 1.77 (4.10) | 0.87 (1.59) | 1.18 (4.87) | 0.29 (0.86) |
| Median | 0.00 | 0.00 | 0.00 | 0.00 | 0.00 |
| Q1; Q3 | 0.00; 1.00 | 0.00; 1.00 | 0.00; 1.00 | 0.00; 0.00 | 0.00; 0.00 |
| Min; Max | 0.0; 19.0 | 0.0; 18.0 | 0.0; 5.0 | 0.0; 28.0 | 0.0; 4.0 |

TABLE 23-continued

Descriptive summary and relative reductions vs. placebo of Total Gd-enhancing T1-hyperintense lesion after 12 weeks of treatment*

| Efficacy parameters (unit) | Placebo (N = 66) | BTKi 5 (N = 33) | BTKi 15 (N = 32) | BTKi 30 (N = 33) | BTKi 60 (N = 32) |
|---|---|---|---|---|---|
| Relative reduction in lesions vs. placebo (%) (95% CI) | | | | | |
| Unadjusted | NA | −30.85 (−236.38, 49.10) | 36.08 (−61.34, 74.68) | 12.84 (−152.99, 69.97) | 78.59 (30.82, 93.37) |
| Adjusted# | NA | −62.16 (−214.44, 16.38) | −47.38 (−312.91, 47.40) | 2.90 (−138.96, 60.54) | 65.05 (−96.21, 93.77) |
| Nominal p-value*** | | 0.1525 | 0.4606 | 0.9490 | 0.2324 |

BTKi: the BTK inhibitor mg daily.

*After 12 weeks of the BTK inhibitor treatment stands for Week 12 for Cohort 1 for the BTK inhibitor treatment, Week 16 for Cohort 2 for the BTK inhibitor treatment, and Week 4 for Cohort 2 placebo.

**The MRI assessment was excluded from the analyses if the participant was receiving systemic corticosteroids within the 30 days prior to the MRI assessment date.

#Negative binomial model adjusting for baseline Gd enhancing T1 hyperintense lesion activity (presence/absence).

***p-value without multiplicity adjustment.

TABLE 24

MCP-Mod for total count of Gd-enhancing T1-hyperintense lesions after 12 weeks of treatment

| | Linear | Quadratic | Logistic | $E_{max}$ ED50 = 10 mg & ED50 = 30 mg | Exponential |
|---|---|---|---|---|---|
| Test statistic | 0.5402 | 0.143 | 0.663 | 0.3512 & 0.0098 | 1.2898 |
| Adjusted p-value | 0.8569 | 0.9964 | 0.7793 | 0.9499 & 1 | 0.3663 |

TABLE 25A

Overview of treatment-emergent adverse events - Weeks 1 to 4

| n (%) | Placebo (N = 65) | BTKi 5 (N = 32) | BTKi 15 (N = 32) | BTKi 30 (N = 33) | BTKi 60 (N = 33) | All (N = 130) |
|---|---|---|---|---|---|---|
| Participants with any TEAE | 19 (29.2) | 8 (25.0) | 14 (43.8) | 14 (42.4) | 14 (42.4) | 50 (38.5) |
| Participants with any severe TEAE | 0 | 0 | 0 | 0 | 0 | 0 |
| Participants with any treatment emergent SAE | 0 | 0 | 0 | 0 | 0 | 0 |
| Participants with any TEAE leading to death | 0 | 0 | 0 | 0 | 0 | 0 |
| Participants with any TEAE leading to study treatment discontinuation | 0 | 0 | 0 | 0 | 0 | 0 |
| Participants with study discontinuation due to any TEAE | 0 | 0 | 0 | 0 | 0 | 0 |
| Participants with any treatment-related TEAE | 5 (7.7) | 4 (12.5) | 1 (3.1) | 4 (12.1) | 3 (9.1) | 12 (9.2) |

TEAE: Treatment emergent adverse event,

SAE: Serious adverse event n (%) = number and percentage of participants with at least one TEAE Note:

Placebo is the Cohort 2 4-week placebo period.

TABLE 25B

| Overview of adverse events - Weeks 1 to 4 | | | | | | |
|---|---|---|---|---|---|---|
| | All Dose Groups (N = 130) | Placebo (N = 66)[1] | BTKi 5 mg (n = 16) | BTKi 15 mg (n = 16) | BTKi 30 mg (n = 16) | BTKi 60 mg (n = 16) |
| Any AE (4 weeks vs. placebo \| 12 weeks) | 38 (29.2%) | 23 (34.8%) | 5 (31.3%) | 3 (18.9%) | 2 (12.5%) | 5 (31.3%) |
| Serious AE | 0 | 0 | 0 | 0 | 0 | 0 |
| AE leading to death | 0 | 0 | 0 | 0 | 0 | 0 |
| AE leading to study discontinuation | 0 | 0 | 0 | 0 | 0 | 0 |
| Any AE leading to study treatment discontinuation | 0 | 0 | 0 | 0 | 0 | 0 |
| Any treatment-related AE | 10 (7.7%) | 7 (10.6&) | 2 (12.5%) | 0 | 0 | 1 (6.3%) |

[1]Includes Cohort 2 placebo arm only, which began the BTKi treatment at Week 4

TABLE 25C

| Overview of adverse events-Weeks 1 to 12 | | | | | |
|---|---|---|---|---|---|
| n (%) | All Dose Groups (N = 130) | BTKi 5 mg (n = 33) | BTKi 15 mg (n = 32) | BTKi 30 mg (n = 33) | BTKi 60 mg (n = 32) |
| Any AE (4 weeks vs. placebo 12 weeks) | 70 (53.8) | 19 (57.6) | 17 (53.1) | 18 (54.5) | 16 (50.0) |
| Serious AE | 1 (0.8) | 0 | 0 | 0 | 1 (3.1) |
| AE leading to death | 0 | 0 | 0 | 0 | 0 |
| AE leading to study discontinuation | 0 | 0 | 0 | 0 | 0 |
| Any AE leading to study treatment discontinuation | 0 | 0 | 0 | 0 | 0 |
| Any treatment-related AE | 17 (13.1) | 5 (15.2) | 1 (3.1) | 4 (12.1) | 7 (21.9) |

TABLE 26

| Overview of treatment-emergent adverse events-the BTK inhibitor treatment period, safety population | | | | | |
|---|---|---|---|---|---|
| n (%) | BTKi 5 (N = 32) | BTKi 15 (N = 32) | BTKi 30 (N = 33) | BTKi 60 (N = 33) | All (N = 130) |
| Participants with any TEAE | 16 (50.0) | 18 (56.3) | 17 (51.5) | 18 (54.5) | 69 (53.1) |
| Participants with any severe TEAE | 0 | 0 | 1 (3.0) | 0 | 1 (0.8) |
| Participants with any treatment emergent SAE | 0 | 0 | 1 (3.0) | 0 | 1 (0.8) |
| Participants with any TEAE leading to death | 0 | 0 | 0 | 0 | 0 |
| Participants with any TEAE leading to study treatment discontinuation | 0 | 0 | 0 | 0 | 0 |

TABLE 26-continued

Overview of treatment-emergent adverse events-the BTK inhibitor treatment period, safety population

| n (%) | BTKi 5 (N = 32) | BTKi 15 (N = 32) | BTKi 30 (N = 33) | BTKi 60 (N = 33) | All (N = 130) |
|---|---|---|---|---|---|
| Participants with study discontinuation due to any TEAE | 0 | 0 | 0 | 0 | 0 |
| Participants with any treatment-related TEAE | 6 (18.8) | 3 (9.4) | 4 (12.1) | 2 (6.1) | 15 (11.5) |

TEAE: Treatment emergent adverse event, SAE: Serious adverse event
n (%) = number and percentage of participants with at least one TEAE

TABLE 27

Serious treatment-emergent adverse events-the BTK inhibitor treatment period, safety population Number (%) of participants with treatment emergent SAE(s) by Primary SOC and PT in the BTK Inhibitor Treatment Period-Safety population

| PRIMARY SYSTEM ORGAN CLASS Preferred Term n (%) | BTKi 5 (N = 32) | BTKi 15 (N = 32) | BTKi 30 (N = 33) | BTKi 60 (N = 33) | All (N = 130) |
|---|---|---|---|---|---|
| Any class | 0 | 0 | 1 (3.0) | 0 | 1 (0.8) |
| NERVOUS SYSTEM DISORDERS | 0 | 0 | 1 (3.0) | 0 | 1 (0.8) |
| Multiple sclerosis relapse | 0 | 0 | 1 (3.0) | 0 | 1 (0.8) |

SAE: Serious adverse event, SOC: System organ class, PT: Preferred term MedDRA 22.1
n (%) = number and percentage of participants with at least one treatment emergent SAE
Note:
Table sorted by SOC internationally agreed order and PT sorted by decreasing frequency according to all TEAE summary

TABLE 28

Treatment-emergent adverse events of special interest - Weeks 1 to 4

| Primary System Organ Class Preferred Term n (%) | Placebo (N = 66) | BTK inhibitor 5 (N = 16) | BTK inhibitor 15 (N = 16) | BTK inhibitor 30 (N = 16) | BTK inhibitor 60 (N = 16) | All (N = 130) |
|---|---|---|---|---|---|---|
| Any AESI | 1 (1.5) | 0 | 0 | 0 | 0 | 1 (0.8) |
| Investigations | 1 (1.5) | 0 | 0 | 0 | 0 | 1 (0.8) |
| Alanice aminotransferase increased | 1 (1.5) | 0 | 0 | 0 | 0 | 1 (0.8) |

TABLE 29

Treatment-emergent adverse events of special interest-the BTK inhibitor treatment period, safety population

| Primary System Organ Class Preferred Term n (%) | BTK inhibitor 5 (N = 33) | BTK inhibitor 15 (N = 32) | BTK inhibitor 30 (N = 33) | BTK inhibitor 60 (N = 32) | All (N = 130) |
|---|---|---|---|---|---|
| Any AESI | 0 | 0 | 1 (3.0) | 1 (3.1) | 2 (1.5) |
| Investigations | 0 | 0 | 1 (3.0) | 1 (3.1) | 2 (1.5) |
| Alanice aminotransferase increased | 0 | 0 | 1 (3.0) | 1 (3.1) | 2 (1.5) |

TABLE 30

| Adverse events occurring in >2 Patients across doses during the 12 weeks treatment | | | | | |
|---|---|---|---|---|---|
| | All Dose Groups (N = 130) | BTKi 5 mg (n = 33) | BTKi 15 mg (n = 32) | BTKi 30 mg (n = 33) | BTKi 60 mg (n = 32) |
| Headache | 9 (7%) | 1 (3%) | 3 (9%) | 1 (3%) | 4 (13%) |
| Upper respiratory tract infection | 6 (5%) | 2 (6%) | 2 (6%) | 1 (3%) | 1 (3%) |
| Nasopharyngitis | 5 (4%) | 1 (3%) | 0 | 1 (3%) | 3 (9%) |
| Back pain | 4 (3%) | 1 (3%) | 1 (3%) | 2 (6%) | 0 |
| Peripheral edema | 4 (3%) | 2 (6%) | 0 | 0 | 2 (6%) |
| Accidental overdose | 3 (2%) | 0 | 0 | 0 | 3 (9%) |
| Gastroenteritis | 3 (2%) | 1 (3%) | 0 | 0 | 2 (6%) |
| Alanine aminotransferase increased | 3 (2%) | 1 (3%) | 0 | 1 (3%) | 1 (3%) |
| Respiratory tract infection | 3 (2%) | 0 | 1 (3%) | 1 (3%) | 1 (3%) |
| Muscle spasticity | 3 (2%) | 0 | 0 | 1 (3%) | 2 (6%) |
| Oropharyngeal pain | 3 (2%) | 1 (3%) | 0 | 1 (3%) | 1 (3%) |
| Alopecia | 3 (2%) | 1 (3%) | 1 (3%) | 0 | 1 (3%) |

Example 3

Using primary mouse microglial cells, the roles of BTK were investigated.

Generation of Primary Mouse Microglial Cells

Collection of Post-Natal Mouse Brains

Primary cultures of microglia were obtained from brains of C57BL/6 postnatal mice. The mice were anesthetized with $CO_2$ and subsequently decapitated with sterilized scissors. Brains were harvested and meninges were removed. The brains were placed in ice cold complete DMEM/F12 medium and kept on ice until processing.

Brain Tissue Processing

The brains were removed from the medium by filtering through a 40 μm cell strainer. The brains were transferred into warm (37° C.) 0.25% trypsin (2 mL/brain) and incubated at 37° C. while rotating for 30 minutes. The dissociation reaction was quenched with an equal volume of complete DMEM/F12. The tissue was centrifuged at 300×g for 7 minutes. The tissue pellet was washed 3 times with complete DMEM/F12, centrifuged at 300×g for 7 minutes. After the final wash, tissue pellet was re-suspended in complete DMEM/F12 (~1 mL/brain), triturated until no chunks are visible, then filtered through a 70 μm cell strainer. The cells were distributed into T150 tissue culture flasks (1 flask/mouse) in the final volume per flask of up to 35 mL with complete DMEM/F12. The cells were fed with a complete medium change every 3-4 days until isolation, beginning on day 5.

Microglial Cell Isolation

After 11 to 14 days in culture, the cells were washed with PBS, and treated with 5 mL 0.25% trypsin, and triturated in 10 mL complete DMEM/F12. The single cell suspensions were filtered through 70 μm cell strainers, centrifuged at 200×g for 6 minutes, and re-suspended at $1\times10^8$ cells/mL in separation media. Up to 4 mL of the cells were transferred to 14 mL polystyrene FACS tubes. 50 μl/mL rat serum was added to each sample and the samples were incubated for 5 minutes. The selection cocktail was prepared by mixing equal parts of Cocktail A and B. (For 1 ml sample mix 25 μl of Cocktail A with 25 μl Cocktail B), and incubating for 5 minutes. The EasySep (Stemcell technologies, Vancouver CA) selection cocktail (50 μL per mL of cells) provided in the kit were added to the FACS tubes, mix well with a pipet tip and incubate in 5 minutes. The EasySep RapidSpheres provided in the kit were vortexed for 30 seconds, 80 μL per mL of cells, were added, mixed with a pipet tip, and incubated at room temperature 3 minutes. The separation media were added to top off the sample to the indicated volume (5 ml for samples <3 ml-10 ml for samples > or =3 ml). The tubes were placed in the EasySep Magnets for 5 minutes. In one fluid motion, the unlabeled cells were poured off in buffer while the tube is still in the magnet and held inverted for 2-3 seconds. The tube was removed from the magnet, and added with the appropriate amount of separation media, and left for another 5 minutes. The magnetic separation/washing process was performed 4 times to remove all unlabeled cells. After the last wash, the labeled CD11b+ microglia cells were resuspended in serum free NbActiv1 media, counted and re-suspended at the desired concentration.

In Vitro Signature Methods

After isolation, microglia were plated at 1 million cells per well on a 12 well plate and rested for 24 hours. Microglia were pre-treated with 2.5 μM the BTK inhibitor for 30 minutes, and aggregated/complexed IgG (50 μg/mL) was added to the stimulated cell groups after pretreatment and the cells were incubated for 6 h or 24 h. Cells were lysed in 200 μL Qiazol and were sent for RNA isolation and sequencing (Genewiz, South Plainfield NJ).

Analysis of the RNASeq library data was conducted within Omicsoft's Array Studio platform following a standard RNAseq protocol. In general, the sequencing reads were quality checked and the samples were mapped to the mouse mm10 reference genome using the ENSEMBL.R89 gene model. Expression measurement (transcripts) were collected as both FPKM and counts. A low count filter was applied per set of 4× biological replicates (groups) where only groups that had transcript counts >15 in at least two replicates were retained. The low counts filter was applied to the FPKM count data. In addition, only transcripts that mapped to coding genes were retained. After applying these filters 12,790 FPKM transcripts remained. The FPKM data was quantile normalized to the 75th percentile. A value of one was added to all samples prior to log 2 transformation.

T-tests were conducted for the following comparisons between the treatment with IgG only and the treatment with IgG and the BTK inhibitor at 6 hours and 24 hours, respectively. In all comparisons, differential expressed genes (DEGs) were determined to be transcripts that met the following criteria: fold change >1.2 or <−1.2 & p-value <0.05 (fc1.2,p0.05).

Figure 4:
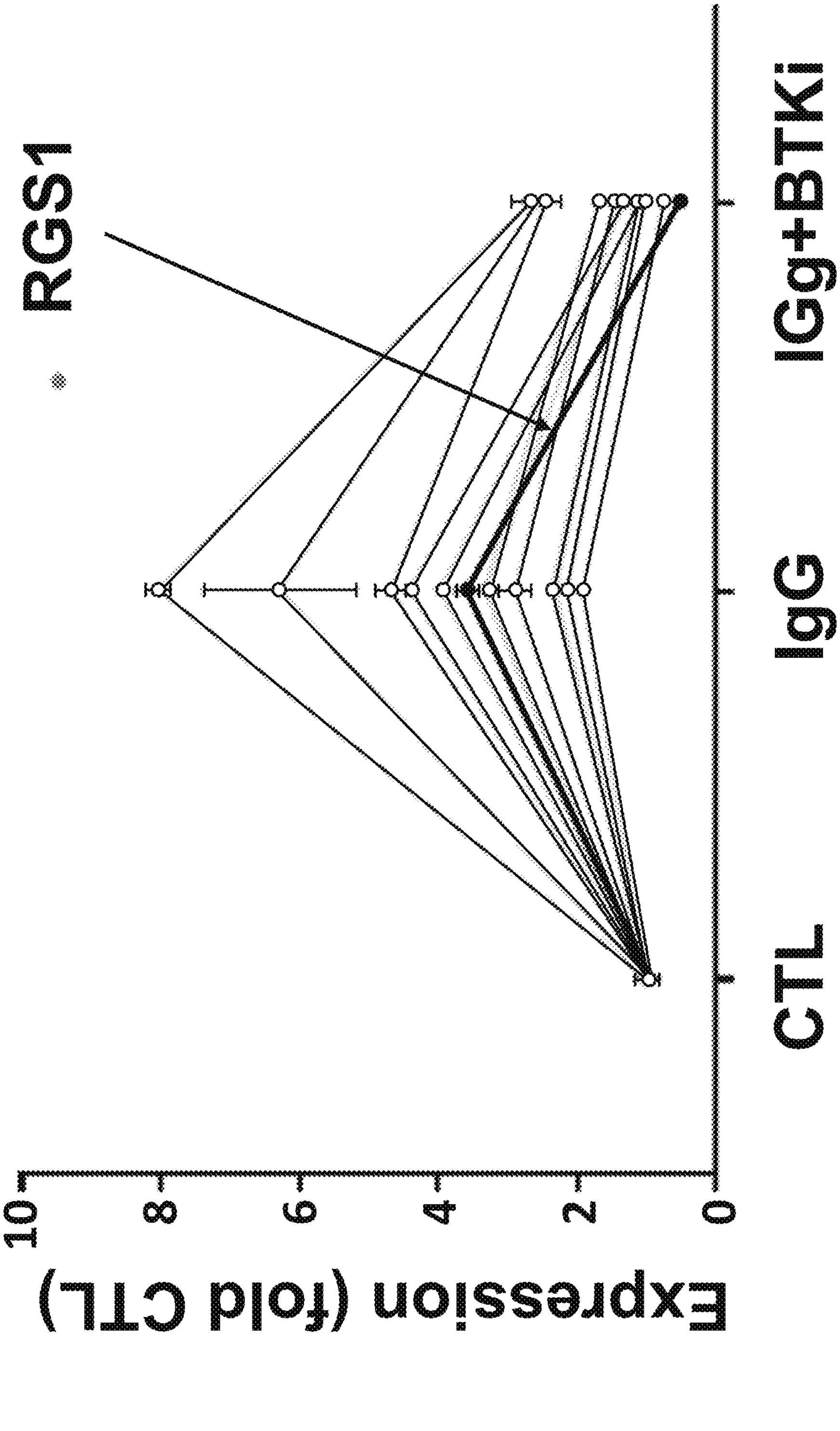
FIG. 4 shows relative expression levels of differential expressed genes (DEGs) in mouse microglia after treatment with IgG, and treatment with IgG and the BTK inhibitor, as compared to the control. CTL=control; IgG=immunoglobulin; RGS1=regulator of G protein signaling 1.

A 6 h BTKi gene signature was established by identifying the DEGs that were increased in the activated state that were corrected upon treatment with the BTK inhibitor. A 24 h BTKi gene signature was established by identifying the DEGs that were increased in the activated state that were corrected upon treatment with the BTK inhibitor, as shown in FIG. 4.

Figure 5B:
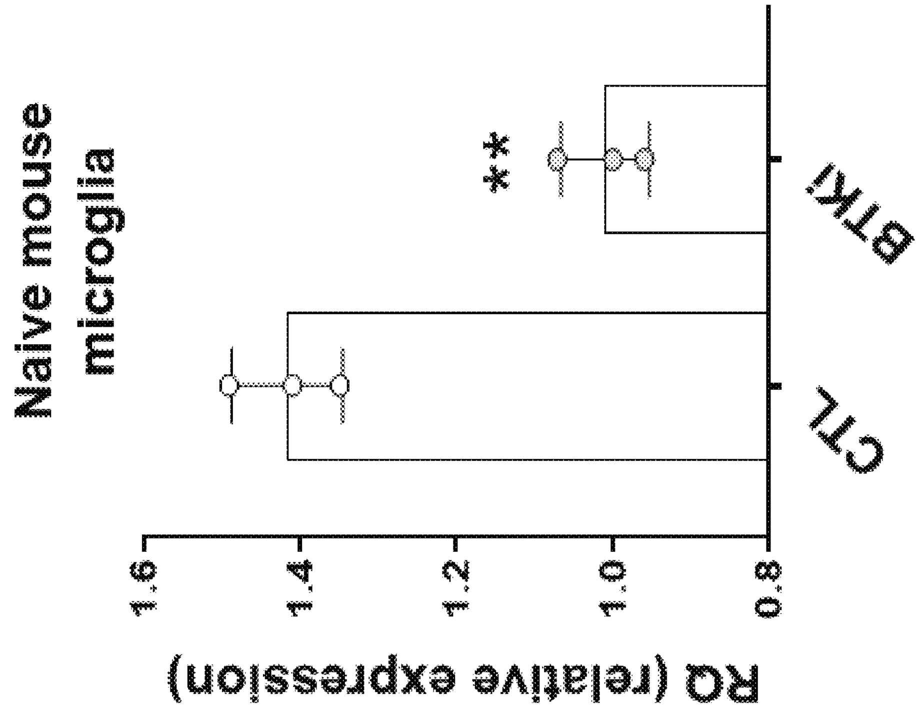
FIGS. 5A-5B show RGS1 mRNA quantitative measurements after in vitro treatment of mouse microglia with IgG only and with IgG and the BTK inhibitor (FIG. 5A) and after in vitro treatment of naïve mouse microglia with the BTK inhibitor (FIG. 5B). CTL=control; IgG=immunoglobulin; mRNA=messenger ribonucleic acid.
Figure 5A:
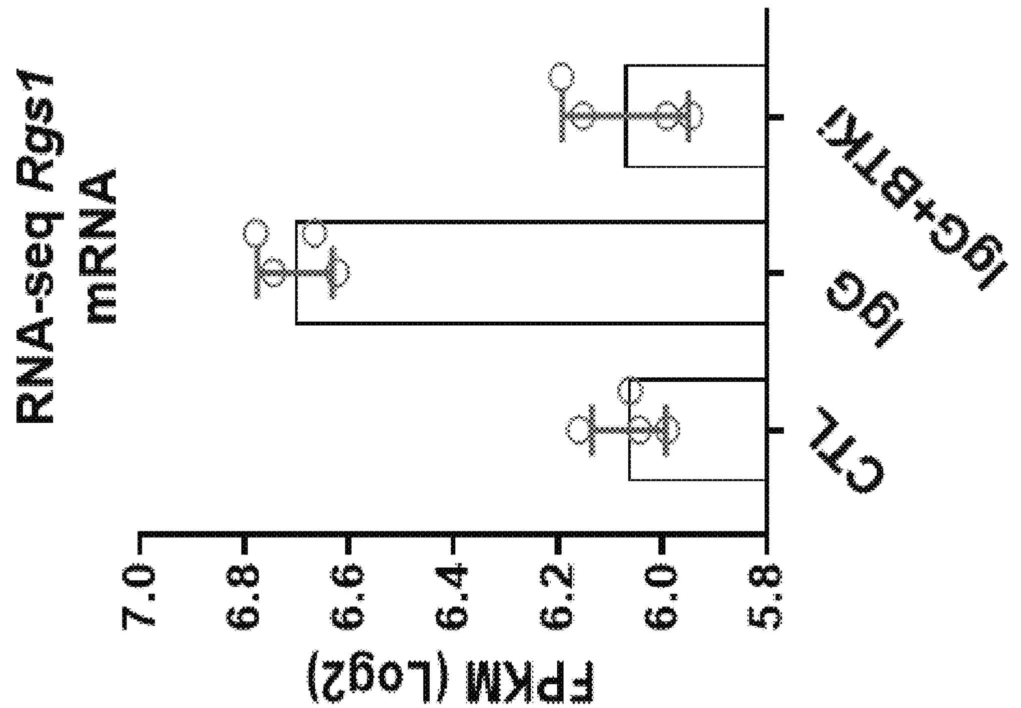

The FPKM comparison of RGS1 mRNA at 24 h were shown in FIG. 5A.

In Vivo Treatment of Naïve Mouse Microglia

Primary mouse microglia were prepared from postnatal mice as described above, and were treated with 2.5 μM of the BTKi inhibitor for 6 and 24 hours. RNA was isolated and was analyzed by quantitative Real time PCR (Taqman, Thermo Fisher). Relative expression levels compared to a control at 6 h is shown in FIG. 5B (t-test, *p<0.05).

In Vivo Mouse Study

Figure 6:
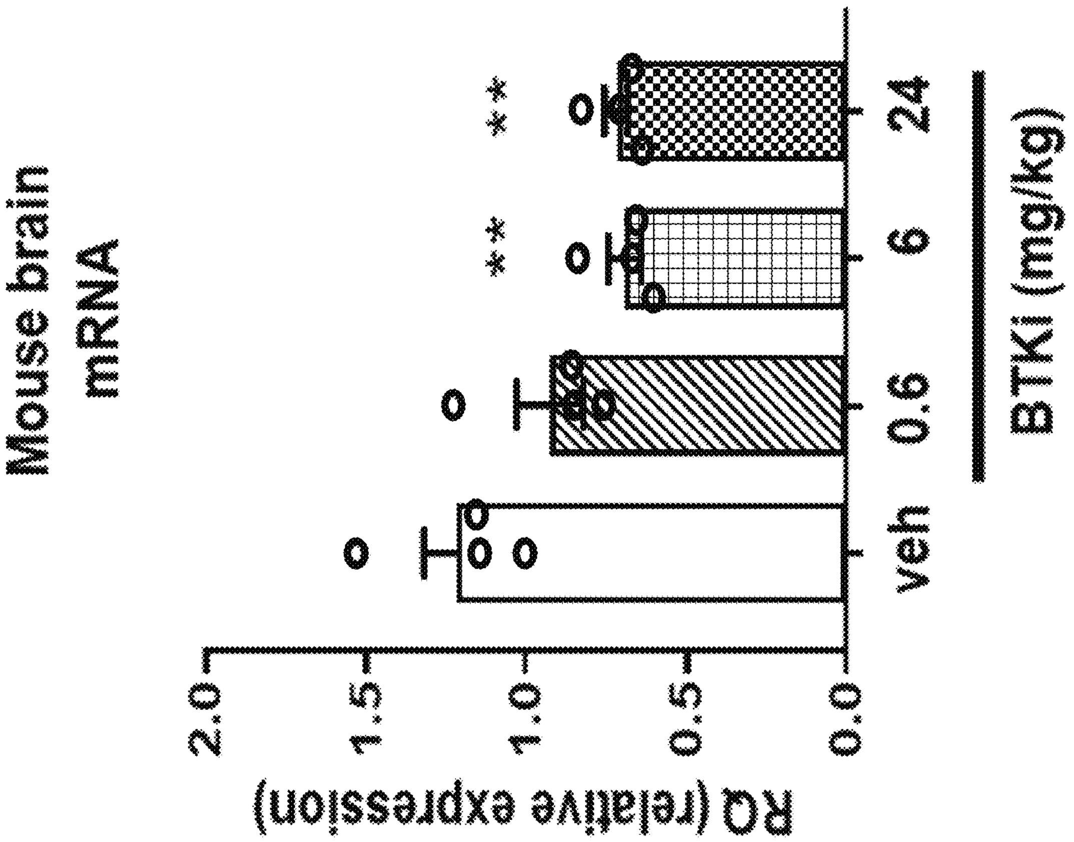
FIG. 6 shows relative RGS1 mRNA expression in microglia after in vivo treatment of naïve mouse with the BTK inhibitor at various doses (0.6, 6, and 24 mg/kg). veh: vehicle (control).

Naïve C57B16 mice were treated daily with an oral solution of the BTK inhibitor or vehicle (100% PEG200) for 5 days. Mice were sacrificed on day 5, 1 h post-final dose, and PBS perfused before brain was isolated. RNA was isolated from brain using the Rneasy Lipid tissue RNA isolation kid (Qiagen). RGS1 was quantified using Real-time PCR and Taqman probe (FIG. 6; one-way ANOVA, **p<0.01).

Human Brain Single Nucleus RNAseq Library Preparation

Patient Samples and Processing

Cryopreserved post-mortem brain specimens were obtained from the UCLA Brain Bank or the Cleveland Clinic Rapid Autopsy Program. Tissue specimens primarily consisted of subcortical white matter with a smaller portion of the surrounding gray matter. Nuclei suspensions were prepared from homogenized tissue following a previously described method with modifications. In brief, approximately 200-400 mg of tissue was processed on ice in a nuclei isolation buffer consisting of 240 mM sucrose, 24 mM KCL, 4.8 mM MgCl2, 9.59 mM Tris (pH 8.0), 0.97 uM DTT, 0.1% (v/v) Triton X-100, 1× protease inhibitor (Fisher, PI78429), 0.4 units/μL RNAseIn (Fisher, PR-N2511), and 0.2 units/μL Superasin (Fisher, AM2694) in nuclease free water. Samples were first placed in a petri dish containing buffer and minced using a razor. The tissue suspension was then then homogenized using a glass dounce homogenizer and the homogenate was filtered through a 100 micron cell strainer. A crude nuclei suspension was prepared from the homogenate by 1-2 rounds of washing (Nuclei PURE store buffer, Sigma, S9183) and centrifugation (700 g for 3 minutes at 4 degrees). Nuclei were then labelled with a nucleic acid binding dye (DAPI, 1:500), washed once more with nuclei isolation buffer, and pelleted by centrifugation (700 g, 2 minutes at 4 degrees). Final nuclei suspensions were prepared by resuspending crude pellets in nuclei isolation buffer and sorting DAPI+ events into a collection buffer (0.5% UltraPure BSA and 1× Superasin in PBS) using a BD Influx cell sorter.

Single Nucleus RNAseq Library Preparation

The isolated nuclei were subjected to snRNA-seq using Chromium single Cell 3' Library Kit with v2 chemistry with a Chromium Controller per the manufacturer's instructions (10× Genomics). The library was sequenced using a Next-seq500 (Illumina).

Single Nucleus RNAseq Data Processing

Sample demultiplexing, barcode processing and single cell counting was performed using the Cell Ranger analysis pipeline (10× Genomics). RNAseq reads were mapped to the human reference genome with pre-mRNA annotations, which account for both exons and introns. The subsequent data analysis was performed using R/Bioconductor and Partek Single Cell Toolkit (Partek). For quality control, nuclei with high mitochondrial content, high UMI and high gene number per cells were removed. Data were normalized using a scaling factor of 1,000,000.

Results

As shown in FIG. 4, the gene expression signature of microglia was altered by activation with IgG, and this was normalized with BTK inhibition. As shown in FIG. 4, RGS1 was identified as one of the genes upregulated in this BTK-dependent microglial signature. RGS1 (regulator of G protein signaling 1) functions as a negative regulator of G protein signaling pathways and has been implicated in various inflammatory diseases. RGS1 has been identified as a MS risk factor and also found to be enriched in microglia (International Multiple Sclerosis Genetics Consortium, Science 365:6460 (2019)).

When the mRNA expression in mouse microglia after the in vivo treatment with IgG only and treatment with IgG and the BTK inhibitor were compared, as shown in FIG. 5A, the mRNA expression of RGS1 was upregulated with IgG treatment and was blocked by the BTK inhibitor. As shown in FIG. 5B, when naïve mouse microglia were treated with the BTK inhibitor, RGS1 mRNA level was reduced.

BTK inhibitor also reduced RGS1 expression in vivo. When the naïve mice were treated with the BTK inhibitor once a day for 5 days, reduction of RGS1 mRNA expression was observed at various doses (0.6, 6, and 24 mg/kg) as shown in FIG. 6. These results indicate that BTK regulates constitutive RGS1 brain expression, which may be indicative of BTK activity, in vitro and in vivo.

Figure 7B:
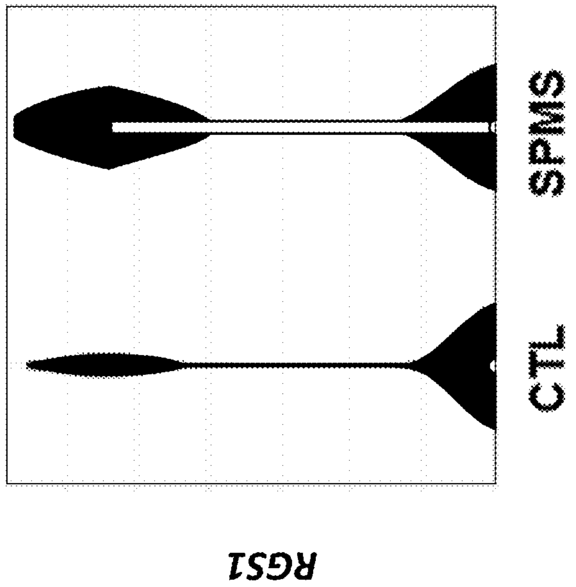
FIG. 7B shows relative RGS1 levels in secondary progressive multiple sclerosis (SPMS) patients and control (FIG. 7B).
Figure 7A:
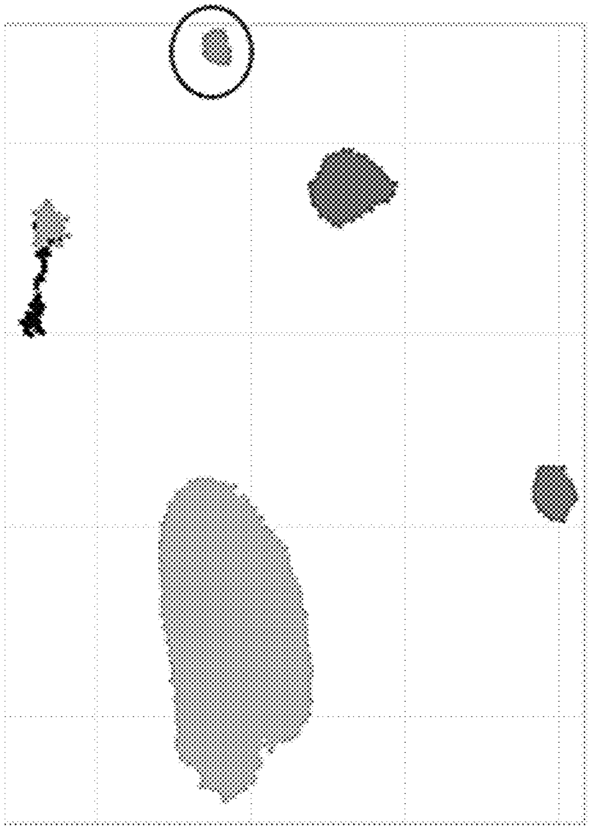
FIG. 7A shows a UMAP (uniform manifold approximation and projection) plot based on a single cell RNAseq dataset where various CNS cells are identified including microglia (in open circle) (FIG. 7A).

FIG. 7A shows that various CNS cells are identified including microglia (in open circle) using the single cell RNA seq dataset from secondary progressive MS (SPMS) microglia. When specific genes in the single cell mRNA sequencing dataset were examined, RGS1 was one of the most upregulated genes in the SPMS microglia (Table 31 and FIG. 7B).

TABLE 31

| Gene | Ratio (SPMS vs. Control), log2 | Gene Name |
|---|---|---|
| SPP1 | 3.14 | Secreted phosphoprotein 1 |
| RGS1 | 2.59 | Regulator of G protein signaling 1 |
| CX3CR1 | −2.1 | C—X3—C motif chemokine receptor 1 |
| P2RY12 | −1.8 | Purinergic receptor P2Y12 |

RGS1 upregulation suggests that BTK may be active in these microglia, and that RGS1 may also have distinct functional relevance to progressive MS microglia phenotype.

Example 4

The effect of food taken with the BTK inhibitor was investigated. The clinical study of Example 1 was conducted, and the results were analyzed to compare the patients treated with the BTK inhibitor in a fasting status and the patients treated in a fed status. Samples from the two groups were obtained and analyzed to evaluate pharmacokinetics parameters as described in Example 1.10 above.

The results confirmed that the administration of the BTK inhibitor in a fed state substantially increased the median AUC (area under curve) when compared to administration in a fasted state. Patients with higher AUC (higher exposure to the BTK inhibitor) resulted in very few or no new Gd-enhancing T1-hyperintense lesions.

What is claimed is:

1. A method of reducing the number of new gadolinium (Gd)-enhancing T1 hyperintense lesions, comprising administering to a human subject in need thereof that has relapsing multiple sclerosis (RMS) an effective amount of (R)-1-(1-acryloylpiperidin-3-yl)-4-amino-3-(4-phenoxyphenyl)-1H-imidazo[4,5-c]pyridin-2(3H)-one, wherein the reduction in the number of new gadolinium (Gd)-enhancing T1 hyperintense lesions is compared to placebo.

2. The method of claim 1, wherein the dose is 60 mg.

3. The method of claim 2, wherein the dose is administered once daily.

4. The method of claim 3, wherein the dose is administered once daily with food.

5. The method of claim 2, wherein administration of (R)-1-(1-acryloylpiperidin-3-yl)-4-amino-3-(4-phenoxyphenyl)-1H-imidazo[4,5-c]pyridin-2(3H)-one reduces the number of new gadolinium (Gd)-enhancing T1 hyperintense lesions as measured by MRI, wherein the reduction in the number of new gadolinium (Gd)-enhancing T1 hyperintense lesions is compared to placebo.

6. The method of claim 5, wherein the number of new Gd-enhancing T1 hyperintense lesions is equal to or less than 1 after 12 weeks of (R)-1-(1-acryloylpiperidin-3-yl)-4-amino-3-(4-phenoxyphenyl)-1H-imidazo[4,5-c]pyridin-2(3H)-one treatment.

7. The method of claim 5, wherein administration of (R)-1-(1-acryloylpiperidin-3-yl)-4-amino-3-(4-phenoxyphenyl)-1H-imidazo[4,5-c]pyridin-2(3H)-one reduces the number of new or enlarging T2 lesions as measured by MRI, wherein the reduction in the number of new or enlarging T2 lesions is compared to placebo.

8. The method of claim 7, wherein the number of new or enlarging T2 lesions is equal to or less than 2 after 12 weeks of (R)-1-(1-acryloylpiperidin-3-yl)-4-amino-3-(4-phenoxyphenyl)-1H-imidazo[4,5-c]pyridin-2(3H)-one treatment.

9. The method of claim 2, wherein the dose is administered once daily, wherein administration of (R)-1-(1-acryloylpiperidin-3-yl)-4-amino-3-(4-phenoxyphenyl)-1H-imidazo[4,5-c]pyridin-2(3H)-one reduces the number of new gadolinium (Gd)-enhancing T1 hyperintense lesions as measured by MRI, wherein the reduction in the number of new gadolinium (Gd)-enhancing T1 hyperintense lesions is compared to placebo.

10. The method of claim 9, wherein the number of new Gd-enhancing T1 hyperintense lesions is equal to or less than 1 after 12 weeks of (R)-1-(1-acryloylpiperidin-3-yl)-4-amino-3-(4-phenoxyphenyl)-1H-imidazo[4,5-c]pyridin-2(3H)-one treatment.

11. The method of claim 9, wherein administration of (R)-1-(1-acryloylpiperidin-3-yl)-4-amino-3-(4-phenoxyphenyl)-1H-imidazo[4,5-c]pyridin-2(3H)-one reduces the number of new or enlarging T2 lesions as measured by MRI, wherein the reduction in the number of new or enlarging T2 lesions is compared to placebo.

12. The method of claim 11, wherein the number of new or enlarging T2 lesions is equal to or less than 2 after 12 weeks of (R)-1-(1-acryloylpiperidin-3-yl)-4-amino-3-(4-phenoxyphenyl)-1H-imidazo[4,5-c]pyridin-2(3H)-one treatment.

13. The method of claim 2, wherein the dose is administered once daily with food, wherein administration of (R)-1-(1-acryloylpiperidin-3-yl)-4-amino-3-(4-phenoxyphenyl)-1H-imidazo[4,5-c]pyridin-2(3H)-one reduces the number of new gadolinium (Gd)-enhancing T1 hyperintense lesions as measured by MRI, wherein the reduction in the number of new gadolinium (Gd)-enhancing T1 hyperintense lesions is compared to placebo.

14. The method of claim 13, wherein the number of new Gd-enhancing T1 hyperintense lesions is equal to or less than 1 after 12 weeks of (R)-1-(1-acryloylpiperidin-3-yl)-4-amino-3-(4-phenoxyphenyl)-1H-imidazo[4,5-c]pyridin-2(3H)-one treatment.

15. The method of claim 13, wherein administration of (R)-1-(1-acryloylpiperidin-3-yl)-4-amino-3-(4-phenoxyphenyl)-1H-imidazo[4,5-c]pyridin-2(3H)-one reduces the number of new or enlarging T2 lesions as measured by MRI, wherein the reduction in the number of new or enlarging T2 lesions is compared to placebo.

16. The method of claim 15, wherein the number of new or enlarging T2 lesions is equal to or less than 2 after 12 weeks of (R)-1-(1-acryloylpiperidin-3-yl)-4-amino-3-(4-phenoxyphenyl)-1H-imidazo[4,5-c]pyridin-2(3H)-one treatment.

17. A method of reducing the number of new gadolinium (Gd)-enhancing T1 hyperintense lesions, comprising administering to a human subject in need thereof that has relapsing multiple sclerosis (RMS) an effective amount of (R)-1-(1-acryloylpiperidin-3-yl)-4-amino-3-(4-phenoxyphenyl)-1H-imidazo[4,5-c]pyridin-2(3H)-one, wherein the reduction in the number of new gadolinium (Gd)-enhancing T1 hyperintense lesions is compared to no treatment.

18. The method of claim 17, wherein the dose is 60 mg.

19. The method of claim 18, wherein the dose is administered once daily.

20. The method of claim 19, wherein the dose is administered once daily with food.

21. The method of claim 18, wherein administration of (R)-1-(1-acryloylpiperidin-3-yl)-4-amino-3-(4-phenoxyphenyl)-1H-imidazo[4,5-c]pyridin-2(3H)-one reduces the number of new gadolinium (Gd)-enhancing T1 hyperintense lesions as measured by MRI, wherein the reduction in the number of new gadolinium (Gd)-enhancing T1 hyperintense lesions is compared to no treatment.

22. The method of claim 21, wherein the number of new Gd-enhancing T1 hyperintense lesions is equal to or less than 1 after 12 weeks of (R)-1-(1-acryloylpiperidin-3-yl)-4-amino-3-(4-phenoxyphenyl)-1H-imidazo[4,5-c]pyridin-2(3H)-one treatment.

23. The method of claim 21, wherein administration of (R)-1-(1-acryloylpiperidin-3-yl)-4-amino-3-(4-phenoxyphenyl)-1H-imidazo[4,5-c]pyridin-2(3H)-one reduces the number of new or enlarging T2 lesions as measured by MRI, wherein the reduction in the number of new or enlarging T2 lesions is compared to no treatment.

24. The method of claim 23, wherein the number of new or enlarging T2 lesions is equal to or less than 2 after 12 weeks of (R)-1-(1-acryloylpiperidin-3-yl)-4-amino-3-(4-phenoxyphenyl)-1H-imidazo[4,5-c]pyridin-2(3H)-one treatment.

25. The method of claim 18, wherein the dose is administered once daily, wherein administration of (R)-1-(1-acryloylpiperidin-3-yl)-4-amino-3-(4-phenoxyphenyl)-1H-imidazo[4,5-c]pyridin-2(3H)-one reduces the number of new gadolinium (Gd)-enhancing T1 hyperintense lesions as measured by MRI, wherein the reduction in the number of new gadolinium (Gd)-enhancing T1 hyperintense lesions is compared to no treatment.

26. The method of claim 25, wherein the number of new Gd-enhancing T1 hyperintense lesions is equal to or less than 1 after 12 weeks of (R)-1-(1-acryloylpiperidin-3-yl)-4-amino-3-(4-phenoxyphenyl)-1H-imidazo[4,5-c]pyridin-2(3H)-one treatment.

27. The method of claim 25, wherein administration of (R)-1-(1-acryloylpiperidin-3-yl)-4-amino-3-(4-phenoxyphenyl)-1H-imidazo[4,5-c]pyridin-2(3H)-one reduces the number of new or enlarging T2 lesions as measured by MRI, wherein the reduction in the number of new or enlarging T2 lesions is compared to no treatment.

28. The method of claim 27, wherein the number of new or enlarging T2 lesions is equal to or less than 2 after 12 weeks of (R)-1-(1-acryloylpiperidin-3-yl)-4-amino-3-(4-phenoxyphenyl)-1H-imidazo[4,5-c]pyridin-2(3H)-one treatment.

29. The method of claim 18, wherein the dose is administered once daily with food, wherein administration of (R)-1-(1-acryloylpiperidin-3-yl)-4-amino-3-(4-phenoxyphenyl)-1H-imidazo[4,5-c]pyridin-2(3H)-one reduces the number of new gadolinium (Gd)-enhancing T1 hyperintense lesions as measured by MRI, wherein the reduction in the number of new gadolinium (Gd)-enhancing T1 hyperintense lesions is compared to no treatment.

30. The method of claim 29, wherein the number of new Gd-enhancing T1 hyperintense lesions is equal to or less than 1 after 12 weeks of (R)-1-(1-acryloylpiperidin-3-yl)-4-amino-3-(4-phenoxyphenyl)-1H-imidazo[4,5-c]pyridin-2(3H)-one treatment.

31. The method of claim 29, wherein administration of (R)-1-(1-acryloylpiperidin-3-yl)-4-amino-3-(4-phenoxyphenyl)-1H-imidazo[4,5-c]pyridin-2(3H)-one reduces the number of new or enlarging T2 lesions as measured by MRI, wherein the reduction in the number of new or enlarging T2 lesions is compared to no treatment.

32. The method of claim 31, wherein the number of new or enlarging T2 lesions is equal to or less than 2 after 12 weeks of (R)-1-(1-acryloylpiperidin-3-yl)-4-amino-3-(4-phenoxyphenyl)-1H-imidazo[4,5-c]pyridin-2(3H)-one treatment.

* * * * *